US012595488B2

(12) United States Patent
Barry et al.

(10) Patent No.: US 12,595,488 B2
(45) Date of Patent: *Apr. 7, 2026

(54) INSECTICIDAL PROTEINS FROM PLANTS AND METHODS FOR THEIR USE

(71) Applicant: PIONEER HI-BRED INTERNATIONAL, INC., Johnston, IA (US)

(72) Inventors: Jennifer Kara Barry, Ames, IA (US); Angel Elizabeth Grace D'Oliviera, Wilmington, DE (US); Ryan Michael Gerber, Apex, NC (US); Kevin Hayes, Urbandale, IA (US); Albert L Lu, West Des Moines, IA (US); Amy Lum, Redwood City, CA (US); Ute Schellenberger, Menlo Park, CA (US); Eric Schepers, Port Deposit, MD (US); Jeffrey Sopa, Rising Sun, MD (US); Weiping Xie, East Palo Alto, CA (US); Nasser Yalpani, Kelowna (CA)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/344,457

(22) Filed: Jun. 29, 2023

(65) Prior Publication Data

US 2023/0348930 A1     Nov. 2, 2023

Related U.S. Application Data

(62) Division of application No. 16/619,984, filed as application No. PCT/US2018/037473 on Jun. 14, 2018, now Pat. No. 11,739,344.

(60) Provisional application No. 62/521,084, filed on Jun. 16, 2017.

(51) Int. Cl.
| | |
|---|---|
| *C12N 15/82* | (2006.01) |
| *A01N 63/50* | (2020.01) |
| *C07K 14/325* | (2006.01) |
| *C07K 14/415* | (2006.01) |
| *C12N 15/11* | (2006.01) |

(52) U.S. Cl.
CPC ......... *C12N 15/8286* (2013.01); *A01N 63/50* (2020.01); *C07K 14/325* (2013.01); *C07K 14/415* (2013.01); *C12N 15/111* (2013.01)

(58) Field of Classification Search
CPC .. C12N 15/8286; C12N 15/111; C12N 15/82; A01N 63/50; C07K 14/325; C07K 14/415; Y02A 40/146; A24D 1/042; A24D 1/045
See application file for complete search history.

(56) References Cited

U.S. PATENT DOCUMENTS

| | | | |
|---|---|---|---|
| 4,149,550 | A | 4/1979 | Green et al. |
| 11,739,344 | B2 * | 8/2023 | Barry .................... C12N 15/82 |
| | | | 514/4.5 |
| 2014/0033361 | A1 | 1/2014 | Altier et al. |
| 2015/0208720 | A1 | 7/2015 | Kadiric |
| 2016/0347799 | A1 | 12/2016 | Barry et al. |

FOREIGN PATENT DOCUMENTS

| | | |
|---|---|---|
| CN | 2484750 Y | 4/2002 |
| CN | 201976724 U | 9/2011 |
| CN | 102742937 A | 10/2012 |
| CN | 202890451 U | 4/2013 |
| CN | 203969190 U | 12/2014 |
| CN | 104323425 A | 2/2015 |
| CN | 204444225 U | 7/2015 |
| CN | 204969449 U | 1/2016 |
| CN | 105707977 A | 6/2016 |
| JP | 2002126428 A | 5/2002 |
| KR | 200301170 Y1 | 1/2003 |
| KR | 20140000921 U | 2/2014 |
| WO | 2015120270 A1 | 8/2015 |
| WO | 2017021422 A1 | 2/2017 |

OTHER PUBLICATIONS

Banks J.A., et al., "The Selaginella Genome Identifies Genetic Changes Associated with the Evolution of Vascular Plants," Science, US, May 20, 2011, vol. 332, No. 6032, pp. 960-963, DOI:10. 1126/science. 1203810, ISSN 0036-8075, XP055758636.
Butala M., et al., "Aegerolysins: Lipid-Binding Proteins with Versatile Functions," Seminars in Cell and Developmental Biology, Academic Press, GB, May 12, 2017, vol. 72, pp. 142-151, Doi: 10.1016/J.SEMCDB.2017.05.002, ISSN 1084-9521, XP085290960.
Extended European Search Report for European Application No. 18817798.4, mailed Apr. 20, 2021, 12 Pages.
Genbank: "Hypothetical Protein LSAT_9X120041 [Lactuca Sativa]," Genbank ID: PLY75840, Jan. 9, 2018, 1 Page.
International Preliminary Report on Patentability for International Application No. PCT/US2018/037473, mailed Dec. 26, 2019, 8 Pages.
International Search Report and Written Opinion for International Application No. PCT/US2018/037473, mailed Oct. 24, 2018, 13 Pages.

(Continued)

*Primary Examiner* — Aaron J Kosar

(57) ABSTRACT

Compositions and methods for controlling pests are provided. The methods involve transforming organisms with a nucleic acid sequence encoding an insecticidal protein. In particular, the nucleic acid sequences are useful for preparing plants and microorganisms that possess insecticidal activity. Thus, transformed bacteria, plants, plant cells, plant tissues and seeds are provided. Compositions are insecticidal nucleic acids and proteins of bacterial species. The sequences find use in the construction of expression vectors for subsequent transformation into organisms of interest including plants, as probes for the isolation of other homologous (or partially homologous) genes. The pesticidal proteins find use in controlling, inhibiting growth or killing Lepidopteran, Coleopteran, Dipteran, fungal, Hemipteran and nematode pest populations and for producing compositions with insecticidal activity.

10 Claims, 10 Drawing Sheets

Specification includes a Sequence Listing.

(56)                    References Cited

OTHER PUBLICATIONS

Park Y., et al., "Enhancement of Bacillus Thuringiensis Cry3Aa and Cry3Bb Toxicities to Coleopteran Larvae by a Toxin-Binding Fragment of an Insect Cadherin," Applied and Environmental Microbiology, May 2009, vol. 75, No. 10, pp. 3086-3092.

Partial Supplementary European Search Report for European Application No. 18817798.4, mailed Jan. 20, 2021, 14 Pages.

UNIPROT: "SubName: Full=17-kDa Protein of Sterile Frond {EC0:0000313 EMBL:BAC55101.1}," UniProtKB/TrEMBL Accession No. Q84LE5, Oct. 14, 2015, 1 Page, [Retrieved on Sep. 19, 2019] Retrieved from URL: www.uniprot.org/uniprot/Q84LE5.textversion=19 Entire Document.

Genbank ID: PLY75840. (Year: 2018).

Park et al. "Enhancement of Bacillus thuringiensis Cry3Aa and Cry3Bb Toxicites to cleopteran Larvae by a Toxin-Binding Fragment of an Insect Cadherin". Applied and Environmental Biology. 75(10): 3086-3092. (Year: 2009).

UniProtKB/RrEMBL Accession No. Q84LE5, Oct. 14, 2015 [online]. [Retrieved on Oct. 11, 2018]. Retrieved from the internet <URL: https://www.uniprot.org/uniprot/Q84LE5.txt?version=19> Entire Document.

International Search Report and Written Opinion for International Application PCT/US18/37473, Mailed Oct. 24, 2018.

UNIPORT: "SubName: Full=Uncharacterized protein {ECO:0000313|EMBL:EFJ10485.1}," Database Accession No. D8SYN2, Oct. 5, 2010, URL: EBI, XP002801409.

UNIPORT: "SubName: Full=Uncharacterized protein {ECO:0000313| EMBL:EFJ25241.1}, Flags: Fragment," Database Accession No. D8RRH1, Oct. 5, 2010, URL: EBI, XP002801410.

* cited by examiner

Fig. 2A

```
          1                                                ▼ ▼                              •                        50
IPD059Aa  (1)   MAATKAVLAVCSCIIVLMG-VMISGGLASDEPTWQEVLTTARTNVVYGPS
IPD059Ab  (1)   MAATKAVLAVCSCIIVLMGVDMISGGLASNEPTWQEVLTTARTNVVYGAS
IPD059Ac  (1)   MAATKAVLAVCSCIIVLMGADMISGGLASNEPTWQEVLTTARTNVVYGAS
IPD059Ad  (1)   MAATKAVLAVCSCIIVLMGADMISGGLASNEPTWQEVLTTARTNVVYGAS
IPD059Ae  (1)   -------------------------------------------------MS
IPD059Ca  (1)   -MATKTLLAVCGCILILMG-VMISGGSAADE-TWQEVLTRAGTNVVYGPS
IPD059Cb  (1)   -MATKTLLTVCGCILILMG-VMISGGSAADE-TWQEVLTRAGTNVVYGPS
IPD059Cc  (1)   -MATKAVSAICGCIMILMG-AMISGALADDE-TWQEVLTTAGTNVVFGAS
IPD059Ag  (1)   -------------------------------------------------MS
IPD059Af  (1)   -------------------------------------------------MS
IPD059Ah  (1)   -------------------------------------------------MS

51                                                                   ▼              100
IPD059Aa  (50)  NTYTIRSMTSGIGYLFRFFFGLGFPGEAVRTDTTITMGRNGDASAIYACI
IPD059Ab  (51)  NTYTIWSQTSGIGYLFRFFFGLGFPGEAVRTDTTITMGRNGDASAIYACI
IPD059Ac  (51)  NTYTIWSQTSGIGYLFRFFFGLGFPGEAVRTDTTITMGRNGDASAIYACI
IPD059Ad  (51)  NTYTIWSQTSGIGYLFRFFFGLGFPGEAVRTDTTITMGRNGDASAIYACI
IPD059Ae  (3)   NTYTIWSQTSGIGYLFRFFFGLGFPGEAVRTDTTITMGRNGYASAIYACI
IPD059Ca  (48)  NTYIIWSTESWIGYVFGFFFGLGFDGEAVRTDTTVTLGRNGDASSIYACI
IPD059Cb  (48)  NTYIIWSTESWIGYVFGFFFGLGFDGEAVRTDTTVTLGRNGDASSIYACI
IPD059Cc  (48)  NTYTIRSRESGIGYLFRFYFGLGGEGEPVRTDTTVTLGRNGDASRIYSCN
IPD059Ag  (3)   NTYTIWSQTSGIGYLFRFFFGLGFPGEAVRTDTTITMGRNGDASAIYACI
IPD059Af  (3)   NTYTIWSQTSGIGYLFRFFFGLGFPGEAVRTNTTITMGRNGDASAIYACI
IPD059Ah  (3)   NTYTIWSQTSGIGYLFRFFFGLGFPGEAVRTDTTITMGRNGDASAIYACI 101                                                              150
IPD059Aa  (100)  DGRLRLVATNTSGTPQNALIRVRFNSTDGYYRLQITQASPAVYVQFVLLS
IPD059Ab  (101)  DGRLQVVATNTSGTPQNALIRVRYNSTDGYYRLQITQASPAVYVQFVLLS
IPD059Ac  (101)  DGRLQVVATNTSGTPQNALIRVRYNSTDGYYRLQITQASPAVYVQFVLLS
IPD059Ad  (101)  DGRLQVVATNTSGTPQNALIRVRYNSTDGYYRLQITQASPAVYVQFVLLS
IPD059Ae  (53)   DGRLQVVATNTSGTPQNALIRVRYNSTDGYYRLQITQASPAVYVQFVLLS
IPD059Ca  (98)   DGKLELVPTNSSGTPQNALIRVRYNSTDGYYRLQITEASPAVYVQFVLLS
IPD059Cb  (98)   DGKLELVPTNSSGTPQNALIRVRYNSTDGYYRLQITEASPAVYVQFVLLS
IPD059Cc  (98)   DGTLELVATNSSGTPQSALIRVRYNSTDGYYRLQITEASPAVYVQFVLLS
IPD059Ag  (53)   DGRLQVVATNTSGTPQNALIRVRYNSTDGYYRLQITQASPAVYVQFVLLS
IPD059Af  (53)   DGRLQVVATNTSGTPQNALIRVRYNSTDGYYRLQITQASPAVYVQFVLLS
IPD059Ah  (53)   DGRLQVVATNTSGTPQNALIRVRYNSTDGYYRLQITQASPAVYVQFVLLS
```

Fig. 2B

```
              151   ▼                                                   200
IPD059Aa  (150)  QGGILCTAGLPGTPLTFTSSSSS-----------------DLRVLHQVVD
IPD059Ab  (151)  QGGILCTAGLPGTPLTFTSSSSSSS---------------DLRVLHQVVD
IPD059Ac  (151)  QGGILCTAGLPGTPLTFTSSSSSSS---------------DLRVLHQVVD
IPD059Ad  (151)  QGGILCTAGLPGTPVTFTSSSSSSS---------------DLRVLHQVVD
IPD059Ae  (103)  QGGILCTAGLPGTPVTFTSSSSSSS---------------DLRVLHQVVD
IPD059Ca  (148)  QGGILCTAGLPGTPIVFTSTSSSSSVSPNRRQGPALVYTPDMHVLRQVVD
IPD059Cb  (148)  QGGILCTAGLPGTPIVFTSTSSSSSVSPNRRQGPALVYTPDMHVLRQVVD
IPD059Cc  (148)  QGGILCTAGLPGTPIVFESSSSSSLSS--RPLGPVLVYTPDMDVLRQVVD
IPD059Ag  (103)  QGGILCTAGLPGTPVTFTSSSSSSS---------------DLRVLHQVVD
IPD059Af  (103)  QGGILCTAGLPGTPLTFTSSSSSSS---------------DLRVLHQVVD
IPD059Ah  (103)  QGGILCTAGLPGTPLTFTSSSSSSS---------------DLRVLHQVVD

201
IPD059Aa  (183)  SSSLS
IPD059Ab  (186)  SSSLA
IPD059Ac  (186)  SSSLA
IPD059Ad  (186)  SSSLA
IPD059Ae  (138)  SSSLA
IPD059Ca  (198)  SSSLA
IPD059Cb  (198)  SSSLA
IPD059Cc  (196)  SSSLA
IPD059Ag  (138)  SSSLA
IPD059Af  (138)  SSSLA
IPD059Ah  (138)  SSSLA
```

Fig. 3

```
                 1                      ▼                       50
IPD059Da    (1)  MANKGGVVAVLWLMTVSSVLMMGCNTVAGDDETWQEVLTTAGTNVVFGAS
IPD059Db    (1)  MATKGGVVAVLWLMTVSSVLMMGCNTVAGDDETWQEVLTTAGTNVVFGAS
IPD059Ea    (1)  MANKGGVVAFWLMIVSCSVLLGCNTVAGTDETWQEVLTTAGTNVVFGAS
IPD059Eb    (1)  MATKGGVVAFWLMIVSCSVLLGCNTVAGTDETWQEVLTTAGTNVVFGAS
IPD059Ec    (1)  MATKGGVVLVCLCMIAL-----GCNTVAGDDETWQEVLTTDGANVVYGAN
IPD059Ed    (1)  MATKGGVVLVCLCMIAL-----GCNTVAGDDETWQEVLTTDGANVVYGAN
IPD059Ee    (1)  MATKGAVVAVCCLVLVS-AMFMGCTTVAGDDETWQEVLTTAGTTVVYGAT
IPD059Ef    (1)  MATKGAVVAVCCLVLVSAILFMGCTTVAGDDETWQEVLTTAGTTVVYGAT
IPD059Eg    (1)  MATKGAVVAVCCLVLVSAILFMGCTTVAGDDETWQEVLTTAGTTVVYGAT

▼
                 51                                           100
IPD059Da   (51)  NTYTIWARDIGIGYLFRFFFGLGSTGEAVRTDTTVTLGAYGDASRVYACT
IPD059Db   (51)  NTYTIWARDIGIGYLFRFFFGLGSTGEAVRTDTTVTLGAYGDASRVYACT
IPD059Ea   (51)  NTYTIRSQETGIGYLFRFYFELGATGEAVRTDTTVTLGAFGDASRIYACV
IPD059Eb   (51)  NTYTIRSQETGIGYLFRFYFELGATGEAVRTDTTVTLGAFGDASRIYACV
IPD059Ec   (46)  NTYTIWARDIGIGYLYRFFFGLGFTGTAVRSDTAVTLGAFADSTRIYACT
IPD059Ed   (46)  NTYTIWARDIGIGYLYRFFFGLGFTGTAVRTDTAVTLGAFADSTRIYACT
IPD059Ee   (50)  NTYTIQAMDIGIRYLYYFFFGLGYTGDAVRTDTAVTLGDLGDASQIYACT
IPD059Ef   (51)  NTYTIQAMDIGIRYLYYFFFGLGYTGDAVRTDTAVTLGDLGDASQIYACT
IPD059Eg   (51)  NTYTIQAMDIGIRYLYYFFFGLGYTGDAVRTDTAVTLGDLGDASQIYACT 101                                          150
IPD059Da  (101)  DGKLQLVAVNSSGTPENAIIRVRYNSTDRNYRLQITENSPAVFVQFTYLS
IPD059Db  (101)  DGKLQLVAVNSSGTPENAIIRVRYNSTDRNYRLQITENSPAVFVQFTYLS
IPD059Ea  (101)  DGKLERVAVNSSGTPENAIFRVRYNSTSSSYLLQITENSPAVFVQFTYLS
IPD059Eb  (101)  DGKLERVAVNSSGTPENAIFRVRYNSTSSSYLLQITENSPAVFVQFTYLS
IPD059Ec   (96)  DGKLELVAVNSSGTPANAIIRVRYNSTDSNYRLQITENSPAVFVQFTYLS
IPD059Ed   (96)  DGKLELVAVNSSGTPANAIIRVRYNSTDSNYRLQITENSPAVFVQFTYLS
IPD059Ee  (100)  DGKLELVAVNSSGTPQNAIIRVRYNSTDGNYGLQITENSPAVFVQFTYLS
IPD059Ef  (101)  DGKLELVAVNSSGTPQNAIIRVRYNSTDGNYGLQITENSPAVFVQFTYLS
IPD059Eg  (101)  DDKLELVAVNSSGTPQNAIIRVRYNSTDGNYGLQITENSPAVFVQFTYLS

151 ▼                                        198
IPD059Da  (151)  QGGLLCTSGVAGTPIRFTFSSSSSLDHVDEP--ATVVLRQVVDA----
IPD059Db  (151)  QGGLLCTSGVAGTPIRFTFSSSSSLDHVDEP--ATVVLRQVVDA----
IPD059Ea  (151)  LGGLLCTSGVAGTPVRFTSASSSSHGHVDEP--ATVDLRQVVDA----
IPD059Eb  (151)  LGGLLCTSGVAGTPVRFTSASSSSHGHVDEP--ATVDLRQVVDA----
IPD059Ec  (146)  LGGLLCTSGVSGTPIRFTSSSSASHDHLHEP--ATVALRQVVET----
IPD059Ed  (146)  LGGLLCTSGVAGTPIRFTSSSSASHDHLHEP--ATVALRQVVET----
IPD059Ee  (150)  LGGLLCTSGVAGTPIRFISSSSASHNHILHKPATTGVLRQVVDASSST
IPD059Ef  (151)  LGGLLCTSGVAGTPIRFISSSSASHNHILHKPATTGVLRQVVDASSST
IPD059Eg  (151)  LGGLLCTSGVAGTPIRFISSSSASHNHILHKPATTGVLRQVVDASSST
```

Fig. 4

```
          1                 ▼▼                              50
IPD059Em  (1)  MAGLK-AAVAMRVMFCCWSVIMILSKAPRVVHAQDEETFEEVTTRNGSTV
IPD059En  (1)  MAGLK-AAVAMRVMFCCWSVIMILSKAPRVVHAQDEETFEEVTTRNGSTV
IPD059Eo  (1)  MAGLK-AAVAMRVMFCCWSVIMILSKAPRVVHAQDEETFEEVTTRNGSTV
IPD059Ep  (1)  MAGLK-AAVAMRVMFCCWSVIMILSKAPRVVHAQDEETFEEVTTRNGSTV
IPD059Eq  (1)  MAGLK-AAVAMRVMFCCWSVIMILSKAPRVVHAQDEETFEEVTTRNGSTV
IPD059Er  (1)  MAGLK-AAVAMRVMFCCWSVIMILSKAPRVVHAQDEETFEEVTTRNGSTV
IPD059Es  (1)  MAGLK-AAVAMRVMFCCWLVIMILSKAPRVVHAHDEETFEEVTTTDGSIV
IPD059Et  (1)  MAGLKAAAVAMRVMFCCWLVIMILSKAPRVVHAHDEETFEEVTTTDGSIV 51                                               100
IPD059Em  (50)  VYGASNTYTIWSRESGIGYYPFHFGLGFEGLAMRTDTPITMGLGSDASRI
IPD059En  (50)  VYGASNTYTIWSRESGIGYYPFHFGLGFEGLAMRTDTPITMGLGSDASRI
IPD059Eo  (50)  VYGANNTYTIWSRESGIGYYPFHFGLGFEGLAMRTDTPITMGLGSDASRI
IPD059Ep  (50)  VYGANNTYTIWSRESGIGYYPFHFGLGFEGLAMRTDTPITMGLGSDASRI
IPD059Eq  (50)  VYGASNTYTIWSRESGIGYYPFHFGLGFEGLAMRTDTPITMGLGSDASRI
IPD059Er  (50)  VYGASNTYTIWSRESGIGYYPFHFGLGFEGLAMRTDTPITMGLGSDASRI
IPD059Es  (50)  VYGASNTYTIWSRESGIGYYPFHFGLGFEGLAMRTDTPITMGLGSDASRI
IPD059Et  (51)  VYGASNTYTIWSRESGIGYYPFHFGLGFEGLAVRTDTAITMGLGSDASRI
                ▼                  ▼
          101                                              150
IPD059Em  (100)  YACVNGTLRRVATDPECTPDNALIRVRLNSTDNYYRLQITQTLPPVYVQL
IPD059En  (100)  YACVNGTLRRVATDPECTPDNALIRVRLNSTHNYYRLQITQTLPPVYVQL
IPD059Eo  (100)  YACVNGTLRRVATDPECTPDNALIRVRLNSTHNYYRLQITQTLPPVYVQL
IPD059Ep  (100)  YACVNGTLRRVATDPECTPDNALIRVRLNSTDNYYRLQITQTLPPVYVQL
IPD059Eq  (100)  YACVNGTLRRVATDPECTPDNALIRVRLNSTDNYYRLQITQTLPPVYVQL
IPD059Er  (100)  YACVNGTLRRVATDPECTPDNALIRVRLNSTHNYYRLQITQTLPPVYVQL
IPD059Es  (100)  YACVNGTLRRVATDPECTPDNALIRVRLNSTDNYYRLQITQTLPPVYVQL
IPD059Et  (101)  YACVNGTLRRVATDPECTPDNALIRVRLNSTHNYYRLQITQTLPPVYVQL

151       ▼                                      200
IPD059Em  (150)  VLLSQGGLLCTSDLPGTPIQFSAVSSTTSTFTPHVPATDPGLVYELGADN
IPD059En  (150)  VLLSQGGLLCTSDLPGTPIQFSAVSSTTSTFTPHVPATDPGLVYELGADN
IPD059Eo  (150)  VLLSQGGLLCTSDLPGTPIQFSAVSSTTSTFTPHVPATDPGLVYELGADN
IPD059Ep  (150)  VLLSQGGLLCTSDLPGTPIQFSAVSSTTSTFTPHVPATDPGLVYELGADN
IPD059Eq  (150)  VLLSQGGLLCTSDLPGTPIQFSAVSSTTSTFTPHVPATDPGLVYELGADN
IPD059Er  (150)  VLLSQGGLLCTSDLPGTPIQFSAVSSTTSTFTPHVPATDPGLVYELGADN
IPD059Es  (150)  VLLSQGGLLCTSDLPGTPIQFSAVSSTTSTFTPHVPATDPGLVYELGADN
IPD059Et  (151)  VLLSQGGLLCTSDLPGTPIQFSAVSSTTSTFTPHVPATDPGLVYELGADN 201       212
IPD059Em  (200)  THILRQVVDGST
IPD059En  (200)  THILRQVVDGST
IPD059Eo  (200)  THILRQVVDGST
IPD059Ep  (200)  THILRQVVDASA
IPD059Eq  (200)  THILRQVVDASA
IPD059Er  (200)  THILRQVVDASA
IPD059Es  (200)  THILRQVVDASA
IPD059Et  (201)  THILRQVVDASA
```

Fig. 5

```
          1                                                   50
IPD098Aa  (1)   MGYAQWVRVTLKNASASGSLEVKQATLQWGKWFKPLPAPEGDKETEVASP
IPD098Ac  (1)   MGYAQWVRVTLKNASASGSLEVKQATLQWGKWFKPLPAPEGDKETEVASP
IPD098Ab  (1)   MGYAQWVRVTLKNASASGSLEVKQATLQWGKWFKPLPAPEGDKETEVASP
IPD098Ba  (1)   MGYAQWVRVTLKSAAASGSLEVKQATLQWGKWYQPMPAPEGDKDTEVASP
IPD098Bb  (1)   MGYAQWVRVTLKNASASGSLEVKQATLQWGKWYQPMPAPEGDKDTEVASP
IPD098Bc  (1)   MGYAQWVRVTLKNASASGSLEVKQATLQWGKWYQPMPAPEGDKDTEVASP
IPD098Bd  (1)   MGYAQWVRVTLKNASASGSLEVKQATLQWGKWFQPMPP-DGDKDTEVASP
IPD098Be  (1)   MGYAQWVRVTLKNASASGSLEVKQATLQWGKWYQPMPAPEGDKDTEVASP
IPD098Bf  (1)   MGYAQWVRVTLKNASASGSLEVKQATLQWGKWYQPMPAREGDKDTEVASP
IPD098Bg  (1)   MGYAQWVRVTLKNGSASGSLEVKQATLQWGKWFQPMPP-DGDKDTEVASP
IPD098Bh  (1)   MGYAQWVRVTPKNGSASGSLEVKQATLQWGKWFQPMPP-DGDKDTEVASP
IPD098Bi  (1)   MGYAQWVRVTLKNGSASGSLEVKQATLQWGKWFQPMPS-DGYKDTEVASP

51                 ▼                     ▼  100
IPD098Aa  (51)  GGDTFQKDAPLVFASCGRENSTSGTQGSVEIWDGSILVVKIAWDCPYVGS
IPD098Ac  (51)  GGDTFQKDAPLVFASCGRENSTSGTQGSVEIWDGSILVVKIAWDCPYVGS
IPD098Ab  (51)  GGDTFQKDAPLVFASCGRENSTSGTQGSVEIWDGSILVVKIAWDCPFLGS
IPD098Ba  (51)  GGETFQTDSPLVFACCGREDSPSGTQGSVEIWDASTLVVKIAWDCPFLGS
IPD098Bb  (51)  GGDTSQKDSPLVFASCGREDSPSGTQGSVEIWDGSTLVVKIAWDCPYVGS
IPD098Bc  (51)  GGDTSQKDSPLVFASCGREDSPSGTQGSVEIWDGSTLVVKIAWDCPYVGS
IPD098Bd  (50)  GGGTFQKGSPLVFASCGRQESPSGTQGSVEVWDGSTLVVKIAWDCPYIGK
IPD098Be  (51)  GGDTSQKDSPLVFASCGREDSPSGTQGSVEIWDGSTLVVKIAWDCPYVGS
IPD098Bf  (51)  GGDTSQKDSPLVFASCGREDSPSGTQGSVEIWDGSTLVVKIAWDCPYVGS
IPD098Bg  (50)  GGGTFQKGSPLVFASCGREESPSGTQGSVEVWDGSTLVVKIAWDCPYIGK
IPD098Bh  (50)  GGGTFQKGSPLVFASCGREESPSGTQGSVEVWDGSTLVVKIAWDCPYIGK
IPD098Bi  (50)  GGGTFQKSSSLVFASCGREESPSGTQGSVEIWDGSTLVVKIAWDCLYIGK 101                           139
IPD098Aa  (101) NSTSLSDQNSDYVVQQVPASVSTGGPLGNITYTIVKLPA
IPD098Ac  (101) NSTSLSDQNSDYVVQQVPASVSTGGPLGNITYTFVKLA-
IPD098Ab  (101) NSTSLSNQSSDYVVQQVPASVSTNGALDNITYTFVKLA-
IPD098Ba  (101) NSTSLSNQSSDYVVQQVPASVSTNGALDNITYTFVKLA-
IPD098Bb  (101) NSTSLTDQSSDYVVQQVPASVSTGGALEDITYTVVKLA-
IPD098Bc  (101) NSTSLTDQSSDYVVQQVPASVSTGGALEDITYTFVKLA-
IPD098Bd  (100) NSTSLTAQNSDYVVQQSPASVSTDGALGNITYTFVKLA-
IPD098Be  (101) NSTSLTDQSSDYVVQQVPASVSTGGALENITYTVVKLA-
IPD098Bf  (101) NSTSLTDQSSDYVVQQVPASVSTGGALENITYTVVKLA-
IPD098Bg  (100) NSTSLTAQNSDYVVQQSPASVSTDGALGNITYTF-----
IPD098Bh  (100) NSTSLTAQNSDYVVQQSPASVSTDGALGNITYTFVKLA-
IPD098Bi  (100) NSTSLTDQNSDYVVQQSPASVSTPS--------------
```

Fig. 6

```
                  1                                                50
IPD098Ga    (1)   ------------------------------------------LRGYPQWVSFK
IPD098Gb    (1)   MLSSSFLLALLSLSIG---GLASAGEEDSVSIFQVTDGKLGGYPQWVSFK
IPD098Fa    (1)   MSSSSFLVALLCVSIGSLASAASAGEKDSVSIFQVTDGKLGGYPQWVSFK
IPD098Gd    (1)   MSSSSFLLALLCISIGSLASAASAGEEDSVSIFQVTDGKLRGYPQWVSFK
IPD098Gc    (1)   MSSSSFLLALLCISIGSLASAASAGEEDSVSIFQVTDGKLGGYPQWVSFK
IPD098Ge    (1)   MSSSSFLLALLCISIGSLASAASAGEEDSVSIFQVTDGKLGGYPQWVSFK 51                                               100
IPD098Ga   (12)   ITNLGPDTLVVRNSVLPWGKWYKYPNKGIDGSSPGGVTIASGATSPTPPF
IPD098Gb   (48)   ITNLGRDTLEVKNSFLSYGKWYKYPNKNDDGSAPGGITIAAGATSPNPPF
IPD098Fa   (51)   ITNLGRDTLEVKNSFLSYGKWYKYPNKNNDGSAPGGITIAAGATSPNPPF
IPD098Gd   (51)   ITNLGRDTLEVKNSFLSYGKWYKYPNKNNDGSAPGGITIAAGATSPNPPF
IPD098Gc   (51)   ITNLGRDTLEVKNSFLSYGKWYKYPNKNNDGSAPGGITIAAGATSPNPAF
IPD098Ge   (51)   ITNLGRDTLEVKNSFLSYGKWYKYPNKNNDGSAPGGITIAAGATSPNPPF 101                                              150
                     ▼                          ▼              ▼  ▼
IPD098Ga   (62)   AACGRENSPSGTEGTFDLYAKEIKVATIYFDCPYIGSNKLSVQYACNTCV
IPD098Gb   (98)   AACGRQGSPSGTTGGFDIYTKGFKVATIHFDCPYTGSNKLSVSDECKNCV
IPD098Fa  (101)   AACGRQGSPSGTTGGFDIYTKGFKVATIHFDCPYTGSNKLSVSDECKNCV
IPD098Gd  (101)   AACGRQGSPSGTTGGFDIYTKGFKVATIHFDCPYTGSNKLSVSDECKNCV
IPD098Gc  (101)   AACGRQGSPSGTTGGFDIYTKGFKVATIHFDCPYTGSNKLSVSDECKNCV
IPD098Ge  (101)   AACGRQGSPSGTTGGFDIYTKGFKVATIHFDCPYTGSNKLSVSDECKNCV 151                         179
IPD098Ga  (112)   VQLPSFSTSGPLGDLVIKVVALVNLEAEA
IPD098Gb  (148)   VQLPSFSTSGALGDLVLKVVALV------
IPD098Fa  (151)   VQLPSFSTSGALGDLVLKVVALV------
IPD098Gd  (151)   VQLPSFSTSGALGDLVLKVVVLV------
IPD098Gc  (151)   VQLPSFSTSGALGDLVLKVVALV------
IPD098Ge  (151)   VQLPSFSTSGALGDLVLKVVALV------
```

Fig. 7A

```
                1                                                    50
IPD108Aa   (1)  --MGTPVNLVATLPRFIAIKGDNGLYLALKPSGILTFDASERTRLATHEV
IPD108Da   (1)  --MAAPADPVATLPRYIAIKGDNGNYLTLTSDGMLKFDSSERNRLATHEV
IPD108Eb   (1)  MAKFEVVSAVPTLPRYISIQGDNGLYLALKSDGLVSFDAKETNNLTTFEV
IPD108Dd   (1)  ----MAANPVALLPRYIALKGDNGMYLSLKSDGLLTFDAAEMTRLATHEV
IPD108Df   (1)  -MASSPANPVALLPRYIAVKGDNGMYLSLKSDGLLTFDAAERTRLATHEV
IPD108Dj   (1)  -MASSLADPVALLPRYIAIKGDNGMYLALKSDGLLTFDAAEITRLATHEV 51                                                   100
IPD108Aa  (49)  LYNADES--TFIIRSANGRFWKRDSSGWVYANLE--EPPATTQADARFKL
IPD108Da  (49)  LYNEDES--TFVIRSQNKRFWTERN-GWICASWEG-QPPTAANKDARFKL
IPD108Eb  (51)  LYDADGA--LLIRSSANRRFWRRDASNYIRATTLN------VTDAGRFKA
IPD108Dd  (47)  LYNEDDPDSTFIIRSQNMRFWRRDSANWIRADREADQPPSAGEHAARFTL
IPD108Df  (50)  LYNEDDPGATFIIRSQNMRFWRRDSANWIRADREADQPPSAADNAARFTL
IPD108Dj  (50)  LYNVDDPDATFIIRSQNMRFWRRDSANWIRADREADQPPSAGDTGARFTL 101                                                  150
IPD108Aa  (95)  VHLDTSDKLAFQSAKDNRYLKRYLA-SENGYNAVMTSLDVHTKVEVSDAS
IPD108Da  (95)  VQLGTG-KLAFQFAKNDNYLKRYNS-GINGYKAAVASPDQYTEIEVSDAS
IPD108Eb  (93)  SKLDTG-NLAFQSTKDDLFLNRYAR-RVDGYNALETVPNQWTEVRVTDAS
IPD108Dd  (97)  VTLASG-KLAFRSAVDSRYIKRYDAGSLKGYNALVPSPDQYSAVEVSDAW
IPD108Df (100)  VTLASG-KLAFQSALDGLYINRYDLGSLKGYNALARSPDQYSAVEVSDAW
IPD108Dj (100)  ARLESG-KLAFRSAVDGLYLNRYNR-DLHGYNALEQTPNQWSEVEVSDAW 151                                                  200
IPD108Aa (144)  EYAVSLPRYIFLKGNNGKYVHISYERSYAWLKFHGDEPGNLWGIAEVVPL
IPD108Da (143)  EYPVSLPQYIYLKGNNGKYVHIYYMDNRKWLKYHGEGPDNLWGMSEVHYL
IPD108Eb (141)  DYAVRLPDYIWLKGNNGKYVHLHYERDLNWLKFHGDSPSDDWGTNQVIPL
IPD108Dd (146)  EYAISLPRYIFLKGNNGMYMQTYNERSINWLKFHGSDPGNLYGTSEVIPL
IPD108Df (149)  EYAVSLPRYIFLKGDNGMYMHAYYERNLNWLKFHGSDPGNLYGTSEVIPL
IPD108Dj (148)  EHPVSLPRHIFLKGDNGMYMHTYNERSLNWLKFHGNDPGNLYGTSEVLHL

201                                 ▼             250
IPD108Aa (194)  LNGSVALYSPHATRFWRNSTNWIWADAQR-DEIATNARCHFEPIKLSSSM
IPD108Da (193)  LDGSIALYSPESTYFWRNSTNWIWTDASK-NEYIDNTRCHFEPVKLSSNM
IPD108Eb (191)  LDGSVALYNVKAGKFWRNSTNWIWADVNKQEDAESNPRCHFEPLKLGSEI
IPD108Dd (196)  LDGSLAFYNPQTDRFWRNSTNWIWTDSSR-SDALTNTRCHFEPIRLSRSM
IPD108Df (199)  LDGSLAFYNPQTDRFWRNGGNWVFTDSSR-SDAITNTRCHFEPIRLSRSM
IPD108Dj (198)  LDGTLAFYSPQTDRFWRNSTNWIWTDSSR-SDAITNTRCHFEPIRLSRSM

251            ▼                                  300
IPD108Aa (243)  LAFRSIFNDRICKRLTDYWTDSMNAAAANTNDVDTRLTVSEATFAKSVFD
IPD108Da (242)  IALKSKFNNQFCKRLTDYWSDSMNAAAGSTSDVETRLTVSEAVSGKYVFD
IPD108Eb (241)  VALKNQFNGLFCKRLTDYWQSCLNAGTGSPNDSEARLIVGDATEKRSIFN
IPD108Dd (245)  LALRNKFNNHICKRLTDYWENCLNAAASNTSDATTHLTVSEAANGRQVFD
IPD108Df (248)  LAVRNKFNNHICKRLSDYWVNCLNAAASNTSDTTTHLTVSEAANGRQVFD
IPD108Dj (247)  VALRNKYNNLICKRLSDYWVNCLNAAASNTSDTTTHLTVSEAANGRQVFD
```

Fig. 7B

```
            301                                                350
IPD108Aa  (293)  VKYLLNLASTSEQRPLAVAHGSARNDSPYTLDMAVTAIISQTVSRSRTWS
IPD108Da  (292)  VKYLLNLASTTDQKPLAVAYGSQVNNSPYQTDLTVTAIVSQSVSRSRTWS
IPD108Eb  (291)  VKYLMNLATTSDQKLQLVGRGSATNNSSNMMDMNVVVTLENKVSKSSTWS
IPD108Dd  (295)  IKYLLNLASTSDQKVLAVGYGSSVNNSSYLTDLVVRVSISQSVSRSYTFS
IPD108Df  (298)  IKYLLNLASTSDQRPLAVGYGSSVNNSSYMSDLVVRVTISQKVSKSYTFS
IPD108Dj  (297)  VKYLLNLASTSDQMPLAVGYGSSINNSSYMTDLVVRVSISQSVSKSYTFS 351                                                400
IPD108Aa  (343)  NSFTFSQSVTTSFKAGFPILAEGKVEVEIGFEQNFSNEWGQTTEQNIGFE
IPD108Da  (342)  NSFTFSQSVTTEFKAGFPFLAEGKVEVQIGFEQSFSNEWGETTEENIEFQ
IPD108Eb  (341)  NSFTFSQKVTTTFKCGVPFIGNAEIGVEIGTEQTFGHEWGETTEETVQFQ
IPD108Dd  (345)  NSFTFSQTVSTEFKAGIPFFGEGKISVEIGLEQSFSNEWGETTEQGIEFE
IPD108Df  (348)  NSFTFSQTVTTEFKAGIPFFGEGTVSVEIGLEQSFSNEWGETTEEGIEFE
IPD108Dj  (347)  NSFTFSQTVSTEFTAGIPFLGGGKISVEIGMEQSFSNEWGETTQRAIEFE

401                     ▼                          450
IPD108Aa  (393)  TQYTVKDVPPGGTASVTVVCSSAKMRIPFTYKSKDTAPDGIDRPTMEYID
IPD108Da  (392)  TQYVVKDVPPGGQASVTVICSAAKMRIPFMYTSKDTAPDGVDRPSMQYID
IPD108Eb  (391)  TGYLVKDIGPGQMASVTVTCSTAKIRIPFTYKCKDTALGGYDRGTVDYID
IPD108Dd  (395)  TQHVVKDVPPGGSASVTITCSTAKMRIPFTYKSKDSAPDGTDRPTQQFVD
IPD108Df  (398)  TQHVVKDVPPGGRASVTVTCSTAKMRIPFTYKSKDSAPDGTDRPTQQFVD
IPD108Dj  (397)  TQHVVKDVPPGGMASVTIICSTAKMRIPFTYKSKDSAPDGTDRPTQEFVD 451                                        496
IPD108Aa  (443)  GIYEGVDAYKIEAQISGSAKSYNVPAKLPL----------------
IPD108Da  (442)  GIYEGVDAYKIEAEINGSAGKETQRLPLKPAGIEKVKFVAPDPTAE
IPD108Eb  (441)  GVYEGVAAYDTRAKVSNGGMVNEVKLRADEEGRAFIL---------
IPD108Dd  (445)  GIFEGVDAYKIEALISDSVKSYTLPVARSYVGAPTSSTELM-----
IPD108Df  (448)  GIFEGVDAYKIEAVISDSVKSYAIPVARSYVSRPAIV---------
IPD108Dj  (447)  GIFEGVDAYKIEAVISDSVRSYVMPVV-------------------
```

INSECTICIDAL PROTEINS FROM PLANTS AND METHODS FOR THEIR USE

CROSS-REFERENCE TO RELATED APPLICATIONS

This Application claims the benefit of U.S. patent application Ser. No. 16/619,984, filed on Dec. 6, 2019, which claims the benefit of International Application PCT/US2018/037473, filed on Jun. 6, 2018, which claims priority to U.S. Provisional Application No. 62/521,084 filed on Jun. 16, 2017, each of which is incorporated herein by reference in its entirety.

REFERENCE TO SEQUENCE LISTING SUBMITTED ELECTRONICALLY

The official copy of the sequence listing is submitted electronically via EFS-Web as an XML formatted sequence listing with a file named "5296USPCD_SequenceListing" created on Jun. 6, 2023 and having a size of 195,000 bytes and is filed concurrently with the specification. The sequence listing contained in this XML formatted document is part of the specification and is herein incorporated by reference in its entirety.

FIELD

This disclosure relates to the field of molecular biology. Provided are novel genes that encode pesticidal proteins. These pesticidal proteins and the nucleic acid sequences that encode them are useful in preparing pesticidal formulations and in the production of transgenic pest-resistant plants.

BACKGROUND

Biological control of insect pests of agricultural significance using a microbial agent, such as fungi, bacteria or another species of insect affords an environmentally friendly and a commercially attractive alternative to synthetic chemical pesticides. The use of biopesticides presents a lower risk of pollution and environmental hazards and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a range of insect pests including Lepidoptera, Diptera, Coleoptera, Hemiptera and others. *Bacillus thuringiensis* (Bt) and *Bacillus popilliae* are among the most successful biocontrol agents discovered to date. Insect pathogenicity has also been attributed to strains of *B. larvae, B. lentimorbus, B. sphaericus* and *B. cereus*. Microbial insecticides, particularly those obtained from *Bacillus* strains, have played an important role in agriculture as alternatives to chemical pest control.

Crop plants have been developed with enhanced insect resistance by genetically engineering crop plants to produce pesticidal proteins from *Bacillus*. For example, corn and cotton plants have been genetically engineered to produce pesticidal proteins isolated from strains of *Bacillus thuringiensis*. These genetically engineered crops are now widely used in agriculture and have provided the farmer with an environmentally friendly alternative to traditional insect-control methods. While they have proven to be very successful commercially, these genetically engineered, insect-resistant crop plants provide resistance to only a narrow range of the economically important insect pests. In some cases, insects can develop resistance to different insecticidal compounds, which raises the need to identify alternative biological control agents for pest control.

Accordingly, there remains a need for new pesticidal proteins with different ranges of insecticidal activity against insect pests, e.g., insecticidal proteins which are active against a variety of insects in the order Lepidoptera and the order Coleoptera including but not limited to insect pests that have developed resistance to existing insecticides.

SUMMARY

In one aspect compositions and methods for conferring pesticidal activity to bacteria, plants, plant cells, tissues and seeds are provided. Compositions include nucleic acid molecules encoding sequences for pesticidal and insecticidal polypeptides, vectors comprising those nucleic acid molecules, and host cells comprising the vectors. Compositions also include the pesticidal polypeptide sequences and antibodies to those polypeptides. Compositions also comprise transformed bacteria, plants, plant cells, tissues and seeds.

In another aspect isolated or recombinant nucleic acid molecules are provided encoding IPD059 polypeptides including amino acid substitutions, deletions, insertions, and fragments thereof. Provided are isolated or recombinant nucleic acid molecules capable of encoding IPD059 polypeptides of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, and SEQ ID NO: 78, as well as amino acid substitutions, deletions, insertions, fragments thereof, and combinations thereof. Nucleic acid sequences that are complementary to a nucleic acid sequence of the embodiments or that hybridize to a sequence of the embodiments are also encompassed. The nucleic acid sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant.

In another aspect IPD059 polypeptides are encompassed. Also provided are isolated or recombinant IPD059 polypeptides of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, and SEQ ID NO: 78, as well as amino acid substitutions, deletions, insertions, fragments thereof and combinations thereof.

In another aspect isolated or recombinant nucleic acid molecules are provided encoding IPD098 polypeptides including amino acid substitutions, deletions, insertions, and fragments thereof. Provided are isolated or recombinant nucleic acid molecules capable of encoding IPD098 polypeptides of SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, and SEQ ID NO: 117, as well as amino acid substitutions, deletions, insertions, fragments thereof, and combinations thereof. Nucleic acid sequences that are complementary to a nucleic acid sequence of the embodiments or that hybridize to a sequence of the embodiments are also encompassed. The nucleic acid sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant.

In another aspect IPD098 polypeptides are encompassed. Also provided are isolated or recombinant IPD098 polypep- tides of SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, and SEQ ID NO: 117, as well as amino acid substitutions, deletions, insertions, fragments thereof and combinations thereof.

In another aspect isolated or recombinant nucleic acid molecules are provided encoding IPD108 polypeptides including amino acid substitutions, deletions, insertions, and fragments thereof. Provided are isolated or recombinant nucleic acid molecules capable of encoding IPD108 poly- peptides of SEQ ID NO: 132, SEQ ID NO: 133, SEQ ID NO: 134, SEQ ID NO: 135, SEQ ID NO: 136, as well as amino acid substitutions, deletions, insertions, fragments thereof, and combinations thereof. Nucleic acid sequences that are complementary to a nucleic acid sequence of the embodiments or that hybridize to a sequence of the embodi- ments are also encompassed. The nucleic acid sequences can be used in DNA constructs or expression cassettes for transformation and expression in organisms, including microorganisms and plants.

The nucleotide or amino acid sequences may be synthetic sequences that have been designed for expression in an organism including, but not limited to, a microorganism or a plant.

In another aspect IPD108 polypeptides are encompassed. Also provided are isolated or recombinant IPD108 polypep- tides of SEQ ID NO: 131, SEQ ID NO: 132, SEQ ID NO: 133, SEQ ID NO: 134, SEQ ID NO: 135, and SEQ ID NO: 136, as well as amino acid substitutions, deletions, insertions, fragments thereof and combinations thereof.

In another aspect isolated or recombinant nucleic acid molecules are provided encoding IPD109 polypeptides including amino acid substitutions, deletions, insertions, and fragments thereof. Provided are isolated or recombinant nucleic acid molecules capable of encoding IPD109 poly- peptides of SEQ ID NO: 138, as well as amino acid substitutions, deletions, insertions, fragments thereof, and combinations thereof. Nucleic acid sequences that are complementary to a nucleic acid sequence of the embodiments or that hybridize to a sequence of the embodiments are also encompassed. The nucleic acid sequences can be used in DNA constructs or expression cassettes for trans- formation and expression in organisms, including microor- ganisms and plants. The nucleotide or amino acid sequences may be synthetic sequences that have been designed for expression in an organism including, but not limited to, a microorganism or a plant.

In another aspect IPD109 polypeptides are encompassed. Also provided are isolated or recombinant IPD109 polypep- tides of SEQ ID NO: 138, as well as amino acid substitu- tions, deletions, insertions, fragments thereof and combina- tions thereof.

In another aspect methods are provided for producing the polypeptides and for using those polypeptides for control- ling or killing a Lepidopteran, Coleopteran, nematode, fungi, and/or Dipteran pests. The transgenic plants of the embodiments express one or more of the pesticidal sequences disclosed herein. In various embodiments, the transgenic plant further comprises one or more additional genes for insect resistance, for example, one or more addi- tional genes for controlling Coleopteran, Lepidopteran, Hemipteran or nematode pests. It will be understood by one of skill in the art that the transgenic plant may comprise any gene imparting an agronomic trait of interest.

In another aspect methods for detecting the nucleic acids and polypeptides of the embodiments in a sample are also included. A kit for detecting the presence of a polypeptide of the disclosure or detecting the presence of a polynucleotide encoding a polypeptide of the disclosure in a sample is provided. The kit may be provided along with all reagents and control samples necessary for carrying out a method for detecting the intended agent, as well as instructions for use.

In another aspect, the compositions and methods of the embodiments are useful to produce organisms with enhanced pest resistance or tolerance. These organisms and compositions comprising the organisms are desirable for agricultural purposes. The compositions of the embodiments are also useful for generating altered or improved proteins that have pesticidal activity or for detecting the presence of IPD059, IPD098, IPD108 or IPD109 polypeptides.

BRIEF DESCRIPTION OF THE FIGURES

FIG. 2A-2B shows an amino acid sequence alignment, using the ALIGNX® module of the Vector NTI® suite, of the IPD059 homologs: IPD059Aa (SEQ ID NO: 39), IPD059Ab (SEQ ID NO: 40), IPD059Ac (SEQ ID NO: 41), IPD059Ad (SEQ ID NO: 42), IPD059Ae (SEQ ID NO: 43), IPD059Af (SEQ ID NO: 44), IPD059Ag (SEQ ID NO: 45), IPD059Ah (SEQ ID NO: 46), IPD059Ca (SEQ ID NO: 47), IPD059Cb (SEQ ID NO: 48), and IPD059Cc (SEQ ID NO: 49). The amino acid sequence diversity between the sequences is highlighted. Conserved cysteine residues are indicated with a "▼" symbol above the alignment. The start of the deletion variant IPD059AaTR1 (SEQ ID NO: 78) is indicated by a "." symbol above residue 29 (Aspartic Acid) of IPD059Aa (SEQ ID NO: 39).

FIG. 3 shows an amino acid sequence alignment, using the ALIGNX® module of the Vector NTI® suite, of the IPD059 homologs: IPD059 Da (SEQ ID NO: 50), IPD059Db (SEQ ID NO: 51), IPD059Ea (SEQ ID NO: 52), IPD059Eb (SEQ ID NO: 53), IPD059Ec (SEQ ID NO: 54), IPD059Ed (SEQ ID NO: 55), IPD059Ee (SEQ ID NO: 56), IPD059Ef (SEQ ID NO: 57), and IPD059Eg (SEQ ID NO: 58). The amino acid sequence diversity between the sequences is highlighted. Conserved cysteine residues are indicated with a "▼" symbol above the alignment.

FIG. 4 shows an amino acid sequence alignment, using the ALIGNX® module of the Vector NTI® suite, of the IPD059 homologs: IPD059Em (SEQ ID NO: 64), IPD059En (SEQ ID NO: 65), IPD059Eo (SEQ ID NO: 66), IPD059Ep (SEQ ID NO: 67), IPD059Eq (SEQ ID NO: 68), IPD059Er (SEQ ID NO: 69), IPD059Es (SEQ ID NO: 70), and IPD059Et (SEQ ID NO: 71). The amino acid sequence diversity between the sequences is highlighted. Conserved cysteine residues are indicated with a "▼" symbol above the alignment.

FIG. 5 shows an amino acid sequence alignment, using the ALIGNX® module of the Vector NTI® suite, of the IPD098 homologs: IPD098Aa (SEQ ID NO: 102), IPD098Ab (SEQ ID NO: 103), IPD098Ac (SEQ ID NO: 104), IPD098Ba (SEQ ID NO: 105), IPD098Bb (SEQ ID NO: 106), IPD098Bc (SEQ ID NO: 107), IPD098Bd (SEQ ID NO: 108), IPD098Be (SEQ ID NO: 109), IPD098Bf (SEQ ID NO: 110), IPD098Bg (SEQ ID NO: 111), IPD098Bh (SEQ ID NO: 112), and IPD098Bi (SEQ ID NO: 113). The amino acid sequence diversity between the sequences is highlighted. Conserved cysteine residues are indicated with a "▼" symbol above the alignment.

FIG. 6 shows an amino acid sequence alignment, using the ALIGNX® module of the Vector NTI® suite, of the IPD098 homologs: IPD098Fa (SEQ ID NO: 118), IPD098Ga (SEQ ID NO: 119), IPD098Gb (SEQ ID NO: 120), IPD098Gc (SEQ ID NO: 121), IPD098Gd (SEQ ID NO: 122), IPD098Ge (SEQ ID NO: 123). The amino acid sequence diversity between the sequences is highlighted. Conserved cysteine residues are indicated with a "▼" symbol above the alignment.

FIG. 7A-7B shows an amino acid sequence alignment, using the ALIGNX® module of the Vector NTI® suite, of the IPD108 homologs: IPD108Aa (SEQ ID NO: 131), IPD108 Da (SEQ ID NO: 132), IPD108Dd (SEQ ID NO: 133), IPD108Df (SEQ ID NO: 134), IPD108Dj (SEQ ID NO: 135), and IPD108Eb (SEQ ID NO: 136). The amino acid sequence diversity between the sequences is highlighted. Conserved cysteine residues are indicated with a "▼" symbol above the alignment.

DETAILED DESCRIPTION

Figure 1:
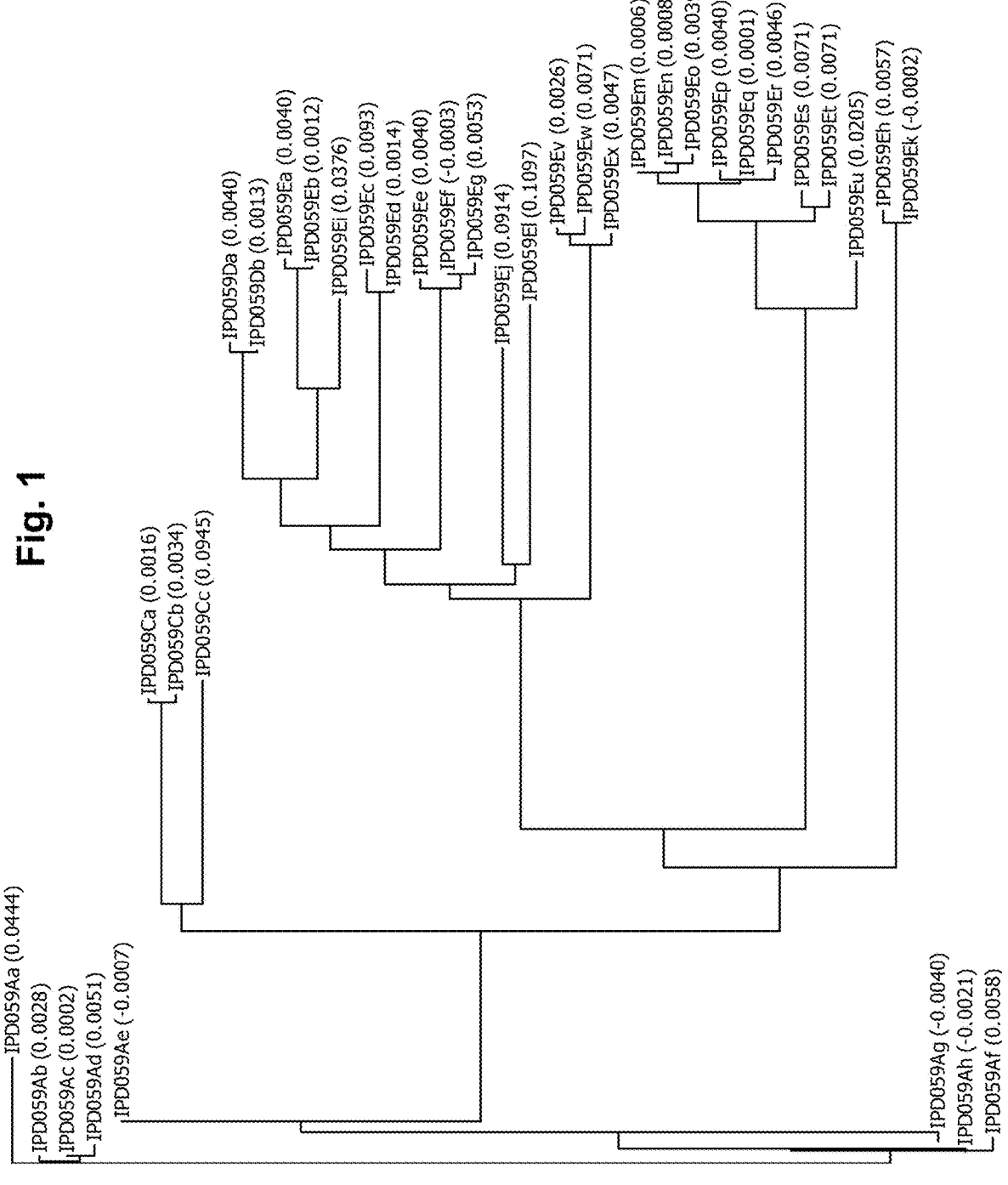
FIG. 1 shows a Phylogenetic tree, generated using the Neighbor Joining Method in the ALIGNX® module of the Vector NTI® suite, of the IPD059 homologs: IPD059Aa (SEQ ID NO: 39), IPD059Ab (SEQ ID NO: 40), IPD059Ac (SEQ ID NO: 41), IPD059Ad (SEQ ID NO: 42), IPD059Ae (SEQ ID NO: 43), IPD059Af (SEQ ID NO: 44), IPD059Ag (SEQ ID NO: 45), IPD059Ah (SEQ ID NO: 46), IPD059Ca (SEQ ID NO: 47), IPD059Cb (SEQ ID NO: 48), IPD059Cc (SEQ ID NO: 49), IPD059 Da (SEQ ID NO: 50), IPD059Db (SEQ ID NO: 51), IPD059Ea (SEQ ID NO: 52), IPD059Eb (SEQ ID NO: 53), IPD059Ec (SEQ ID NO: 54), IPD059Ed (SEQ ID NO: 55), IPD059Ee (SEQ ID NO: 56), IPD059Ef (SEQ ID NO: 57), IPD059Eg (SEQ ID NO: 58), IPD059Eh (SEQ ID NO: 59), IPD059Ei (SEQ ID NO: 60), IPD059Ej (SEQ ID NO: 61), IPD059Ek (SEQ ID NO: 62), IPD059El (SEQ ID NO: 63), IPD059Em (SEQ ID NO: 64), IPD059En (SEQ ID NO: 65), IPD059Eo (SEQ ID NO: 66), IPD059Ep (SEQ ID NO: 67), IPD059Eq (SEQ ID NO: 68), IPD059Er (SEQ ID NO: 69), IPD059Es (SEQ ID NO: 70), IPD059Et (SEQ ID NO: 71), IPD059Eu (SEQ ID NO: 72), IPD059Ev (SEQ ID NO: 73), IPD059Ew (SEQ ID NO: 74), and IPD059Ex (SEQ ID NO: 75).
Figure 8:
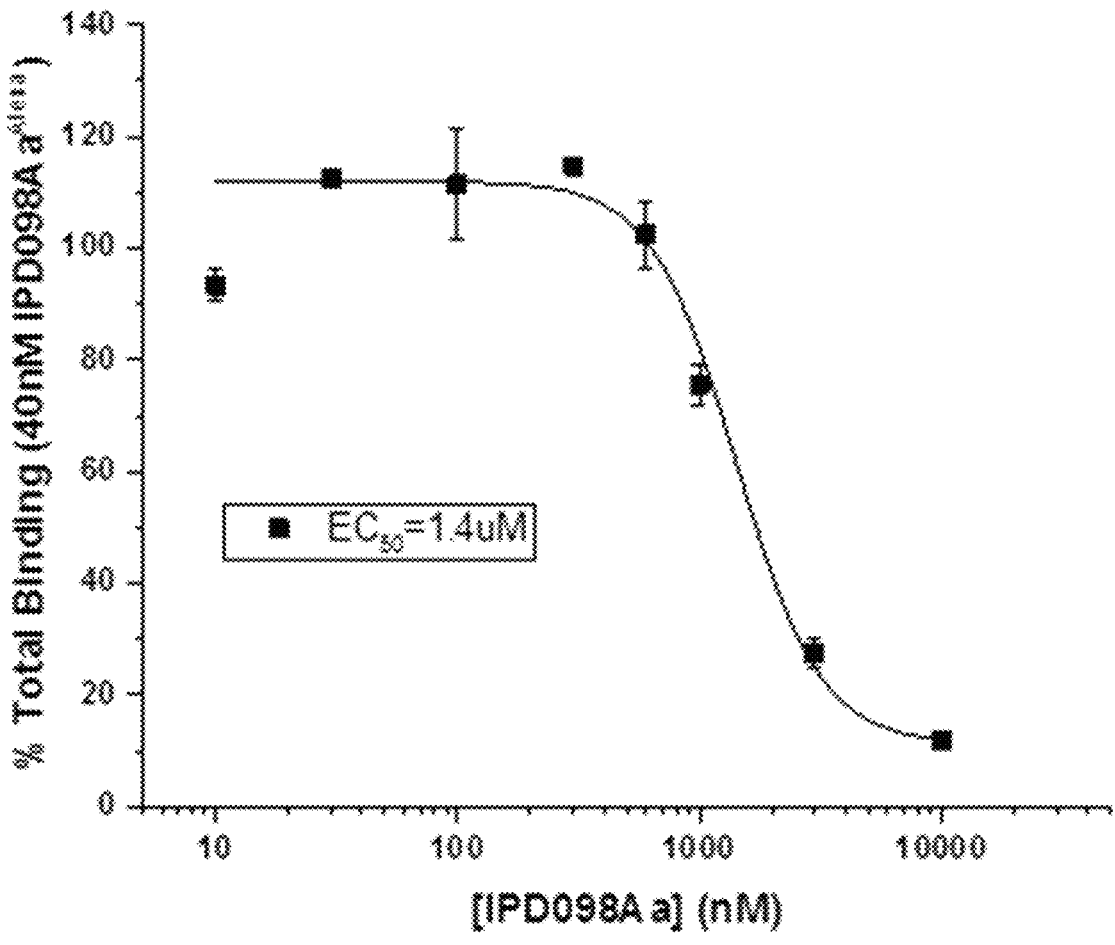
FIG. 8 shows a curve reflecting densitometry values of in-gel fluorescence, from the SDS-PAGE gel of Example 12, for homologous competition of 40 nM Alexa-labeled IPD098Aa polypeptide (SEQ ID NO: 102) by unlabeled IPD098Aa polypeptide (SEQ ID NO: 102) as the percentage of total binding (in absence of competitor) to WCRW BBMVs versus the concentration of unlabeled IPD098Aa polypeptide (SEQ ID NO: 102).

It is to be understood that this disclosure is not limited to the particular methodology, protocols, cell lines, genera, and reagents described, as such may vary. It is also to be understood that the terminology used herein is for describing particular embodiments only, and is not intended to limit the scope of the present disclosure.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this disclosure belongs unless clearly indicated otherwise.

The present disclosure is drawn to compositions and methods for controlling pests. The methods involve transforming organisms with nucleic acid sequences encoding a polypeptide of the disclosure. The nucleic acid sequences of the embodiments are useful for preparing plants and microorganisms that possess pesticidal activity. Thus, transformed bacteria, plants, plant cells, plant tissues and seeds are provided. The compositions include pesticidal nucleic acids and proteins of bacterial species. The nucleic acid sequences find use in the construction of expression vectors for subsequent transformation into organisms of interest, as probes for the isolation of other homologous (or partially homologous) genes, and for the generation of altered IPD059, IPD098, IPD108 or IPD109 polypeptides by methods known in the art, such as site directed mutagenesis, domain swapping or DNA shuffling. The IPD059, IPD098, IPD108 or IPD109 polypeptides find use in controlling or killing Lepidopteran, Coleopteran, Dipteran, fungal, Hemipteran and nematode pest populations and for producing compositions with pesticidal activity. Insect pests of interest include, but are not limited to, Lepidoptera species including but not limited to: Corn Earworm, (CEW) (*Helicoverpa zea*); European Corn Borer (ECB) (*Ostrinia nubialis*), diamond-back moth, e.g., *Helicoverpa zea* Boddie; soybean looper, e.g., *Pseudoplusia includens* Walker; and velvet bean caterpillar e.g., *Anticarsia gemmatalis* Hübner and Coleoptera species including but not limited to Western corn rootworm (*Diabrotica virgifera*)—WCRW, Southern corn rootworm (*Diabrotica undecimpunctata howardi*)—SCRW, and Northern corn rootworm (*Diabrotica barberi*)—NCRW.

By "pesticidal toxin" or "pesticidal protein" is used herein to refer to a toxin that has toxic activity against one or more pests, including, but not limited to, members of the Lepidoptera, Diptera, Hemiptera and Coleoptera orders or the Nematoda phylum or a protein that has homology to such a protein. Pesticidal proteins have been isolated from organisms including, for example, *Bacillus* sp., *Pseudomonas* sp., *Photorhabdus* sp., Xenorhabdus sp., *Clostridium bifermentans* and *Paenibacillus popilliae*. Pesticidal proteins include but are not limited to: insecticidal proteins from *Pseudomonas* sp. such as PSEEN3174 (Monalysin; (2011) PLoS Pathogens 7:1-13); from *Pseudomonas protegens* strain CHAO and Pf-5 (previously *fluorescens*) (Pechy-Tarr, (2008) Environmental Microbiology 10:2368-2386; GenBank Accession No. EU400157); from *Pseudomonas taiwanensis* (Liu, et al., (2010) J. Agric. Food Chem., 58:12343-12349) and from *Pseudomonas pseudoalcali-genes* (Zhang, et al., (2009) Annals of Microbiology 59:45-50 and Li, et al., (2007) Plant Cell Tiss. Organ Cult. 89:159-168); insecticidal proteins from *Photorhabdus* sp. and Xenorhabdus sp. (Hinchliffe, et al., (2010) The Open Toxicology Journal, 3:101-118 and Morgan, et al., (2001) Applied and Envir. Micro. 67:2062-2069); U.S. Pat. Nos. 6,048,838, and 6,379,946; a PIP-1 polypeptide of U.S. Pat. No. 9,688,730; an AfIP-1A and/or AfIP-1B polypeptide of U.S. Pat. No. 9,475,847; a PIP-47 polypeptide of US Publication Number US20160186204; an IPD045 polypeptide, an IPD064 polypeptide, an IPD074 polypeptide, an IPD075 polypeptide, and an IPD077 polypeptide of PCT Publication Number WO 2016/114973; an IPD080 polypeptide of PCT Serial Number PCT/US17/56517; an IPD078 polypeptide, an IPD084 polypeptide, an IPD085 polypeptide, an IPD086 polypeptide, an IPD087 polypeptide, an IPD088 polypeptide, and an IPD089 polypeptide of Serial Number PCT/US17/54160; PIP-72 polypeptide of US Patent Publication Number US20160366891; a PtIP-50 polypeptide and a PtIP-65 polypeptide of US Publication Number US20170166921; an IPD098 polypeptide, an IPD059 polypeptide, an IPD108 polypeptide, an IPD109 polypeptide of U.S. Ser. No. 62/521,084; a PtIP-83 polypeptide of US Publication Number US20160347799; a PtIP-96 polypeptide of US Publication Number US20170233440; an IPD079 polypeptide of PCT Publication Number WO2017/23486; an IPD082 polypeptide of PCT Publication Number WO 2017/105987, an IPD090 polypeptide of Serial Number PCT/US17/30602, an IPD093 polypeptide of U.S. Ser. No. 62/434,020; an IPD103 polypeptide of Serial Number PCT/US17/39376; an IPD101 polypeptide of U.S. Ser. No. 62/438,179; an IPD121 polypeptide of US Serial Number U.S. 62/508,514; and δ-endotoxins including, but not limited to a Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry29, Cry30, Cry31, Cry32, Cry33, Cry34, Cry35, Cry36, Cry37, Cry38, Cry39, Cry40, Cry41, Cry42, Cry43, Cry44, Cry45, Cry46, Cry47, Cry49, Cry50, Cry51, Cry52, Cry53, Cry54, Cry55, Cry56, Cry57, Cry58, Cry59, Cry60, Cry61, Cry62, Cry63, Cry64, Cry65, Cry66, Cry67, Cry68, Cry69, Cry70, Cry71, and Cry 72 classes of δ-endotoxin polypeptides and the *B. thuringiensis* cytolytic cyt1 and cyt2 genes. Members of these classes of *B. thuringiensis* insecticidal proteins well known to one skilled in the art (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix).

Examples of δ-endotoxins also include but are not limited to Cry1A proteins of U.S. Pat. Nos. 5,880,275, 7,858,849, and 8,878,007; a Cry1Ac mutant of U.S. Pat. No. 9,512,187; a DIG-3 or DIG-11 toxin (N-terminal deletion of α-helix 1 and/or α-helix 2 variants of cry proteins such as Cry1A, Cry3A) of U.S. Pat. Nos. 8,304,604, 8,304,605 and 8,476, 226; Cry1B of U.S. patent application Ser. No. 10/525,318, US Patent Application Publication Number US20160194364, and U.S. Pat. Nos. 9,404,121 and 8,772, 577; Cry1B variants of PCT Publication Number WO2016/61197 and Serial Number PCT/US17/27160; Cry1C of U.S. Pat. No. 6,033,874; Cry1D protein of US20170233759; a Cry1E protein of PCT Serial Number PCT/US17/53178; a Cry1F protein of U.S. Pat. Nos. 5,188,960 and 6,218,188; Cry1A/F chimeras of U.S. Pat. Nos. 7,070,982; 6,962,705 and 6,713,063; a Cry1I protein of PCT Publication number WO 2017/0233759; a Cry1J variant of US Publication US20170240603; a Cry2 protein such as Cry2Ab protein of U.S. Pat. No. 7,064,249 and Cry2A.127 protein of U.S. Pat. No. 7,208,474; a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476, 781, 7,105,332, 7,339,092, 7,378,499, 7,462,760, and 9,593, 345; a Cry9 protein such as such as members of the Cry9A, Cry9B, Cry9C, Cry9D, Cry9E and Cry9F families including the Cry9 protein of U.S. Pat. Nos. 9,000,261 and 8,802,933, and US Serial Number WO 2017/132188; a Cry15 protein of Naimov, et al., (2008) Applied and Environmental Microbiology, 74:7145-7151; a Cry14 protein of U.S. Pat. No. 8,933,299; a Cry22, a Cry34Ab1 protein of U.S. Pat. Nos. 6,127,180, 6,624,145 and 6,340,593; a truncated Cry34 protein of U.S. Pat. No. 8,816,157; a CryET33 and cryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083, 499, 6,548,291 and 6,340,593; a Cry46 protein of U.S. Pat. No. 9,403,881, a Cry 51 protein, a Cry binary toxin; a TIC901 or related toxin; TIC807 of US Patent Application Publication Number 2008/0295207; TIC853 of U.S. Pat. No. 8,513,493; ET29, ET37, TIC809, TIC810, TIC812, TIC127, TIC128 of PCT US 2006/033867; engineered Hemipteran toxic proteins of US Patent Application Publication Number US20160150795, AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020 and AXMI-021 of WO 2006/083891; AXMI-010 of WO 2005/038032; AXMI-003 of WO 2005/021585; AXMI-008 of US Patent Application Publication Number 2004/0250311; AXMI-006 of US Patent Application Publication Number 2004/0216186; AXMI-007 of US Patent Application Publication Number 2004/0210965; AXMI-009 of US Patent Application Number 2004/0210964; AXMI-014 of US Patent Application Publication Number 2004/0197917; AXMI-004 of US Patent Application Publication Number 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US Patent Application Publication Number 2011/0023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063 and AXMI-064 of US Patent Application Publication Number 2011/0263488; AXM1046, AXM1048, AXM1050, AXM1051, AXM1052, AXM1053, AXM1054, AXM1055, AXM1056, AXM1057, AXM1058, AXM1059, AXM1060, AXM1061, AXM1067, AXM1069, AXM1071, AXM1072, AXM1073, AXM1074, AXM1075, AXM1087, AXM1088, AXM1093, AXM1070, AXM1080, AXM1081, AXM1082, AXM1091, AXM1092, AXM1096, AXM1097, AXM1098, AXM1099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI125, AXMI126, AXMI127, AXMI129, AXMI151, AXMI161, AXMI164, AXMI183, AXMI1132, AXMI1137, AXM1138 of U.S. Pat. Nos. 8,461,421 and 8,461,422; AXMI-R1 and related proteins of US Patent Application Publication Number 2010/0197592; AXM1221Z, AXM1222z, AXM1223z, AXM1224z and AXM1225z of WO 2011/103248; AXM1218, AXM1219, AXM1220, AXM1226, AXM1227, AXM1228, AXM1229, AXM1230 and AXM1231 of WO 2011/103247; AXMI-115, AXMI-113, AXMI-005, AXMI-163 and AXMI-184 of U.S. Pat. No. 8,334,431; AXMI-001, AXMI-002, AXMI-030, AXMI-035 and AXMI-045 of US Patent Application Publication Number 2010/0298211; AXMI-066 and AXMI-076 of US Patent Application Publication Number 2009/0144852; AXM1128, AXM1130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXM1079, AXM1080, AXM1081, AXM1082, AXM1091, AXM1092, AXM1096, AXM1097, AXM1098, AXM1099, AXM1100, AXM1101, AXM1102, AXM1103, AXM1104, AXM1107, AXM1108, AXM1109, AXM1110, dsAXM1111, AXM1112, AXM1114, AXM1116, AXM1117, AXM1118, AXM1119, AXM1120, AXM1121, AXM1122, AXM1123, AXM1124, AXM11257, AXM11268, AXM1127, AXM1129, AXM1164, AXM1151, AXM1161, AXM1183, AXM1132, AXM1138, AXM1137 of U.S. Pat. No. 8,461,421; AXM1192 of U.S. Pat. No. 8,461,415; AXM1281 of US Patent Application Publication Number US20160177332; AXM1422 of U.S. Pat. No. 8,252,872; cry proteins such as Cry1A and Cry3A having modified proteolytic sites of U.S. Pat. No. 8,319,019; a Cry1Ac, Cry2Aa and Cry1Ca toxin protein from *Bacillus thuringiensis* strain VBTS 2528 of US Patent Application Publication Number 2011/0064710. The Cry proteins MP032, MP049, MP051, MP066, MP068, MP070, MP091S, MP109S, MP114, MP121, MP134S, MP183S, MP185S, MP186S, MP195S, MP197S, MP208S, MP209S, MP212S, MP214S, MP217S, MP222S, MP234S, MP235S, MP237S, MP242S, MP243, MP248, MP249S, MP251M, MP252S, MP253, MP259S, MP287S, MP288S, MP295S, MP296S, MP297S, MP300S, MP304S, MP306S, MP310S, MP312S, MP314S, MP319S, MP325S, MP326S, MP327S, MP328S, MP334S, MP337S, MP342S, MP349S, MP356S, MP359S, MP360S, MP437S, MP451S, MP452S, MP466S, MP468S, MP476S, MP482S, MP522S, MP529S, MP548S, MP552S, MP562S, MP564S, MP566S, MP567S, MP569S, MP573S, MP574S, MP575S, MP581S, MP590, MP594S, MP596S, MP597, MP599S, MP600S, MP601S, MP602S, MP604S, MP626S, MP629S, MP630S, MP631S, MP632S, MP633S, MP634S, MP635S, MP639S, MP640S, MP644S, MP649S, MP651S, MP652S, MP653S, MP661S, MP666S, MP672S, MP696S, MP704S, MP724S, MP729S, MP739S, MP755S, MP773S, MP799S, MP800S, MP801S, MP802S, MP803S, MP805S, MP809S, MP815S, MP828S, MP831S, MP844S, MP852, MP865S, MP879S, MP887S, MP891S, MP896S, MP898S, MP935S, MP968, MP989, MP993, MP997, MP1049, MP1066, MP1067, MP1080, MP1081, MP1200, MP1206, MP1233, and MP1311 of U.S. Ser. No. 62/607,372. The insecticidal activity of Cry proteins is well known to one skilled in the art (for review, see, van Frannkenhuyzen, (2009) J. Invert. Path. 101:1-16). The use of Cry proteins as transgenic plant traits is well known to one skilled in the art and Cry-transgenic plants including but not limited to plants expressing Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) Plant Biotech Journal 9:283-300 and the CERA. (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682); Cry1BE & Cry1F (US2012/0311746); Cry1CA & Cry1AB (US2012/0311745); Cry1F & CryCa (US2012/0317681); Cry1 DA & Cry1BE (US2012/0331590); Cry1DA & Cry1Fa (US2012/0331589); Cry1AB & Cry1 BE (US2012/0324606); Cry1Fa & Cry2Aa and Cry1I & Cry1E (US2012/0324605); Cry34Ab/35Ab & Cry6Aa (US20130167269); Cry34Ab/VCry35Ab & Cry3Aa (US20130167268); Cry1 Da & Cry1Ca (U.S. Pat. No. 9,796,982); Cry3Aa & Cry6Aa (U.S. Pat. No. 9,798,963); and Cry3A & Cry1Ab or Vip3Aa (U.S. Pat. No. 9,045,766). Pesticidal proteins also include insecticidal lipases including lipid acyl hydrolases of U.S. Pat. No. 7,491,869, and cholesterol oxidases such as from *Streptomyces* (Purcell et al. (1993) Biochem Biophys Res Commun 15:1406-1413). Pesticidal proteins also include VIP (vegetative insecticidal proteins) toxins of U.S. Pat. Nos. 5,877,012, 6,107,279 6,137,033, 7,244,820, 7,615,686, and 8,237,020 and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include Cyt proteins including Cyt1A variants of PCT Serial Number PCT/US2017/000510; Pesticidal proteins also include toxin complex (TC) proteins, obtainable from organisms such as Xenorhabdus, *Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus*, Xenorhabdus or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but not limited to lycotoxin-1 peptides and mutants thereof (U.S. Pat. No. 8,334,366). The combinations generated can also include multiple copies of any one of the polynucleotides of interest.

In some embodiments, the IPD059, IPD098, IPD108 or IPD109 polypeptide includes an amino acid sequence deduced from the full-length nucleic acid sequence disclosed herein and amino acid sequences that are shorter than the full-length sequences, either due to the use of an alternate downstream start site or due to processing that produces a shorter protein having pesticidal activity. Processing may occur in the organism the protein is expressed in or in the pest after ingestion of the protein.

Thus, provided herein are novel isolated or recombinant nucleic acid sequences that confer pesticidal activity. Also provided are the amino acid sequences of IPD059, IPD098, IPD108 or IPD109 polypeptides. The protein resulting from translation of these IPD059, IPD098, IPD108 or IPD109 genes allows cells to control or kill certain pests that ingest it.

IPD059 Proteins and Variants and Fragments Thereof

IPD059 polypeptides are encompassed by the disclosure. "IPD059 polypeptide" and "IPD059 protein" as used herein interchangeably refers to a polypeptide having insecticidal activity including but not limited to insecticidal activity against one or more insect pests of the Lepidoptera and/or Coleoptera orders, and is sufficiently homologous to the IPD059Aa polypeptide of SEQ ID NO: 39. A variety of IPD059 polypeptides are contemplated. Sources of IPD059 polypeptides or related proteins include fern or other primitive plant species selected from but not limited to Polypodium species, Colysis species, Asplenium species, *Polystichum* species or *Phyllitis* species.

In some embodiments, the IPD059 polypeptide is derived from a fern species in the Order Polypodiales, Family Polypodiaceae, and Genus Polypodium L. In some embodiments, the IPD059 polypeptide is derived from a fern species in the Genus Polypodium L. selected from but not limited to *Polypodium absidatum, Polypodium acutifolium, Polypodium adiantiforme, Polypodium aequale, Polypodium affine, Polypodium albidopaleatum, Polypodium alcicorne, Polypodium alfarii, Polypodium alfredii, Polypodium alfredii* var. *curtii, Polypodium allosuroides, Polypodium alsophilicola, Polypodium amamianum, Polypodium amoenum, Polypodium amorphum, Polypodium anetioides, Polypodium anfractuosum, Polypodium anguinum, Polypodium angustifolium f. remotifolia, Polypodium angustifolium* var. *amphostenon, Polypodium angustifolium* var. *heterolepis, Polypodium angustifolium* var. *monstrosa, Polypodium angustipaleatum, Polypodium angustissimum, Polypodium anisomeron* var. *pectinatum, Polypodium antioquianum, Polypodium aoristisorum, Polypodium apagolepis, Polypodium apicidens, Polypodium apiculatum, Polypodium apoense, Polypodium appalachianum, Polypodium appressum, Polypodium arenarium, Polypodium argentinum, Polypodium argutum, Polypodium armatum, Polypodium aromaticum, Polypodium aspersum, Polypodium assurgens, Polypodium atrum, Polypodium auriculatum, Polypodium balaonense, Polypodium balliviani, Polypodium bamleri, Polypodium bangii, Polypodium bartlettii, Polypodium basale, Polypodium bernoullii, Polypodium biauritum, Polypodium bifrons, Polypodium blepharodes, Polypodium bolivari, Polypodium bolivianum, Polypodium bolobense, Polypodium bombycinum, Polypodium bombycinum* var. *insularum, Polypodium bradeorum, Polypodium bryophilum, Polypodium bryopodum, Polypodium buchtienii, Polypodium buesii, Polypodium bulbotrichum, Polypodium caceresii, Polypodium californicum f. brauscombii, Polypodium californicum f. parsonsiae, Polypodium californicum, Polypodium calophlebium, Polypodium calvum, Polypodium camptophyllarium* var. *abbreviatum, Polypodium capitellatum, Polypodium carpinterae, Polypodium chachapoyense, Polypodium chartaceum, Polypodium chimantense, Polypodium chiricanum, Polypodium choquetangense, Polypodium christensenii, Polypodium christii, Polypodium chrysotrichum, Polypodium ciliolepis, Polypodium cinerascens, Polypodium collinsii, Polypodium colysoides, Polypodium confluens, Polypodium conforme, Polypodium confusum, Polypodium congregatifolium, Polypodium connellii, Polypodium consimile* var. *bourgaeanum, Polypodium consimile* var. *minor, Polypodium conterminans, Polypodium contiguum, Polypodium cookii, Polypodium coriaceum, Polypodium coronans, Polypodium costaricense, Polypodium costatum, Polypodium crassifolium f. angustissimum, Polypodium crassifolium* var. *longipes, Polypodium crassulum, Polypodium craterisorum, Polypodium cryptum, Polypodium crystalloneuron, Polypodium cucullatum* var. *planum, Polypodium cuencanum, Polypodium cumingianum, Polypodium cupreolepis, Polypodium curranii, Polypodium curvans, Polypodium cyathicola, Polypodium cyathisorum, Polypodium cyclocolpon, Polypodium daguense, Polypodium damunense, Polypodium dareiformioides, Polypodium dasypleura, Polypodium decipiens, Polypodium decorum, Polypodium delicatulum, Polypodium deltoideum, Polypodium demeraranum, Polypodium denticulatum, Polypodium diaphanum, Polypodium dilatatum, Polypodium dispersum, Polypodium dissectum, Polypodium dissimulans, Polypodium dolichosorum, Polypodium dolorense, Polypodium donnell-smithii, Polypodium drymoglossoides, Polypodium ebeninum, Polypodium eggersii, Polypodium elmeri, Polypodium elongatum, Polypodium enterosoroides, Polypodium erubescens, Polypodium erythrolepis, Polypodium erythrotrichum, Polypodium eurybasis, Polypodium eurybasis* var. *villosum, Polypodium exornans, Polypodium falcoideum, Polypodium fallacissimum, Polypodium farinosum, Polypodium faucium, Polypodium feei, Polypodium ferrugineum, Polypodium feuillei, Polypodium firmulum, Polypodium firmum, Polypodium flaccidum, Polypodium flagellare, Polypodium flexuosum, Polypodium flexuosum* var. *ekmanii, Polypodium forbesii, Polypodium formosanum, Polypodium fraxinifolium* subsp. *articulatum, Polypodium fraxinifolium* subsp. *luridum, Polypodium fructuosum, Polypodium fucoides, Polypodium fulvescens, Polypodium galeottii, Polypodium glaucum, Polypodium glycyrrhiza, Polypodium gracillimum, Polypodium gramineum, Polypodium grandifolium, Polypodium gratum, Polypodium graveolens, Polypodium griseo-nigrum, Polypodium griseum, Polypodium guttatum, Polypodium haalilioanum, Polypodium hammatisorum, Polypodium hancockii, Polypodium haplophlebicum, Polypodium harrisii, Polypodium hastatum* var. *simplex, Polypodium hawaiiense, Polypodium heanophyllum, Polypodium helleri, Polypodium hemionitidium, Polypodium henryi, Polypodium herzogii, Polypodium hesperium, Polypodium hessii, Polypodium hombersleyi, Polypodium hostmannii, Polypodium humile, Polypodium hyalinum, Polypodium iboense, Polypodium induens* var. *subdentatum, Polypodium insidiosum, Polypodium insigne, Polypodium intermedium* subsp. *masafueranum* var. *obtuseserratum, Polypodium intramarginale, Polypodium involutum, Polypodium itatiayense, Polypodium javanicum, Polypodium juglandifolium, Polypodium kaniense, Polypodium knowltoniorum, Polypodium kyimbilense, Polypodium l'herminieri* var. *costaricense, Polypodium lachniferum f. incurvata, Polypodium lachniferum* var. *glabrescens, Polypodium lachnopus, Polypodium lanceolatum* var. *complanatum, Polypodium lanceolatum* 15 var. *trichophorum, Polypodium latevagans, Polypodium laxifrons, Polypodium laxifrons* var. *lividum, Polypodium lehmannianum, Polypodium leiorhizum, Polypodium leptopodon, Polypodium leuconeuron* var. *angustifolia, Polypodium leuconeuron* var. *latifolium, Polypodium leucosticta, Polypodium limulum, Polypodium lindigii, Polypodium lineatum, Polypodium lomarioides, Polypodium longifrons, Polypodium loretense, Polypodium loriceum* var. *umbraticum, Polypodium loriforme, Polypodium loxogramme f. gigas, Polypodium ludens, Polypodium luzonicum, Polypodium lycopodioides f. obtusum, Polypodium lycopodioides* L., *Polypodium mac-* rolepis, *Polypodium macrophyllum*, *Polypodium macrosorum*, *Polypodium macrosphaerum*, *Polypodium maculosum*, *Polypodium madrense*, *Polypodium manmeiense*, *Polypodium margaritiferum*, *Polypodium maritimum*, *Polypodium martensii*, *Polypodium mayoris*, *Polypodium megalolepis*, *Polypodium melanotrichum*, *Polypodium menisciifolium* var. *pubescens*, *Polypodium meniscioides*, *Polypodium merrillii*, *Polypodium mettenii*, *Polypodium mexiae*, *Polypodium microsorum*, *Polypodium militare*, *Polypodium minimum*, *Polypodium minusculum*, *Polypodium mixtum*, *Polypodium mollendense*, *Polypodium mollissimum*, *Polypodium moniliforme* var. *minus*, *Polypodium monoides*, *Polypodium monticola*, *Polypodium montigenum*, *Polypodium moritzianum*, *Polypodium moultonii*, *Polypodium multicaudatum*, *Polypodium multilineatum*, *Polypodium multisorum*, *Polypodium munchii*, *Polypodium muscoides*, *Polypodium myriolepis*, *Polypodium myriophyllum*, *Polypodium myriotrichum*, *Polypodium nematorhizon*, *Polypodium nemorale*, *Polypodium nesioticum*, *Polypodium nigrescentium*, *Polypodium nigripes*, *Polypodium nigrocinctum*, *Polypodium nimbatum*, *Polypodium nitidissimum*, *Polypodium nitidissimum* var. *latior*, *Polypodium nubrigenum*, *Polypodium oligolepis*, *Polypodium oligosorum*, *Polypodium oligosorum*, *Polypodium olivaceum*, *Polypodium olivaceum* var. *elatum*, *Polypodium oodes*, *Polypodium oosphaerum*, *Polypodium oreophilum*, *Polypodium ornatissimum*, *Polypodium ornatum*, *Polypodium ovatum*, *Polypodium oxylobum*, *Polypodium oxypholis*, *Polypodium pakkaense*, *Polypodium pallidum*, *Polypodium palmatopedatum*, *Polypodium palmeri*, *Polypodium panamense*, *Polypodium parvum*, *Polypodium patagonicum*, *Polypodium paucisorum*, *Polypodium pavonianum*, *Polypodium pectinatum* var. *caliense*, *Polypodium pectinatum* var. *hispidum*, *Polypodium pellucidum*, *Polypodium pendulum* var. *boliviense*, *Polypodium percrassum*, *Polypodium perpusillum*, *Polypodium peruvianum* var. *subgibbosum*, *Polypodium phyllitidis* var. *elongatum*, *Polypodium pichinchense*, *Polypodium pilosissimum*, *Polypodium pilosissimum* var. *glabriusculum*, *Polypodium pilossimum* var. *tunguraquensis*, *Polypodium pityrolepis*, *Polypodium platyphyllum*, *Polypodium playfairii*, *Polypodium plebeium* var. *cooperi*, *Polypodium plectolepidioides*, *Polypodium pleolepis*, *Polypodium plesiosorum* var.i, *Polypodium podobasis*, *Polypodium podocarpum*, *Polypodium poloense*, *Polypodium polydatylon*, *Polypodium polypodioides* var. *aciculare*, *Polypodium polypodioides* var. *michauxianum*, *Polypodium praetermissum*, *Polypodium preslianum* var. *immersum*, *Polypodium procerum*, *Polypodium procerum*, *Polypodium productum*, *Polypodium productum*, *Polypodium prolongilobum*, *Polypodium propinguum*, *Polypodium proteus*, *Polypodium pruinatum*, *Polypodium pseudocapillare*, *Polypodium pseudofraternum*, *Polypodium pseudonutans*, *Polypodium pseudoserratum*, *Polypodium pulcherrimum*, *Polypodium pulogense*, *Polypodium pungens*, *Polypodium purpusii*, *Polypodium radicale*, *Polypodium randallii*, *Polypodium ratiborii*, *Polypodium reclinatum*, *Polypodium recreense*, *Polypodium repens* var. *abruptum*, *Polypodium revolvens*, *Polypodium rhachipterygium*, *Polypodium rhomboideum*, *Polypodium rigens*, *Polypodium robustum*, *Polypodium roraimense*, *Polypodium roraimense*, *Polypodium rosei*, *Polypodium rosenstockii*, *Polypodium rubidum*, *Polypodium rudimentum*, *Polypodium rusbyi*, *Polypodium sablanianum*, *Polypodium sarmentosum*, *Polypodium saxicola*, *Polypodium schenckii*, *Polypodium schlechteri*, *Polypodium scolopendria*, *Polypodium scolopendria*, *Polypodium scolopendrium*, *Polypodium scouleri*, *Polypodium scutulatum*, *Polypodium segregatum*, *Polypodium semihirsutum*, *Poly-* podium semihirsutum var. *fuscosetosum*, *Polypodium senile* var. *minor*, *Polypodium sericeolanatum*, *Polypodium serraeforme*, *Polypodium serricula*, *Polypodium sesquipedala*, *Polypodium sessilifolium*, *Polypodium setosum* var. *calvum*, *Polypodium setulosum*, *Polypodium shaferi*, *Polypodium sibomense*, *Polypodium siccum*, *Polypodium simacense*, *Polypodium simulans*, *Polypodium singeri*, *Polypodium sinicum*, *Polypodium sintenisii*, *Polypodium skutchii*, *Polypodium sloanei*, *Polypodium sodiroi*, *Polypodium sordidulum*, *Polypodium sordidum*, *Polypodium sphaeropteroides*, *Polypodium sphenodes*, *Polypodium sprucei*, *Polypodium sprucei* var. *furcativenosa*, *Polypodium steirolepis*, *Polypodium stenobasis*, *Polypodium stenolepis*, *Polypodium stenopterum*, *Polypodium subcapillare*, *Polypodium subflabelliforme*, *Polypodium subhemionitidium*, *Polypodium subinaequale*, *Polypodium subintegrum*, *Polypodium subspathulatum*, *Polypodium subtile*, *Polypodium subvestitum*, *Polypodium subviride*, *Polypodium superficiale* var. *attenuatum*, *Polypodium superficiale* var. *chinensis*, *Polypodium sursumcurrens*, *Polypodium tablazianum*, *Polypodium taenifolium*, *Polypodium tamandarei*, *Polypodium tatei*, *Polypodium tenuiculum* var. *acrosora*, *Polypodium tenuiculum* var. *brasiliense*, *Polypodium tenuilore*, *Polypodium tenuinerve*, *Polypodium tepuiense*, *Polypodium teresae*, *Polypodium tetragonum* var. *incompletum*, *Polypodium thysanolepis* var. *bipinnatifidum*, *Polypodium thysanolepis*, var. *thysanolepis*, *Polypodium thysanolepsi*, *Polypodium tobagense*, *Polypodium trichophyllum*, *Polypodium tridactylum*, *Polypodium tridentatum*, *Polypodium trifurcatum* var. *brevipes*, *Polypodium triglossum*, *Polypodium truncatulum*, *Polypodium truncicola* var. *major*, *Polypodium truncicola* var. *minor*, *Polypodium tuberosum*, *Polypodium tunguraguae*, *Polypodium turquinum*, *Polypodium turrialbae*, *Polypodium ursipes*, *Polypodium vagans*, *Polypodium valdealatum*, *Polypodium versteegii*, *Polypodium villagranii*, *Polypodium virginianum* f. *cambroideum*, *Polypodium virginianum* f. *peraferens*, *Polypodium vittarioides*, *Polypodium vulgare*, *Polypodium vulgare* L., *Polypodium vulgare* subsp. *oreophilum*, *Polypodium vulgare* var. *acuminatum*, *Polypodium vulpinum*, *Polypodium williamsii*, *Polypodium wobbense*, *Polypodium* x *fallacissimum-guttatum*, *Polypodium xantholepis*, *Polypodium xiphopteris*, *Polypodium yarumalense*, *Polypodium yungense*, and *Polypodium zosteriforme*.

In some embodiments, the IPD059 polypeptide is derived from a fern species in the Order Polypodiales, Family Polypodiaceae or Genus Colysis. In some embodiments, the IPD059 polypeptide is derived from a fern species in the Genus Colysis selected from but not limited to *Colysis ampla*, *Colysis digitata*, *Colysis elegans*, *Colysis elliptica*, *Colysis flexiloba*, *Colysis hemionitidea*, *Colysis hemitoma*, *Colysis henryi*, *Colysis insignis*, *Colysis intermedia*, *Colysis leveillei*, *Colysis longipes*, *Colysis pentaphylla*, *Colysis pothifolia*, *Colysis pteropus*, *Colysis shintenensis*, *Colysis simplicifrons*, *Colysis triphylla*, and *Colysis wrightii*.

In some embodiments, the IPD059 polypeptide is derived from a fern species in the Order Polypodiales, Family Aspleniaceae, and Genus Asplenium. In some embodiments, the IPD059 polypeptide is derived from a fern species in the Genus Asplenium selected from but not limited to *Asplenium abscissum*, *Asplenium actinopteroides*, *Asplenium adiantum-nigrum*, *Asplenium aegaeum*, *Asplenium aethiopicum*, *Asplenium* aff. *hallbergii*, *Asplenium* aff. *heterochroum*, *Asplenium affine*, *Asplenium alatum*, *Asplenium amboinense*, *Asplenium anceps*, *Asplenium angustum*, *Asplenium anisophyllum*, *Asplenium anogrammoides*, *Asplenium anogrammoides* x *Asplenium*, *Asplenium antiquum*,

*Asplenium antrophyoides, Asplenium apogamum, Asplenium appendiculatum, Asplenium aureum, Asplenium auriculatum, Asplenium auritum, Asplenium australasicum, Asplenium azoricum, Asplenium barclayanum, Asplenium billotii, Asplenium bipartitum, Asplenium blepharodes, Asplenium boltonii, Asplenium boreale, Asplenium bourgaei, Asplenium bulbiferum, Asplenium bulbiferum* x *Asplenium bulbiferum* subsp. *gracillimum, Asplenium bullatum, Asplenium capillipes, Asplenium castaneum, Asplenium caudatum, Asplenium ceterach, Asplenium chathamense, Asplenium christii, Asplenium cimmeriorum, Asplenium coenobiale, Asplenium compressum, Asplenium contiguum, Asplenium cordatum, Asplenium crinicaule, Asplenium cristatum, Asplenium cuneatiforme, Asplenium cuneifolium, Asplenium currorii, Asplenium cuspidatum, Asplenium cymbifolium, Asplenium cyprium, Asplenium dalhousiae, Asplenium dareoides, Asplenium daucifolium, Asplenium decompositum, Asplenium delicatulum, Asplenium dielerectum, Asplenium difforme, Asplenium dimorphum, Asplenium dissectum, Asplenium dregeanum, Asplenium elliottii, Asplenium emarginatum, Asplenium ensiforme, Asplenium erectum, Asplenium exiguum, Asplenium feei, Asplenium fibrillosum, Asplenium filipes, Asplenium finlaysonianum, Asplenium fissum, Asplenium flabellifolium, Asplenium flaccidum, Asplenium fontanum, Asplenium foresiense, Asplenium formosum, Asplenium fragile, Asplenium friesiorum, Asplenium gemmiferum, Asplenium griffithianum, Asplenium gulingense, Asplenium hallbergii, Asplenium harpeodes, Asplenium hastatum, Asplenium haughtonii, Asplenium haurakiense, Asplenium hemionitis, Asplenium hemitomum, Asplenium heterochroum, Asplenium heteroresiliens, Asplenium hispanicum, Asplenium hobdyi, Asplenium hookerianum, Asplenium hostmannii, Asplenium hybridum, Asplenium incisum, Asplenium interjectum, Asplenium jahandiezii, Asplenium juglandifolium, Asplenium kukkonenii, Asplenium laciniatum, Asplenium laetum, Asplenium lamprophyllum, Asplenium laserpitiifolium, Asplenium lividum, Asplenium lolegnamense, Asplenium loriceum, Asplenium loxoscaphoides, Asplenium lucidum, Asplenium lunulatum, Asplenium lushanense, Asplenium lyallii, Asplenium majoricum, Asplenium majus, Asplenium mannii, Asplenium marinum, Asplenium mauritiensis, Asplenium micantifrons, Asplenium milnei, Asplenium monanthes, Asplenium montanum, Asplenium myriophyllum, Asplenium nidus, Asplenium nitens, Asplenium normale, Asplenium northlandicum, Asplenium obliquissimum, Asplenium obliquum, Asplenium oblongifolium, Asplenium obovatum, Asplenium obtusatum, Asplenium octoploideum, Asplenium oligophlebium, Asplenium onopteris, Asplenium palmeri, Asplenium papaverifolium, Asplenium parvifolium, Asplenium paucivenosum, Asplenium pauperequitum, Asplenium pekinense, Asplenium pellucidum, Asplenium petiolulatum, Asplenium petrarchae, Asplenium phillipsianum, Asplenium phyllitidis, Asplenium planicaule, Asplenium platyneuron, Asplenium polyodon, Asplenium polyphyllum, Asplenium praegracile, Asplenium praemorsum, Asplenium preussii, Asplenium prolongatum, Asplenium protensum, Asplenium pseudolaserpitiifolium, Asplenium pseudowilfordii, Asplenium pteridoides, Asplenium pteropus, Asplenium punjabense, Asplenium radicans, Asplenium resiliens, Asplenium rhizophyllum, Asplenium richardii, Asplenium riparium, Asplenium ritoense, Asplenium ruprechtii, Asplenium ruta-muraria, Asplenium rutifolium, Asplenium sagittatum, Asplenium salicifolium, Asplenium sandersonii, Asplenium sarelii, Asplenium scalare, Asplenium scleropium, Asplenium scolopendrium, Asplenium seelosii, Asplenium septentrionale, Asplenium serratum, Asplenium setoi, Asplenium*

*lenium shimurae, Asplenium shuttleworthianum, Asplenium simplicifrons, Asplenium smedsii, Asplenium soleirolioides, Asplenium sphenotomum, Asplenium squamulatum, Asplenium stoloniferum, Asplenium subglandulosus, Asplenium sulcatum, Asplenium surrogatum, Asplenium tenerum, Asplenium tenuicaule, Asplenium theciferum, Asplenium thunbergii, Asplenium tricholepis, Asplenium trichomanes, Asplenium trigonopterum, Asplenium tripteropus, Asplenium variabile, Asplenium varians, Asplenium viellardii, Asplenium viride, Asplenium volkensii, Asplenium vulcanicum, Asplenium wilfordii, Asplenium wrightii, Asplenium wrightioides, Asplenium* x *adulterinum, Asplenium* x *chasmophilum, Asplenium* x *lessinense, Asplenium* x *mantoniae, Asplenium* x *protomajoricum, Asplenium* x *tenuivarians, Asplenium yoshinagae,* and *Asplenium yunnanense.*

In some embodiments, the IPD059 polypeptide is derived from a fern species in the Order Polypodiales, Family Dryopteridaceae, and Genus *Polystichum.* In some embodiments, the IPD059 polypeptide is derived from a fern species in the Genus *Polystichum* selected from but not limited to *Polystichum acanthophyllum, Polystichum aculeatum, Polystichum acutidens, Polystichum acutipinnulum, Polystichum adungense, Polystichum alcicorne, Polystichum altum, Polystichum anomalum, Polystichum articulatipilosum, Polystichum assurgentipinnum, Polystichum atkinsonii, Polystichum attenuatum, Polystichum auriculum, Polystichum bakerianum, Polystichum baoxingense, Polystichum biaristatum, Polystichum bifidum, Polystichum bigemmatum, Polystichum bissectum, Polystichum bomiense, Polystichum brachypterum, Polystichum braunii, Polystichum capillipes, Polystichum castaneum, Polystichum chingiae, Polystichum christii, Polystichum chunii, Polystichum consimile, Polystichum costularisorum, Polystichum craspedosorum, Polystichum crassinervium, Polystichum cringerum, Polystichum cuneatiforme, Polystichum cyclolobum, Polystichum daguanense, Polystichum dangii, Polystichum delavayi, Polystichum deltodon, Polystichum dielsii, Polystichum diffundens, Polystichum discretum, Polystichum disjunctum, Polystichum duthiei, Polystichum elevatovenusum, Polystichum erosum, Polystichum exauriforme, Polystichum excellens, Polystichum excelsius, Polystichum fimbriatum, Polystichum formosanum, Polystichum frigidicola, Polystichum fugongense, Polystichum gongboense, Polystichum grandifrons, Polystichum guangxiense, Polystichum gymnocarpium, Polystichum habaense, Polystichum hancockii, Polystichum hecatopteron, Polystichum herbaceum, Polystichum houchangense, Polystichum huae, Polystichum ichangense, Polystichum inaense, Polystichum incisopinnulum, Polystichum integrilimbum, Polystichum integrilobum, Polystichum jinfoshaense, Polystichum jiulaodongense, Polystichum jizhushanense, Polystichum kangdingense, Polystichum kungianum, Polystichum kwangtungense, Polystichum lachenense, Polystichum lanceolatum, Polystichum langchungense, Polystichum latilepis, Polystichum lentum, Polystichum leveillei, Polystichum liui, Polystichum lonchitis, Polystichum longiaristatum, Polystichum longidens, Polystichum longipaleatum, Polystichum longipes, Polystichum longipinnulum, Polystichum longispinosum, Polystichum longissimum, Polystichum macrochlaenum, Polystichum makinoi, Polystichum manmeiense, Polystichum martinii, Polystichum mayebarae, Polystichum medogense, Polystichum mehrae, Polystichum meiguense, Polystichum melanostipes, Polystichum mollissimum, Polystichum morii, Polystichum moupinense, Polystichum muscicola, Polystichum nayongense, Polystichum neoliuii, Polystichum neolobatum, Polystichum nepalense, Polystichum nigrum, Polystichum ningshenense,*

*Polystichum nudisorum, Polystichum obliquum, Polystichum oblongum, Polystichum oligocarpum, Polystichum omeiense, Polystichum oreodoxa, Polystichum orientalitibeticum, Polystichum otophorum, Polystichum ovato-paleaceum, Polystichum paramoupinense, Polystichum parvifoliolatum, Polystichum parvipinnulum, Polystichum pianmaense, Polystichum piceo-paleaceum, Polystichum polyblepharum, Polystichum prescottianum, Polystichum prionolepis, Polystichum pseudocastaneum, Polystichum pseudolanceolatum, Polystichum pseudomakinoi, Polystichum pseudorhomboideum, Polystichum pseudosetosum, Polystichum pseudoxiphophyllum, Polystichum punctiferum, Polystichum puteicola, Polystichum pycnopterum, Polystichum qamdoense, Polystichum retrosopaleaceum, Polystichum revolutum, Polystichum rhombiforme, Polystichum rigens, Polystichum robustum, Polystichum rufopaleaceum, Polystichum saxicola, Polystichum semifertile, Polystichum setillosum, Polystichum shandongense, Polystichum shensiense, Polystichum shimurae, Polystichum simplicipinnum, Polystichum sinense, Polystichum sinotsussimense, Polystichum sozanense, Polystichum speluncicola, Polystichum squarrosum, Polystichum stenophyllum, Polystichum stimulans, Polystichum subacutidens, Polystichum subdeltodon, Polystichum subfimbriatum, Polystichum submarginale, Polystichum submite, Polystichum subulatum, Polystichum tacticopterum, Polystichum taizhongense, Polystichum tangmaiense, Polystichum thomsonii, Polystichum tibeticum, Polystichum tonkinense, Polystichum tripteron, Polystichum tsingkanshanense, Polystichum tsussimense, Polystichum wattii, Polystichum xiphophyllum, Polystichum yadongense, Polystichum yuanum, Polystichum yunnanense,* and *Polystichum zayuense.*

"Sufficiently homologous" is used herein to refer to an amino acid sequence that has at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. In some embodiments, the sequence homology is against the full-length sequence of an IPD059 polypeptide.

In some embodiments the IPD059 polypeptide has at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75 or SEQ ID NO: 78. The term "about" when used herein in context with percent sequence identity means/−0.5%. One of skill in the art will recognize that these values can be appropriately adjusted to determine corresponding homology of proteins taking into account amino acid similarity and the like.

In some embodiments, the IPD059 polypeptide has an N-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or more amino acids from the N-terminus relative to IPD059 polypeptides of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75 or SEQ ID NO: 78.

In some embodiments, the IPD059 polypeptide has an N-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, from the N-terminus relative to IPD059 polypeptides of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75 or SEQ ID NO: 78.

IPD098 Proteins and Variants and Fragments Thereof

IPD098 polypeptides are encompassed by the disclosure. "IPD098 polypeptide" and "IPD098 protein" as used herein interchangeably refers to a polypeptide having insecticidal activity including but not limited to insecticidal activity against one or more insect pests of the Lepidoptera and/or Coleoptera orders, and is sufficiently homologous to the IPD098Aa polypeptide of SEQ ID NO: 102. A variety of IPD098 polypeptides are contemplated. Sources of IPD098 polypeptides or related proteins include fern or other primitive plant species selected from but not limited to *Asplenium* species, *Platycerium* species, *Aspergillus* species or *Selaginella* species.

In some embodiments, the IPD098 polypeptide is derived from a fern species in the Order Polypodiales, Family Aspleniaceae, and Genus Asplenium. In some embodiments, the IPD098 polypeptide is derived from a fern species in the Genus Asplenium selected from but not limited to *Asplenium abscissum, Asplenium actinopteroides, Asplenium adiantum-nigrum, Asplenium aegaeum, Asplenium aethiopicum, Asplenium aff. hallbergii, Asplenium aff. heterochroum, Asplenium affine, Asplenium alatum, Asplenium amboinense, Asplenium anceps, Asplenium angustum, Asplenium anisophyllum, Asplenium anogrammoides, Asplenium anogrammoides* x *Asplenium, Asplenium antiquum, Asplenium antrophyoides, Asplenium apogamum, Asplenium appendiculatum, Asplenium aureum, Asplenium auriculatum, Asplenium auritum, Asplenium australasicum, Asplenium azoricum, Asplenium barclayanum, Asplenium billotii, Asplenium bipartitum, Asplenium blepharodes, Asplenium boltonii, Asplenium boreale, Asplenium bourgaei, Asplenium bulbiferum, Asplenium bulbiferum* x *Asplenium bulbiferum* subsp. *gracillimum, Asplenium bullatum, Asplenium capillipes, Asplenium castaneum, Asplenium caudatum, Asplenium ceterach, Asplenium chathamense, Asplenium christii,*

*Asplenium cimmeriorum, Asplenium coenobiale, Asplenium compressum, Asplenium contiguum, Asplenium cordatum, Asplenium crinicaule, Asplenium cristatum, Asplenium cuneatiforme, Asplenium cuneifolium, Asplenium currorii, Asplenium cuspidatum, Asplenium cymbifolium, Asplenium cyprium, Asplenium dalhousiae, Asplenium dareoides, Asplenium daucifolium, Asplenium decompositum, Asplenium delicatulum, Asplenium dielerectum, Asplenium difforme, Asplenium dimorphum, Asplenium dissectum, Asplenium dregeanum, Asplenium elliottii, Asplenium emarginatum, Asplenium ensiforme, Asplenium erectum, Asplenium exiguum, Asplenium feei, Asplenium fibrillosum, Asplenium filipes, Asplenium finlaysonianum, Asplenium fissum, Asplenium flabellifolium, Asplenium flaccidum, Asplenium fontanum, Asplenium foresiense, Asplenium formosum, Asplenium fragile, Asplenium friesiorum, Asplenium gemmiferum, Asplenium griffithianum, Asplenium gulingense, Asplenium hallbergii, Asplenium harpeodes, Asplenium hastatum, Asplenium haughtonii, Asplenium haurakiense, Asplenium hemionitis, Asplenium hemitomum, Asplenium heterochroum, Asplenium heteroresiliens, Asplenium hispanicum, Asplenium hobdyi, Asplenium hookerianum, Asplenium hostmannii, Asplenium hybridum, Asplenium incisum, Asplenium interjectum, Asplenium jahandiezii, Asplenium juglandifolium, Asplenium kukkonenii, Asplenium laciniatum, Asplenium laetum, Asplenium lamprophyllum, Asplenium laserpitiifolium, Asplenium lividum, Asplenium lolegnamense, Asplenium loriceum, Asplenium loxoscaphoides, Asplenium lucidum, Asplenium lunulatum, Asplenium lushanense, Asplenium lyallii, Asplenium majoricum, Asplenium majus, Asplenium mannii, Asplenium marinum, Asplenium mauritiensis, Asplenium micantifrons, Asplenium milnei, Asplenium monanthes, Asplenium montanum, Asplenium myriophyllum, Asplenium nidus, Asplenium nitens, Asplenium normale, Asplenium northlandicum, Asplenium obliquissimum, Asplenium obliquum, Asplenium oblongifolium, Asplenium obovatum, Asplenium obtusatum, Asplenium octoploideum, Asplenium oligophlebium, Asplenium onopteris, Asplenium palmeri, Asplenium papaverifolium, Asplenium parvifolium, Asplenium paucivenosum, Asplenium pauperequitum, Asplenium pekinense, Asplenium pellucidum, Asplenium petiolulatum, Asplenium petrarchae, Asplenium phillipsianum, Asplenium phyllitidis, Asplenium planicaule, Asplenium platyneuron, Asplenium polyodon, Asplenium polyphyllum, Asplenium praegracile, Asplenium praemorsum, Asplenium preussii, Asplenium prolongatum, Asplenium protensum, Asplenium pseudolaserpitiifolium, Asplenium pseudowilfordii, Asplenium pteridoides, Asplenium pteropus, Asplenium punjabense, Asplenium radicans, Asplenium resiliens, Asplenium rhizophyllum, Asplenium richardii, Asplenium riparium, Asplenium ritoense, Asplenium ruprechtii, Asplenium ruta-muraria, Asplenium rutifolium, Asplenium sagittatum, Asplenium salicifolium, Asplenium sandersonii, Asplenium sarelii, Asplenium scalare, Asplenium scleropium, Asplenium scolopendrium, Asplenium seelosii, Asplenium septentrionale, Asplenium serratum, Asplenium setoi, Asplenium shimurae, Asplenium shuttleworthianum, Asplenium simplicifrons, Asplenium smedsii, Asplenium soleirolioides, Asplenium sphenotomum, Asplenium squamulatum, Asplenium stoloniferum, Asplenium subglandulosum, Asplenium sulcatum, Asplenium surrogatum, Asplenium tenerum, Asplenium tenuicaule, Asplenium theciferum, Asplenium thunbergii, Asplenium tricholepis, Asplenium trichomanes, Asplenium trigonopterum, Asplenium tripteropus, Asplenium variabile, Asplenium varians, Asplenium viellardii, Asplenium viride, Asplenium volkensii, Asplenium vulcanicum, Asplenium wilfordii, Asplenium wrightii, Asplenium wrightioides, Asplenium x adulterinum, Asplenium x chasmophilum, Asplenium x lessinense, Asplenium x mantoniae, Asplenium x protomajoricum, Asplenium x tenuivarians, Asplenium yoshinagae,* and *Asplenium yunnanense.*

In some embodiments, the IPD098 polypeptide is derived from a species in the Class Isoetopsida Order Selaginales. In some embodiments, the IPD098 polypeptide is derived from a fern species in the Class Isoetopsida, Order Selaginales, Family Selaginellaceae. In some embodiments, the IPD098 polypeptide is derived from a species in the Genus *Selaginella*. In some embodiments the IPD098 polypeptide is derived from a *Selaginella* species selected from but not limited to *Selaginella acanthonota, Selaginella apoda, Selaginella arbuscula, Selaginella arenicola, Selaginella arizonica, Selaginella armata, Selaginella asprella, Selaginella biformis, Selaginella bigelovii, Selaginella braunii, Selaginella cinerascens, Selaginella cordifolia, Selaginella deflexa, Selaginella delicatula, Selaginella densa, Selaginella douglasii, Selaginella eatonii, Selaginella eclipes, Selaginella eremophila, Selaginella erythropus, Selaginella flabellata, Selaginella hansenii, Selaginella heterodonta, Selaginella kraussiana, Selaginella krugii, Selaginella laxifolia, Selaginella lepidophylla, Selaginella leucobryoides, Selaginella ludoviciana, Selaginella mutica, Selaginella oregana, Selaginella ovifolia, Selaginella pallescens, Selaginella peruviana, Selaginella pilifera, Selaginella plana, Selaginella plumosa, Selaginella pulcherrima, Selaginella rupestris, Selaginella rupincola, Selaginella scopulorum, Selaginella selaginoides, Selaginella sibirica, Selaginella standleyi, Selaginella stellata, Selaginella subcaulescens, Selaginella substipitata, Selaginella tenella, Selaginella tortipila, Selaginella uliginosa, Selaginella umbrosa, Selaginella uncinata, Selaginella underwoodii, Selaginella utahensis, Selaginella victoriae, Selaginella viridissima, Selaginella wallacei, Selaginella watsonii, Selaginella weatherbiana, Selaginella willdenowii, Selaginella wrightii* and *Selaginella X neomexicana.*

In some embodiments, the IPD098 polypeptide is derived from a fern species in the Order Polypodiales, Family Polypodiaceae, and Genus Platycerium. In some embodiments, the IPD098 polypeptide is derived from a species in the Genus *Platycerium*. In some embodiments the IPD098 polypeptide is derived from a *Platycerium* species selected from but not limited to *Platycerium alcicorne, Platycerium andinum, Platycerium angolense, Platycerium bifurcatum, Platycerium coronarium, Platycerium elephantotis, Platycerium ellisii, Platycerium grande, Platycerium hillii, Platycerium holttumii, Platycerium madagascariense, Platycerium quadridichotomum, Platycerium ridleyi, Platycerium* sp. ES-2011, *Platycerium stemaria, Platycerium superbum, Platycerium veitchii, Platycerium wallichii, Platycerium wandae,* and *Platycerium willinckii.*

In some embodiments, the IPD098 polypeptide is derived from a mold species in the Order Eurotiales, Family Trichocomaceae, and Genus Aspergillus. In some embodiments, the IPD098 polypeptide is derived from a species in the Genus *Aspergillus*. In some embodiments the IPD098 polypeptide is derived from an *Aspergillus* species selected from but not limited to *Aspergillus acidus, Aspergillus aculeatinus, Aspergillus aculeatus, Aspergillus aeneus, Aspergillus affinis, Aspergillus alabamensis, Aspergillus alliaceus, Aspergillus amazonicus, Aspergillus ambiguus, Aspergillus amoenus, Aspergillus amstelodami, Aspergillus amyloliquefaciens, Aspergillus amylovorus, Aspergillus anomalus, Aspergillus anthodesmis, Aspergillus apicalis, Aspergillus appendiculatus, Aspergillus arachidicola,*

*Aspergillus arenarius, Aspergillus arvii, Aspergillus asperescens, Aspergillus assulatus, Aspergillus astellatus, Aspergillus aurantiobrunneus, Aspergillus aureofulgens, Aspergillus aureolatus, Aspergillus aureoterreus, Aspergillus aureus, Aspergillus auricomus, Aspergillus australensis, Aspergillus austroafricanus, Aspergillus avenaceus, Aspergillus awamori, Aspergillus baeticus, Aspergillus bahamensis, Aspergillus biplanus, Aspergillus bisporus, Aspergillus bombycis, Aspergillus brasiliensis, Aspergillus brevipes, Aspergillus brevistipitatus, Aspergillus bridgeri, Aspergillus brunneo-uniseriatus, Aspergillus brunneoviolaceu, Aspergillus caelatus, Aspergillus caesiellus, Aspergillus caespitosus, Aspergillus calidoustus, Aspergillus campestris, Aspergillus candidus, Aspergillus capensis, Aspergillus carbonarius, Aspergillus carneus, Aspergillus cavernicola, Aspergillus cavernicola, Aspergillus cervinus, Aspergillus chevalieri, Aspergillus chungii, Aspergillus cibarius, Aspergillus clavatoflavus, Aspergillus clavatonanicus, Aspergillus clavatus, Aspergillus conicus, Aspergillus conjunctus, Aspergillus conversis, Aspergillus coreanus, Aspergillus coremiiformis, Aspergillus costaricensis, Aspergillus costiformis, Aspergillus creber, Aspergillus cretensis, Aspergillus cristatus, Aspergillus crustosus, Aspergillus crystallinus, Aspergillus cvjetkovicii, Aspergillus deflectus, Aspergillus delacroixii, Aspergillus delicatus, Aspergillus densus, Aspergillus dentatulus, Aspergillus depauperatus, Aspergillus dessyi, Aspergillus digitatus, Aspergillus dimorphicus, Aspergillus diplocystis, Aspergillus discophorus, Aspergillus disjunctus, Aspergillus diversus, Aspergillus dorothicus, Aspergillus dubius, Aspergillus dubius, Aspergillus duricaulis, Aspergillus dybowskii, Aspergillus eburneocremeus, Aspergillus eburneus, Aspergillus echinosporus, Aspergillus echinulatus, Aspergillus ecuadorensis, Aspergillus effusus, Aspergillus egyptiacus, Aspergillus elatior, Aspergillus elegans, Aspergillus ellipsoideus, Aspergillus ellipticus, Aspergillus elongatus, Aspergillus equitis, Aspergillus erythrocephalus, Aspergillus falconensis, Aspergillus fasciculatus, Aspergillus fennelliae, Aspergillus ferrugineus, Aspergillus ferrugineus, Aspergillus ficuum, Aspergillus fiemonthi, Aspergillus filifera, Aspergillus fimetarius, Aspergillus fimeti, Aspergillus fischeri, Aspergillus fischerianus, Aspergillus flaschentraegeri, Aspergillus flavescens, Aspergillus flavidus, Aspergillus flavipes, Aspergillus flavofurcatus, Aspergillus flavoviridescens, Aspergillus flavus, Aspergillus flocculosus, Aspergillus floriformis, Aspergillus foeniculicola, Aspergillus foetidus, Aspergillus fonsecaeus, Aspergillus foutoynontii, Aspergillus foveolatus, Aspergillus fresenii, Aspergillus fructus, Aspergillus fruticans, Aspergillus fruticulosus, Aspergillus fujiokensis, Aspergillus fuliginosus, Aspergillus fulvus, Aspergillus fumaricus, Aspergillus fumigatiaffinis, Aspergillus fumigatoides, Aspergillus fumigatus, Aspergillus fumisynnematus, Aspergillus fungoides, Aspergillus funiculosus, Aspergillus fuscus, Aspergillus galeritus, Aspergillus giganteus, Aspergillus gigantosulphureus, Aspergillus gigas, Aspergillus glaber, Aspergillus glaucoaffinis, Aspergillus glauconiveus, Aspergillus glaucus, Aspergillus globosus, Aspergillus godfrini, Aspergillus gorakhpurensis, Aspergillus gracilis, Aspergillus granulatus, Aspergillus granulosus, Aspergillus gratioti, Aspergillus greconis, Aspergillus griseus, Aspergillus guttifer, Aspergillus gymnosardae, Aspergillus halophilicus, Aspergillus halophilus, Aspergillus helicothrix, Aspergillus hennebergii, Aspergillus herbariorum, Aspergillus heterocaryoticus, Aspergillus heteromorphus, Aspergillus heterothallicus, Aspergillus heyangensis, Aspergillus hiratsukae, Aspergillus hollandicus, Aspergillus homomorphus, Aspergillus hortae, Aspergillus humicola, Aspergillus humus, Aspergillus iberi-*

*cus, Aspergillus igneus, Aspergillus iizukae, Aspergillus implicatus, Aspergillus incrassatus, Aspergillus indicus, Aspergillus indohii, Aspergillus ingratus, Aspergillus insecticola, Aspergillus insuetus, Aspergillus insulicola, Aspergillus intermedius, Aspergillus inuii, Aspergillus itaconicus, Aspergillus ivoriensis, Aspergillus janus, Aspergillus japonicus, Aspergillus jeanselmei, Aspergillus jensenii, Aspergillus kambarensis, Aspergillus kanagawaensis, Aspergillus kassunensis, Aspergillus katsuobushi, Aspergillus keveli, Aspergillus koningii, Aspergillus laciniosus, Aspergillus lacticoffeatus, Aspergillus laneus, Aspergillus lanosus, Aspergillus laokiashanensis, Aspergillus lateralis, Aspergillus lentulus, Aspergillus lepidophyton, Aspergillus leporis, Aspergillus leucocarpus, Aspergillus lignieresii, Aspergillus longivesica, Aspergillus longobasidia, Aspergillus luchensi, Aspergillus luchuensis, Aspergillus lucknowensis, Aspergillus luteoniger, Aspergillus luteovirescens, Aspergillus lutescens, Aspergillus luteus, Aspergillus macfiei, Aspergillus macrosporus, Aspergillus malignus, Aspergillus malodoratus, Aspergillus malvaceus, Aspergillus mandshuricus, Aspergillus manginii, Aspergillus mannitosus, Aspergillus maritimus, Aspergillus mattletii, Aspergillus maximus, Aspergillus medius, Aspergillus melitensis, Aspergillus melleus, Aspergillus mellinus, Aspergillus mencieri, Aspergillus michelii, Aspergillus microcephalus, Aspergillus microcysticus, Aspergillus microsporus, Aspergillus microthecius, Aspergillus microviridicitrinus, Aspergillus minimus, Aspergillus minisclerotigenes, Aspergillus minor, Aspergillus minutus, Aspergillus miyajii, Aspergillus miyakoensis, Aspergillus mollis, Aspergillus montenegroi, Aspergillus montevidensis, Aspergillus mucoroides, Aspergillus mucoroideus, Aspergillus muelleri, Aspergillus multicolor, Aspergillus multiplicatus, Aspergillus muricatus, Aspergillus muscivora, Aspergillus mutabilis, Aspergillus mycetomivillabruzzii, Aspergillus mycobanche, Aspergillus nakazawae, Aspergillus nantae, Aspergillus nanus, Aspergillus navahoensis, Aspergillus neobridgeri, Aspergillus neocarnoyi, Aspergillus neoellipticus, Aspergillus neoglaber, Aspergillus nidulans, Aspergillus nidulellus, Aspergillus niger, Aspergillus nigrescens, Aspergillus nigricans, Aspergillus nishimurae, Aspergillus niveoglaucus, Aspergillus niveus, Aspergillus noelting, Aspergillus nominus, Aspergillus nomius, Aspergillus novofumigatus, Aspergillus novus, Aspergillus ochraceopetaliformis, Aspergillus ochraceoroseus, Aspergillus ochraceoruber, Aspergillus ochraceus, Aspergillus okazakii, Aspergillus olivaceofuscus, Aspergillus olivaceus, Aspergillus olivascens, Aspergillus olivicola, Aspergillus omanensis, Aspergillus onikii, Aspergillus oosporus, Aspergillus ornatulus, Aspergillus ornatus, Aspergillus oryzae, Aspergillus ostianus, Aspergillus otanii, Aspergillus ovalispermus, Aspergillus paleaceus, Aspergillus pallidus, Aspergillus panamensis, Aspergillus paradoxus, Aspergillus parasiticus, Aspergillus parrulus, Aspergillus parvathecius, Aspergillus parvisclerotigenus, Aspergillus parviverruculosus, Aspergillus parvulu, Aspergillus paulistensis, Aspergillus penicillatus, Aspergillus penicilliformis, Aspergillus penicillioides, Aspergillus penicillioideum, Aspergillus penicillopsis, Aspergillus periconioides, Aspergillus perniciosus, Aspergillus persii, Aspergillus petrakii, Aspergillus peyronelii, Aspergillus phaeocephalus, Aspergillus phialiseptatus, Aspergillus phoenicis, Aspergillus pidoplichknovii, Aspergillus piperis, Aspergillus polychromus, Aspergillus pouchetii, Aspergillus primulinus, Aspergillus profusus, Aspergillus proliferans, Aspergillus protuberus, Aspergillus pseudocaelatus, Aspergillus pseudocarbonarius, Aspergillus pseudocitricus, Aspergillus pseudoclavatus, Aspergillus pseudodeflectus,*

*Aspergillus pseudoelatior, Aspergillus pseudoelegans, Aspergillus pseudoflavus, Aspergillus pseudoglaucus, Aspergillus pseudoheteromorphus, Aspergillus pseudoniger, Aspergillus pseudoniger, Aspergillus pseudonomius, Aspergillus pseudotamarii, Aspergillus pulchellus, Aspergillus pulmonum-hominis, Aspergillus pulverulentus, Aspergillus pulvinus, Aspergillus puniceus, Aspergillus purpureofuscus, Aspergillus purpureus, Aspergillus pusillus, Aspergillus puulaauensis, Aspergillus pyramidus, Aspergillus pyri, Aspergillus qinqixianii, Aspergillus qizutongii, Aspergillus quadricinctus, Aspergillus quadricingens, Aspergillus quadrifidus, Aspergillus quadrilineatus, Aspergillus quercinus, Aspergillus quininae, Aspergillus quitensis, Aspergillus racemosus, Aspergillus raianus, Aspergillus rambellii, Aspergillus ramosus, Aspergillus raperi, Aspergillus recurvatus, Aspergillus rehmii, Aspergillus repandus, Aspergillus repens, Aspergillus reptans, Aspergillus restrictus, Aspergillus rhizopodus, Aspergillus robustus, Aspergillus roseoglobosus, Aspergillus roseoglobulosus, Aspergillus roseovelutinus, Aspergillus roseus, Aspergillus roseus, Aspergillus ruber, Aspergillus rubrobrunneus, Aspergillus rubrum, Aspergillus rufescens, Aspergillus rugulosus, Aspergillus rugulovalvus, Aspergillus rutilans, Aspergillus sacchari, Aspergillus saitoi, Aspergillus salviicola, Aspergillus sartoryi, Aspergillus scheelei, Aspergillus schiemanniae, Aspergillus sclerogenus, Aspergillus sclerotiicarbonarius, Aspergillus sclerotioniger, Aspergillus sclerotiorum, Aspergillus sejunctus, Aspergillus septatus, Aspergillus sepultus, Aspergillus silvaticus, Aspergillus simplex, Aspergillus sojae, Aspergillus sparsus, Aspergillus spathulatus, Aspergillus spectabilis, Aspergillus spelunceus, Aspergillus spiculosus, Aspergillus spinosus, Aspergillus spinulosus, Aspergillus spiralis, Aspergillus stella-maris, Aspergillus stellatus, Aspergillus stellifer, Aspergillus stercoreus, Aspergillus sterigmatophorus, Aspergillus steynii, Aspergillus stramenius, Aspergillus striatulus, Aspergillus striatus, Aspergillus stromatoides, Aspergillus strychni, Aspergillus subfuscus, Aspergillus subgriseus, Aspergillus sublatus, Aspergillus sublevisporus, Aspergillus subolivaceus, Aspergillus subsessilis, Aspergillus subunguis, Aspergillus subversicolor, Aspergillus sulphureus, Aspergillus sunderbanii, Aspergillus sydowii, Aspergillus sylvaticus, Aspergillus syncephalis, Aspergillus tabacinus, Aspergillus taichungensis, Aspergillus takakii, Aspergillus taklimakanensis, Aspergillus tamari, Aspergillus tapirirae, Aspergillus tardus, Aspergillus tatenoi, Aspergillus tennesseensis, Aspergillus terrestris, Aspergillus terreus, Aspergillus terricola, Aspergillus testaceocolorans, Aspergillus tetrazonus, Aspergillus thermomutatus, Aspergillus thomi, Aspergillus tiraboschii, Aspergillus togoensis, Aspergillus tokelau, Aspergillus tonophilus, Aspergillus toxicarius, Aspergillus tritici, Aspergillus tsurutae, Aspergillus tuberculatus, Aspergillus tubingensis, Aspergillus tunetanus, Aspergillus udagawae, Aspergillus umbrinus, Aspergillus umbrosus, Aspergillus undulatus, Aspergillus unguis, Aspergillus unilateralis, Aspergillus usamii, Aspergillus ustilago, Aspergillus ustus, Aspergillus uvarum, Aspergillus vadensis, Aspergillus vancampenhoutii, Aspergillus varanasensis, Aspergillus variabilis, Aspergillus varians, Aspergillus variecolor, Aspergillus variegatus, Aspergillus velutinus, Aspergillus venenatus, Aspergillus venezuelensis, Aspergillus versicolor, Aspergillus vinosobubalinus, Aspergillus violaceobrunneus, Aspergillus violaceofuscus, Aspergillus violaceus, Aspergillus virens, Aspergillus viridigriseus, Aspergillus viridinutans, Aspergillus vitellinus, Aspergillus vitis, Aspergillus vitricola, Aspergillus wangduanlii, Aspergillus warcupii, Aspergillus wehmeri, Aspergillus welwitschiae, Aspergillus wentii,*

*Aspergillus westendorpii, Aspergillus westerdijkiae, Aspergillus xerophilus, Aspergillus yezoensis, Aspergillus zhaoqingensis,* and *Aspergillus zonatus.*

"Sufficiently homologous" is used herein to refer to an amino acid sequence that has at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. In some embodiments, the sequence homology is against the full-length sequence of an IPD098 polypeptide.

In some embodiments the IPD098 polypeptide has at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116 or SEQ ID NO: 117. The term "about" when used herein in context with percent sequence identity means/−0.5%. One of skill in the art will recognize that these values can be appropriately adjusted to determine corresponding homology of proteins taking into account amino acid similarity and the like.

IPD108 Proteins and Variants and Fragments Thereof

IPD108 polypeptides are encompassed by the disclosure. "IPD108 polypeptide" and "IPD108 protein" as used herein interchangeably refers to a polypeptide having insecticidal activity including but not limited to insecticidal activity against one or more insect pests of the Lepidoptera and/or Coleoptera orders, and is sufficiently homologous to the IPD108Aa polypeptide of SEQ ID NO: 131. A variety of IPD108 polypeptides are contemplated. Sources of IPD108 polypeptides or related proteins include fern or other primitive plant species selected from but not limited to Selaginella species, Athyrium species or *Onoclea* species.

In some embodiments, the IPD108 polypeptide is derived from a species in the Class Isoetopsida Order Selaginales. In some embodiments, the IPD108 polypeptide is derived from a fern species in the Class Isoetopsida, Order Selaginales, and Family Selaginellaceae. In some embodiments, the IPD108 polypeptide is derived from a species in the Genus Selaginella. In some embodiments the IPD108 polypeptide is derived from a Selaginella species selected from but not limited to *Selaginella acanthonota, Selaginella apoda, Selaginella arbuscula, Selaginella arenicola, Selaginella arizonica, Selaginella armata, Selaginella asprella, Selaginella biformis, Selaginella bigelovii, Selaginella braunii, Selaginella cinerascens, Selaginella cordifolia, Selaginella deflexa, Selaginella delicatula, Selaginella densa, Selaginella douglasii, Selaginella eatonii, Selaginella eclipes, Selaginella eremophila, Selaginella erythropus, Selaginella flabellata, Selaginella hansenii, Selaginella heterodonta, Selaginella kraussiana, Selaginella krugii, Selaginella laxifolia, Selaginella lepidophylla, Selaginella leucobryoides, Selaginella ludoviciana, Selaginella mutica, Selaginella oregana, Selaginella ovifolia, Selaginella pallescens, Selaginella peruviana, Selaginella pilifera, Selaginella plana, Selaginella plumosa, Selaginella pulcherrima, Selaginella* rupestris, Selaginella rupincola, Selaginella scopulorum, Selaginella selaginoides, Selaginella sibirica, Selaginella standleyi, Selaginella stellata, Selaginella subcaulescens, Selaginella substipitata, Selaginella tenella, Selaginella tortipila, Selaginella uliginosa, Selaginella umbrosa, Selaginella uncinata, Selaginella underwoodii, Selaginella utahensis, Selaginella victoriae, Selaginella viridissima, Selaginella wallacei, Selaginella watsonii, Selaginella weatherbiana, Selaginella willdenowii, Selaginella wrightii and Selaginella X neomexicana.

In some embodiments, the IPD108 polypeptide is derived from a species in the Class Polypodiopsida and Order Polypodiales. In some embodiments, the IPD108 polypeptide is derived from a fern species in the Class Polypodiopsida Order Polypodiales, and Family Athyriaceae. In some embodiments, the IPD108 polypeptide is derived from a species in the Genus Athyrium. In some embodiments the IPD108 polypeptide is derived from an Athyrium species selected from but not limited to Athyrium arisanense, Athyrium atkinsonii, Athyrium biserrulatum, Athyrium brevifrons, Athyrium chingianum, Athyrium clarkei, Athyrium clivicola, Athyrium cryptogrammoides, Athyrium cumingianum, Athyrium cuspidatum, Athyrium deltoidofrons, Athyrium distentifolium, Athyrium dolosa, Athyrium epirachis, Athyrium eremicola, Athyrium fangii, Athyrium filix-femina, Athyrium frangulum, Athyrium giraldii, Athyrium iseanum, Athyrium kirisimaense, Athyrium kuratae, Athyrium masamunei, Athyrium melanolepis, Athyrium monomachi, Athyrium multidentatum, Athyrium nakanoi, Athyrium neglectum, Athyrium nigripes, Athyrium nikkoense, Athyrium niponicum, Athyrium nyalamense, Athyrium oblitescens, Athyrium otophorum, Athyrium palustre, Athyrium pinetorum, Athyrium pubicostatum, Athyrium reflexipinnum, Athyrium rhachidosorum, Athyrium rupestre, Athyrium scandicinum, Athyrium setuligerum, Athyrium sheareri, Athyrium silvicola, Athyrium sinense, Athyrium skinneri, Athyrium sp., Athyrium sp. YCL-2009, Athyrium spinulosum, Athyrium strigillosum, Athyrium subrigescens, Athyrium subtriangulare, Athyrium supraspinescens, Athyrium tashiroi, Athyrium tozanense, Athyrium vidalii, Athyrium viridescentipes, Athyrium wardii, Athyrium x akiense, Athyrium x hisatsuanum, Athyrium x tokashikii, Athyrium yokoscense, and Athyrium yui.

In some embodiments, the IPD108 polypeptide is derived from a fern species in the Class Polypodiopsida Order Polypodiales, and Family Onocleaceae. In some embodiments, the IPD108 polypeptide is derived from a species in the Genus Onoclea. In some embodiments, the IPD108 polypeptide is derived from Onoclea sensibilis, Onoclea orientalis, Onoclea interrupta, Onoclea interrupta or Onoclea hintonii.

"Sufficiently homologous" is used herein to refer to an amino acid sequence that has at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. In some embodiments, the sequence homology is against the full-length sequence of an IPD108 polypeptide.

In some embodiments the IPD108 polypeptide has at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 131, SEQ ID NO: 132, SEQ ID NO: 133, SEQ ID NO: 134 or SEQ ID NO: 135. The term "about" when used herein in context with percent sequence identity means/−0.5%. One of skill in the art will recognize that these values can be appropriately adjusted to determine corresponding homology of proteins taking into account amino acid similarity and the like.

IPD109 Proteins and Variants and Fragments Thereof

IPD109 polypeptides are encompassed by the disclosure. "IPD109 polypeptide" and "IPD109 protein" as used herein interchangeably refers to a polypeptide having insecticidal activity including but not limited to insecticidal activity against one or more insect pests of the Lepidoptera and/or Coleoptera orders, and is sufficiently homologous to the IPD109Aa polypeptide of SEQ ID NO: 138. A variety of IPD109 polypeptides are contemplated. Sources of IPD109 polypeptides or related proteins include fern or other primitive plant species selected from but not limited to a Selaginella species.

In some embodiments, the IPD109 polypeptide is derived from a species in the Class Isoetopsida Order Selaginales. In some embodiments, the IPD109 polypeptide is derived from a fern species in the Class Isoetopsida, Order Selaginales, Family Selaginellaceae. In some embodiments, the IPD109 polypeptide is derived from a species in the Genus Selaginella. In some embodiments the IPD109 polypeptide is derived from a Selaginella species selected from but not limited to Selaginella acanthonota, Selaginella apoda, Selaginella arbuscula, Selaginella arenicola, Selaginella arizonica, Selaginella armata, Selaginella asprella, Selaginella biformis, Selaginella bigelovii, Selaginella braunii, Selaginella cinerascens, Selaginella cordifolia, Selaginella deflexa, Selaginella delicatula, Selaginella densa, Selaginella douglasii, Selaginella eatonii, Selaginella eclipes, Selaginella eremophila, Selaginella erythropus, Selaginella flabellata, Selaginella hansenii, Selaginella heterodonta, Selaginella kraussiana, Selaginella krugii, Selaginella laxifolia, Selaginella lepidophylla, Selaginella leucobryoides, Selaginella ludoviciana, Selaginella mutica, Selaginella oregana, Selaginella ovifolia, Selaginella pallescens, Selaginella peruviana, Selaginella pilifera, Selaginella plana, Selaginella plumosa, Selaginella pulcherrima, Selaginella rupestris, Selaginella rupincola, Selaginella scopulorum, Selaginella selaginoides, Selaginella sibirica, Selaginella standleyi, Selaginella stellata, Selaginella subcaulescens, Selaginella substipitata, Selaginella tenella, Selaginella tortipila, Selaginella uliginosa, Selaginella umbrosa, Selaginella uncinata, Selaginella underwoodii, Selaginella utahensis, Selaginella victoriae, Selaginella viridissima, Selaginella wallacei, Selaginella watsonii, Selaginella weatherbiana, Selaginella willdenowii, Selaginella wrightii and Selaginella X neomexicana.

"Sufficiently homologous" is used herein to refer to an amino acid sequence that has at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. In some embodiments, the sequence homology is against the full-length sequence of an IPD109 polypeptide.

In some embodiments the IPD109 polypeptide has at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 138. The term "about" when used herein in context with percent sequence identity means/−0.5%. One of skill in the art will recognize that these values can be appropriately adjusted to determine corresponding homology of proteins taking into account amino acid similarity and the like.

In some embodiments, the sequence identity is calculated using ClustalW algorithm in the ALIGNX® module of the Vector NTI® Program Suite (Invitrogen Corporation, Carlsbad, Calif.) with all default parameters. In some embodiments, the sequence identity is across the entire length of polypeptide calculated using ClustalW algorithm in the ALIGNX® module of the Vector NTI® Program Suite (Invitrogen Corporation, Carlsbad, Calif.) with all default parameters.

As used herein, the terms "protein," "peptide molecule," or "polypeptide" includes any molecule that comprises five or more amino acids. It is well known in the art that protein, peptide or polypeptide molecules may undergo modification, including post-translational modifications, such as, but not limited to, disulfide bond formation, glycosylation, phosphorylation or oligomerization. Thus, as used herein, the terms "protein," "peptide molecule" or "polypeptide" includes any protein that is modified by any biological or non-biological process. The terms "amino acid" and "amino acids" refer to all naturally occurring L-amino acids.

A "recombinant protein" is used herein to refer to a protein that is no longer in its natural environment, for example in vitro or in a recombinant bacterial or plant host cell. A polypeptide that is substantially free of cellular material includes preparations of protein having less than about 30%, 20%, 10% or 5% (by dry weight) of non-pesticidal protein (also referred to herein as a "contaminating protein").

"Variants" as used herein refers to proteins or polypeptides having an amino acid sequence that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater identical to the parental amino acid sequence.

In some embodiments, the sequence identity is across the entire length of the polypeptide calculated using ClustalW algorithm in the ALIGNX® module of the Vector NTI® Program Suite (Invitrogen Corporation, Carlsbad, Calif.) with all default parameters.

Methods for such manipulations are generally known in the art. For example, amino acid sequence variants of a protein can be prepared by mutations in the DNA. This may also be accomplished by one of several forms of mutagenesis and/or in directed evolution.

In some aspects, the changes encoded in the amino acid sequence will not substantially affect the function of the protein. Such variants will possess the desired pesticidal activity. However, it is understood that the ability of a protein to confer pesticidal activity may be improved using such techniques upon the compositions of this disclosure. For example, conservative amino acid substitutions may be made at one or more predicted nonessential amino acid residues. A "nonessential" amino acid residue is a residue that can be altered from the wild-type sequence of a protein without altering the biological activity. Alignment of the amino acid sequences of protein homologs (for example—FIGS. 2-6), allows for the identification of residues that are highly conserved amongst the natural homologs of this family as well as residues or regions tolerant to amino acid diversity. A "conservative amino acid substitution" is one in which the amino acid residue is replaced with an amino acid residue having a similar side chain. Families of amino acid residues having similar side chains have been defined in the art. These families include: amino acids with basic side chains (e.g., lysine, arginine, histidine); acidic side chains (e.g., aspartic acid, glutamic acid); polar, negatively charged residues and their amides (e.g., aspartic acid, asparagine, glutamic, acid, glutamine; uncharged polar side chains (e.g., glycine, asparagine, glutamine, serine, threonine, tyrosine, cysteine); small aliphatic, nonpolar or slightly polar residues (e.g., Alanine, serine, threonine, proline, glycine); nonpolar side chains (e.g., alanine, valine, leucine, isoleucine, proline, phenylalanine, methionine, tryptophan); large aliphatic, nonpolar residues (e.g., methionine, leucine, isoleucine, valine, cystine); beta-branched side chains (e.g., threonine, valine, isoleucine); aromatic side chains (e.g., tyrosine, phenylalanine, tryptophan, histidine); large aromatic side chains (e.g., tyrosine, phenylalanine, tryptophan).

Amino acid substitutions may be made in nonconserved regions that retain function. In general, such substitutions would not be made for conserved amino acid residues or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the embodiments (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the embodiments (e.g., residues that have only conservative substitutions between all proteins contained in the alignment homologous proteins). However, one of skill in the art would understand that functional variants may have minor conserved or nonconserved alterations in the conserved residues. Guidance as to appropriate amino acid substitutions that do not affect biological activity of the protein of interest may be found in the model of Dayhoff, et al., (1978) *Atlas of Protein Sequence and Structure* (Natl. Biomed. Res. Found., Washington, D.C.), herein incorporated by reference.

In making such changes, the hydropathic index of amino acids may be considered. The importance of the hydropathic amino acid index in conferring interactive biologic function on a protein is generally understood in the art (Kyte and Doolittle, (1982) *J Mol Biol.* 157(1):105-32). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It is known in the art that certain amino acids may be substituted by other amino acids having a similar hydropathic index or score and still result in a protein with similar biological activity, i.e., still obtain a biological functionally equivalent protein. Each amino acid has been assigned a hydropathic index on the basis of its hydrophobicity and charge characteristics (Kyte and Doolittle, ibid). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9) and arginine (−4.5). In making such changes, the substitution of amino acids whose hydropathic indices are within 2 is preferred, those which are within 1 are particularly preferred, and those within 0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0.+0.1); glutamate (+3.0.+0.1); serine (+0.3); asparagine (+0.2); glutamine (+0.2); glycine (0); threonine (−0.4); proline (−0.5.+0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Alternatively, alterations may be made to the protein sequence of many proteins at the amino or carboxy terminus without substantially affecting activity. This can include insertions, deletions or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity or epitope to facilitate either protein purification, protein detection or other experimental uses known in the art (3) target secretion or translation of a protein to a subcellular organelle, such as the periplasmic space of Gram-negative bacteria, mitochondria or chloroplasts of plants or the endoplasmic reticulum of eukaryotic cells, the latter of which often results in glycosylation of the protein.

Variant nucleotide and amino acid sequences of the disclosure also encompass sequences derived from mutagenic and recombinogenic procedures such as DNA shuffling. With such a procedure, one or more different homolog polypeptides coding regions can be used to create a new polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene and other known pesticidal genes to obtain a new gene coding for a protein with an improved property of interest, such as an increased insecticidal activity. Strategies for such DNA shuffling are known in the art. See, for example, Stemmer, (1994) *Proc. Natl. Acad. Sci. USA* 91:10747-10751; Stemmer, (1994) *Nature* 370:389-391; Crameri, et al., (1997) *Nature Biotech.* 15:436-438; Moore, et al., (1997) *J. Mol. Biol.* 272:336-347; Zhang, et al., (1997) *Proc. Natl. Acad. Sci. USA* 94:4504-4509; Crameri, et al., (1998) *Nature* 391:288-291; and U.S. Pat. Nos. 5,605,793 and 5,837,458.

Domain swapping or shuffling is another mechanism for generating altered polypeptides. Domains may be swapped between polypeptide homologs resulting in hybrid or chimeric toxins with improved insecticidal activity or target spectrum. Methods for generating recombinant proteins and testing them for pesticidal activity are well known in the art (see, for example, Naimov, et al., (2001) *Appl. Environ. Microbiol.* 67:5328-5330; de Maagd, et al., (1996) *Appl. Environ. Microbiol.* 62:1537-1543; Ge, et al., (1991) *J. Biol. Chem.* 266:17954-17958; Schnepf, et al., (1990) *J. Biol. Chem.* 265:20923-20930; Rang, et al., 91999) *Appl. Environ. Microbiol.* 65:2918-2925).

Phylogenetic, sequence motif, and structural analyses of insecticidal protein families. A sequence and structure analysis method can be employed, which is composed of four components: phylogenetic tree construction, protein sequence motifs finding, secondary structure prediction, and alignment of protein sequences and secondary structures. Details about each component are illustrated below.

Phylogenetic Tree Construction

The phylogenetic analysis can be performed using the software MEGA5. Protein sequences can be subjected to ClustalW version 2 analysis (Larkin M. A et al (2007) Bioinformatics 23(21): 2947-2948) for multiple sequence alignment. The evolutionary history is then inferred by the Maximum Likelihood method based on the JTT matrix-based model. The tree with the highest log likelihood is obtained, exported in Newick format, and further processed to extract the sequence IDs in the same order as they appeared in the tree. A few clades representing sub-families can be manually identified for each insecticidal protein family.

Protein Sequence Motifs Finding

Protein sequences are re-ordered according to the phylogenetic tree built previously, and fed to the MOTIF analysis tool MEME (Multiple EM for MOTIF Elicitation) (Bailey T. L., and Elkan C., *Proceedings of the Second International Conference on Intelligent Systems for Molecular Biology*, pp. 28-36, AAAI Press, Menlo Park, California, 1994.) for identification of key sequence motifs. MEME is setup as follows: Minimum number of sites 2, Minimum motif width 5, and Maximum number of motifs 30. Sequence motifs unique to each sub-family were identified by visual observation. The distribution of MOTIFs across the entire gene family could be visualized in HTML webpage. The MOTIFs are numbered relative to the ranking of the E-value for each MOTIF.

Secondary Structure Prediction

PSIPRED, top ranked secondary structure prediction method (Jones DT. (1999) *J. Mol. Biol.* 292: 195-202), can be used for protein secondary structure prediction. The tool provides accurate structure prediction using two feed-forward neural networks based on the PSI-BLAST output. The PSI-BLAST database is created by removing low-complexity, transmembrane, and coiled-coil regions in Uniref100. The PSIPRED results contain the predicted secondary structures (Alpha helix: H, Beta strand: E, and Coil: C) and the corresponding confidence scores for each amino acid in a given protein sequence.

Alignment of Protein Sequences and Secondary Structures

A script can be developed to generate gapped secondary structure alignment according to the multiple protein sequence alignment from step 1 for all proteins. All aligned protein sequences and structures are concatenated into a single FASTA file, and then imported into MEGA for visualization and identification of conserved structures.

In some embodiments, the IPD059, IPD098, IPD108 or IPD109 polypeptide has a modified physical property. As used herein, the term "physical property" refers to any parameter suitable for describing the physical-chemical characteristics of a protein. As used herein, "physical property of interest" and "property of interest" are used interchangeably to refer to physical properties of proteins that are being investigated and/or modified. Examples of physical properties include, but are not limited to, net surface charge and charge distribution on the protein surface, net hydrophobicity and hydrophobic residue distribution on the protein surface, surface charge density, surface hydrophobicity density, total count of surface ionizable groups, surface tension, protein size and its distribution in solution, melting temperature, heat capacity, and second virial coefficient. Examples of physical properties also include, IPD059, IPD098, IPD108 or IPD109 polypeptide having increased expression, increased solubility, decreased phytotoxicity, and digestibility of proteolytic fragments in an insect gut. Models for digestion by simulated gastric fluids are known to one skilled in the art (Fuchs, R. L. and J. D. Astwood. *Food Technology* 50: 83-88, 1996; Astwood, J. D., et al *Nature Biotechnology* 14: 1269-1273, 1996; Fu T J et al *J. Agric Food Chem.* 50: 7154-7160, 2002).

In some embodiments variants include polypeptides that differ in amino acid sequence due to mutagenesis. Variant proteins encompassed by the disclosure are biologically active, that is they continue to possess the desired biological activity (i.e. pesticidal activity) of the native protein. In some embodiments, the variant will have at least about 10%, at least about 30%, at least about 50%, at least about 70%, at least about 80% or more of the insecticidal activity of the native protein. In some embodiments, the variants may have improved activity over the native protein.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present disclosure and may be used in the methods of the present disclosure. It will be understood that, when expressed in plants, it will be necessary to alter the alternate start codon to ATG for proper translation.

One skilled in the art understands that the polynucleotide coding sequence can be modified to add a codon at the position following the methionine start codon to create a restriction enzyme site for recombinant cloning purposes and/or for expression purposes. In some embodiments, the polypeptides of the disclosure further comprise an alanine residue at the position after the translation initiator methionine.

In some embodiments, the translation initiator methionine of a polypeptide of the disclosure is cleaved off post translationally. One skilled in the art understands that the N-terminal translation initiator methionine can be removed by methionine aminopeptidase in many cellular expression systems.

In some embodiments, chimeric polypeptides are provided comprising regions of at least two different IPD059, IPD098, IPD108 or IPD109 polypeptides of the disclosure. In some embodiments, chimeric polypeptides are provided comprising regions of at least two different IPD098 polypeptides of the disclosure. In some embodiments, chimeric polypeptides are provided comprising regions of at least two different IPD059, IPD098, IPD108 or IPD109 polypeptides of the disclosure. In some embodiments, chimeric polypeptides are provided comprising regions of at least two different IPD059, IPD098, IPD108 or IPD109 polypeptides of the disclosure.

In other embodiments, the polypeptides of the disclosure may be expressed as a precursor protein with an intervening sequence that catalyzes multi-step, post translational protein splicing. Protein splicing involves the excision of an intervening sequence from a polypeptide with the concomitant joining of the flanking sequences to yield a new polypeptide (Chong, et al., (1996) *J. Biol. Chem.*, 271:22159-22168). This intervening sequence or protein splicing element, referred to as inteins, which catalyze their own excision through three coordinated reactions at the N-terminal and C-terminal splice junctions: an acyl rearrangement of the N-terminal cysteine or serine; a transesterification reaction between the two termini to form a branched ester or thioester intermediate and peptide bond cleavage coupled to cyclization of the intein C-terminal asparagine to free the intein (Evans, et al., (2000) *J. Biol. Chem.*, 275:9091-9094. The elucidation of the mechanism of protein splicing has led to a number of intein-based applications (Comb, et al., U.S. Pat. No. 5,496,714; Comb, et al., U.S. Pat. No. 5,834,247; Camarero and Muir, (1999) *J. Amer. Chem. Soc.* 121:5597-5598; Chong, et al., (1997) *Gene* 192:271-281, Chong, et al., (1998) *Nucleic Acids Res.* 26:5109-5115; Chong, et al., (1998) *J. Biol. Chem.* 273:10567-10577; Cotton, et al., (1999) *J. Am. Chem. Soc.* 121:1100-1101; Evans, et al., (1999) *J. Biol. Chem.* 274:18359-18363; Evans, et al., (1999) *J. Biol. Chem.* 274:3923-3926; Evans, et al., (1998) *Protein Sci.* 7:2256-2264; Evans, et al., (2000) *J. Biol. Chem.* 275:9091-9094; Iwai and Pluckthun, (1999) *FEBS Lett.* 459:166-172; Mathys, et al., (1999) *Gene* 231:1-13; Mills, et al., (1998) *Proc. Natl. Acad. Sci. USA* 95:3543-3548; Muir, et al., (1998) *Proc. Natl. Acad. Sci. USA* 95:6705-6710; Otomo, et al., (1999) *Biochemistry* 38:16040-16044; Otomo, et al., (1999) *J. Biolmol. NMR* 14:105-114; Scott, et al., (1999) *Proc. Natl. Acad. Sci. USA* 96:13638-13643; Severinov and Muir, (1998) *J. Biol. Chem.* 273:16205-16209; Shingledecker, et al., (1998) *Gene* 207:187-195; Southworth, et al., (1998) *EMBO J.* 17:918-926; Southworth, et al., (1999) *Biotechniques* 27:110-120; Wood, et al., (1999) *Nat. Biotechnol.* 17:889-892; Wu, et al., (1998a) *Proc. Natl. Acad. Sci. USA* 95:9226-9231; Wu, et al., (1998b) *Biochim Biophys Acta* 1387:422-432; Xu, et al., (1999) *Proc. Natl. Acad. Sci. USA* 96:388-393; Yamazaki, et al., (1998) *J. Am. Chem. Soc.*, 120:5591-5592). For the application of inteins in plant transgenes, see, Yang, et al., (*Transgene Res* 15:583-593 (2006)) and Evans, et al., (*Annu. Rev. Plant Biol.* 56:375-392 (2005)).

In another embodiment, the polypeptides of the disclosure may be encoded by two separate genes where the intein of the precursor protein comes from the two genes, referred to as a split-intein, and the two portions of the precursor are joined by a peptide bond formation. This peptide bond formation is accomplished by intein-mediated trans-splicing. For this purpose, a first and a second expression cassette comprising the two separate genes further code for inteins capable of mediating protein trans-splicing. By trans-splicing, the proteins and polypeptides encoded by the first and second fragments may be linked by peptide bond formation. Trans-splicing inteins may be selected from the nucleolar and organellar genomes of different organisms including eukaryotes, archaebacteria and eubacteria. Inteins that may be used for are listed at neb.com/neb/inteins.html, which can be accessed on the world-wide web using the "www" prefix). The nucleotide sequence coding for an intein may be split into a 5' and a 3' part that code for the 5' and the 3' part of the intein, respectively. Sequence portions not necessary for intein splicing (e.g. homing endonuclease domain) may be deleted. The intein coding sequence is split such that the 5' and the 3' parts are capable of trans-splicing. For selecting a suitable splitting site of the intein coding sequence, the considerations published by Southworth, et al., (1998) EMBO J. 17:918-926 may be followed. In constructing the first and the second expression cassette, the 5' intein coding sequence is linked to the 3' end of the first fragment coding for the N-terminal part of the IPD059, IPD098, IPD108 or IPD109 polypeptide of the disclosure and the 3' intein coding sequence is linked to the 5' end of the second fragment coding for the C-terminal part of the IPD059, IPD098, IPD108 or IPD109 polypeptide.

In general, the trans-splicing partners can be designed using any split intein, including any naturally-occurring or artificially-split split intein. Several naturally-occurring split inteins are known, for example: the split intein of the DnaE gene of *Synechocystis* sp. PCC6803 (see, Wu, et al., (1998) *Proc Natl Acad Sci USA.* 95(16):9226-31 and Evans, et al., (2000) *J Biol Chem.* 275(13):9091-4 and of the DnaE gene from *Nostoc punctiforme* (see, Iwai, et al., (2006) FEBS Lett. 580(7):1853-8). Non-split inteins have been artificially split in the laboratory to create new split inteins, for example: the artificially split Ssp DnaB intein (see, Wu, et al., (1998) *Biochim Biophys Acta.* 1387:422-32) and split Sce VMA intein (see, Brenzel, et al., (2006) *Biochemistry.* 45(6):1571-8) and an artificially split fungal mini-intein (see, Elleuche, et al., (2007) *Biochem Biophys Res Commun.* 355(3):830-4). There are also intein databases available that catalogue known inteins (see for example the online-database available at: bioinformatics.weizmann.ac.il/~pietro/inteins/Inteinstable.html, which can be accessed on the world-wide web using the "www" prefix).

Naturally-occurring non-split inteins may have endonuclease or other enzymatic activities that can typically be removed when designing an artificially-split split intein. Such mini-inteins or minimized split inteins are well known in the art and are typically less than 200 amino acid residues long (see, Wu, et al., (1998) Biochim Biophys Acta. 1387: 422-32). Suitable split inteins may have other purification enabling polypeptide elements added to their structure, provided that such elements do not inhibit the splicing of the split intein or are added in a manner that allows them to be removed prior to splicing. Protein splicing has been reported using proteins that comprise bacterial intein-like (BIL) domains (see, Amitai, et al., (2003) Mol Microbiol. 47:61-73) and hedgehog (Hog) auto-processing domains (the latter is combined with inteins when referred to as the Hog/intein superfamily or HINT family (see, Dassa, et al., (2004) J Biol Chem. 279:32001-7) and domains such as these may also be used to prepare artificially-split inteins. In particular, non-splicing members of such families may be modified by molecular biology methodologies to introduce or restore splicing activity in such related species. Recent studies demonstrate that splicing can be observed when a N-terminal split intein component is allowed to react with a C-terminal split intein component not found in nature to be its "partner"; for example, splicing has been observed utilizing partners that have as little as 30 to 50% homology with the "natural" splicing partner (see, Dassa, et al., (2007) Biochemistry. 46(1):322-30). Other such mixtures of disparate split intein partners have been shown to be unreactive one with another (see, Brenzel, et al., (2006) Biochemistry. 45(6):1571-8). However, it is within the ability of a person skilled in the relevant art to determine whether a particular pair of polypeptides is able to associate with each other to provide a functional intein, using routine methods and without the exercise of inventive skill.

In some embodiments, a polypeptide of the disclosure is a circular permuted variant. The development of recombinant DNA methods has made it possible to study the effects of sequence transposition on protein folding, structure and function. The approach used in creating new sequences resembles that of naturally occurring pairs of proteins that are related by linear reorganization of their amino acid sequences (Cunningham, et al., (1979) *Proc. Natl. Acad. Sci. U.S.A.* 76:3218-3222; Teather and Erfle, (1990) *J. Bacteriol.* 172:3837-3841; Schimming, et al., (1992) *Eur. J. Biochem.* 204:13-19; Yamiuchi and Minamikawa, (1991) *FEBS Lett.* 260:127-130; MacGregor, et al., (1996) *FEBS Lett.* 378:263-266). The first in vitro application of this type of rearrangement to proteins was described by Goldenberg and Creighton (*J. Mol. Biol.* 165:407-413, 1983). In creating a circular permuted variant, a new N-terminus is selected at an internal site (breakpoint) of the original sequence, the new sequence having the same order of amino acids as the original from the breakpoint until it reaches an amino acid that is at or near the original C-terminus. At this point the new sequence is joined, either directly or through an additional portion of sequence (linker), to an amino acid that is at or near the original N-terminus and the new sequence continues with the same sequence as the original until it reaches a point that is at or near the amino acid that was N-terminal to the breakpoint site of the original sequence, this residue forming the new C-terminus of the chain. The length of the amino acid sequence of the linker can be selected empirically or with guidance from structural information or by using a combination of the two approaches. When no structural information is available, a small series of linkers can be prepared for testing using a design whose length is varied in order to span a range from 0 to 50 Å and whose sequence is chosen in order to be consistent with surface exposure (hydrophilicity, Hopp and Woods, (1983) *Mol. Immunol.* 20:483-489; Kyte and Doolittle, (1982) *J. Mol. Biol.* 157: 105-132; solvent exposed surface area, Lee and Richards, (1971) *J. Mol. Biol.* 55:379-400) and the ability to adopt the necessary conformation without deranging the configuration of the pesticidal polypeptide (conformationally flexible; Karplus and Schulz, (1985) *Naturwissenschaften* 72:212-213). Assuming an average of translation of 2.0 to 3.8 Å per residue, this would mean the length to test would be between 0 to 30 residues, with 0 to 15 residues being the preferred range. Exemplary of such an empirical series would be to construct linkers using a cassette sequence such as Gly-Gly-Gly-Ser repeated n times, where n is 1, 2, 3 or 4. Those skilled in the art will recognize that there are many such sequences that vary in length or composition that can serve as linkers with the primary consideration being that they be neither excessively long nor short (cf., Sandhu, (1992) *Critical Rev. Biotech.* 12:437-462); if they are too long, entropy effects will likely destabilize the three-dimensional fold, and may also make folding kinetically impractical, and if they are too short, they will likely destabilize the molecule because of torsional or steric strain. Those skilled in the analysis of protein structural information will recognize that using the distance between the chain ends, defined as the distance between the c-alpha carbons, can be used to define the length of the sequence to be used or at least to limit the number of possibilities that must be tested in an empirical selection of linkers. They will also recognize that it is sometimes the case that the positions of the ends of the polypeptide chain are ill-defined in structural models derived from x-ray diffraction or nuclear magnetic resonance spectroscopy data, and that when true, this situation will therefore need to be taken into account in order to properly estimate the length of the linker required. From those residues, whose positions are well defined are selected two residues that are close in sequence to the chain ends, and the distance between their c-alpha carbons is used to calculate an approximate length for a linker between them. Using the calculated length as a guide, linkers with a range of number of residues (calculated using 2 to 3.8 Å per residue) are then selected. These linkers may be composed of the original sequence, shortened or lengthened as necessary, and when lengthened the additional residues may be chosen to be flexible and hydrophilic as described above; or optionally the original sequence may be substituted for using a series of linkers, one example being the Gly-Gly-Gly-Ser cassette approach mentioned above; or optionally a combination of the original sequence and new sequence having the appropriate total length may be used. Sequences of pesticidal polypeptides capable of folding to biologically active states can be prepared by appropriate selection of the beginning (amino terminus) and ending (carboxyl terminus) positions from within the original polypeptide chain while using the linker sequence as described above. Amino and carboxyl termini are selected from within a common stretch of sequence, referred to as a breakpoint region, using the guidelines described below. A novel amino acid sequence is thus generated by selecting amino and carboxyl termini from within the same breakpoint region. In many cases the selection of the new termini will be such that the original position of the carboxyl terminus immediately preceded that of the amino terminus. However, those skilled in the art will recognize that selections of termini anywhere within the region may function, and that these will effectively lead to either deletions or additions to the amino or carboxyl portions of the new sequence. It is a central tenet of molecular biology that the primary amino acid sequence of a protein dictates folding to the three-dimensional structure necessary for expression of its biological function. Methods are known to those skilled in the art to obtain and interpret three-dimensional structural information using x-ray diffraction of single protein Crystals or nuclear magnetic resonance spectroscopy of protein solutions. Examples of structural information that are relevant to the identification of breakpoint regions include the location and type of protein secondary structure (alpha and 3-10 helices, parallel and anti-parallel beta sheets, chain reversals and turns, and loops; Kabsch and Sander, (1983) *Biopolymers* 22:2577-2637; the degree of solvent exposure of amino acid residues, the extent and type of interactions of residues with one another (Chothia, (1984) *Ann. Rev. Biochem.* 53:537-572) and the static and dynamic distribution of conformations along the polypeptide chain (Alber and Mathews, (1987) *Methods Enzymol.* 154:511-533). In some cases, additional information is known about solvent exposure of residues; one example is a site of post-translational attachment of carbohydrate which is necessarily on the surface of the protein. When experimental structural information is not available or is not feasible to obtain, methods are also available to analyze the primary amino acid sequence in order to make predictions of protein tertiary and secondary structure, solvent accessibility and the occurrence of turns and loops. Biochemical methods are also sometimes applicable for empirically determining surface exposure when direct structural methods are not feasible; for example, using the identification of sites of chain scission following limited proteolysis in order to infer surface exposure (Gentile and Salvatore, (1993) *Eur. J. Biochem.* 218:603-621). Using either, the experimentally derived structural information or predictive methods (e.g., Srinivisan and Rose, (1995) *Proteins: Struct., Funct. & Genetics* 22:81-99) the parental amino acid sequence is inspected to classify regions according to whether or not they are integral to the maintenance of secondary and tertiary structure. The occurrence of sequences within regions that are known to be involved in periodic secondary structure (alpha and 3-10 helices, parallel and anti-parallel beta sheets) are regions that should be avoided. Similarly, regions of amino acid sequence that are observed or predicted to have a low degree of solvent exposure are more likely to be part of the so-called hydrophobic core of the protein and should also be avoided for selection of amino and carboxyl termini. In contrast, those regions that are known or predicted to be in surface turns or loops, and especially those regions that are known not to be required for biological activity, are the preferred sites for location of the extremes of the polypeptide chain. Continuous stretches of amino acid sequence that are preferred based on the above criteria are referred to as a breakpoint region. Polynucleotides encoding circular permuted IPD059, IPD098, IPD108 or IPD109 polypeptides with new N-terminus/C-terminus which contain a linker region separating the original C-terminus and N-terminus can be made essentially following the method described in Mullins, et al., (1994) *J. Am. Chem. Soc.* 116:5529-5533. Multiple steps of polymerase chain reaction (PCR) amplifications are used to rearrange the DNA sequence encoding the primary amino acid sequence of the protein. Polynucleotides encoding circular permuted IPD059, IPD098, IPD108 or IPD109 polypeptides with new N-terminus/C-terminus which contain a linker region separating the original C-terminus and N-terminus can be made based on the tandem-duplication method described in Horlick, et al., (1992) *Protein Eng.* 5:427-431. Polymerase chain reaction (PCR) amplification of the new N-terminus/C-terminus genes is performed using a tandemly duplicated template DNA.

In another embodiment, fusion proteins are provided that include within its amino acid sequence an amino acid sequence comprising a polypeptide of the disclosure. Methods for design and construction of fusion proteins (and polynucleotides encoding same) are known to those of skill in the art. Polynucleotides encoding a polypeptide of the embodiments may be fused to signal sequences which will direct the localization of the polypeptide of the embodiments to particular compartments of a prokaryotic or eukaryotic cell and/or direct the secretion of the polypeptide of the embodiments from a prokaryotic or eukaryotic cell. For example, in *E. coli*, one may wish to direct the expression of the protein to the periplasmic space. Examples of signal sequences or proteins (or fragments thereof) to which the polypeptide of the disclosure may be fused in order to direct the expression of the polypeptide to the periplasmic space of bacteria include, but are not limited to, the peiB signal sequence, the maltose binding protein (MBP) signal sequence, MBP, the ompA signal sequence, the signal sequence of the periplasmic *E. coli* heat-labile enterotoxin B-subunit and the signal sequence of alkaline phosphatase. Several vectors are commercially available for the construction of fusion proteins which will direct the localization of a protein, such as the pMAL series of vectors (particularly the pMAL-p series) available from New England Biolabs. In a specific embodiment, the IPD059, IPD098, IPD108 or IPD109 polypeptide may be fused to the peiB pectate lyase signal sequence to increase the efficiency of expression and purification of such polypeptides in Gram-negative bacteria (see, U.S. Pat. Nos. 5,576,195 and 5,846,818). Plant plastid transit peptide/polypeptide fusions are well known in the art. Apoplast transit peptides such as rice or barley alpha-amylase secretion signal are also well known in the art. The plastid transit peptide is generally fused N-terminal to the polypeptide to be targeted (e.g., the fusion partner). In one embodiment, the fusion protein consists essentially of the plastid transit peptide and the polypeptide of the disclosure to be targeted. In another embodiment, the fusion protein comprises the plastid transit peptide and the polypeptide to be targeted. In such embodiments, the plastid transit peptide is preferably at the N-terminus of the fusion protein. However, additional amino acid residues may be N-terminal to the plastid transit peptide providing that the fusion protein is at least partially targeted to a plastid. In a specific embodiment, the plastid transit peptide is in the N-terminal half, N-terminal third or N-terminal quarter of the fusion protein. Most or all of the plastid transit peptide is generally cleaved from the fusion protein upon insertion into the plastid. The position of cleavage may vary slightly between plant species, at different plant developmental stages, as a result of specific intercellular conditions or the particular combination of transit peptide/fusion partner used. In one embodiment, the plastid transit peptide cleavage is homogenous such that the cleavage site is identical in a population of fusion proteins. In another embodiment, the plastid transit peptide is not homogenous, such that the cleavage site varies by 1-10 amino acids in a population of fusion proteins. The plastid transit peptide can be recombinantly fused to a second protein in one of several ways. For example, a restriction endonuclease recognition site can be introduced into the nucleotide sequence of the transit peptide at a position corresponding to its C-terminal end and the same or a compatible site can be engineered into the nucleotide sequence of the protein to be targeted at its N-terminal end. Care must be taken in designing these sites to ensure that the coding sequences of the transit peptide and the second protein are kept "in frame" to allow the synthesis of the desired fusion protein. In some cases, it may be preferable to remove the initiator methionine of the second protein when the new restriction site is introduced. The introduction of restriction endonuclease recognition sites on both parent molecules and their subsequent joining through recombinant DNA techniques may result in the addition of one or more extra amino acids between the transit peptide and the second protein. This generally does not affect targeting activity as long as the transit peptide cleavage site remains accessible and the function of the second protein is not altered by the addition of these extra amino acids at its N-terminus. Alternatively, one skilled in the art can create a precise cleavage site between the transit peptide and the second protein (with or without its initiator methionine) using gene synthesis (Stemmer, et al., (1995) *Gene* 164:49-53) or similar methods. In addition, the transit peptide fusion can intentionally include amino acids downstream of the cleavage site. The amino acids at the N-terminus of the mature protein can affect the ability of the transit peptide to target proteins to plastids and/or the efficiency of cleavage following protein import. This may be dependent on the protein to be targeted. See, e.g., Comai, et al., (1988) *J. Biol. Chem.* 263(29): 15104-9.

In some embodiments, the polypeptide of the disclosure is fused to a heterologous signal peptide or heterologous transit peptide.

In some embodiments, fusion proteins are provide comprising a polypeptide of the disclosure represented by a formula selected from the group consisting of:

$R^1$-L-$R^2$, $R^2$-L-$R^1$, $R^1$-$R^2$ or $R^2$-$R^1$ wherein $R^1$ is a polypeptide of the disclosure and $R^2$ is a protein of interest. In some embodiments $R^1$ and $R^2$ are a polypeptide of the disclosure. The $R^1$ polypeptide is fused either directly or through a linker (L) segment to the $R^2$ polypeptide. The term "directly" defines fusions in which the polypeptides are joined without a peptide linker. Thus "L" represents a chemical bound or polypeptide segment to which both $R^1$ and $R^2$ are fused in frame, most commonly L is a linear peptide to which $R^1$ and $R^2$ are bound by amide bonds linking the carboxy terminus of $R^1$ to the amino terminus of L and carboxy terminus of L to the amino terminus of $R^2$. By "fused in frame" is meant that there is no translation termination or disruption between the reading frames of $R^1$ and $R^2$. The linking group (L) is generally a polypeptide of between 1 and 500 amino acids in length. The linkers joining the two molecules are preferably designed to (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains and (4) provide steric separation of $R^1$ and $R^2$ such that $R^1$ and $R^2$ could interact simultaneously with their corresponding receptors on a single cell. Typically surface amino acids in flexible protein regions include Gly, Asn and Ser. Virtually any permutation of amino acid sequences containing Gly, Asn and Ser would be expected to satisfy the above criteria for a linker sequence. Other neutral amino acids, such as Thr and Ala, may also be used in the linker sequence. Additional amino acids may also be included in the linkers due to the addition of unique restriction sites in the linker sequence to facilitate construction of the fusions.

In some embodiments, the linkers comprise sequences selected from the group of formulas: $(Gly_3Ser)_n$, $(Gly_4Ser)_n$, $(Gly_5Ser)_n$, $(GlynSer)_n$ or $(AlaGlySer)_n$ where n is an integer. One example of a highly-flexible linker is the (GlySer)-rich spacer region present within the pIII protein of the filamentous bacteriophages, e.g. bacteriophages M13 or fd (Schaller, et al., 1975). This region provides a long, flexible spacer region between two domains of the pIII surface protein. Also included are linkers in which an endopeptidase recognition sequence is included. Such a cleavage site may be valuable to separate the individual components of the fusion to determine if they are properly folded and active in vitro. Examples of various endopeptidases include, but are not limited to, Plasmin, Enterokinase, Kallikerin, Urokinase, Tissue Plasminogen activator, clostripain, Chymosin, Collagenase, Russell's Viper Venom Protease, Postproline cleavage enzyme, V8 protease, Thrombin and factor Xa. In some embodiments, the linker comprises the amino acids EEKKN (SEQ ID NO: 156) from the multi-gene expression vehicle (MGEV), which is cleaved by vacuolar proteases as disclosed in US Patent Application Publication Number US 2007/0277263. In other embodiments, peptide linker segments from the hinge region of heavy chain immunoglobulins IgG, IgA, IgM, IgD or IgE provide an angular relationship between the attached polypeptides. Especially useful are those hinge regions where the cysteines are replaced with serines. Linkers of the present disclosure include sequences derived from murine IgG gamma 2b hinge region in which the cysteines have been changed to serines. The fusion proteins are not limited by the form, size or number of linker sequences employed and the only requirement of the linker is that functionally it does not interfere adversely with the folding and function of the individual molecules of the fusion.

Nucleic Acid Molecules, and Variants and Fragments Thereof

Isolated or recombinant nucleic acid molecules comprising nucleic acid sequences encoding polypeptides or biologically active portions thereof, as well as nucleic acid molecules sufficient for use as hybridization probes to identify nucleic acid molecules encoding proteins with regions of sequence homology are provided. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule (or DNA) is used herein to refer to a nucleic acid sequence (or DNA) that is no longer in its natural environment, for example in vitro. A "recombinant" nucleic acid molecule (or DNA) is used herein to refer to a nucleic acid sequence (or DNA) that is in a recombinant bacterial or plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes. For example, in various embodiments, the recombinant nucleic acid molecules encoding polypeptides of the disclosure can contain less than about 5 kb, 4 kb, 3 kb, 2 kb, 1 kb, 0.5 kb or 0.1 kb of nucleic acid sequences that naturally flank the nucleic acid molecule in genomic DNA of the cell from which the nucleic acid is derived.

In some embodiments, an isolated nucleic acid molecule encoding a polypeptide of the disclosure has one or more change in the nucleic acid sequence compared to the native or genomic nucleic acid sequence. In some embodiments the change in the native or genomic nucleic acid sequence includes but is not limited to: changes in the nucleic acid sequence due to the degeneracy of the genetic code; changes in the nucleic acid sequence due to the amino acid substitution, insertion, deletion and/or addition compared to the native or genomic sequence; removal of one or more intron; deletion of one or more upstream or downstream regulatory regions; and deletion of the 5' and/or 3' untranslated region associated with the genomic nucleic acid sequence. In some embodiments, the nucleic acid molecule encoding a polypeptide of the disclosure is a non-genomic sequence.

A variety of polynucleotides that encode the polypeptides of the disclosure or related proteins are contemplated. Such polynucleotides are useful for production of the polypeptides of the disclosure in host cells when operably linked to a suitable promoter, transcription termination and/or polyadenylation sequences. Such polynucleotides are also useful as probes for isolating homologous or substantially homologous polynucleotides that encode polypeptides of the disclosure or related proteins.

Polynucleotides Encoding IPD059 Polypeptides

One source of polynucleotides that encode IPD059 polypeptides or related proteins is a fern or other primitive plant species selected from but not limited to limited to Polypodium species, Colysis species, Asplenium species, *Polystichum* species or a *Phyllitis* species, which contains an IPD059 polynucleotide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37 encoding an IPD059 polypeptide of SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74 or SEQ ID NO: 75, respectively. The polynucleotides of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37, can be used to express IPD059 polypeptides in recombinant bacterial hosts that include but are not limited to *Agrobacterium, Bacillus, Escherichia, Salmonella, Pseudomonas* and *Rhizobium* bacterial host cells. The polynucleotides are also useful as probes for isolating homologous or substantially homologous polynucleotides that encode IPD059 polypeptides or related proteins. Such probes can be used to identify homologous or substantially homologous polynucleotides derived from fern or other primitive plant species selected from but not limited *Polypodium* species, *Colysis* species, *Asplenium* species, *Polystichum* species or *Phyllitis* species.

Polynucleotides that encode IPD059 polypeptides can also be synthesized de novo from an IPD059 polypeptide sequence. The sequence of the polynucleotide gene can be deduced from an IPD059 polypeptide sequence through use of the genetic code. Computer programs such as "Back-Translate" (GCG™ Package, Acclerys, Inc. San Diego, Calif.) can be used to convert a peptide sequence to the corresponding nucleotide sequence encoding the peptide. Examples of IPD059 polypeptide sequences that can be used to obtain corresponding nucleotide encoding sequences include, but are not limited to the IPD059 polypeptides of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, and SEQ ID NO: 78. Furthermore, synthetic IPD059 polynucleotide sequences of the disclosure can be designed so that they will be expressed in plants.

In some embodiments the nucleic acid molecule encoding an IPD059 polypeptide is a polynucleotide having the sequence set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37, and variants, fragments and complements thereof. "Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments, the nucleic acid molecule encoding the IPD059 polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments, the non-genomic nucleic acid molecule is a synthetic nucleic acid sequence. In some embodiments, the non-genomic nucleic acid molecule is a cDNA.

In some embodiments, the nucleic acid molecule encoding an IPD059 polypeptide is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to the nucleic acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37, wherein the IPD059 polypeptide has insecticidal activity.

In some embodiments, the nucleic acid molecule encodes an IPD059 polypeptide comprising an amino acid sequence of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75 or SEQ ID NO: 78, having 1,2, 3,4, 5,6, 7, 8, 9,10,11,12,13,14,15,16,17,18,19, 20,21,22,23,24,25,26,27, 28, 29, 30, 31, 32, 33, 34, 35, 36, 37, 38, 39, 40, 41, 42, 43, 44, 45, 46, 47, 48 or more amino acid substitutions, deletions and/or insertions compared to the native amino acid at the corresponding position of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75 or SEQ ID NO: 78.

Also provided are nucleic acid molecules that encode transcription and/or translation products that are subsequently spliced to ultimately produce functional IPD059 polypeptides. Splicing can be accomplished in vitro or in vivo, and can involve cis- or trans-splicing. The substrate for splicing can be polynucleotides (e.g., RNA transcripts) or polypeptides. An example of cis-splicing of a polynucleotide is where an intron inserted into a coding sequence is removed and the two flanking exon regions are spliced to generate an IPD059 polypeptide encoding sequence. An example of trans-splicing would be where a polynucleotide is encrypted by separating the coding sequence into two or more fragments that can be separately transcribed and then spliced to form the full-length pesticidal encoding sequence. The use of a splicing enhancer sequence, which can be introduced into a construct, can facilitate splicing either in cis or trans-splicing of polypeptides (U.S. Pat. Nos. 6,365, 377 and 6,531,316). Thus, in some embodiments the polynucleotides do not directly encode a full-length IPD059 polypeptide, but rather encode a fragment or fragments of an IPD059 polypeptide. These polynucleotides can be used to express a functional IPD059 polypeptide through a mechanism involving splicing, where splicing can occur at the level of polynucleotide (e.g., intron/exon) and/or polypeptide (e.g., intein/extein). This can be useful, for example, in controlling expression of pesticidal activity, since a functional pesticidal polypeptide will only be expressed if all required fragments are expressed in an environment that permits splicing processes to generate functional product. In another example, introduction of one or more insertion sequences into a polynucleotide can facilitate recombination with a low homology polynucleotide; use of an intron or intein for the insertion sequence facilitates the removal of the intervening sequence, thereby restoring function of the encoded variant.

Nucleic acid molecules that are fragments of these nucleic acid sequences encoding IPD059 polypeptides are also encompassed by the embodiments. "Fragment" as used herein refers to a portion of the nucleic acid sequence encoding an IPD059 polypeptide. A fragment of a nucleic acid sequence may encode a biologically active portion of an IPD059 polypeptide or it may be a fragment that can be used as a hybridization probe or PCR primer using methods disclosed below. Nucleic acid molecules that are fragments of a nucleic acid sequence encoding an IPD059 polypeptide comprise at least about 150, 180, 210, 240, 270, 300, 330 or 360, contiguous nucleotides or up to the number of nucleotides present in a full-length nucleic acid sequence encoding an IPD059 polypeptide disclosed herein, depending upon the intended use. "Contiguous nucleotides" is used herein to refer to nucleotide residues that are immediately adjacent to one another. Fragments of the nucleic acid sequences of the embodiments will encode protein fragments that retain the biological activity of the IPD059 polypeptide and, hence, retain insecticidal activity. "Retains insecticidal activity" is used herein to refer to a polypeptide having at least about 10%, at least about 30%, at least about 50%, at least about 70%, 80%, 90%, 95% or higher of the insecticidal activity of the full-length IPD059Aa polypeptide (SEQ ID NO: 39). In some embodiments, the insecticidal activity is against a Lepidopteran species. In one embodiment, the insecticidal activity is against a Coleopteran species.

In some embodiments, the IPD059 polypeptide is encoded by a nucleic acid sequence sufficiently homologous to the nucleic acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37. "Sufficiently homologous" is used herein to refer to an amino acid or nucleic acid sequence that has at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins encoded by two nucleic acid sequences by taking into account degeneracy, amino acid similarity, reading frame positioning, and the like. In some embodiments, the sequence homology is against the full-length sequence of the polynucleotide encoding an IPD059 polypeptide or against the full-length sequence of an IPD059 polypeptide.

In some embodiments, the nucleic acid encodes an IPD059 polypeptide having at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75 or SEQ ID NO: 78.

In some embodiments, the sequence identity is calculated using ClustalW algorithm in the ALIGNX® module of the Vector NTI® Program Suite (Invitrogen Corporation, Carlsbad, Calif.) with all default parameters. In some embodiments, the sequence identity is across the entire length of polypeptide calculated using ClustalW algorithm in the ALIGNX module of the Vector NTI Program Suite (Invitrogen Corporation, Carlsbad, Calif.) with all default parameters.

To determine the percent identity of two or more amino acid sequences or of two or more nucleic acid sequences, the sequences are aligned for optimal comparison purposes. The percent identity between the two sequences is a function of the number of identical positions shared by the sequences (i.e., percent identity=number of identical positions/total number of positions (e.g., overlapping positions×100).

In one embodiment, the two sequences are the same length. In another embodiment, the comparison is across the entirety of the reference sequence (e.g., across the entirety of SEQ ID NO: 39). The percent identity between two sequences can be determined using techniques similar to those described below, with or without allowing gaps. In calculating percent identity, typically exact matches are counted.

Another non-limiting example of a mathematical algorithm utilized for the comparison of sequences is the algorithm of Needleman and Wunsch, (1970) *J. Mol. Biol.* 48(3):443-453, used GAP Version 10 software to determine sequence identity or similarity using the following default parameters: % identity and % similarity for a nucleic acid sequence using GAP Weight of 50 and Length Weight of 3, and the nwsgapdna.cmpii scoring matrix; % identity or % similarity for an amino acid sequence using GAP weight of 8 and length weight of 2, and the BLOSUM62 scoring program. Equivalent programs may also be used. "Equivalent program" is used herein to refer to any sequence comparison program that, for any two sequences in question, generates an alignment having identical nucleotide residue matches and an identical percent sequence identity when compared to the corresponding alignment generated by GAP Version 10.

In some embodiments, the IPD059 polynucleotide encodes an IPD059 polypeptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of SEQ ID NO: 39.

In some embodiments polynucleotides are provided encoding chimeric polypeptides comprising regions of at least two different IPD059 polypeptides of the disclosure.

In some embodiments, polynucleotides are provided encoding chimeric polypeptides comprising regions of at least two different IPD059 polypeptides selected from SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75 or SEQ ID NO: 78.

In some embodiments, an IPD059 polynucleotide encodes the IPD059 polypeptide comprising an amino acid sequence of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75 or SEQ ID NO: 78.

Polynucleotides Encoding IPD098 Polypeptides

One source of polynucleotides that encode IPD098 polypeptides or related proteins is a fern or other primitive plant species selected from but not limited to limited to Asplenium species, *Platycerium* species, *Aspergillus* species or a Selaginella species, which contains an IPD098 polynucleotide of SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93 or SEQ ID NO: 94, encoding an IPD098 polypeptide of SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116 or SEQ ID NO: 117, respectively. The polynucleotides of SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93 or SEQ ID NO: 94, can be used to express IPD098 polypeptides in recombinant bacterial hosts that include but are not limited to *Agrobacterium, Bacillus, Escherichia, Salmonella, Pseudomonas* and *Rhizobium* bacterial host cells. The polynucleotides are also useful as probes for isolating homologous or substantially homologous polynucleotides that encode IPD098 polypeptides or related proteins. Such probes can be used to identify homologous or substantially homologous polynucleotides derived from fern or other primitive plant species selected from but not limited *Polypodium* species, *Colysis* species, *Asplenium* species, *Polystichum* species or *Phyllitis* species.

Polynucleotides that encode IPD098 polypeptides can also be synthesized de novo from an IPD098 polypeptide sequence. The sequence of the polynucleotide gene can be deduced from an IPD098 polypeptide sequence through use of the genetic code. Computer programs such as "Back-Translate" (GCG™ Package, Acclerys, Inc. San Diego, Calif.) can be used to convert a peptide sequence to the corresponding nucleotide sequence encoding the peptide. Examples of IPD098 polypeptide sequences that can be used to obtain corresponding nucleotide encoding sequences include, but are not limited to the IPD098 polypeptides of SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116 and SEQ ID NO: 117. Furthermore, synthetic IPD098 polynucleotide sequences of the disclosure can be designed so that they will be expressed in plants.

In some embodiments the nucleic acid molecule encoding an IPD098 polypeptide is a polynucleotide having the sequence set forth in SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93 or SEQ ID NO: 94, and variants, fragments and complements thereof. "Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments, the nucleic acid molecule encoding the IPD098 polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments, the non-genomic nucleic acid molecule is a synthetic nucleic acid sequence. In some embodiments, the non-genomic nucleic acid molecule is a cDNA.

In some embodiments the nucleic acid molecule encoding an IPD098 polypeptide is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to the nucleic acid sequence of SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93 or SEQ ID NO: 94, wherein the IPD098 polypeptide has insecticidal activity.

In some embodiments the nucleic acid molecule encodes an IPD098 polypeptide comprising an amino acid sequence of SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116 or SEQ ID NO: 117, having 1, 2, 3, 4, 5, 6, 7, 8, 9, 10, 11, 12, 13, 14, 15, 16, 17, 18,19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or more amino acid substitutions, deletions and/or insertions compared to the native amino acid at the corresponding position of SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116 or SEQ ID NO: 117.

Also provided are nucleic acid molecules that encode transcription and/or translation products that are subsequently spliced to ultimately produce functional IPD098 polypeptides. Splicing can be accomplished in vitro or in vivo, and can involve cis- or trans-splicing. The substrate for splicing can be polynucleotides (e.g., RNA transcripts) or polypeptides. An example of cis-splicing of a polynucleotide is where an intron inserted into a coding sequence is removed and the two flanking exon regions are spliced to generate an IPD098 polypeptide encoding sequence. An example of trans-splicing would be where a polynucleotide is encrypted by separating the coding sequence into two or more fragments that can be separately transcribed and then spliced to form the full-length pesticidal encoding sequence. The use of a splicing enhancer sequence, which can be introduced into a construct, can facilitate splicing either in cis or trans-splicing of polypeptides (U.S. Pat. Nos. 6,365,377 and 6,531,316). Thus, in some embodiments the polynucleotides do not directly encode a full-length IPD098 polypeptide, but rather encode a fragment or fragments of an IPD098 polypeptide. These polynucleotides can be used to express a functional IPD098 polypeptide through a mechanism involving splicing, where splicing can occur at the level of polynucleotide (e.g., intron/exon) and/or polypeptide (e.g., intein/extein). This can be useful, for example, in controlling expression of pesticidal activity, since a functional pesticidal polypeptide will only be expressed if all required fragments are expressed in an environment that permits splicing processes to generate functional product. In another example, introduction of one or more insertion sequences into a polynucleotide can facilitate recombination with a low homology polynucleotide; use of an intron or intein for the insertion sequence facilitates the removal of the intervening sequence, thereby restoring function of the encoded variant.

Nucleic acid molecules that are fragments of these nucleic acid sequences encoding IPD098 polypeptides are also encompassed by the embodiments. "Fragment" as used herein refers to a portion of the nucleic acid sequence encoding an IPD098 polypeptide. A fragment of a nucleic acid sequence may encode a biologically active portion of an IPD098 polypeptide or it may be a fragment that can be used as a hybridization probe or PCR primer using methods disclosed below. Nucleic acid molecules that are fragments of a nucleic acid sequence encoding an IPD098 polypeptide comprise at least about 150, 180, 210, 240, 270, 300, 330 or 360, contiguous nucleotides or up to the number of nucleotides present in a full-length nucleic acid sequence encoding an IPD098 polypeptide disclosed herein, depending upon the intended use. "Contiguous nucleotides" is used herein to refer to nucleotide residues that are immediately adjacent to one another. Fragments of the nucleic acid sequences of the embodiments will encode protein fragments that retain the biological activity of the IPD098 polypeptide and, hence, retain insecticidal activity. "Retains insecticidal activity" is used herein to refer to a polypeptide having at least about 10%, at least about 30%, at least about 50%, at least about 70%, 80%, 90%, 95% or higher of the insecticidal activity of the full-length IPD098Aa polypeptide (SEQ ID NO: 102). In some embodiments, the insecticidal activity is against a Lepidopteran species. In one embodiment, the insecticidal activity is against a Coleopteran species.

In some embodiments, the IPD098 polypeptide is encoded by a nucleic acid sequence sufficiently homologous to the nucleic acid sequence of SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93 or SEQ ID NO: 94. "Sufficiently homologous" is used herein to refer to an amino acid or nucleic acid sequence that has at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins encoded by two nucleic acid sequences by taking into account degeneracy, amino acid similarity, reading frame positioning, and the like. In some embodiments, the sequence homology is against the full-length sequence of the polynucleotide encoding an IPD098 polypeptide or against the full-length sequence of an IPD098 polypeptide.

In some embodiments the nucleic acid encodes an IPD098 polypeptide having at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116 or SEQ ID NO: 117.

In some embodiments, the sequence identity is calculated using ClustalW algorithm in the ALIGNX® module of the Vector NTI® Program Suite (Invitrogen Corporation, Carlsbad, Calif.) with all default parameters. In some embodiments, the sequence identity is across the entire length of polypeptide calculated using ClustalW algorithm in the ALIGNX module of the Vector NTI Program Suite (Invitrogen Corporation, Carlsbad, Calif.) with all default parameters.

To determine the percent identity of two or more amino acid sequences or of two or more nucleic acid sequences, the sequences are aligned for optimal comparison purposes. The percent identity between the two sequences is a function of the number of identical positions shared by the sequences (i.e., percent identity=number of identical positions/total number of positions (e.g., overlapping positions x100).

In one embodiment, the two sequences are the same length. In another embodiment, the comparison is across the entirety of the reference sequence (e.g., across the entirety of SEQ ID NO: 102). The percent identity between two sequences can be determined using techniques similar to those described below, with or without allowing gaps. In calculating percent identity, typically exact matches are counted.

Another non-limiting example of a mathematical algorithm utilized for the comparison of sequences is the algorithm of Needleman and Wunsch, (1970) *J. Mol. Biol.* 48(3):443-453, used GAP Version 10 software to determine sequence identity or similarity using the following default parameters: % identity and % similarity for a nucleic acid sequence using GAP Weight of 50 and Length Weight of 3, and the nwsgapdna.cmpii scoring matrix; % identity or % similarity for an amino acid sequence using GAP weight of 8 and length weight of 2, and the BLOSUM62 scoring program. Equivalent programs may also be used. "Equivalent program" is used herein to refer to any sequence comparison program that, for any two sequences in question, generates an alignment having identical nucleotide residue matches and an identical percent sequence identity when compared to the corresponding alignment generated by GAP Version 10.

In some embodiments, the/PD098 polynucleotide encodes an IPD098 polypeptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of SEQ ID NO: 102.

In some embodiments, polynucleotides are provided encoding chimeric polypeptides comprising regions of at least two different IPD098 polypeptides of the disclosure.

In some embodiments, polynucleotides are provided encoding chimeric polypeptides comprising regions of at least two different IPD098 polypeptides selected from SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116 and SEQ ID NO: 117.

In some embodiments, an IPD098 polynucleotide encodes a IPD098 polypeptide comprising an amino acid sequence of SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116 and SEQ ID NO: 117.

Polynucleotides Encoding IPD108 Polypeptides

One source of polynucleotides that encode IPD108 polypeptides or related proteins is a fern or other primitive plant species selected from but not limited to limited to Selaginella species, Athyrium species or *Onoclea* species, which contains an IPD108 polynucleotide of SEQ ID NO: 125, SEQ ID NO: 126, SEQ ID NO: 127, SEQ ID NO: 128 or SEQ ID NO: 129 encoding an IPD108 polypeptide of SEQ ID NO: 131, SEQ ID NO: 132, SEQ ID NO: 133, SEQ ID NO: 134 or SEQ ID NO: 135, respectively. The polynucleotides of SEQ ID NO: 125, SEQ ID NO: 126, SEQ ID NO: 127, SEQ ID NO: 128 or SEQ ID NO: 129 can be used to express IPD108 polypeptides in recombinant bacterial hosts that include but are not limited to *Agrobacterium, Bacillus, Escherichia, Salmonella, Pseudomonas* and *Rhizobium* bacterial host cells. The polynucleotides are also useful as probes for isolating homologous or substantially homologous polynucleotides that encode IPD108 polypeptides or related proteins. Such probes can be used to identify homologous or substantially homologous polynucleotides derived from fern or other primitive plant species selected from but not limited Selaginella species, Athyrium species or *Onoclea* species.

Polynucleotides that encode IPD108 polypeptides can also be synthesized de novo from an IPD108 polypeptide sequence. The sequence of the polynucleotide gene can be deduced from an IPD108 polypeptide sequence through use of the genetic code. Computer programs such as "Back-Translate" (GCG™ Package, Acclerys, Inc. San Diego, Calif.) can be used to convert a peptide sequence to the corresponding nucleotide sequence encoding the peptide. Examples of IPD108 polypeptide sequences that can be used to obtain corresponding nucleotide encoding sequences include, but are not limited to the IPD108 polypeptides of SEQ ID NO: 131, SEQ ID NO: 132, SEQ ID NO: 133, SEQ ID NO: 134, and SEQ ID NO: 135. Furthermore, synthetic IPD108 polynucleotide sequences of the disclosure can be designed so that they will be expressed in plants.

In some embodiments, the nucleic acid molecule encoding an IPD108 polypeptide is a polynucleotide having the sequence set forth in SEQ ID NO: 125, SEQ ID NO: 126, SEQ ID NO: 127, SEQ ID NO: 128 or SEQ ID NO: 129, and variants, fragments and complements thereof. "Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments, the nucleic acid molecule encoding the IPD108 polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments, the non-genomic nucleic acid molecule is a synthetic nucleic acid sequence. In some embodiments, the non-genomic nucleic acid molecule is a cDNA.

In some embodiments, the nucleic acid molecule encoding an IPD108 polypeptide is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to the nucleic acid sequence of SEQ ID NO: 125, SEQ ID NO: 126, SEQ ID NO: 127, SEQ ID NO: 128 or SEQ ID NO: 129, wherein the IPD108 polypeptide has insecticidal activity.

In some embodiments, the nucleic acid molecule encodes an IPD108 polypeptide comprising an amino acid sequence of SEQ ID NO: 131, SEQ ID NO: 132, SEQ ID NO: 133, SEQ ID NO: 134, and SEQ ID NO: 135 having 1, 2, 3, 4, 5, 6, 7, 8, 9, 10, 11, 12, 13, 14, 15, 16, 17, 18,19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or more amino acid substitutions, deletions and/or insertions compared to the native amino acid at the corresponding position of SEQ ID NO: 131, SEQ ID NO: 132, SEQ ID NO: 133, SEQ ID NO: 134, and SEQ ID NO: 135.

Also provided are nucleic acid molecules that encode transcription and/or translation products that are subsequently spliced to ultimately produce functional IPD108 polypeptides. Splicing can be accomplished in vitro or in vivo, and can involve cis- or trans-splicing. The substrate for splicing can be polynucleotides (e.g., RNA transcripts) or polypeptides. An example of cis-splicing of a polynucleotide is where an intron inserted into a coding sequence is removed and the two flanking exon regions are spliced to generate an IPD108 polypeptide encoding sequence. An example of trans-splicing would be where a polynucleotide is encrypted by separating the coding sequence into two or more fragments that can be separately transcribed and then spliced to form the full-length pesticidal encoding sequence. The use of a splicing enhancer sequence, which can be introduced into a construct, can facilitate splicing either in cis or trans-splicing of polypeptides (U.S. Pat. Nos. 6,365, 377 and 6,531,316). Thus, in some embodiments the polynucleotides do not directly encode a full-length IPD108 polypeptide, but rather encode a fragment or fragments of an IPD108 polypeptide. These polynucleotides can be used to express a functional IPD108 polypeptide through a mechanism involving splicing, where splicing can occur at the level of polynucleotide (e.g., intron/exon) and/or polypeptide (e.g., intein/extein). This can be useful, for example, in controlling expression of pesticidal activity, since a functional pesticidal polypeptide will only be expressed if all required fragments are expressed in an environment that permits splicing processes to generate functional product. In another example, introduction of one or more insertion sequences into a polynucleotide can facilitate recombination with a low homology polynucleotide; use of an intron or intein for the insertion sequence facilitates the removal of the intervening sequence, thereby restoring function of the encoded variant.

Nucleic acid molecules that are fragments of these nucleic acid sequences encoding IPD108 polypeptides are also encompassed by the embodiments. "Fragment" as used herein refers to a portion of the nucleic acid sequence encoding an IPD108 polypeptide. A fragment of a nucleic acid sequence may encode a biologically active portion of an IPD108 polypeptide or it may be a fragment that can be used as a hybridization probe or PCR primer using methods disclosed below. Nucleic acid molecules that are fragments of a nucleic acid sequence encoding an IPD108 polypeptide comprise at least about 150, 180, 210, 240, 270, 300, 330 or 360, contiguous nucleotides or up to the number of nucleotides present in a full-length nucleic acid sequence encoding an IPD108 polypeptide disclosed herein, depending upon the intended use. "Contiguous nucleotides" is used herein to refer to nucleotide residues that are immediately adjacent to one another. Fragments of the nucleic acid sequences of the embodiments will encode protein fragments that retain the biological activity of the IPD108 polypeptide and, hence, retain insecticidal activity. "Retains insecticidal activity" is used herein to refer to a polypeptide having at least about 10%, at least about 30%, at least about 50%, at least about 70%, 80%, 90%, 95% or higher of the insecticidal activity of the full-length IPD108Aa polypeptide (SEQ ID NO: 131). In some embodiments, the insecticidal activity is against a Lepidopteran species. In one embodiment, the insecticidal activity is against a Coleopteran species.

In some embodiments, the IPD108 polypeptide is encoded by a nucleic acid sequence sufficiently homologous to the nucleic acid sequence of SEQ ID NO: 125, SEQ ID NO: 126, SEQ ID NO: 127, SEQ ID NO: 128 or SEQ ID NO: 129. "Sufficiently homologous" is used herein to refer to an amino acid or nucleic acid sequence that has at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins encoded by two nucleic acid sequences by taking into account degeneracy, amino acid similarity, reading frame positioning, and the like. In some embodiments, the sequence homology is against the full-length sequence of the polynucleotide encoding an IPD108 polypeptide or against the full-length sequence of an IPD108 polypeptide.

In some embodiments the nucleic acid encodes an IPD108 polypeptide having at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 131, SEQ ID NO: 132, SEQ ID NO: 133, SEQ ID NO: 134 or SEQ ID NO: 135.

In some embodiments, the sequence identity is calculated using ClustalW algorithm in the ALIGNX® module of the Vector NTI® Program Suite (Invitrogen Corporation, Carlsbad, Calif.) with all default parameters. In some embodiments, the sequence identity is across the entire length of polypeptide calculated using ClustalW algorithm in the ALIGNX module of the Vector NTI Program Suite (Invitrogen Corporation, Carlsbad, Calif.) with all default parameters.

To determine the percent identity of two or more amino acid sequences or of two or more nucleic acid sequences, the sequences are aligned for optimal comparison purposes. The percent identity between the two sequences is a function of the number of identical positions shared by the sequences (i.e., percent identity=number of identical positions/total number of positions (e.g., overlapping positions x100).

In one embodiment, the two sequences are the same length. In another embodiment, the comparison is across the entirety of the reference sequence (e.g., across the entirety of SEQ ID NO: 131). The percent identity between two sequences can be determined using techniques similar to those described below, with or without allowing gaps. In calculating percent identity, typically exact matches are counted.

Another non-limiting example of a mathematical algorithm utilized for the comparison of sequences is the algorithm of Needleman and Wunsch, (1970) *J. Mol. Biol.* 48(3):443-453, used GAP Version 10 software to determine sequence identity or similarity using the following default parameters: % identity and % similarity for a nucleic acid sequence using GAP Weight of 50 and Length Weight of 3, and the nwsgapdna.cmpii scoring matrix; % identity or % similarity for an amino acid sequence using GAP weight of 8 and length weight of 2, and the BLOSUM62 scoring program. Equivalent programs may also be used. "Equivalent program" is used herein to refer to any sequence comparison program that, for any two sequences in question, generates an alignment having identical nucleotide residue matches and an identical percent sequence identity when compared to the corresponding alignment generated by GAP Version 10.

In some embodiments, the IPD108 polynucleotide encodes an IPD108 polypeptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of SEQ ID NO: 131.

In some embodiments polynucleotides are provided encoding chimeric polypeptides comprising regions of at least two different IPD108 polypeptides of the disclosure.

In some embodiments, polynucleotides are provided encoding chimeric polypeptides comprising regions of at least two different IPD108 polypeptides selected from SEQ ID NO: 131, SEQ ID NO: 132, SEQ ID NO: 133, SEQ ID NO: 134, and SEQ ID NO: 135.

In some embodiments, an IPD108 polynucleotide encodes the IPD108 polypeptide comprising an amino acid sequence of SEQ ID NO: 131, SEQ ID NO: 132, SEQ ID NO: 133, SEQ ID NO: 134 or SEQ ID NO: 135.

Polynucleotides Encoding IPD109 Polypeptides

One source of polynucleotides that encode IPD109 polypeptides or related proteins is a fern or other primitive plant species selected from but not limited to limited to Selaginella species, which contains an IPD109 polynucleotide of SEQ ID NO: 137 encoding an IPD109 polypeptide of SEQ ID NO: 138. The polynucleotide of SEQ ID NO: 137 can be used to express IPD109 polypeptides in recombinant bacterial hosts that include but are not limited to *Agrobacterium, Bacillus, Escherichia, Salmonella, Pseudomonas* and *Rhizobium* bacterial host cells. The polynucleotides are also useful as probes for isolating homologous or substantially homologous polynucleotides that encode IPD109 polypeptides or related proteins. Such probes can be used to identify homologous or substantially homologous polynucleotides derived from fern or other primitive plant species selected from but not limited to Selaginella species.

Polynucleotides that encode IPD109 polypeptides can also be synthesized de novo from an IPD109 polypeptide sequence. The sequence of the polynucleotide gene can be deduced from an IPD109 polypeptide sequence through use of the genetic code. Computer programs such as "Back-Translate" (GCG™ Package, Acclerys, Inc. San Diego, Calif.) can be used to convert a peptide sequence to the corresponding nucleotide sequence encoding the peptide. Examples of IPD109 polypeptide sequences that can be used to obtain corresponding nucleotide encoding sequences include, but are not limited to the IPD109 polypeptides of SEQ ID NO: 137. Furthermore, synthetic IPD109 polynucleotide sequences of the disclosure can be designed so that they will be expressed in plants.

In some embodiments, the nucleic acid molecule encoding an IPD109 polypeptide is a polynucleotide having the sequence set forth in SEQ ID NO: 137 and variants, fragments and complements thereof. "Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments, the nucleic acid molecule encoding the IPD109 polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments, the non-genomic nucleic acid molecule is a synthetic nucleic acid sequence. In some embodiments, the non-genomic nucleic acid molecule is a cDNA.

In some embodiments, the nucleic acid molecule encoding an IPD109 polypeptide is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to the nucleic acid sequence of SEQ ID NO: 137, wherein the IPD109 polypeptide has insecticidal activity.

In some embodiments, the nucleic acid molecule encodes an IPD109 polypeptide comprising an amino acid sequence of SEQ ID NO: 138 having 1, 2, 3, 4, 5, 6, 7, 8, 9, 10, 11, 12, 13,14, 15,16, 17,18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or more amino acid substitutions, deletions and/or insertions compared to the native amino acid at the corresponding position of SEQ ID NO: 138.

Also provided are nucleic acid molecules that encode transcription and/or translation products that are subsequently spliced to ultimately produce functional IPD109 polypeptides. Splicing can be accomplished in vitro or in vivo, and can involve cis- or trans-splicing. The substrate for splicing can be polynucleotides (e.g., RNA transcripts) or polypeptides. An example of cis-splicing of a polynucleotide is where an intron inserted into a coding sequence is removed and the two flanking exon regions are spliced to generate an IPD109 polypeptide encoding sequence. An example of trans-splicing would be where a polynucleotide is encrypted by separating the coding sequence into two or more fragments that can be separately transcribed and then spliced to form the full-length pesticidal encoding sequence. The use of a splicing enhancer sequence, which can be introduced into a construct, can facilitate splicing either in cis or trans-splicing of polypeptides (U.S. Pat. Nos. 6,365,377 and 6,531,316). Thus, in some embodiments the polynucleotides do not directly encode a full-length IPD109 polypeptide, but rather encode a fragment or fragments of an IPD109 polypeptide. These polynucleotides can be used to express a functional IPD109 polypeptide through a mechanism involving splicing, where splicing can occur at the level of polynucleotide (e.g., intron/exon) and/or polypeptide (e.g., intein/extein). This can be useful, for example, in controlling expression of pesticidal activity, since a functional pesticidal polypeptide will only be expressed if all required fragments are expressed in an environment that permits splicing processes to generate functional product. In another example, introduction of one or more insertion sequences into a polynucleotide can facilitate recombination with a low homology polynucleotide; use of an intron or intein for the insertion sequence facilitates the removal of the intervening sequence, thereby restoring function of the encoded variant.

Nucleic acid molecules that are fragments of these nucleic acid sequences encoding IPD109 polypeptides are also encompassed by the embodiments. "Fragment" as used herein refers to a portion of the nucleic acid sequence encoding an IPD109 polypeptide. A fragment of a nucleic acid sequence may encode a biologically active portion of an IPD109 polypeptide or it may be a fragment that can be used as a hybridization probe or PCR primer using methods disclosed below. Nucleic acid molecules that are fragments of a nucleic acid sequence encoding an IPD109 polypeptide comprise at least about 150, 180, 210, 240, 270, 300, 330 or 360, contiguous nucleotides or up to the number of nucleotides present in a full-length nucleic acid sequence encoding an IPD109 polypeptide disclosed herein, depending upon the intended use. "Contiguous nucleotides" is used herein to refer to nucleotide residues that are immediately adjacent to one another. Fragments of the nucleic acid sequences of the embodiments will encode protein fragments that retain the biological activity of the IPD109 polypeptide and, hence, retain insecticidal activity. "Retains insecticidal activity" is used herein to refer to a polypeptide having at least about 10%, at least about 30%, at least about 50%, at least about 70%, 80%, 90%, 95% or higher of the insecticidal activity of the full-length IPD109Aa polypeptide (SEQ ID NO: 138). In some embodiments, the insecticidal activity is against a Lepidopteran species. In one embodiment, the insecticidal activity is against a Coleopteran species.

In some embodiments, the IPD109 polypeptide is encoded by a nucleic acid sequence sufficiently homologous to the nucleic acid sequence of SEQ ID NO: 137. "Sufficiently homologous" is used herein to refer to an amino acid or nucleic acid sequence that has at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence homology compared to a reference sequence using one of the alignment programs described herein using standard parameters. One of skill in the art will recognize that these values can be appropriately adjusted to determine corresponding homology of proteins encoded by two nucleic acid sequences by taking into account degeneracy, amino acid similarity, reading frame positioning, and the like. In some embodiments, the sequence homology is against the full-length sequence of the polynucleotide encoding an IPD109 polypeptide or against the full-length sequence of an IPD109 polypeptide.

In some embodiments, the nucleic acid encodes an IPD109 polypeptide having at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 138.

In some embodiments, the sequence identity is calculated using ClustalW algorithm in the ALIGNX® module of the Vector NTI® Program Suite (Invitrogen Corporation, Carlsbad, Calif.) with all default parameters. In some embodiments, the sequence identity is across the entire length of polypeptide calculated using ClustalW algorithm in the ALIGNX module of the Vector NTI Program Suite (Invitrogen Corporation, Carlsbad, Calif.) with all default parameters.

To determine the percent identity of two or more amino acid sequences or of two or more nucleic acid sequences, the sequences are aligned for optimal comparison purposes. The percent identity between the two sequences is a function of the number of identical positions shared by the sequences (i.e., percent identity=number of identical positions/total number of positions (e.g., overlapping positions x100).

In another embodiment, the comparison is across the entirety of the reference sequence (e.g., across the entirety of SEQ ID NO: 138). The percent identity between two sequences can be determined using techniques similar to those described below, with or without allowing gaps. In calculating percent identity, typically exact matches are counted.

Another non-limiting example of a mathematical algorithm utilized for the comparison of sequences is the algorithm of Needleman and Wunsch, (1970) *J. Mol. Biol.* 48(3):443-453, used GAP Version 10 software to determine sequence identity or similarity using the following default parameters: % identity and % similarity for a nucleic acid sequence using GAP Weight of 50 and Length Weight of 3, and the nwsgapdna.cmpii scoring matrix; % identity or % similarity for an amino acid sequence using GAP weight of 8 and length weight of 2, and the BLOSUM62 scoring program. Equivalent programs may also be used. "Equivalent program" is used herein to refer to any sequence comparison program that, for any two sequences in question, generates an alignment having identical nucleotide residue matches and an identical percent sequence identity when compared to the corresponding alignment generated by GAP Version 10.

In some embodiments, the IPD109 polynucleotide encodes an IPD109 polypeptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of SEQ ID NO: 138.

In some embodiments polynucleotides are provided encoding chimeric polypeptides comprising regions of at least two different IPD109 polypeptides of the disclosure.

In some embodiments, an IPD109 polynucleotide encodes the IPD109 polypeptide comprising the amino acid sequence of SEQ ID NO: 138.

The embodiments also encompass nucleic acid molecules encoding variants of the polypeptides of the disclosure. "Variants" of the polypeptides of the disclosure encoding nucleic acid sequences include those sequences that encode the polypeptides disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis but which still encode the polypeptides disclosed as discussed below.

The skilled artisan will further appreciate that changes can be introduced by mutation of the nucleic acid sequences thereby leading to changes in the amino acid sequence of the encoded polypeptides of the disclosure, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Alternatively, variant nucleic acid sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional pesticidal polypeptide homologues and fragments thereof with desired properties. A variety of such reactions are known, including those developed by the inventors and their co-workers. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries and any recombinant polynucleotide produced by such methods. Additionally, such methods optionally comprise selecting a variant polynucleotide from such libraries based on pesticidal activity, as is wherein such recursive recombination is done in vitro or in vivo.

A variety of diversity generating protocols, including nucleic acid recursive recombination protocols are available and fully described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods herein or otherwise available to one of skill, any nucleic acids that are produced can be selected for a desired activity or property, e.g. pesticidal activity or, such activity at a desired pH, etc. This can include identifying any activity that can be detected, for example, in an automated or automatable format, by any of the assays in the art, see, e.g., discussion of screening of insecticidal activity, infra. A variety of related (or even unrelated) properties can be evaluated, in serial or in parallel, at the discretion of the practitioner.

Descriptions of a variety of diversity generating procedures for generating modified nucleic acid sequences, e.g., those coding for polypeptides having pesticidal activity or fragments thereof, are found in the following publications and the references cited therein: Soong, et al., (2000) *Nat Genet* 25(4):436-439; Stemmer, et al., (1999) *Tumor Targeting* 4:1-4; Ness, et al., (1999) *Nat Biotechnol* 17:893-896; Chang, et al., (1999) *Nat Biotechnol* 17:793-797; Minshull and Stemmer, (1999) *Curr Opin Chem Biol* 3:284-290; Christians, et al., (1999) *Nat Biotechnol* 17:259-264; Crameri, et al., (1998) *Nature* 391:288-291; Crameri, et al., (1997) *Nat Biotechnol* 15:436-438; Zhang, et al., (1997) *PNAS USA* 94:4504-4509; Patten, et al., (1997) *Curr Opin Biotechnol* 8:724-733; Crameri, et al., (1996) *Nat Med* 2:100-103; Crameri, et al., (1996) *Nat Biotechnol* 14:315-319; Gates, et al., (1996) *J Mol Biol* 255:373-386; Stemmer, (1996) "Sexual PCR and Assembly PCR" In: *The Encyclopedia of Molecular Biology*. VCH Publishers, New York. pp. 447-457; Crameri and Stemmer, (1995) *BioTechniques* 18:194-195; Stemmer, et al., (1995) *Gene,* 164:49-53; Stemmer, (1995) *Science* 270:1510; Stemmer, (1995) *Bio/Technology* 13:549-553; Stemmer, (1994) *Nature* 370:389-391 and Stemmer, (1994) *PNAS USA* 91:10747-10751.

Mutational methods of generating diversity include, for example, site-directed mutagenesis (Ling, et al., (1997) *Anal Biochem* 254(2):157-178; Dale, et al., (1996) *Methods Mol Biol* 57:369-374; Smith, (1985) *Ann Rev Genet* 19:423-462; Botstein and Shortle, (1985) *Science* 229:1193-1201; Carter, (1986) *Biochem J* 237:1-7 and Kunkel, (1987) "The efficiency of oligonucleotide directed mutagenesis" in *Nucleic Acids & Molecular Biology (Eckstein and Lilley, eds.,* Springer Verlag, Berlin)); mutagenesis using uracil containing templates (Kunkel, (1985) *PNAS USA* 82:488-492; Kunkel, et al., (1987) *Methods Enzymol* 154:367-382 and Bass, et al., (1988) *Science* 242:240-245); oligonucleotide-directed mutagenesis (Zoller and Smith, (1983) *Methods Enzymol* 100:468-500; Zoller and Smith, (1987) *Methods Enzymol* 154:329-350 (1987); *Zoller and Smith,* (1982) *Nucleic Acids Res* 10:6487-6500), phosphorothioate-modified DNA mutagenesis (Taylor, et al., (1985) *Nucl Acids Res* 13:8749-8764; Taylor, et al., (1985) *Nucl Acids Res* 13:8765-8787 (1985); *Nakamaye and Eckstein,* (1986) *Nucl Acids Res* 14:9679-9698; Sayers, et al., (1988) *Nucl Acids Res* 16:791-802 and Sayers, et al., (1988) *Nucl Acids Res* 16:803-814); mutagenesis using gapped duplex DNA (Kramer, et al., (1984) *Nucl Acids Res* 12:9441-9456; Kramer and Fritz, (1987) *Methods Enzymol* 154:350-367; Kramer, et al., (1988) *Nucl Acids Res* 16:7207 and Fritz, et al., (1988) *Nucl Acids Res* 16:6987-6999). Additional suitable methods include point mismatch repair (Kramer, et al., (1984) *Cell* 38:879-887), mutagenesis using repair-deficient host strains (Carter, et al., (1985) *Nucl Acids Res* 13:4431-4443 and Carter, (1987) *Methods in Enzymol* 154:382-403), deletion mutagenesis (Eghtedarzadeh and Henikoff, (1986) *Nucl Acids Res* 14:5115), restriction-selection and restriction-purification (Wells, et al., (1986) *Phil Trans R Soc Lond A* 317:415-423), mutagenesis by total gene synthesis (Nambiar, et al., (1984) *Science* 223:1299-1301; Sakamar and Khorana, (1988) *Nucl Acids Res* 14:6361-6372; Wells, et al., (1985) *Gene* 34:315-323 and Grundström, et al., (1985) *Nucl Acids Res* 13:3305-3316), double-strand break repair (Mandecki, (1986) *PNAS USA,* 83:7177-7181 and Arnold, (1993) *Curr Opin Biotech* 4:450-455). Additional details on many of the above methods can be found in *Methods Enzymol* Volume 154, which also describes useful controls for trouble-shooting problems with various mutagenesis methods.

Additional details regarding various diversity generating methods can be found in the following US Patents, PCT Publications and Applications and EPO publications: U.S. Pat. Nos. 5,723,323, 5,763,192, 5,814,476, 5,817,483, 5,824,514, 5,976,862, 5,605,793, 5,811,238, 5,830,721, 5,834,252, 5,837,458, WO 1995/22625, WO 1996/33207, WO 1997/20078, WO 1997/35966, WO 1999/41402, WO 1999/41383, WO 1999/41369, WO 1999/41368, EP 752008, EP 0932670, WO 1999/23107, WO 1999/21979, WO 1998/31837, WO 1998/27230, WO 1998/27230, WO 2000/00632, WO 2000/09679, WO 1998/42832, WO 1999/29902, WO 1998/41653, WO 1998/41622, WO 1998/42727, WO 2000/18906, WO 2000/04190, WO 2000/42561, WO 2000/42559, WO 2000/42560, WO 2001/23401 and PCT/USO1/06775.

The nucleotide sequences of the embodiments can also be used to isolate corresponding sequences from a fern or other primitive plant. In this manner, methods such as PCR, hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, New York), hereinafter "Sambrook". See also, Innis, et al., eds. (1990) *PCR Protocols: A Guide to Methods and Applications (Academic Press, New York); Innis and Gelfand, eds.* (1995) *PCR Strategies (Academic Press, New York); and Innis and Gelfand, eds.* (1999) *PCR Methods Manual (Academic Press,* New York). Known methods of PCR include, but are not limited to, methods using paired primers, nested primers, single specific primers, degenerate primers, gene-specific primers, vector-specific primers, partially-mismatched primers, and the like.

To identify potential insecticidal polypeptides from fern or other primitive plants, the fern or other primitive plant cell lysates can be screened with antibodies generated against a polypeptide of the disclosure using Western blotting and/or ELISA methods. This type of assays can be performed in a high throughput fashion. Positive samples can be further analyzed by various techniques such as antibody based protein purification and identification. Methods of generating antibodies are well known in the art as discussed infra.

Alternatively, mass spectrometry based protein identification method can be used to identify homologs of polypeptides of the disclosure using protocols in the literatures (Scott Patterson, (1998), 10.22, 1-24, Current Protocol in Molecular Biology published by John Wiley & Son Inc). Specifically, LC-MS/MS based protein identification method is used to associate the MS data of given cell lysate or desired molecular weight enriched samples (excised from SDS-PAGE gel of relevant molecular weight bands) with sequence information of a polypeptide of the disclosure and their homologs. Any match in peptide sequences indicates the potential of having the homologous proteins in the samples. Additional techniques (protein purification and molecular biology) can be used to isolate the protein and identify the sequences of the homologs.

In hybridization methods, all or part of the pesticidal nucleic acid sequence can be used to screen cDNA or genomic libraries. Methods for construction of such cDNA and genomic libraries are generally known in the art and are disclosed in Sambrook and Russell, (2001), supra. The so-called hybridization probes may be genomic DNA fragments, cDNA fragments, RNA fragments or other oligonucleotides and may be labeled with a detectable group such as 32P or any other detectable marker, such as other radio-isotopes, a fluorescent compound, an enzyme or an enzyme co-factor. Probes for hybridization can be made by labeling synthetic oligonucleotides based on the polypeptide-encoding nucleic acid sequence disclosed herein. Degenerate primers designed on the basis of conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequence encoding an IPD059, IPD098, IPD108 or IPD109 polypeptide of the disclosure or a fragment or variant thereof. Methods for the preparation of probes for hybridization are generally known in the art and are disclosed in Sambrook and Russell, (2001), supra, herein incorporated by reference.

For example, an entire nucleic acid sequence, encoding a polypeptide, disclosed herein or one or more portions thereof may be used as a probe capable of specifically hybridizing to corresponding nucleic acid sequences encoding polypeptide sequences of the disclosure and messenger RNAs. To achieve specific hybridization under a variety of conditions, such probes include sequences that are unique and are preferably at least about 10 nucleotides in length or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook, et al., (1989) *Molecular Cloning: A Laboratory Manual* (2d ed., Cold Spring Harbor Laboratory Press, Cold Spring Harbor, N.Y.).

Hybridization of such sequences may be carried out under stringent conditions. "Stringent conditions" or "stringent hybridization conditions" is used herein to refer to conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length Compositions Compositions comprising at least one IPD059, IPD098, IPD108 or IPD109 polypeptide or IPD059, IPD098, IPD108 or IPD109 chimeric polypeptide of the disclosure are also embraced. In some embodiments, the composition comprises comprising at least one IPD059, IPD098, IPD108 or IPD109 polypeptide of the disclosure and an agricultural carrier.

Antibodies

Antibodies to an IPD059, IPD098, IPD108 or IPD109 polypeptide of the embodiments or to variants or fragments thereof are also encompassed. The antibodies of the disclosure include polyclonal and monoclonal antibodies as well as fragments thereof which retain their ability to bind to an IPD059, IPD098, IPD108 or IPD109 polypeptide found in the insect gut. An antibody, monoclonal antibody or fragment thereof is said to be capable of binding a molecule if it is capable of specifically reacting with the molecule to thereby bind the molecule to the antibody, monoclonal antibody or fragment thereof. The term "antibody" (Ab) or "monoclonal antibody" (Mab) is meant to include intact molecules as well as fragments or binding regions or domains thereof (such as, for example, Fab and F(ab).sub.2 fragments) which are capable of binding hapten. Such fragments are typically produced by proteolytic cleavage, such as papain or pepsin. Alternatively, hapten-binding fragments can be produced through the application of recombinant DNA technology or through synthetic chemistry. Methods for the preparation of the antibodies of the present disclosure are generally known in the art. For example, see, Antibodies, A Laboratory Manual, Ed Harlow and David Lane (eds.) Cold Spring Harbor Laboratory, N.Y. (1988), as well as the references cited therein. Standard reference works setting forth the general principles of immunology include: Klein, J. Immunology: The Science of Cell-Noncell Discrimination, John Wiley & Sons, N.Y. (1982); Dennett, et al., Monoclonal Antibodies, Hybridoma: A New Dimension in Biological Analyses, Plenum Press, N.Y. (1980) and Campbell, "Monoclonal Antibody Technology," In Laboratory Techniques in Biochemistry and Molecular Biology, Vol. 13, Burdon, et al., (eds.), Elsevier, Amsterdam (1984). See also, U.S. Pat. Nos. 4,196,265; 4,609,893; 4,713,325; 4,714,681; 4,716,111; 4,716,117 and 4,720,459. Antibodies against IPD059, IPD098, IPD108 or IPD109 polypeptides or antigen-binding portions thereof can be produced by a variety of techniques, including conventional monoclonal antibody methodology, for example the standard somatic cell hybridization technique of Kohler and Milstein, (1975) *Nature* 256:495. Other techniques for producing monoclonal antibody can also be employed such as viral or oncogenic transformation of B lymphocytes. An animal system for preparing hybridomas is a murine system. Immunization protocols and techniques for isolation of immunized splenocytes for fusion are known in the art. Fusion partners (e.g., murine myeloma cells) and fusion procedures are also known. The antibody and monoclonal antibodies of the disclosure can be prepared by utilizing an IPD059, IPD098, IPD108 or IPD109 polypeptide as antigens.

A kit for detecting the presence of an IPD059, IPD098, IPD108 or IPD109 polypeptide or detecting the presence of a nucleotide sequence encoding an IPD059, IPD098, IPD108 or IPD109 polypeptide in a sample is provided. In one embodiment, the kit provides antibody-based reagents for detecting the presence of an IPD059, IPD098, IPD108 or IPD109 polypeptide in a tissue sample. In another embodiment, the kit provides labeled nucleic acid probes useful for detecting the presence of one or more polynucleotides encoding an IPD059, IPD098, IPD108 or IPD109 polypeptide. The kit is provided along with appropriate reagents and controls for carrying out a detection method, as well as instructions for use of the kit.

Receptor Identification and Isolation

Receptors to the IPD059, IPD098, IPD108 or IPD109 polypeptide of the embodiments or to variants or fragments thereof are also encompassed. Methods for identifying receptors are well known in the art (see, Hofmann, et. al., (1988) *Eur. J. Biochem.* 173:85-91; Gill, et al., (1995) *J. Biol. Chem.* 27277-27282) can be employed to identify and isolate the receptor that recognizes the IPD059, IPD098, IPD108 or IPD109 polypeptide using the brush-border membrane vesicles from susceptible insects. In addition to the radioactive labeling method listed in the cited literatures, an IPD059, IPD098, IPD108 or IPD109 polypeptide can be labeled with fluorescent dye and other common labels such as streptavidin. Brush-border membrane vesicles (BBMV) of susceptible insects such as soybean looper and stink bugs can be prepared according to the protocols listed in the references and separated on SDS-PAGE gel and blotted on suitable membrane. Labeled IPD059, IPD098, IPD108 or IPD109 polypeptide can be incubated with blotted membrane of BBMV and labeled IPD059, IPD098, IPD108 or IPD109 polypeptide can be identified with the labeled reporters. Identification of protein band(s) that interact with the IPD059, IPD098, IPD108 or IPD109 polypeptide can be detected by N-terminal amino acid gas phase sequencing or mass spectrometry based protein identification method (Patterson, (1998) 10.22, 1-24, Current Protocol in Molecular Biology published by John Wiley & Son Inc). Once the protein is identified, the corresponding gene can be cloned from genomic DNA or cDNA library of the susceptible insects and binding affinity can be measured directly with the IPD059, IPD098, IPD108 or IPD109 polypeptide. Receptor function for insecticidal activity by the IPD059, IPD098, IPD108 or IPD109 polypeptide can be verified by accomplished by RNAi type of gene knock out method (Rajagopal, et al., (2002) *J. Biol. Chem.* 277:46849-46851).

Nucleotide Constructs, Expression Cassettes and Vectors

The use of the term "nucleotide constructs" herein is not intended to limit the embodiments to nucleotide constructs comprising DNA. Those of ordinary skill in the art will recognize that nucleotide constructs particularly polynucleotides and oligonucleotides composed of ribonucleotides and combinations of ribonucleotides and deoxyribonucleotides may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant and insect cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the IPD059, IPD098, IPD108 or IPD109 polypeptide gene sequence of the disclosure to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments, the DNA construct comprises a polynucleotide encoding an IPD059, IPD098, IPD108 or IPD109 polypeptide of the embodiments.

In some embodiments, the DNA construct comprises: a polynucleotide encoding an IPD059 polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75 or SEQ ID NO: 78; and a heterologous regulatory element.

In some embodiments, the DNA construct comprises: a polynucleotide encoding an IPD098 polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO 123 or SEQ ID NO: 124; and a heterologous regulatory element.

In some embodiments, the DNA construct comprises: a polynucleotide encoding an IPD098 polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116 or SEQ ID NO: 117; and a heterologous regulatory element.

In some embodiments, the DNA construct comprises: a polynucleotide encoding an IPD108 polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 131, SEQ ID NO: 132, SEQ ID NO: 133, SEQ ID NO: 134, SEQ ID NO: 135 or SEQ ID NO: 136; and a heterologous regulatory element.

In some embodiments, the DNA construct comprises: a polynucleotide encoding an IPD108 polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 131, SEQ ID NO: 132, SEQ ID NO: 133, SEQ ID NO: 134 or SEQ ID NO: 135; and a heterologous regulatory element.

In some embodiments, the DNA construct comprises: a polynucleotide encoding an IPD109 polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 138; and a heterologous regulatory element.

In some embodiments, the DNA construct comprises a polynucleotide encoding a chimeric IPD059, IPD098, IPD108 or IPD109 polypeptide of the embodiments.

In some embodiments, the DNA construct comprises a polynucleotide encoding a fusion protein comprising an IPD059, IPD098, IPD108 or IPD109 polypeptide of the embodiments.

In some embodiments, the DNA construct comprises: a polynucleotide encoding a polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 118, SEQ ID NO: 119, SEQ ID NO: 120, SEQ ID NO: 121, SEQ ID NO: 122, SEQ ID NO: 123 or SEQ ID NO: 124; and a heterologous regulatory element.

In some embodiments, the DNA construct comprises: a polynucleotide encoding a polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 136; and a heterologous regulatory element.

In some embodiments, the DNA construct comprises: a polynucleotide encoding a polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 136; and a heterologous regulatory element.

In some embodiments, the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers are known in the art including for example, introns with gene expression enhancing properties in plants (US Patent Application Publication Number 2009/0144863, the ubiquitin intron (i.e., the maize ubiquitin intron 1 (see, for example, NCBI sequence S94464)), the omega enhancer or the omega prime enhancer (Gallie, et al., (1989) *Molecular Biology of RNA ed. Cech* (*Liss*, New York) 237-256 and Gallie, et al., (1987) *Gene* 60:217-25), the CaMV 35S enhancer (see, e.g., Benfey, et al., (1990) *EMBO J.* 9:1685-96) and the enhancers of U.S. Pat. No. 7,803,992 may also be used, each of which is incorporated by reference. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) Cell 64:671-674; Sanfacon, etal., (1991) *Genes Dev.* 5:141-149; Mogen, etal., (1990) *Plant Cell* 2:1261-1272; Munroe, etal., (1990) *Gene* 91:151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred usage. For example, although nucleic acid sequences of the embodiments may be expressed in both monocotyledonous and dicotyledonous plant species, sequences can be modified to account for the specific preferences and GC content preferences of monocotyledons or dicotyledons as these preferences have been shown to differ (Murray et al. (1989) *Nucleic Acids Res.* 17:477-498). Thus, the maize-preferred for a particular amino acid may be derived from known gene sequences from maize. Maize usage for 28 genes from maize plants is listed in Table 4 of Murray, et al., supra. Methods are available in the art for synthesizing plant-preferred genes. See, for example, Murray, et al., (1989) *Nucleic Acids Res.* 17:477-498, and Liu H et al. *Mol Bio Rep* 37:677-684, 2010, herein incorporated by reference. A *Zea* maize usage table can be also found at kazusa.or.jp//cgi-bin/show.cgi?species=4577, which can be accessed using the www prefix. A *Glycine max* usage table can be found at kazusa.or.jp//cgi-bin/show.cgi?species=3847&aa=1&style=N, which can be accessed using the www prefix.

In some embodiments, the recombinant nucleic acid molecule encoding an IPD059, IPD098, IPD108 or IPD109 polypeptide has maize optimized codons.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli* or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus), human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA, ed. Cech* (*Liss*, New York), pp. 237-256) and maize chlorotic mottle virus leader (MCMV) (Lommel, et al., (1991) *Virology* 81:382-385). See also, Della-Cioppa, et al., (1987) *Plant Physiol.* 84:965-968. Such constructs may also contain a "signal sequence" or "leader sequence" to facilitate co-translational or post-translational transport of the peptide to certain intracellular structures such as the chloroplast (or other plastid), endoplasmic reticulum or Golgi apparatus.

"Signal sequence" as used herein refers to a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are proteolytically activated in the gut of the target pest (Chang, (1987) *Methods Enzymol.* 153:507-516). In some embodiments, the signal sequence is located in the native sequence or may be derived from a sequence of the embodiments. "Leader sequence" as used herein refers to any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like. Nuclear-encoded proteins targeted to the chloroplast thylakoid lumen compartment have a characteristic bipartite transit peptide, composed of a stromal targeting signal peptide and a lumen targeting signal peptide. The stromal targeting information is in the amino-proximal portion of the transit peptide. The lumen targeting signal peptide is in the carboxyl-proximal portion of the transit peptide, and contains all the information for targeting to the lumen. Recent research in proteomics of the higher plant chloroplast has achieved in the identification of numerous nuclear-encoded lumen proteins (Kieselbach et al. *FEBS LETT* 480:271-276, 2000; Peltier et al. *Plant Cell* 12:319-341, 2000; Bricker et al. *Biochim. Biophys Acta* 1503:350-356, 2001), the lumen targeting signal peptide of which can potentially be used in accordance with the present disclosure. About 80 proteins from *Arabidopsis*, as well as homologous proteins from spinach and garden pea, are reported by Kieselbach et al., *Photosynthesis Research,* 78:249-264, 2003. In particular, Table 2 of this publication, which is incorporated into the description herewith by reference, discloses 85 proteins from the chloroplast lumen, identified by their accession number (see also US Patent Application Publication 2009/09044298). In addition, the recently published draft version of the rice genome (Goff et al, *Science* 296:92-100, 2002) is a suitable source for lumen targeting signal peptide which may be used in accordance with the present disclosure.

Suitable chloroplast transit peptides (CTP) are well known to one skilled in the art also include chimeric CT's comprising but not limited to, an N-terminal domain, a central domain or a C-terminal domain from a CTP from *Oryza sativa* 1-decoy-D xylose-5-Phosphate Synthase *Oryza sativa*-Superoxide dismutase *Oryza sativa*-soluble starch synthase *Oryza sativa*-NADP-dependent Malic acid enzyme *Oryza sativa*-Phospho-2-dehydro-3-deoxyheptonate Aldolase 2 *Oryza sativa*-L-Ascorbate peroxidase 5 *Oryza sativa*-Phosphoglucan water dikinase, *Zea Mays* ssRUBISCO, *Zea Mays*-beta-glucosidase, *Zea Mays*-Malate dehydrogenase, *Zea Mays* Thioredoxin M-type US Patent Application Publication 2012/0304336).

The IPD059, IPD098, IPD108 or IPD109 polypeptide gene to be targeted to the chloroplast may be optimized for expression in the chloroplast to account for differences in usage between the plant nucleus and this organelle. In this manner, the nucleic acids of interest may be synthesized using chloroplast-preferred sequences.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible or other promoters for expression in the host organism. Suitable constitutive promoters for use in a plant host cell include, for example, the core promoter of the Rsyn7 promoter and other constitutive promoters disclosed in WO 1999/43838 and U.S. Pat. No. 6,072,050; the core CaMV 35S promoter (Odell, et al., (1985) *Nature* 313:810-812); rice actin (McElroy, et al., (1990) Plant Cell 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142 and 6,177,611.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin 1I) gene (Ryan, (1990) *Ann. Rev. Phytopath.* 28:425-449; Duan, et al., (1996) *Nature Biotechnology* 14:494-498); wun1 and wun2, U.S. Pat. No. 5,428,148; win1 and win2 (Stanford, et al., (1989) *Mol. Gen. Genet.* 215:200-208); systemin (McGurl, et al., (1992) *Science* 225:1570-1573); WIP1 (Rohmeier, et al., (1993) *Plant Mol. Biol.* 22:783-792; Eckelkamp, et al., (1993) *FEBS Letters* 323:73-76); MPI gene (Corderok, et al., (1994) *Plant J.* 6(2):141-150) and the like, herein incorporated by reference.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi, et al., (1983) *Neth. J. Plant Pathol.* 89:245-254; Uknes, et al., (1992) *Plant Cell* 4: 645-656 and Van Loon, (1985) *Plant Mol. Virol.* 4:111-116. See also, WO 1999/43819, herein incorporated by reference.

Of interest are promoters that are expressed locally at or near the site of pathogen infection. See, for example, Marineau, et al., (1987) *Plant Mol. Biol.* 9:335-342; Matton, et al., (1989) *Molecular Plant-Microbe Interactions* 2:325-331; Somsisch, et al., (1986) *Proc. Natl. Acad. Sci. USA* 83:2427-2430; Somsisch, et al., (1988) *Mol. Gen. Genet.* 2:93-98 and Yang, (1996) *Proc. Natl. Acad. Sci. USA* 93:14972-14977. See also, Chen, et al., (1996) *Plant J.* 10:955-966; Zhang, et al., (1994) *Proc. Natl. Acad. Sci. USA* 91:2507-2511; Warner, et al., (1993) *Plant J.* 3:191-201; Siebertz, et al., (1989) *Plant Cell* 1:961-968; U.S. Pat. No. 5,750,386 (nematode-inducible) and the references cited therein. Of particular interest is the inducible promoter for the maize PRms gene, whose expression is induced by the pathogen *Fusarium moniliforme* (see, for example, Cordero, et al., (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the gluco-corticoid-inducible promoter in Schena, et al., (1991) *Proc. Natl. Acad. Sci. USA* 88:10421-10425 and McNellis, et al., (1998) *Plant J.* 14(2):247-257) and tetracycline-inducible and tetracycline-repressible promoters (see, for example, Gatz, et al., (1991) *Mol. Gen. Genet.* 227:229-237 and U.S. Pat. Nos. 5,814,618 and 5,789,156), herein incorporated by reference.

Tissue-preferred promoters can be utilized to target enhanced an IPD059, IPD098, IPD108 or IPD109 polypeptide expression within a particular plant tissue. Tissue-preferred promoters include those discussed in Yamamoto, et al., (1997) *Plant J.* 12(2)255-265; Kawamata, et al., (1997) *Plant Cell Physiol.* 38(7):792-803; Hansen, et al., (1997) *Mol. Gen Genet.* 254(3):337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5):773-778; Lam, (1994) *Results Probl. Cell Differ.* 20:181-196; Orozco, et al., (1993) *Plant Mol Biol.* 23(6):1129-1138; Matsuoka, et al., (1993) *Proc Natl. Acad. Sci. USA* 90(20):9586-9590 and Guevara-Garcia, et al., (1993) *Plant J.* 4(3):495-505. Such promoters can be modified, if necessary, for weak expression.

Leaf-preferred promoters are known in the art. See, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138 and Matsuoka, et al., (1993) *Proc. Natl. Acad. Sci. USA* 90(20):9586-9590.

Root-preferred or root-specific promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 14(3):433-443

(root-specific promoter of the mannopine synthase (MAS) gene of *Agrobacterium tumefaciens*) and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed rolC and rolD root-inducing genes of *Agrobacterium rhizogenes* (see, Plant Science (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2 gene is root specific in the intact plant and stimulated by wounding in leaf tissue, an especially desirable combination of characteristics for use with an insecticidal or larvicidal gene (see, *EMBO J.* 8(2): 343-350). The TR1 gene fused to nptll (neomycin phospho-transferase II) showed similar characteristics. Additional root-preferred promoters include the VfENOD-GRP3 gene promoter (Kuster, et al., (1995) *Plant Mol. Biol.* 29(4):759-772) and rolB promoter (Capana, et al., (1994) *Plant Mol. Biol.* 25(4):681-691. See also, U.S. Pat. Nos. 5,837,876; 5,750,386; 5,633,363; 5,459,252; 5,401,836; 5,110,732 and 5,023,179. *Arabidopsis thaliana* root-preferred regulatory sequences are disclosed in US20130117883.

"Seed-preferred" promoters include both "seed-specific" promoters (those promoters active during seed development such as promoters of seed storage proteins) as well as "seed-germinating" promoters (those promoters active during seed germination). See, Thompson, et al., (1989) *BioEssays* 10:108, herein incorporated by reference. Such seed-preferred promoters include, but are not limited to, Ciml (cytokinin-induced message); cZ19B1 (maize 19 kDa zein); and milps (myo-inositol-1-phosphate synthase) (see, U.S. Pat. No. 6,225,529, herein incorporated by reference). Gamma-zein and Glb-1 are endosperm-specific promoters. For dicots, seed-specific promoters include, but are not limited to, Kunitz trypsin inhibitor 3 (KTi3) (Jofuku and Goldberg, (1989) *Plant Cell* 1:1079-1093), bean β-phaseolin, napin, β-conglycinin, glycinin 1, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also, WO 2000/12733, where seed-preferred promoters from end1 and end2 genes are disclosed; herein incorporated by reference. In dicots, seed specific promoters include but are not limited to seed coat promoter from *Arabidopsis*, pBAN; and the early seed promoters from *Arabidopsis*, p26, p63, and p63tr (U.S. Pat. Nos. 7,294,760 and 7,847,153). A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of between about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 1999/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142 and 6,177,611, herein incorporated by reference.

The above list of promoters is not meant to be limiting. Any appropriate promoter can be used in the embodiments.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones and 2,4-dichlorophenoxyacetate (2,4-D). Additional examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213 and Meijer, et al., (1991) *Plant Mol. Biol.* 16:807-820); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-136); bromoxynil (Stalker, et al., (1988) *Science* 242:419-423); glyphosate (Shaw, et al., (1986) *Science* 233:478-481 and U.S. patent application Ser. Nos. 10/004,357 and 10/427,692); phosphinothricin (DeBlock, et al., (1987) *EMBO J.* 6:2513-2518). See generally, Yarranton, (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff, (1992) *Mol. Microbiol.* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Sci. USA* 86:5400-5404; Fuerst, et al., (1989) *Proc. Natl. Acad. Sci. USA* 86:2549-2553; Deuschle, et al., (1990) *Science* 248:480-483; Gossen, (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, etal., (1991) *NucleicAcids Res.* 19:4647-4653; Hillenand-Wissman, (1989) *Topics Mol. Struc. Biol.* 10:143-162; Degenkolb, et al., (1991) *Antimicrob. Agents Chemother.* 35:1591-1595; Kleinschnidt, etal., (1988) *Biochemistry* 27:1094-1104; Bonin, (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental*

*Pharmacology*, Vol. 78 (Springer-Verlag, Berlin) and Gill, et al., (1988) *Nature* 334:721-724. Such disclosures are herein incorporated by reference.

The above list of selectable marker genes is not meant to be limiting. Any selectable marker gene can be used in the embodiments.

Plant Transformation

The methods of the embodiments involve introducing a polypeptide or polynucleotide into a plant. "Introducing" is as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in Plant Cell, Tissue, and Organ Culture: Fundamental Methods, ed. Gamborg and Phillips, (Springer-Verlag, Berlin) and McCabe, et al., (1988) *Biotechnology* 6:923-926) and Led transformation (WO 00/28058). For potato transformation see, Tu, et al., (1998) *Plant Molecular Biology* 37:829-838 and Chong, et al., (2000) *Transgenic Research* 9:71-78. Additional transformation procedures can be found in Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) Biotechnology6: 559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in The Experimental Manipulation ofOvule Tissues, ed. Chapman, et al., (*Longman*, New York), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*); all of which are herein incorporated by reference.

In specific embodiments, the sequences of the embodiments can be provided to a plant using a variety of transient transformation methods. Such transient transformation methods include, but are not limited to, the introduction of the IPD059, IPD098, IPD108 or IPD109 polynucleotide or variants and fragments thereof directly into the plant or the introduction of the IPD059, IPD098, IPD108 or IPD109 polypeptide transcript into the plant. Such methods include, for example, microinjection or particle bombardment. See, for example, Crossway, et al., (1986) *Mol Gen. Genet.* 202:179-185; Nomura, et al., (1986) *Plant Sci.* 44:53-58; Hepler, et al., (1994) *Proc. Natl. Acad. Sci.* 91:2176-2180 and Hush, et al., (1994) *The Journal of Cell Science* 107: 775-784, all of which are herein incorporated by reference. Alternatively, the IPD059, IPD098, IPD108 or IPD109 polynucleotide can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylamine (PEI; Sigma #P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO 1999/25821, WO 1999/25854, WO 1999/25840, WO 1999/25855 and WO 1999/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

Plant transformation vectors may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux, (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g., immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one can identify and proliferate the cells that are transformed with the plasmid vector. Molecular and biochemical methods can then be used to confirm the presence of the integrated heterologous gene of interest into the genome of the transgenic plant.

Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g., Hiei, et al., (1994) *The Plant Journal* 6:271-282; Ishida, et al., (1996) *Nature Biotechnology* 14:745-750). Explants are typically transferred to a fresh supply of the same medium and cultured routinely. A general description of the techniques and methods for generating transgenic plants are found in Ayres and Park, (1994) *Critical Reviews in Plant Science* 13:219-239 and Bommineni and Jauhar, (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired IPD059, IPD098, IPD108 or IPD109 polypeptide. It is also recognized that such a viral polyprotein, comprising at least a portion of the amino acid sequence of an IPD059, IPD098, IPD108 or IPD109 of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules, are known in the art. See, for example, U.S. Pat. Nos. 5,889,191; 5,889,190; 5,866,785; 5,589,367 and 5,316,931; herein incorporated by reference.

Methods for transformation of chloroplasts are known in the art. See, for example, Svab, et al., (1990) *Proc. Natl. Acad. Sci. USA* 87:8526-8530; Svab and Maliga, (1993) *Proc. Natl. Acad.* Sci. USA 90:913-917; Svab and Maliga, (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride, et al., (1994) *Proc. Natl. Acad. Sci. USA* 91:7301-7305.

The embodiments further relate to plant-propagating material of a transformed plant of the embodiments including, but not limited to, seeds, tubers, corms, bulbs, leaves and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (Carthamus tinctorius), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus* casica), guava (*Psidium guajava*), mango (*Mangifera indica*), olive (*Olea europaea*), papaya (*Carica papaya*), cashew (*Anacardium occidentale*), macadamia (Macadamia *integrifolia*), almond (*Prunus* amygdalus), sugar beets (*Beta vulgaris*), sugarcane (*Saccharum* spp.), oats, barley, vegetables ornamentals, and conifers.

Vegetables include tomatoes (*Lycopersicon esculentum*), lettuce (e.g., *Lactuca sativa*), green beans (*Phaseolus vulgaris*), lima beans (*Phaseolus* limensis), peas (*Lathyrus* spp.), and members of the genus *Cucumis* such as cucumber (*C. sativus*), cantaloupe (C. cantalupensis), and musk melon (*C. melo*). Ornamentals include azalea (*Rhododendron* spp.), hydrangea (*Macrophylla hydrangea*), hibiscus (Hibiscus rosasanensis), roses (Rosa spp.), tulips (Tulipa spp.), daffodils (*Narcissus* spp.), petunias (*Petunia hybrida*), carnation (*Dianthus* caryophyllus), poinsettia (*Euphorbia pulcherrima*), and *chrysanthemum*. Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true first such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Turf grasses include, but are not limited to: annual bluegrass (*Poa annua*); annual ryegrass (*Lolium multiflorum*); Canada bluegrass (*Poa compressa*); Chewing's fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchard grass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithii*); Bermuda grass (*Cynodon* spp.); St. Augustine grass (Stenotaphrum *secundatum*); zoysia grass (*Zoysia* spp.); Bahia grass (*Paspalum notatum*); carpet grass (*Axonopus affinis*); centipede grass (Eremochloa ophiuroides); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive, etc. Leguminous plants include beans and peas. Beans include guar, locust bean, fenugreek, soybean, garden beans, cowpea, mung bean, lima bean, fava bean, lentils, chickpea, etc.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell, (2001) Molecular Cloning: A Laboratory Manual. Cold Spring Harbor Laboratory Press, Cold Spring Harbor, NY). PCR is carried out using oligonucleotide primers specific to the gene of interest or *Agrobacterium* vector background, etc.

Plant transformation may be confirmed by Southern blot analysis of genomic DNA (Sambrook and Russell, (2001) supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled 32P target DNA fragment to confirm the integration of introduced gene into the plant genome according to standard techniques (Sambrook and Russell, (2001) supra).

In Northern blot analysis, RNA is isolated from specific tissues of transformant, fractionated in a formaldehyde agarose gel, and blotted onto a nylon filter according to standard procedures that are routinely used in the art (Sambrook and Russell, (2001) supra). Expression of RNA encoded by the pesticidal gene is then tested by hybridizing the filter to a radioactive probe derived from a pesticidal gene, by methods known in the art (Sambrook and Russell, (2001) supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the IPD059, IPD098, IPD108 or IPD109 polypeptide.

Methods to Introduce Genome Editing Technologies into Plants

In some embodiments, the disclosed IPD059, IPD098, IPD108 or IPD109 polynucleotide compositions can be introduced into the genome of a plant using genome editing technologies or previously introduced IPD059, IPD098, IPD108 or IPD109 polynucleotides in the genome of a plant may be edited using genome editing technologies. For example, the disclosed polynucleotides can be introduced into a desired location in the genome of a plant through the use of double-stranded break technologies such as TALENs, meganucleases, zinc finger nucleases, CRISPR-Cas, and the like. For example, the disclosed polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In some embodiments, where the disclosed IPD059, IPD098, IPD108 or IPD109 polynucleotide has previously been introduced into a genome, genome editing technologies may be used to alter or modify the introduced polynucleotide sequence. Site specific modifications that can be introduced into the disclosed IPD059, IPD098, IPD108 or IPD109 polynucleotide compositions include those produced using any method for introducing site specific modification, including, but not limited to, through the use of gene repair oligonucleotides (e.g. US Publication 2013/0019349) or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional insecticidally-active proteins in close proximity to the disclosed IPD059, IPD098, IPD108 or IPD109 polynucleotide compositions disclosed herein within the genome of a plant, in order to generate molecular stacks of insecticidally-active proteins.

An "altered target site," "altered target sequence" "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide or (iv) any combination of (i)-(iii).

Stacking of Traits in Transgenic Plant

Transgenic plants may comprise a stack of one or more insecticidal polynucleotides disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

In some embodiments the polynucleotides encoding the IPD059, IPD098, IPD108 or IPD109 polypeptide disclosed herein, alone or stacked with one or more additional insect resistance traits can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). Thus, the polynucleotide embodiments can be used to provide a complete agronomic package of improved crop quality with the ability to flexibly and cost effectively control any number of agronomic pests.

Transgenes Useful for Stacking Include but are not Limited to:

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example, Jones, et al., (1994) *Science* 266:789 (cloning of the tomato Cf-9 gene for resistance to *Cladosporium fulvum*); Martin, et al., (1993) *Science* 262:1432 (tomato Pto gene for resistance to *Pseudomonas syringae* pv. tomato encodes a protein kinase); Mindrinos, et al., (1994) *Cell* 78:1089 (*Arabidopsis* RSP2 gene for resistance to *Pseudomonas syringae*), McDowell and Woffenden, (2003) *Trends Biotechnol.* 21(4):178-83 and Toyoda, et al., (2002) *Transgenic Res.* 11(6):567-82. A plant resistant to a disease is one that is more resistant to a pathogen as compared to the wild type plant.

(B) Genes encoding a *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC® Accession Numbers 40098, 67136, 31995 and 31998. Other non-limiting examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; 5,986,177; 6,023,013, 6,060,594, 6,063,597, 6,077,824, 6,620, 988, 6,642,030, 6,713,259, 6,893,826, 7,105,332; 7,179,965, 7,208,474; 7,227,056, 7,288,643, 7,323, 556, 7,329,736, 7,449,552, 7,468,278, 7,510,878, 7,521,235, 7,544,862, 7,605,304, 7,696,412, 7,629, 504, 7,705,216, 7,772,465, 7,790,846, 7,858,849 and WO 1991/14778; WO 1999/31248; WO 2001/12731; WO 1999/24581 and WO 1997/40162.

Genes encoding pesticidal proteins may also be stacked including but are not limited to: insecticidal proteins from *Pseudomonas* sp. such as PSEEN3174 (Monalysin; (2011) *PLoS Pathogens* 7:1-13); from *Pseudomonas protegens* strain CHAO and Pf-5 (previously *fluorescens*) (Pechy-Tarr, (2008) *Environmental Microbiology* 10:2368-2386; GenBank Accession No. EU400157); from *Pseudomonas taiwanensis* (Liu, et al., (2010) *J. Agric. Food Chem.*, 58:12343-12349) and from *Pseudomonas pseudoalcali-*

*genes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and Xenorhabdus sp. (Hinchliffe, et al., (2010) *The Open Toxicology Journal,* 3:101-118 and Morgan, et al., (2001) *Applied and Envir. Micro.* 67:2062-2069); U.S. Pat. Nos. 6,048,838, and 6,379,946; a PIP-1 polypeptide of U.S. Pat. No. 9,688,730; an AfIP-1A and/or AfIP-1B polypeptide of U.S. Pat. No. 9,475,847; a PIP-47 polypeptide of US Publication Number US20160186204; an IPD045 polypeptide, an IPD064 polypeptide, an IPD074 polypeptide, an IPD075 polypeptide, and an IPD077 polypeptide of PCT Publication Number WO 2016/114973; an IPD080 polypeptide of PCT Serial Number PCT/US17/56517; an IPD078 polypeptide, an IPD084 polypeptide, an IPD085 polypeptide, an IPD086 polypeptide, an IPD087 polypeptide, an IPD088 polypeptide, and an IPD089 polypeptide of Serial Number PCT/US17/54160; PIP-72 polypeptide of US Patent Publication Number US20160366891; a PtIP-50 polypeptide and a PtIP-65 polypeptide of US Publication Number US20170166921; an IPD098 polypeptide, an IPD059 polypeptide, an IPD108 polypeptide, an IPD109 polypeptide of U.S. Ser. No. 62/521,084; a PtIP-83 polypeptide of US Publication Number US20160347799; a PtIP-96 polypeptide of US Publication Number US20170233440; an IPD079 polypeptide of PCT Publication Number WO2017/23486; an IPD082 polypeptide of PCT Publication Number WO 2017/105987, an IPD090 polypeptide of Serial Number PCT/US17/30602, an IPD093 polypeptide of U.S. Ser. No. 62/434,020; an IPD103 polypeptide of Serial Number PCT/US17/39376; an IPD101 polypeptide of U.S. Ser. No. 62/438,179; an IPD121 polypeptide of US Serial Number U.S. 62/508,514; and 5-endotoxins including, but not limited to a Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry29, Cry30, Cry31, Cry32, Cry33, Cry34, Cry35, Cry36, Cry37, Cry38, Cry39, Cry40, Cry41, Cry42, Cry43, Cry44, Cry45, Cry46, Cry47, Cry49, Cry50, Cry51, Cry52, Cry53, Cry54, Cry55, Cry56, Cry57, Cry58, Cry59, Cry60, Cry61, Cry62, Cry63, Cry64, Cry65, Cry66, Cry67, Cry68, Cry69, Cry70, Cry71, and Cry 72 classes of 5-endotoxin polypeptides and the *B. thuringiensis* cytolytic cyt1 and cyt2 genes. Members of these classes of *B. thuringiensis* insecticidal proteins well known to one skilled in the art (see, Crickmore, et al., "*Bacillus thuringiensis* toxin nomenclature" (2011), at lifesci.sussex.ac.uk/home/Neil_Crickmore/Bt/which can be accessed on the world-wide web using the "www" prefix).

Examples of 5-endotoxins also include but are not limited to Cry1A proteins of U.S. Pat. Nos. 5,880,275, 7,858,849, and 8,878,007; a Cry1Ac mutant of U.S. Pat. No. 9,512,187; a DIG-3 or DIG-11 toxin (N-terminal deletion of α-helix 1 and/or α-helix 2 variants of cry proteins such as Cry1A, Cry3A) of U.S. Pat. Nos. 8,304,604, 8,304,605 and 8,476, 226; Cry1B of U.S. patent application Ser. No. 10/525,318, US Patent Application Publication Number US20160194364, and U.S. Pat. Nos. 9,404,121 and 8,772, 577; Cry1B variants of PCT Publication Number WO2016/61197 and Serial Number PCT/US17/27160; Cry1C of U.S. Pat. No. 6,033,874; Cry1D protein of US20170233759; a Cry1E protein of PCT Serial Number PCT/US17/53178; a Cry1F protein of U.S. Pat. Nos. 5,188,960 and 6,218,188; Cry1A/F chimeras of U.S. Pat. Nos. 7,070,982; 6,962,705 and 6,713,063; a Cry11 protein of PCT Publication number WO 2017/0233759; a Cry1J variant of US Publication US20170240603; a Cry2 protein such as Cry2Ab protein of U.S. Pat. No. 7,064,249 and Cry2A.127 protein of U.S. Pat. No. 7,208,474; a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476, 781, 7,105,332, 7,339,092, 7,378,499, 7,462,760, and 9,593, 345; a Cry9 protein such as such as members of the Cry9A, Cry9B, Cry9C, Cry9D, Cry9E and Cry9F families including the Cry9 protein of U.S. Pat. Nos. 9,000,261 and 8,802,933, and US Serial Number WO 2017/132188; a Cry15 protein of Naimov, et al., (2008) *Applied and Environmental Microbiology*, 74:7145-7151; a Cry14 protein of U.S. Pat. No. 8,933,299; a Cry22, a Cry34Ab1 protein of U.S. Pat. Nos. 6,127,180, 6,624,145 and 6,340,593; a truncated Cry34 protein of U.S. Pat. No. 8,816,157; a CryET33 and cryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083, 499, 6,548,291 and 6,340,593; a Cry46 protein of U.S. Pat. No. 9,403,881, a Cry 51 protein, a Cry binary toxin; a TIC901 or related toxin; TIC807 of US Patent Application Publication Number 2008/0295207; TIC853 of U.S. Pat. No. 8,513,493; ET29, ET37, TIC809, TIC810, TIC812, TIC127, TIC128 of PCT US 2006/033867; engineered Hemipteran toxic proteins of US Patent Application Publication Number US20160150795, AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020 and AXMI-021 of WO 2006/083891; AXMI-010 of WO 2005/038032; AXMI-003 of WO 2005/021585; AXMI-008 of US Patent Application Publication Number 2004/0250311; AXMI-006 of US Patent Application Publication Number 2004/0216186; AXMI-007 of US Patent Application Publication Number 2004/0210965; AXMI-009 of US Patent Application Number 2004/0210964; AXMI-014 of US Patent Application Publication Number 2004/0197917; AXMI-004 of US Patent Application Publication Number 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US Patent Application Publication Number 2011/0023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063 and AXMI-064 of US Patent Application Publication Number 2011/0263488; AXM1046, AXM1048, AXM1050, AXM1051, AXM1052, AXM1053, AXM1054, AXM1055, AXM1056, AXM1057, AXM1058, AXM1059, AXM1060, AXM1061, AXM1067, AXM1069, AXM1071, AXM1072, AXM1073, AXM1074, AXM1075, AXM1087, AXM1088, AXM1093, AXM1070, AXM1080, AXM1081, AXM1082, AXM1091, AXM1092, AXM1096, AXM1097, AXM1098, AXM1099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI125, AXMI126, AXMI127, AXMI129, AXMI151, AXMI161, AXMI164, AXMI183, AXMI132, AXMI137, AXMI138 of U.S. Pat. Nos. 8,461,421 and 8,461,422; AXMI-R1 and related proteins of US Patent Application Publication Number 2010/

0197592; AXM1221Z, AXM1222z, AXM1223z, AXM1224z and AXM1225z of WO 2011/103248; AXM1218, AXM1219, AXM1220, AXM1226, AXM1227, AXM1228, AXM1229, AXM1230 and AXM1231 of WO 2011/103247; AXMI-115, AXMI-113, AXMI-005, AXMI-163 and AXMI-184 of U.S. Pat. No. 8,334,431; AXMI-001, AXMI-002, AXMI-030, AXMI-035 and AXMI-045 of US Patent Application Publication Number 2010/0298211; AXMI-066 and AXMI-076 of US Patent Application Publication Number 2009/0144852; AXM1128, AXM1130, AXM1131, AXM1133, AXM1140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXM1079, AXM1080, AXM1081, AXM1082, AXM1091, AXM1092, AXM1096, AXM1097, AXM1098, AXM1099, AXMI100, AXMI101, AXMI102, AXM1103, AXM1104, AXM1107, AXM1108, AXM1109, AXM1110, dsAXM1111, AXM1112, AXM1114, AXM1116, AXM1117, AXM1118, AXM1119, AXM1120, AXM1121, AXM1122, AXM1123, AXM1124, AXM11257, AXM11268, AXMI127, AXMI129, AXMI164, AXMI151, AXMI161, AXMI183, AXMI132, AXM1138, AXM1137 of U.S. Pat. No. 8,461, 421; AXM1192 of U.S. Pat. No. 8,461,415; AXM1281 of US Patent Application Publication Number US20160177332; AXM1422 of U.S. Pat. No. 8,252,872; cry proteins such as Cry1A and Cry3A having modified proteolytic sites of U.S. Pat. No. 8,319,019; a Cry1Ac, Cry2Aa and Cry1Ca toxin protein from *Bacillus thuringiensis* strain VBTS 2528 of US Patent Application Publication Number 2011/0064710. The Cry proteins MP032, MP049, MP051, MP066, MP068, MP070, MP091S, MP109S, MP114, MP121, MP134S, MP183S, MP185S, MP186S, MP195S, MP197S, MP208S, MP209S, MP212S, MP214S, MP217S, MP222S, MP234S, MP235S, MP237S, MP242S, MP243, MP248, MP249S, MP251M, MP252S, MP253, MP259S, MP287S, MP288S, MP295S, MP296S, MP297S, MP300S, MP304S, MP306S, MP310S, MP312S, MP314S, MP319S, MP325S, MP326S, MP327S, MP328S, MP334S, MP337S, MP342S, MP349S, MP356S, MP359S, MP360S, MP437S, MP451S, MP452S, MP466S, MP468S, MP476S, MP482S, MP522S, MP529S, MP548S, MP552S, MP562S, MP564S, MP566S, MP567S, MP569S, MP573S, MP574S, MP575S, MP581S, MP590, MP594S, MP596S, MP597, MP599S, MP600S, MP601S, MP602S, MP604S, MP626S, MP629S, MP630S, MP631S, MP632S, MP633S, MP634S, MP635S, MP639S, MP640S, MP644S, MP649S, MP651S, MP652S, MP653S, MP661S, MP666S, MP672S, MP696S, MP704S, MP724S, MP729S, MP739S, MP755S, MP773S, MP799S, MP800S, MP801S, MP802S, MP803S, MP805S, MP809S, MP815S, MP828S, MP831S, MP844S, MP852, MP865S, MP879S, MP887S, MP891S, MP896S, MP898S, MP935S, MP968, MP989, MP993, MP997, MP1049, MP1066, MP1067, MP1080, MP1081, MP1200, MP1206, MP1233, and MP1311 of U.S. Ser. No. 62/607,372. The insecticidal activity of Cry proteins is well known to one skilled in the art (for review, see, van Frannkenhuyzen, (2009) *J. Invert. Path*. 101:1-16). The use of Cry proteins as transgenic plant traits is well known to one skilled in the art and Cry-transgenic plants including but not limited to plants expressing Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sana-huja, (2011) *Plant Biotech Journal* 9:283-300 and the CERA. (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682); Cry1BE & Cry1F (US2012/0311746); Cry1CA & Cry1AB (US2012/0311745); Cry1F & CryCa (US2012/0317681); Cry1 DA & Cry1BE (US2012/0331590); Cry1DA & Cry1Fa (US2012/0331589); Cry1AB & Cry1 BE (US2012/0324606); Cry1Fa & Cry2Aa and Cry1I & Cry1E (US2012/0324605); Cry34Ab/35Ab & Cry6Aa (US20130167269); Cry34Ab/VCry35Ab & Cry3Aa (US20130167268); Cry1 Da & Cry1Ca (U.S. Pat. No. 9,796,982); Cry3Aa & Cry6Aa (U.S. Pat. No. 9,798, 963); and Cry3A & Cry1Ab or Vip3Aa (U.S. Pat. No. 9,045,766). Pesticidal proteins also include insecticidal lipases including lipid acyl hydrolases of U.S. Pat. No. 7,491,869, and cholesterol oxidases such as from *Strepto-myces* (Purcell et al. (1993) *Biochem Biophys Res Commun* 15:1406-1413). Pesticidal proteins also include VIP (veg-etative insecticidal proteins) toxins of U.S. Pat. Nos. 5,877, 012, 6,107,279 6,137,033, 7,244,820, 7,615,686, and 8,237, 020 and the like. Other VIP proteins are well known to one skilled in the art (see, lifesci.sussex.ac.uk/home/Neil_Crickmore/Bt/vip.html which can be accessed on the world-wide web using the "www" prefix). Pesticidal pro-teins also include Cyt proteins including Cyt1A variants of PCT Serial Number PCT/US2017/000510; Pesticidal pro-teins also include toxin complex (TC) proteins, obtainable from organisms such as Xenorhabdus, *Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus*, Xenorhab-dus or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal pro-teins also include spider, snake and scorpion venom pro-teins. Examples of spider venom peptides include but not limited to lycotoxin-1 peptides and mutants thereof (U.S. Pat. No. 8,334,366). The combinations generated can also include multiple copies of any one of the polynucleotides of interest.

(C) A polynucleotide encoding an insect-specific hormone or pheromone such as an ecdysteroid and juvenile hormone, a variant thereof, a mimetic based thereon or an antagonist or agonist thereof. See, for example, the disclosure by Hammock, et al., (1990) *Nature* 344:458, of baculovirus expression of cloned juvenile hormone esterase, an inactivator of juvenile hormone.

(D) A polynucleotide encoding an insect-specific peptide which, upon expression, disrupts the physiology of the affected pest. For example, see the disclosures of, Regan, (1994) *J. Biol. Chem.* 269:9 (expression cloning yields DNA coding for insect diuretic hormone recep-tor); Pratt, et al., (1989) *Biochem. Biophys. Res. Comm.* 163:1243 (an allostatin is identified in *Diploptera pun-tata*); Chattopadhyay, et al., (2004) *Critical Reviews in Microbiology* 30(1):33-54; Zjawiony, (2004) *J Nat Prod* 67(2):300-310; Carlini and Grossi-de-Sa, (2002) *Toxicon* 40(11):1515-1539; Ussuf, et al., (2001) *Curr Sci.* 80(7):847-853 and Vasconcelos and Oliveira, (2004) *Toxicon* 44(4):385-403. See also, U.S. Pat. No. 5,266,317 to Tomalski, et al., who disclose genes encoding insect-specific toxins.

(E) A polynucleotide encoding an enzyme responsible for a hyperaccumulation of a monoterpene, a sesquiter-pene, a steroid, hydroxamic acid, a phenylpropanoid derivative or another non-protein molecule with insec-ticidal activity.

(F) A polynucleotide encoding an enzyme involved in the modification, including the post-translational modifi-cation, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phos-phorylase, a polymerase, an elastase, a chitinase and a glucanase, whether natural or synthetic. See, PCT Application WO 1993/02197 in the name of Scott, et al., which discloses the nucleotide sequence of a callase gene. DNA molecules which contain chitinase-encod-ing sequences can be obtained, for example, from the ATCC® under Accession Numbers 39637 and 67152. See also, Kramer, et al., (1993) *Insect Biochem. Molec. Biol.* 23:691, who teach the nucleotide sequence of a cDNA encoding tobacco hookworm chitinase and Kawalleck, et al., (1993) *Plant Molec. Biol.* 21:673, who provide the nucleotide sequence of the parsley ubi4-2 polyubiquitin gene, and U.S. Pat. Nos. 6,563, 020; 7,145,060 and 7,087,810.

(G) A polynucleotide encoding a molecule that stimulates signal transduction. For example, see the disclosure by Botella, et al., (1994) *Plant Molec. Biol.* 24:757, of nucleotide sequences for mung bean calmodulin cDNA clones, and Griess, et al., (1994) *Plant Physiol.* 104: 1467, who provide the nucleotide sequence of a maize calmodulin cDNA clone.

(H) A polynucleotide encoding a hydrophobic moment peptide. See, PCT Application WO 1995/16776 and U.S. Pat. No. 5,580,852 disclosure of peptide deriva-tives of Tachyplesin which inhibit fungal plant patho-gens) and PCT Application WO 1995/18855 and U.S. Pat. No. 5,607,914 (teaches synthetic antimicrobial peptides that confer disease resistance).

(I) A polynucleotide encoding a membrane permease, a channel former or a channel blocker. For example, see the disclosure by Jaynes, et al., (1993) *Plant Sci.* 89:43, of heterologous expression of a cecropin-beta lytic peptide analog to render transgenic tobacco plants resistant to *Pseudomonas solanacearum*.

(J) A gene encoding a viral-invasive protein or a complex toxin derived therefrom. For example, the accumula-tion of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28:451. Coat protein-mediated resistance has been con-ferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) A gene encoding an insect-specific antibody or an immunotoxin derived therefrom. Thus, an antibody targeted to a critical metabolic function in the insect gut would inactivate an affected enzyme, killing the insect. Cf. Taylor, et al., Abstract #497, SEVENTH INT'L SYMPOSIUM ON MOLECULAR PLANT-MI-CROBE INTERACTIONS (Edinburgh, Scotland, 1994) (enzymatic inactivation in transgenic tobacco via production of single-chain antibody fragments).

(L) A gene encoding a virus-specific antibody. See, for example, Tavladoraki, et al., (1993) *Nature* 366:469, who show that transgenic plants expressing recombinant antibody genes are protected from virus attack.

(M) A polynucleotide encoding a developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) *Bio/Technology* 10:1436. The cloning and characterization of a gene which encodes a bean endopolygalacturonase-inhibiting protein is described by Toubart, et al., (1992) *Plant J.* 2:367.

(N) A polynucleotide encoding a developmental-arrestive protein produced in nature by a plant. For example, Logemann, et al., (1992) *Bio/Technology* 10:305, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) *Current Biology* 5(2), Pieterse and Van Loon, (2004) *Curr. Opin. Plant Bio.* 7(4):456-64 and Somssich, (2003) *Cell* 113(7):815-6.

(P) Antifungal genes (Cornelissen and Melchers, (1993) *Pl. Physiol.* 101:709-712 and Parijs, et al., (1991) *Planta* 183:258-264 and Bushnell, et al., (1998) *Can. J. of Plant Path.* 20(2):137-149. Also see, U.S. patent application Ser. Nos. 09/950,933; 11/619,645; 11/657,710; 11/748,994; 11/774,121 and U.S. Pat. Nos. 6,891,085 and 7,306,946. LysM Receptor-like kinases for the perception of chitin fragments as a first step in plant defense response against fungal pathogens (US 2012/0110696).

(Q) Detoxification genes, such as for fumonisin, beauvericin, moniliformin and zearalenone and their structurally related derivatives. For example, see, U.S. Pat. Nos. 5,716,820; 5,792,931; 5,798,255; 5,846,812; 6,083,736; 6,538,177; 6,388,171 and 6,812,380.

(R) A polynucleotide encoding a Cystatin and cysteine proteinase inhibitors. See, U.S. Pat. No. 7,205,453.

(S) Defensin genes. See, WO 2003/000863 and U.S. Pat. Nos. 6,911,577; 6,855,865; 6,777,592 and 7,238,781.

(T) Genes conferring resistance to nematodes. See, e.g., PCT Application WO 1996/30517; PCT Application WO 1993/19181, WO 2003/033651 and Urwin, et al., (1998) *Planta* 204:472-479, Williamson, (1999) *Curr Opin Plant Bio.* 2(4):327-31; U.S. Pat. Nos. 6,284,948 and 7,301,069 and miR164 genes (WO 2012/058266).

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker, et al., *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035 and incorporated by reference for this purpose.

(W) Genes that confer resistance to *Colletotrichum*, such as described in US Patent Application Publication US 2009/0035765 and incorporated by reference for this purpose. This includes the Rcg locus that may be utilized as a single locus conversion. 2. Transgenes that Confer Resistance to a Herbicide, for Example:

(A) A polynucleotide encoding resistance to a herbicide that inhibits the growing point or meristem, such as an imidazolinone or a sulfonylurea. Exemplary genes in this category code for mutant ALS and AHAS enzyme as described, for example, by Lee, et al., (1988) *EMBO J.* 7:1241 and Miki, et al., (1990) *Theor. Appl. Genet.* 80:449, respectively. See also, U.S. Pat. Nos. 5,605, 011; 5,013,659; 5,141,870; 5,767,361; 5,731,180; 5,304,732; 4,761,373; 5,331,107; 5,928,937 and 5,378, 824; U.S. patent application Ser. No. 11/683,737 and International Publication WO 1996/33270.

(B) A polynucleotide encoding a protein for resistance to Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566, 587; 6,338,961; 6,248,876; 6,040,497; 5,804,425; 5,633,435; 5,145,783; 4,971,908; 5,312,910; 5,188, 642; 5,094,945, 4,940,835; 5,866,775; 6,225,114; 6,130,366; 5,310,667; 4,535,060; 4,769,061; 5,633, 448; 5,510,471; Re. 36,449; RE 37,287 E and 5,491, 288 and International Publications EP 1173580; WO 2001/66704; EP 1173581 and EP 1173582, which are incorporated herein by reference for this purpose. Glyphosate resistance is also imparted to plants that express a gene encoding a glyphosate oxido-reductase enzyme as described more fully in U.S. Pat. Nos. 5,776,760 and 5,463,175, which are incorporated herein by reference for this purpose. In addition, glyphosate resistance can be imparted to plants by the over expression of genes encoding glyphosate N-acetyl-transferase. See, for example, U.S. Pat. Nos. 7,462,481; 7,405,074 and US Patent Application Publication Number US 2008/0234130. A DNA molecule encoding a mutant aroA gene can be obtained under ATCC® Accession Number 39256, and the nucleotide sequence of the mutant gene is disclosed in U.S. Pat. No. 4,769,061 to Comai. EP Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in EP Application Numbers 0 242 246 and 0 242 236 to Leemans, et al.; De Greef, et al., (1989) *Bio/Technology* 7:61, describe the production of transgenic plants that express chimeric bar genes coding for phosphinothricin acetyl transferase activity. See also, U.S. Pat. Nos. 5,969,213; 5,489,520; 5,550,318; 5,874, 265; 5,919,675; 5,561,236; 5,648,477; 5,646,024; 6,177,616 and 5,879,903, which are incorporated herein by reference for this purpose. Exemplary genes conferring resistance to phenoxy proprionic acids and cyclohexones, such as sethoxydim and haloxyfop, are the Acc1-S1, Acc1-S2 and Acc1-S3 genes described by Marshall, et al., (1992) *Theor. Appl.* Genet. 83:435.

(C) A polynucleotide encoding a protein for resistance to herbicide that inhibits photosynthesis, such as a triazine (psbA and gs+ genes) and a benzonitrile (nitrilase gene). Przibilla, etal., (1991) *Plant Cell* 3:169, describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC® Accession Numbers 53435, 67441 and 67442. Cloning and expression of DNA coding for a glutathione S-transferase is described by Hayes, et al., (1992) *Biochem. J.* 285:173.

(D) A polynucleotide encoding a protein for resistance to Acetohydroxy acid synthase, which has been found to make plants that express this enzyme resistant to multiple types of herbicides, has been introduced into a variety of plants (see, e.g., Hattori, et al., (1995) *Mol Gen Genet.* 246:419). Other genes that confer resistance to herbicides include: a gene encoding a chimeric protein of rat cytochrome P4507A1 and yeast NADPH-cytochrome P450 oxidoreductase (Shiota, et al., (1994) *Plant Physiol* 106:17), genes for glutathione reductase and superoxide dismutase (Aono, et al., (1995) *Plant Cell Physiol* 36:1687) and genes for various phospho-transferases (Datta, et al., (1992) *Plant Mol Biol* 20:619).

(E) A polynucleotide encoding resistance to a herbicide targeting Protoporphyrinogen oxidase (protox) which is necessary for the production of chlorophyll. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. No. 6,288,306; 6,282,83 and 5,767,373 and International Publication WO 2001/12825.

(F) The aad-1 gene (originally from *Sphingobium herbicidovorans*) encodes the aryloxyalkanoate dioxygenase (AAD-1) protein. The trait confers tolerance to 2,4-dichlorophenoxyacetic acid and aryloxyphenoxypropionate (commonly referred to as "fop" herbicides such as quizalofop) herbicides. The aad-1 gene, itself, for herbicide tolerance in plants was first disclosed in WO 2005/107437 (see also, US 2009/0093366). The aad-12 gene, derived from *Delftia acidovorans*, which encodes the aryloxyalkanoate dioxygenase (AAD-12) protein that confers tolerance to 2,4-dichlorophenoxyacetic acid and pyridyloxyacetate herbicides by deactivating several herbicides with an aryloxyalkanoate moiety, including phenoxy auxin (e.g., 2,4-D, MCPA), as well as pyridyloxy auxins (e.g., fluroxypyr, triclopyr).

(G) A polynucleotide encoding a herbicide resistant dicamba monooxygenase disclosed in US Patent Application Publication 2003/0135879 for imparting dicamba tolerance;

(H) A polynucleotide molecule encoding bromoxynil nitrilase (Bxn) disclosed in U.S. Pat. No. 4,810,648 for imparting bromoxynil tolerance;

(I) A polynucleotide molecule encoding phytoene (crtl) described in Misawa, et al., (1993) *Plant J.* 4:833-840 and in Misawa, et al., (1994) *Plant J.* 6:481-489 for norflurazon tolerance.

3. Transgenes that Confer or Contribute to an Altered Grain Characteristic

Such as:

(A) Altered fatty acids, for example, by (1) Down-regulation of stearoyl-ACP to increase stearic acid content of the plant. See, Knultzon, et al., (1992) *Proc. Natl. Acad. Sci. USA* 89:2624 and WO 1999/64579 (Genes to Alter Lipid Profiles in Corn).

(2) Elevating oleic acid via FAD-2 gene modification and/or decreasing linolenic acid via FAD-3 gene modification (see, U.S. Pat. Nos. 6,063,947; 6,323,392; 6,372,965 and WO 1993/11245).

(3) Altering conjugated linolenic or linoleic acid content, such as in WO 2001/12800.

(4) Altering LEC1, AGP, Dek1, Superal1, mi ps, and various Ipa genes such as Ipa1, Ipa3, hpt or hggt. For example, see, WO 2002/42424, WO 1998/22604, WO 2003/011015, WO 2002/057439, WO 2003/011015, U.S. Pat. Nos. 6,423,886, 6,197,561, 6,825,397 and US Patent Application Publication Numbers US 2003/0079247, US 2003/0204870 and Rivera-Madrid, et al., (1995) *Proc. Natl. Acad. Sci.* 92:5620-5624.

(5) Genes encoding delta-8 desaturase for making long-chain polyunsaturated fatty acids (U.S. Pat. Nos. 8,058, 571 and 8,338,152), delta-9 desaturase for lowering saturated fats (U.S. Pat. No. 8,063,269), *Primula* A6-desaturase for improving omega-3 fatty acid profiles.

(6) Isolated nucleic acids and proteins associated with lipid and sugar metabolism regulation, in particular, lipid metabolism protein (LMP) used in methods of producing transgenic plants and modulating levels of seed storage compounds including lipids, fatty acids, starches or seed storage proteins and use in methods of modulating the seed size, seed number, seed weights, root length and leaf size of plants (EP 2404499).

(7) Altering expression of a High-Level Expression of Sugar-Inducible 2 (HS12) protein in the plant to increase or decrease expression of HS12 in the plant. Increasing expression of HS12 increases oil content while decreasing expression of HS12 decreases abscisic acid sensitivity and/or increases drought resistance (US Patent Application Publication Number 2012/0066794).

(8) Expression of cytochrome b5 (Cb5) alone or with FAD2 to modulate oil content in plant seed, particularly to increase the levels of omega-3 fatty acids and improve the ratio of omega-6 to omega-3 fatty acids (US Patent Application Publication Number 2011/0191904).

(9) Nucleic acid molecules encoding wrinkled1-like polypeptides for modulating sugar metabolism (U.S. Pat. No. 8,217,223).

(B) Altered phosphorus content, for example, by the (1) Introduction of a phytase-encoding gene would enhance breakdown of phytate, adding more free phosphate to the transformed plant. For example, see, Van Hartingsveldt, et al., (1993) *Gene* 127:87, for a disclosure of the nucleotide sequence of an *Aspergillus niger* phytase gene.

(2) Modulating a gene that reduces phytate content. In maize, this, for example, could be accomplished, by cloning and then re-introducing DNA associated with one or more of the alleles, such as the LPA alleles, identified in maize mutants characterized by low levels of phytic acid, such as in WO 2005/113778 and/or by altering inositol kinase activity as in WO 2002/059324, US Patent Application Publication Number 2003/0009011, WO 2003/027243, US Patent Application Publication Number 2003/0079247, WO 1999/05298, U.S. Pat. Nos. 6,197,561, 6,291,224, 6,391,348, WO 2002/059324, US Patent Application Publication Number 2003/0079247, WO 1998/45448, WO 1999/55882, WO 2001/04147.

(C) Altered carbohydrates affected, for example, by altering a gene for an enzyme that affects the branching pattern of starch or, a gene altering thioredoxin such as NTR and/or TRX (see, U.S. Pat. No. 6,531,648. which is incorporated by reference for this purpose) and/or a gamma zein knock out or mutant such as cs27 or TUSC27 or en27 (see, U.S. Pat. No. 6,858,778 and US Patent Application Publication Number 2005/0160488, US Patent Application Publication Number 2005/0204418, which are incorporated by reference for this purpose). See, Shiroza, et al., (1988) *J. Bacteriol.* 170:810 (nucleotide sequence of *Streptococcus* mutant fructosyltransferase gene), Steinmetz, et al., (1985) *Mol. Gen. Genet.* 200:220 (nucleotide sequence of *Bacillus subtilis* levansucrase gene), Pen, et al., (1992) *Bio/Technology* 10:292 (production of transgenic plants that express *Bacillus licheniformis* alpha-amylase), Elliot, et al., (1993) *Plant Molec. Biol.* 21:515 (nucleotide sequences of tomato invertase genes), Søgaard, et al., (1993) *J. Biol. Chem.* 268:22480 (site-directed mutagenesis of barley alpha-amylase gene) and Fisher, et al., (1993) *Plant Physiol.* 102:1045 (maize endosperm starch branching enzyme II), WO 1999/10498 (improved digestibility and/or starch extraction through modification of UDP-D-xylose 4-epimerase, Fragile 1 and 2, Refl, HCHL, C4H), U.S. Pat. No. 6,232,529 (method of producing high oil seed by modification of starch levels (AGP)). The fatty acid modification genes mentioned herein may also be used to affect starch content and/or composition through the interrelationship of the starch and oil pathways.

(D) Altered antioxidant content or composition, such as alteration of tocopherol or tocotrienols. For example, see, U.S. Pat. No. 6,787,683, US Patent Application Publication Number 2004/0034886 and WO 2000/68393 involving the manipulation of antioxidant levels and WO 2003/082899 through alteration of a homogentisate geranyl geranyl transferase (hggt).

(E) Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 1999/40209 (alteration of amino acid compositions in seeds), WO 1999/29882 (methods for altering amino acid content of proteins), U.S. Pat. No. 5,850,016 (alteration of amino acid compositions in seeds), WO 1998/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441, 274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 1998/56935 (plant amino acid biosynthetic enzymes), WO 1998/45458 (engineered seed protein having higher percentage of essential amino acids), WO 1998/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO 1996/01905 (increased threonine), WO 1995/15392 (increased lysine), US Patent Application Publication Number 2003/0163838, US Patent Application Publication Number 2003/0150014, US Patent Application Publication Number 2004/0068767, U.S. Pat. No. 6,803,498, WO 2001/79516.

4. Genes that Control Male-Sterility:

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing or turning "on", the promoter, which in turn allows the gene that, confers male fertility to be transcribed.

(A) Introduction of a deacetylase gene under the control of a tapetum-specific promoter and with the application of the chemical N—Ac-PPT (WO 2001/29237).

(B) Introduction of various stamen-specific promoters (WO 1992/13956, WO 1992/13957).

(C) Introduction of the barnase and the barstar gene (Paul, et al., (1992) *Plant Mol. Biol.* 19:611-622).

For additional examples of nuclear male and female sterility systems and genes, see also, U.S. Pat. Nos. 5,859,341; 6,297,426; 5,478,369; 5,824,524; 5,850,014 and 6,265,640, all of which are hereby incorporated by reference.

5. Genes that Create a Site for Site Specific DNA Integration.

This includes the introduction of FRT sites that may be used in the FLP/FRT system and/or Lox sites that may be used in the Cre/Loxp system. For example, see, Lyznik, et al., (2003) *Plant Cell Rep* 21:925-932 and WO 1999/25821, which are hereby incorporated by reference. Other systems that may be used include the Gin recombinase of phage Mu (Maeser, et al., (1991) Vicki Chandler, *The Maize Handbook* ch. 118 (Springer-Verlag 1994), the Pin recombinase of *E. coli* (Enomoto, et al., 1983) and the R/RS system of the pSRi plasmid (Araki, et al., 1992).

6. Genes that Affect Abiotic Stress Resistance

Including but not limited to flowering, ear and seed development, enhancement of nitrogen utilization efficiency, altered nitrogen responsiveness, drought resistance or tolerance, cold resistance or tolerance and salt resistance or tolerance and increased yield under stress.

(A) For example, see: WO 2000/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801, 104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 199809521.

(B) WO 199938977 describing genes, including CBF genes and transcription factors effective in mitigating the negative effects of freezing, high salinity and drought on plants, as well as conferring other positive effects on plant phenotype.

(C) US Patent Application Publication Number 2004/0148654 and WO 2001/36596 where abscisic acid is altered in plants resulting in improved plant phenotype such as increased yield and/or increased tolerance to abiotic stress.

(D) WO 2000/006341, WO 2004/090143, U.S. Pat. Nos. 7,531,723 and 6,992,237 where cytokinin expression is modified resulting in plants with increased stress tolerance, such as drought tolerance, and/or increased yield. Also see, WO 2002/02776, WO 2003/052063, JP 2002/281975, U.S. Pat. No. 6,084,153, WO 2001/64898, U.S. Pat. No. 6,177,275 and U.S. Pat. No. 6,107,547 (enhancement of nitrogen utilization and altered nitrogen responsiveness).

(E) For ethylene alteration, see, US Patent Application Publication Number 2004/0128719, US Patent Application Publication Number 2003/0166197 and WO 2000/32761.

(F) For plant transcription factors or transcriptional regulators of abiotic stress, see, e.g., US Patent Application Publication Number 2004/0098764 or US Patent Application Publication Number 2004/0078852.

(G) Genes that increase expression of vacuolar pyrophosphatase such as AVP1 (U.S. Pat. No. 8,058,515) for increased yield; nucleic acid encoding a HSFA4 or a HSFA5 (Heat Shock Factor of the class A4 or A5) polypeptides, an oligopeptide transporter protein (OPT4-like) polypeptide; a plastochron2-like (PLA2-like) polypeptide or a Wuschel related homeobox 1-like (WOX1-like) polypeptide (U. Patent Application Publication Number US 2011/0283420).

(H) Down regulation of polynucleotides encoding poly (ADP-ribose) polymerase (PARP) proteins to modulate programmed cell death (U.S. Pat. No. 8,058,510) for increased vigor.

(I) Polynucleotide encoding DTP21 polypeptides for conferring drought resistance (US Patent Application Publication Number US 2011/0277181).

(J) Nucleotide sequences encoding ACC Synthase 3 (ACS3) proteins for modulating development, modulating response to stress, and modulating stress tolerance (US Patent Application Publication Number US 2010/0287669).

(K) Polynucleotides that encode proteins that confer a drought tolerance phenotype (DTP) for conferring drought resistance (WO 2012/058528).

(L) Tocopherol cyclase (TC) genes for conferring drought and salt tolerance (US Patent Application Publication Number 2012/0272352).

(M) CAAX amino terminal family proteins for stress tolerance (U.S. Pat. No. 8,338,661).

(N) Mutations in the SAL1 encoding gene have increased stress tolerance, including increased drought resistant (US Patent Application Publication Number 2010/0257633).

(O) Expression of a nucleic acid sequence encoding a polypeptide selected from the group consisting of: GRF polypeptide, RAA1-like polypeptide, SYR polypeptide, ARKL polypeptide, and YTP polypeptide increasing yield-related traits (US Patent Application Publication Number 2011/0061133).

(P) Modulating expression in a plant of a nucleic acid encoding a Class Ill Trehalose Phosphate Phosphatase (TPP) polypeptide for enhancing yield-related traits in plants, particularly increasing seed yield (US Patent Application Publication Number 2010/0024067).

Other genes and transcription factors that affect plant growth and agronomic traits such as yield, flowering, plant growth and/or plant structure, can be introduced or introgressed into plants, see e.g., WO 1997/49811 (LHY), WO 1998/56918 (ESD4), WO 1997/10339 and U.S. Pat. No. 6,573,430 (TFL), U.S. Pat. No. 6,713,663 (FT), WO 1996/14414 (CON), WO 1996/38560, WO 2001/21822 (VRN1), WO 2000/44918 (VRN2), WO 1999/49064 (GI), WO 2000/46358 (FR1), WO 1997/29123, U.S. Pat. Nos. 6,794,560, 6,307,126 (GAI), WO 1999/09174 (D8 and Rht) and WO 2004/076638 and WO 2004/031349 (transcription factors).

7. Genes that Confer Increased Yield (A) A transgenic crop plant transformed by a 1-Amino-Cyclopropane-1-Carboxylate Deaminase-like Polypeptide (ACCDP) coding nucleic acid, wherein expression of the nucleic acid sequence in the crop plant results in the plant's increased root growth, and/or increased yield, and/or increased tolerance to environmental stress as compared to a wild type variety of the plant (U.S. Pat. No. 8,097,769).

(B) Over-expression of maize zinc finger protein gene (Zm-ZFP1) using a seed preferred promoter has been shown to enhance plant growth, increase kernel number and total kernel weight per plant (US Patent Application Publication Number 2012/0079623).

(C) Constitutive over-expression of maize lateral organ boundaries (LOB) domain protein (Zm-LOBDP1) has been shown to increase kernel number and total kernel weight per plant (US Patent Application Publication Number 2012/0079622).

(D) Enhancing yield-related traits in plants by modulating expression in a plant of a nucleic acid encoding a VIM1 (Variant in Methylation 1)-like polypeptide or a VTC2-like (GDP-L-galactose phosphorylase) polypeptide or a DUF1685 polypeptide or an ARF6-like (Auxin Responsive Factor) polypeptide (WO 2012/038893).

(E) Modulating expression in a plant of a nucleic acid encoding a Ste20-like polypeptide or a homologue thereof gives plants having increased yield relative to control plants (EP 2431472).

(F) Genes encoding nucleoside diphosphatase kinase (NDK) polypeptides and homologs thereof for modifying the plant's root architecture (US Patent Application Publication Number 2009/0064373).

8. Genes that Confer Plant Digestibility.

(A) Altering the level of xylan present in the cell wall of a plant by modulating expression of xylan synthase (U.S. Pat. No. 8,173,866).

In some embodiment the stacked trait may be a trait or event that has received regulatory approval including but not limited to the events with regulatory approval that are well known to one skilled in the art and can be found at the Center for Environmental Risk Assessment (cera-gmc.org/?action=gm_crop_database, which can be accessed using the www prefix) and at the International Service for the Acquisition of Agri-Biotech Applications (isaaa.org/gmap-provaldatabase/default.asp, which can be accessed using the www prefix).

Gene Silencing

In some embodiments, the stacked trait may be in the form of silencing of one or more polynucleotides of interest resulting in suppression of one or more target pest polypeptides. In some embodiments, the silencing is achieved through the use of a suppression DNA construct.

In some embodiments one or more polynucleotide encoding the polypeptides of the IPD059, IPD098, IPD108 or IPD109 polypeptide or fragments or variants thereof may be stacked with one or more polynucleotides encoding one or more polypeptides having insecticidal activity or agronomic traits as set forth supra and optionally may further include one or more polynucleotides providing for gene silencing of one or more target polynucleotides as discussed infra.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The term "suppression" includes lower, reduce, decline, decrease, inhibit, eliminate and prevent. "Silencing" or "gene silencing" does not specify mechanism and is inclusive, and not limited to, anti-sense, cosuppression, viral-suppression, hairpin suppression, stem-loop suppression, RNAi-based approaches and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50% or any integer between 51% and 100% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target protein.

"Antisense RNA" refers to an RNA transcript that is complementary to all or part of a target primary transcript or mRNA and that blocks the expression of a target isolated nucleic acid fragment. The complementarity of an antisense RNA may be with any part of the specific gene transcript, i.e., at the 5' non-coding sequence, 3' non-coding sequence, introns or the coding sequence.

"Cosuppression" refers to the production of sense RNA transcripts capable of suppressing the expression of the target protein. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see, Vaucheret, et al., (1998) *Plant J.* 16:651-659 and Gura, (2000) *Nature* 404:804-808).

Another variation describes the use of plant viral sequences to direct the suppression of proximal mRNA encoding sequences (PCT Publication WO 1998/36083).

Recent work has described the use of "hairpin" structures that incorporate all or part, of an mRNA encoding sequence in a complementary orientation that results in a potential "stem-loop" structure for the expressed RNA (PCT Publication WO 1999/53050). In this case the stem is formed by polynucleotides corresponding to the gene of interest inserted in either sense or anti-sense orientation with respect to the promoter and the loop is formed by some polynucleotides of the gene of interest, which do not have a complement in the construct. This increases the frequency of cosuppression or silencing in the recovered transgenic plants. For review of hairpin suppression, see, Wesley, et al., (2003) Methods in Molecular Biology, Plant Functional Genomics: Methods and Protocols 236:273-286.

A construct where the stem is formed by at least 30 nucleotides from a gene to be suppressed and the loop is formed by a random nucleotide sequence has also effectively been used for suppression (PCT Publication WO 1999/61632).

The use of poly-T and poly-A sequences to generate the stem in the stem-loop structure has also been described (PCT Publication WO 2002/00894).

Yet another variation includes using synthetic repeats to promote formation of a stem in the stem-loop structure. Transgenic organisms prepared with such recombinant DNA fragments have been shown to have reduced levels of the protein encoded by the nucleotide fragment forming the loop as described in PCT Publication WO 2002/00904.

RNA interference refers to the process of sequence-specific post-transcriptional gene silencing in animals mediated by short interfering RNAs (siRNAs) (Fire, et al., (1998) *Nature* 391:806). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire, et al., (1999) *Trends Genet.* 15:358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease Ill enzyme referred to as dicer. Dicer is involved in the processing of the dsRNA into short pieces of dsRNA known as short interfering RNAs (siRNAs) (Berstein, et al., (2001) *Nature* 409:363). Short interfering RNAs derived from dicer activity are typically about 21 to about 23 nucleotides in length and comprise about 19 base pair duplexes (Elbashir, et al., (2001) *Genes Dev.* 15:188). Dicer has also been implicated in the excision of 21- and 22-nucleotide small temporal RNAs (stRNAs) from precursor RNA of conserved structure that are implicated in translational control (Hutvagner, et al., (2001) *Science* 293: 834). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex (Elbashir, et al., (2001) *Genes Dev.* 15:188). In addition, RNA interference can also involve small RNA (e.g., miRNA) mediated gene silencing, presumably through cellular mechanisms that regulate chromatin structure and thereby prevent transcription of target gene sequences (see, e.g., Allshire, (2002) *Science* 297:1818-1819; Volpe, et al., (2002) *Science* 297: 1833-1837; Jenuwein, (2002) *Science* 297:2215-2218 and Hall, et al., (2002) *Science* 297:2232-2237). As such, miRNA molecules of the disclosure can be used to mediate gene silencing via interaction with RNA transcripts or alternately by interaction with particular gene sequences, wherein such interaction results in gene silencing either at the transcriptional or post-transcriptional level.

Methods and compositions are further provided which allow for an increase in RNAi produced from the silencing element. In such embodiments, the methods and compositions employ a first polynucleotide comprising a silencing element for a target pest sequence operably linked to a promoter active in the plant cell; and, a second polynucleotide comprising a suppressor enhancer element comprising the target pest sequence or an active variant or fragment thereof operably linked to a promoter active in the plant cell. The combined expression of the silencing element with suppressor enhancer element leads to an increased amplification of the inhibitory RNA produced from the silencing element over that achievable with only the expression of the silencing element alone. In addition to the increased amplification of the specific RNAi species itself, the methods and compositions further allow for the production of a diverse population of RNAi species that can enhance the effectiveness of disrupting target gene expression. As such, when the suppressor enhancer element is expressed in a plant cell in combination with the silencing element, the methods and composition can allow for the systemic production of RNAi throughout the plant; the production of greater amounts of RNAi than would be observed with just the silencing element construct alone; and, the improved loading of RNAi into the phloem of the plant, thus providing better control of phloem feeding insects by an RNAi approach. Thus, the various methods and compositions provide improved methods for the delivery of inhibitory RNA to the target organism. See, for example, US Patent Application Publication 2009/0188008.

As used herein, a "suppressor enhancer element" comprises a polynucleotide comprising the target sequence to be suppressed or an active fragment or variant thereof. It is recognized that the suppressor enhancer element need not be identical to the target sequence, but rather, the suppressor enhancer element can comprise a variant of the target sequence, so long as the suppressor enhancer element has sufficient sequence identity to the target sequence to allow for an increased level of the RNAi produced by the silencing element over that achievable with only the expression of the silencing element. Similarly, the suppressor enhancer element can comprise a fragment of the target sequence, wherein the fragment is of sufficient length to allow for an increased level of the RNAi produced by the silencing element over that achievable with only the expression of the silencing element.

It is recognized that multiple suppressor enhancer elements from the same target sequence or from different target sequences or from different regions of the same target sequence can be employed. For example, the suppressor enhancer elements employed can comprise fragments of the target sequence derived from different region of the target sequence (i.e., from the 3'UTR, coding sequence, intron, and/or 5'UTR). Further, the suppressor enhancer element can be contained in an expression cassette, as described elsewhere herein, and in specific embodiments, the suppressor enhancer element is on the same or on a different DNA vector or construct as the silencing element. The suppressor enhancer element can be operably linked to a promoter as disclosed herein. It is recognized that the suppressor enhancer element can be expressed constitutively or alternatively, it may be produced in a stage-specific manner employing the various inducible or tissue-preferred or developmentally regulated promoters that are discussed elsewhere herein.

In specific embodiments, employing both a silencing element and the suppressor enhancer element the systemic production of RNAi occurs throughout the entire plant. In further embodiments, the plant or plant parts of the disclosure have an improved loading of RNAi into the phloem of the plant than would be observed with the expression of the silencing element construct alone and, thus provide better control of phloem feeding insects by an RNAi approach. In specific embodiments, the plants, plant parts and plant cells of the disclosure can further be characterized as allowing for the production of a diversity of RNAi species that can enhance the effectiveness of disrupting target gene expression.

In specific embodiments, the combined expression of the silencing element and the suppressor enhancer element increases the concentration of the inhibitory RNA in the plant cell, plant, plant part, plant tissue or phloem over the level that is achieved when the silencing element is expressed alone.

As used herein, an "increased level of inhibitory RNA" comprises any statistically significant increase in the level of RNAi produced in a plant having the combined expression when compared to an appropriate control plant. For example, an increase in the level of RNAi in the plant, plant part or the plant cell can comprise at least about a 1%, about a 1%-5%, about a 5%-10%, about a 10%-20%, about a 20%-30%, about a 30%-40%, about a 40%-50%, about a 50%-60%, about 60-70%, about 70%-80%, about a 80%-90%, about a 90%-100% or greater increase in the level of RNAi in the plant, plant part, plant cell or phloem when compared to an appropriate control.

In other embodiments, the increase in the level of RNAi in the plant, plant part, plant cell or phloem can comprise at least about a 1 fold, about a 1 fold-5 fold, about a 5 fold-10 fold, about a 10 fold-20 fold, about a 20 fold-30 fold, about a 30 fold-40 fold, about a 40 fold-50 fold, about a 50 fold-60 fold, about 60 fold-70 fold, about 70 fold-80 fold, about a 80 fold-90 fold, about a 90 fold-100 fold or greater increase in the level of RNAi in the plant, plant part, plant cell or phloem when compared to an appropriate control. Examples of combined expression of the silencing element with suppressor enhancer element for the control of Stinkbugs and *Lygus* can be found in US Patent Application Publication 2011/0301223 and US Patent Application Publication 2009/0192117.

Some embodiments relate to down-regulation of expression of target genes in insect pest species by interfering ribonucleic acid (RNA) molecules. PCT Publication WO 2007/074405 describes methods of inhibiting expression of target genes in invertebrate pests including Colorado potato beetle. PCT Publication WO 2005/110068 describes methods of inhibiting expression of target genes in invertebrate pests including in particular Western corn rootworm as a means to control insect infestation. Furthermore, PCT Publication WO 2009/091864 describes compositions and methods for the suppression of target genes from insect pest species including pests from the *Lygus* genus. Nucleic acid molecules including RNAi for targeting the vacuolar ATPase H subunit, useful for controlling a coleopteran pest population and infestation as described in US Patent Application Publication 2012/0198586. PCT Publication WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect β-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein and an insect Tbp-1 such as Tat-binding protein. PCT publication WO 2007/035650 describes ribonucleic acid (RNA or double stranded RNA) that inhibits or down regulates the expression of a target gene that encodes Snf7. US Patent Application publication 2011/0054007 describes polynucleotide silencing elements targeting RPS10. US Patent Application publications 2014/0275208 and US2015/0257389 describe polynucleotide silencing elements targeting RyanR and PAT3. PCT Patent Application publication WO2016/138106 describes polynucleotide silencing elements targeting coatomer alpha or gamma. US Patent Application Publications 2012/029750, US 20120297501, and 2012/0322660 describe interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1a Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosy-lation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubuliln Homologous Sequence.

Use in Pesticidal Control

General methods for employing strains comprising a nucleic acid sequence of the embodiments or a variant thereof, in pesticide control or in engineering other organisms as pesticidal agents are known in the art.

Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene expressing the IPD059, IPD098, IPD108 or IPD109 polypeptide and desirably provide for improved protection of the pesticide from environmental degradation and inactivation.

Alternatively, the IPD059, IPD098, IPD108 or IPD109 polypeptide is produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated IPD059, IPD098, IPD108 or IPD109 polypeptides may then be formulated in accordance with conventional techniques for application to the environment hosting a target pest, e.g., soil, water, and foliage of plants. See, for example EPA 0192319, and the references cited therein.

Pesticidal Compositions

In some embodiments, the active ingredients can be applied in the form of compositions and can be applied to the crop area or plant to be treated, simultaneously or in succession, with other compounds. These compounds can be fertilizers, weed killers, Cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise, the formulations may be prepared into edible "baits" or fashioned into pest "traps" to permit feeding or ingestion by a target pest of the pesticidal formulation.

Methods of applying an active ingredient or an agrochemical composition that contains at least one of the IPD059, IPD098, IPD108 or IPD109 polypeptide produced by the bacterial strains include leaf application, seed coating and soil application. The number of applications and the rate of application depend on the intensity of infestation by the corresponding pest.

The composition may be formulated as a powder, dust, pellet, granule, spray, emulsion, colloid, solution or such like, and may be prepared by such conventional means as desiccation, lyophilization, homogenation, extraction, filtration, centrifugation, sedimentation or concentration of a culture of cells comprising the polypeptide. In all such compositions that contain at least one such pesticidal polypeptide, the polypeptide may be present in a concentration of from about 1% to about 99% by weight.

Lepidopteran, Dipteran, Heteropteran, nematode, Hemiptera or Coleopteran pests may be killed or reduced in numbers in a given area by the methods of the disclosure or may be prophylactically applied to an environmental area to prevent infestation by a susceptible pest. Preferably the pest ingests or is contacted with, a pesticidally-effective amount of the polypeptide. "Pesticidally-effective amount" as used herein refers to an amount of the pesticide that is able to bring about death to at least one pest or to noticeably reduce pest growth, feeding or normal physiological development. This amount will vary depending on such factors as, for example, the specific target pests to be controlled, the specific environment, location, plant, crop or agricultural site to be treated, the environmental conditions and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating the bacterial cell, Crystal and/or spore suspension or isolated protein component with the desired agriculturally-acceptable carrier. The compositions may be formulated prior to administration in an appropriate means such as lyophilized, freeze-dried, desiccated or in an aqueous carrier, medium or suitable diluent, such as saline or other buffer. The formulated compositions may be in the form of a dust or granular material or a suspension in oil (vegetable or mineral) or water or oil/water emulsions or as a wettable powder or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference. The plants can also be treated with one or more chemical compositions, including one or more herbicide, insecticides or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, FluaCrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, Indoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2,2-difluorethyl)amino]furan-2(5H)-on; FruitsNeqetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, loxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron Methyl, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethonmethyl, Pirimicarb, Methiocarb; Maize Herbicides: Atrazine, Alachlor, Bromoxynil, Acetochlor, Dicamba, Clopyralid, (S-) Dimethenamid, Glufosinate, Glyphosate, Isoxaflutole, (S-) Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumuron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluoroethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-) Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluoroethyl)amino]furan-2 (5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluoroethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides: Carbofuran organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluoroethyl)amino]furan-2(5H)-on.

In some embodiments, the herbicide is Atrazine, Bromacil, Diuron, Chlorsulfuron, Metsulfuron, Thifensulfuron Methyl, Tribenuron, Acetochlor, Dicamba, Isoxaflutole, Nicosulfuron, Rimsulfuron, Pyrithiobac-sodium, Flumioxazin, Chlorimuron-Ethyl, Metribuzin, Quizalofop, S-metolachlor, Hexazinne or combinations thereof.

In some embodiments, the insecticide is Esfenvalerate, Chlorantraniliprole, Methomyl, Indoxacarb, Oxamyl or combinations thereof.

Pesticidal and Insecticidal Activity

"Pest" includes but is not limited to, insects, fungi, bacteria, nematodes, mites, ticks and the like. Insect pests include insects selected from the orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Lepidoptera and Coleoptera.

Those skilled in the art will recognize that not all compounds are equally effective against all pests. Compounds of the embodiments display activity against insect pests, which may include economically important agronomic, forest, greenhouse, nursery ornamentals, food and fiber, public and animal health, domestic and commercial structure, household and stored product pests.

Larvae of the order Lepidoptera include, but are not limited to, armyworms, cutworms, loopers and heliothines in the family Noctuidae *Spodoptera frugiperda* JE Smith (fall armyworm); *S. exigua* Hübner (beet armyworm); *S. litura* Fabricius (tobacco cutworm, cluster caterpillar); *Mamestra* configurata Walker (bertha armyworm); *M. brassicae* Linnaeus (cabbage moth); *Agrotis ipsilon* Hufnagel (black cutworm); *A. orthogonia* Morrison (western cutworm); *A. subterranea* Fabricius (granulate cutworm); *Alabama argillacea* Hubner (cotton leaf worm); *Trichoplusia ni* Hübner (cabbage looper); *Pseudoplusia includens* Walker (soybean looper); *Anticarsia gemmatalis* Hübner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hübner (American bollworm); *H. zea* Boddie (corn earworm or cotton bollworm); *Melanchra picta* Harris (zebra caterpillar); *Egira* (Xylomyges) curialis Grote (citrus cutworm); borers, casebearers, webworms, coneworms, and skeletonizers from the family Pyralidae *Ostrinia nubilalis* Hübner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hübner (tobacco (cacao) moth); *Galleria mellonella* Linnaeus (greater wax moth); *Herpetogramma licarsisalis* Walker (sod webworm); Homoeosoma electellum Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hübner (Indian meal moth); *Scirpophaga incertulas* Walker (yellow stem borer); *Udea rubigalis* Guenée (celery leaftier); and leafrollers, budworms, seed worms and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana*

Fischer von Rösslerstamm (summer fruit *tortrix* moth); *Cochylis hospes* Walsingham (banded sunflower moth); *Cydia latiferreana* Walsingham (filbertworm); *C. pomonella* Linnaeus (coding moth); *Platynota flavedana* Clemens (variegated leafroller); *P. stultana* Walsingham (omnivorous leafroller); *Lobesia botrana* Denis & Schiffermuller (European grape vine moth); *Spilonota ocellana* Denis & Schiffermuller (eyespotted bud moth); *Endopiza viteana* Clemens (grape berry moth); *Eupoecilia ambiguella* Hubner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guerin-Meneville (Chinese Oak Tussah Moth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hubner (elm spanworm); *Erannis tiliaria* Harris (linden looper); *Euproctis chrysorrhoea* Linnaeus (browntail moth); *Harrisina americana* Guerin-Meneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria* fiscellaria Hulst (Eastern hemlock looper); *L. fiscellaria* lugubrosa Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval and Leconte (Southern cabbageworm); *Sabulodes aegrotata* Guenee (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenee; *Malacosoma* spp. and *Orgyia* spp.

Of interest are larvae and adults of the order Coleoptera including weevils from the families Anthribidae, Bruchidae and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith and Lawrence (northern corn rootworm); *D. undecimpunctata howardi* Barber (southern corn rootworm); *Chaetocnema pulicaria* Melsheimer (corn flea beetle); *Phyllotreta* cruciferae Goeze (Crucifer flea beetle); *Phyllotreta striolata* (stripped flea beetle); *Colaspis brunnea* Fabricius (grape *colaspis*); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Adults and immatures of the order Diptera are of interest, including leafminers *Agromyza parvicornis* Loew (corn blotch leafminer); midges (including, but not limited to: *Contarinia sorghicola* Coquillett (sorghum midge); *Mayetiola destructor* Say (Hessian fly); *Sitodiplosis mosellana* Gehin (wheat midge); *Neolasioptera murtfeldtiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctata* Fallen (wheat bulb fly) and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp. and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds) and other Brachycera, mosquitoes *Aedes* spp.; *Anopheles* spp.; *Culex* spp.; black flies *Prosimulium* spp.; *Simulium* spp.; biting midges, sand flies, sciarids, and other Nematocera.

Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, Issidae and Delphacidae, treehoppers from the family Membracidae, psyllids from the family Psyllidae, whiteflies from the family Aleyrodidae, aphids from the family Aphididae, *phylloxera* from the family Phylloxeridae, mealybugs from the family Pseudococcidae, scales from the families Asterolecanidae, Coccidae, Dactylopiidae, Diaspididae, Eriococcidae Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae and red bugs and cotton stainers from the family Pyrrhocoridae.

Agronomically important members from the order Homoptera further include, but are not limited to: *Acyrthi-*

*siphon pisum* Harris (pea aphid); *Aphis craccivora* Koch (cowpea aphid); *A. fabae* Scopoli (black bean aphid); *A. gossypii* Glover (cotton aphid, melon aphid); A. maidiradicis Forbes (corn root aphid); *A. pomi* De Geer (apple aphid); *A. spiraecola* Patch (spirea aphid); *Aulacorthum solani* Kalten-bach (foxglove aphid); *Chaetosiphon fragaefolii* Cockerell (strawberry aphid); *Diuraphis noxia* Kurdjumov/Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-po-tato aphid, green peach aphid); *Nasonovia ribisnigri* Mosley (lettuce aphid); *Pemphigus* spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Tox-optera aurantii* Boyer de Fonscolombe (black citrus aphid) and *T. citricida* Kirkaldy (brown citrus aphid); *Adelges* spp. (adelgids); *Phylloxera devastatrix* Pergande (pecan *phyllox-era*); *Bemisia tabaci* Gennadius (tobacco whitefly, sweet-potato whitefly); *B. argentifolii* Bellows & Perring (silver-leaf whitefly); *Dialeurodes citri* Ashmead (citrus whitefly); *Trialeurodes abutiloneus* (bandedwinged whitefly) and *T. vaporariorum* Westwood (greenhouse whitefly); *Empoasca fabae* Harris (potato leafhopper); *Laodelphax striatellus* Fallen (smaller brown planthopper); Macro/estes quadri/ineatus Forbes (aster leafhopper); *Nephotettix cinticeps* Uhler (green leafhopper); *N. nigropictus* Stal (rice leafhop-per); *Nilaparvata lugens* Stal (brown planthopper); *Peregri-nus maidis* Ashmead (corn planthopper); *Sogatella furcifera* Horvath (white-backed planthopper); *Sogatodes orizicola* Muir (rice delphacid); *Typhlocyba pomaria* McAtee (white apple leafhopper); *Erythroneoura* spp. (grape leafhoppers); *Magicicada septendecim* Linnaeus (periodical cicada); *Icerya purchasi* Maskell (cottony cushion scale); *Quadras-pidiotus perniciosus* Comstock (San Jose scale); *Planococ-cus citri* Risso (citrus mealybug); Pseudococcus spp. (other mealybug complex); *Cacopsylla pyricola* Foerster (pear psylla); *Trioza diospyri* Ashmead (persimmon *psylla*).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Her-rich-Schsffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); L. *Hesperus* Knight (Western tarnished plant bug); *L. prat-ensis* Linnaeus (common meadow bug); *L. rugulipennis* Poppius (European tarnished plant bug); *Lygocoris pabuli-nus* Linnaeus (common green capsid); *Nezara viridula* Lin-naeus (southern green stink bug); *Oebalus pugnax* Fabricius (rice stink bug); *Oncopeltus fasciatus* Dallas (large milk-weed bug); *Pseudatomoscelis seriatus* Reuter (cotton flea-hopper).

Furthermore, embodiments may be effective against Hemiptera such, *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphno-coris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp. and *Cimicidae* spp.

Also included are adults and larvae of the order Acari (mites) such as *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites impor-tant in human and animal health, i.e., dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabi-lis* Say (American dog tick); *Amblyomma americanum* Lin-naeus (lone star tick) and scab and itch mites in the families Psoroptidae, Pyemotidae and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch and Mulaik (brown recluse spider) and the *Latrodectus mactans* Fabricius (black widow spider) and centipedes in the order Scutigeromorpha such as *Scutigera coleoptrata* Linnaeus (house centipede).

Insect pest of interest include the superfamily of stink bugs and other related insects including but not limited to species belonging to the family Pentatomidae (*Nezara viridula, Halyomorpha halys, Piezodorus guildini, Euschis-tus servus, Acrosternum hilare, Euschistus heros, Euschistus tristigmus, Acrosternum hilare, Dichelops furcatus, Dich-elops melacanthus*, and *Bagrada hilaris* (Bagrada Bug)), the family Plataspidae (*Megacopta cribraria*-Bean plataspid) and the family Cydnidae (*Scaptocoris castanea*-Root stink bug) and Lepidoptera species including but not limited to: diamond-back moth, e.g., *Helicoverpa zea* Boddie; soybean looper, e.g., *Pseudoplusia includens* Walker and velvet bean caterpillar e.g., *Anticarsia gemmatalis* Hubner.

Methods for measuring pesticidal activity are well known in the art. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743, 477, all of which are herein incorporated by reference in their entirety. Generally, the protein is mixed and used in feeding assays. See, for example Marrone, et al., (1985) *J. of Economic Entomology* 78:290-293. Such assays can include contacting plants with one or more pests and deter-mining the plant's ability to survive and/or cause the death of the pests. Nematodes include parasitic nematodes such as root-knot, cyst and lesion nematodes, including *Heterodera* spp., *Meloidogyne* spp. and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode) and *Globodera rostochiensis* and *Globodera pailida* (potato cyst nematodes). Lesion nematodes include *Pratylenchus* spp.

Seed Treatment

To protect and to enhance yield production and trait technologies, seed treatment options can provide additional crop plan flexibility and cost effective control against insects, weeds and diseases. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematocides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in *The Pesticide Manual*: A World Compendium, C. D. S. Tomlin Ed., Published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis* species), *bradyrhizobium* spp. (including one or more of *betae, canariense, elkanii, iriomotense, japonicum*, liaonigense, *pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, *penicillium*, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *trichoderma*, trifloxystrobin, triticonazole and/or zinc. PCNB seed coat refers to EPA Registration Number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

Methods for Killing an Insect Pest and Controlling an Insect Population

In some embodiments methods are provided for killing an insect pest, comprising contacting the insect pest, either simultaneously or sequentially, with an insecticidally-effective amount of a recombinant IPD059, IPD098, IPD108 or IPD109 polypeptide of the disclosure.

In some embodiments, methods are provided for killing an insect pest, comprising contacting the insect pest with an insecticidally-effective amount of a recombinant IPD059, polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75 or SEQ ID NO: 78.

In some embodiments, methods are provided for killing an insect pest, comprising contacting the insect pest with an insecticidally-effective amount of a recombinant IPD098 polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116 or SEQ ID NO: 117.

In some embodiments, methods are provided for killing an insect pest, comprising contacting the insect pest with an insecticidally-effective amount of a recombinant IPD108 polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 131, SEQ ID NO: 132, SEQ ID NO: 133, SEQ ID NO: 134 or SEQ ID NO: 135.

In some embodiments, methods are provided for killing an insect pest, comprising contacting the insect pest with an insecticidally-effective amount of a recombinant IPD109 polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 138.

In some embodiments, methods are provided for controlling an insect pest population, comprising contacting the insect pest population, either simultaneously or sequentially, with an insecticidally-effective amount of a recombinant IPD059, IPD098, IPD108 or IPD109 polypeptide of the disclosure.

In some embodiments, methods are provided for controlling an insect pest population, comprising contacting the insect pest population with an insecticidally-effective amount of a recombinant IPD059 polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75 or SEQ ID NO: 78.

In some embodiments, methods are provided for controlling an insect pest population, comprising contacting the insect pest population with an insecticidally-effective amount of a recombinant IPD098 polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116 or SEQ ID NO: 117.

In some embodiments, methods are provided for controlling an insect pest population, comprising contacting the insect pest population with an insecticidally-effective amount of a recombinant IPD108 polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 131, SEQ ID NO: 132, SEQ ID NO: 133, SEQ ID NO: 134 or SEQ ID NO: 135.

In some embodiments, methods are provided for controlling an insect pest population, comprising contacting the insect pest population with an insecticidally-effective amount of a recombinant IPD109 polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 138.

As used herein, "controlling a pest population" or "controls a pest" refers to any effect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack or deterring the pests from eating the plant.

In some embodiments, methods are provided for controlling an insect pest population resistant to a pesticidal protein, comprising contacting the insect pest population, either simultaneously or sequentially, with an insecticidally-effective amount of a recombinant IPD059, IPD098, IPD108 or IPD109 polypeptide of the disclosure.

In some embodiments, methods are provided for protecting a plant from an insect pest, comprising expressing in the plant or cell thereof at least one recombinant polynucleotide encoding an IPD059, IPD098, IPD108 or IPD109 polypeptide of the disclosure.

In some embodiments, methods are provided for protecting a plant from an insect pest, comprising expressing in the plant or cell thereof a recombinant polynucleotide encoding an IPD059 polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75 or SEQ ID NO: 78.

In some embodiments, methods are provided for protecting a plant from an insect pest, comprising expressing in the plant or cell thereof a recombinant polynucleotide encoding an IPD098 polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116 or SEQ ID NO: 117.

In some embodiments, methods are provided for protecting a plant from an insect pest, comprising expressing in the plant or cell thereof a recombinant polynucleotide encoding an IPD098 polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 118, SEQ ID NO: 119, SEQ ID NO: 120, SEQ ID NO: 121, SEQ ID NO: 122, SEQ ID NO: 123 or SEQ ID NO: 124.

In some embodiments, methods are provided for protecting a plant from an insect pest, comprising expressing in the plant or cell thereof a recombinant polynucleotide encoding an IPD108 polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 131, SEQ ID NO: 132, SEQ ID NO: 133, SEQ ID NO: 134 or SEQ ID NO: 135.

In some embodiments, methods are provided for protecting a plant from an insect pest, comprising expressing in the plant or cell thereof a recombinant polynucleotide encoding an IPD108 polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 136.

In some embodiments, methods are provided for protecting a plant from an insect pest, comprising expressing in the plant or cell thereof a recombinant polynucleotide encoding an IPD109 polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to SEQ ID NO: 138.

Insect Resistance Management (IRM) Strategies Expression of *B. thuringiensis* δ-endotoxins in transgenic corn plants has proven to be an effective means of controlling agriculturally important insect pests (Perlak, et al., 1990; 1993). However, insects have evolved that are resistant to *B. thuringiensis* δ-endotoxins expressed in transgenic plants. Such resistance, should it become widespread, would clearly limit the commercial value of germplasm containing genes encoding such *B. thuringiensis* δ-endotoxins.

One way to increasing the effectiveness of the transgenic insecticides against target pests and contemporaneously reducing the development of insecticide-resistant pests is to use provide non-transgenic (i.e., non-insecticidal protein) refuges (a section of non-insecticidal crops/corn) for use with transgenic crops producing a single insecticidal protein active against target pests. The United States Environmental Protection Agency (epa.gov/oppbppdl/biopesticides/pips/bt_corn_refuge_2006.htm, which can be accessed using the www prefix) publishes the requirements for use with transgenic crops producing a single Bt protein active against target pests. In addition, the National Corn Growers Association, on their website: (ncga.com/insect-resistance-management-fact-sheet-bt-corn, which can be accessed using the www prefix) also provides similar guidance regarding refuge requirements. Due to losses to insects within the refuge area, larger refuges may reduce overall yield.

Another way of increasing the effectiveness of the transgenic insecticides against target pests and contemporaneously reducing the development of insecticide-resistant pests would be to have a repository of insecticidal genes that are effective against groups of insect pests and which manifest their effects through different modes of action.

Expression in a plant of two or more insecticidal compositions toxic to the same insect species, each insecticide being expressed at efficacious levels would be another way to achieve control of the development of resistance. This is based on the principle that evolution of resistance against two separate modes of action is far more unlikely than only one. Roush, for example, outlines two-toxin strategies, also called "pyramiding" or "stacking," for management of insecticidal transgenic crops. (The Royal Society. *Phil.*

*Trans. R. Soc. Lond. B*. (1998) 353:1777-1786). Stacking or pyramiding of two different proteins each effective against the target pests and with little or no cross-resistance can allow for use of a smaller refuge. The US Environmental Protection Agency requires significantly less (generally 5%) structured refuge of non-Bt corn be planted than for single trait products (generally 20%). There are various ways of providing the IRM effects of a refuge, including various geometric planting patterns in the fields and in-bag seed mixtures, as discussed further by Roush.

In some embodiments, the IPD059, IPD098, IPD108, AND IPD109 polypeptides of the disclosure are useful as an insect resistance management strategy in combination (i.e., pyramided) with other pesticidal proteins include but are not limited to Bt toxins, Xenorhabdus sp. or *Photorhabdus* sp. insecticidal proteins, other insecticidally active proteins, and the like.

Provided are methods of controlling Lepidoptera and/or Coleoptera insect infestation(s) in a transgenic plant that promote insect resistance management, comprising expressing in the plant at least two different insecticidal proteins having different modes of action.

In some embodiments, the methods of controlling Lepidoptera and/or Coleoptera insect infestation in a transgenic plant and promoting insect resistance management comprises the presentation of at least one IPD059, IPD098, IPD108 or IPD109 polypeptide insecticidal proteins of the disclosure against insects in the order Lepidoptera and/or Coleoptera.

In some embodiments, the methods of controlling Lepidoptera and/or Coleoptera insect infestation in a transgenic plant and promoting insect resistance management comprise expressing in the transgenic plant an IPD059, IPD098, IPD108 or IPD109 polypeptide of the disclosure and a Cry protein or other insecticidal protein having different modes of action against insects in the order Lepidoptera and/or Coleoptera.

Also provided are methods of reducing likelihood of emergence of Lepidoptera and/or Coleoptera insect resistance to transgenic plants expressing in the plants insecticidal proteins to control the insect species, comprising expression of an IPD059, IPD098, IPD108 or IPD109 polypeptide of the disclosure in combination with a second insecticidal protein having different modes of action against the insect species.

Also provided are means for effective Lepidoptera and/or Coleoptera insect resistance management of transgenic plants, comprising co-expressing at high levels in the plants two or more insecticidal proteins toxic to Lepidoptera and/or Coleoptera insects but each exhibiting a different mode of effectuating its killing activity, wherein the two or more insecticidal proteins comprise an IPD059, IPD098, IPD108 or IPD109 polypeptide of the disclosure and a Cry protein.

In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that the IPD059, IPD098, IPD108 or IPD109 polypeptide does not compete with binding sites for Cry proteins in such insects.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with a pest against which the polypeptide has pesticidal activity. In some embodiments, the polypeptide has pesticidal activity against a Lepidopteran, Coleopteran, Dipteran, Hemipteran or nematode pest, and the field is infested with a Lepidopteran, Hemipteran, Coleopteran, Dipteran or nematode pest.

As defined herein, the "yield" of the plant refers to the quality and/or quantity of biomass produced by the plant. "Biomass" as used herein refers to any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

In specific methods, plant yield is increased as a result of improved pest resistance of a plant expressing an IPD059, IPD098, IPD108 or IPD109 polypeptide disclosed herein. Expression of the IPD059, IPD098, IPD108 or IPD109 polypeptide results in a reduced ability of a pest to infest or feed on the plant, thus improving plant yield.

Methods of Processing

Further provided are methods of processing a plant, plant part or seed to obtain a food or feed product from a plant, plant part or seed comprising an IPD059, IPD098, IPD108 or IPD109 polynucleotide. The plants, plant parts or seeds provided herein, can be processed to yield oil, protein products and/or by-products that are derivatives obtained by processing that have commercial value. Non-limiting examples include transgenic seeds comprising a nucleic acid molecule encoding an IPD059, IPD098, IPD108, and IPD109 polypeptide which can be processed to yield soy oil, soy products and/or soy by-products.

"Processing" refers to any physical and chemical methods used to obtain any soy product and includes, but is not limited to, heat conditioning, flaking and grinding, extrusion, solvent extraction or aqueous soaking and extraction of whole or partial seeds.

The following examples are offered by way of illustration and not by way of limitation.

EXPERIMENTALS

Example 1—Insect Feeding Assays

Insecticidal activity bioassay screens were conducted on the clarified and desalted extract from plant tissue described below to evaluate the effects of its proteins on a variety of Lepidoptera species (European corn borer (*Ostrinia nubilalis*), corn earworm (*Helicoverpa zea*), black cutworm (*Agrotis ipsilon*), fall armyworm (*Spodoptera frugiperda*), Soybean looper (*Pseudoplusia includens*) and Velvetbean caterpillar (*Anticarsia gemmatalis*)), and a Coleopteran species (Western corn rootworm (*Diabrotica virgifera*)).

Lepidopteran Assays

Lepidopteran in-vitro feeding assays were conducted on an artificial agar based diet (Southland Products Inc., Lake Village, AR) in 96 well format. The diet (100 μL) was overlaid with clarified and desalted sample (25 μL) and allowed to dry. Control wells were overlaid with 25 μL of 50 mM Tris buffer, pH 8.0. Two to five neonate larvae were placed into each well to feed for 72 to 96 hours at 27° C. The effects of the protein on the larvae were scored for neonate mortality, severity of stunting or no effect. Scores were recorded numerically as dead (3), severely stunted (2) (little or no growth but alive and equivalent to a 1st instar larvae), stunted (1) (growth to second instar but not equivalent to controls), or normal (0) (similar to larvae feeding on diet with only buffer applied). Each sample was subjected to proteinase K and heat treatments which resulted in loss of activity indicating that the sample was proteinaceous in nature. Each sample was assayed on European corn borer (*Ostrinia nubilalis*), corn earworm (*Helicoverpa zea*), black cutworm (*Agrotis ipsilon*), fall armyworm (*Spodoptera frugiperda*), Soybean looper (*Pseudoplusia includens*) and Velvetbean caterpillar (*Anticarsia gemmatalis*).

Coleopteran Assays

Coleopteran in-vitro feeding assays were conducted on an artificial agar based diet (Southland Products Inc., Lake Village, AR) in 96 well format. The diet (75 μL) was overlaid with clarified and desalted sample (25 μL) and allowed to dry. Control wells were overlaid with 25 μL of 50 mM Tris buffer, pH 8.0. Three to six neonate Western corn rootworm (*Diabrotica virgifera*) larvae were placed into each well to feed for 72 hours at 27° C. The effects of the protein on the larvae were scored for neonate mortality, severity of stunting or no effect. Scores were recorded numerically as dead (3), severely stunted (2) (little or no growth but alive and equivalent to a 1st instar larvae), stunted (1) (growth to second instar but not equivalent to controls), or normal (0) (similar to larvae feeding on diet with only buffer applied). Each sample was subjected to proteinase K and heat treatments which resulted in loss of activity indicating that the sample was proteinaceous in nature. Each sample was assayed on Western corn rootworm (*Diabrotica virgifera*).

Example 2—Screening of Plant Extracts for Insecticidal Activity

Insecticidal activities against ECB and WCRW were observed from clarified and desalted plant extracts. Plants were collected and flash frozen in liquid $N_2$ and stored at −80° C. for future use. The frozen sample was removed from storage and ground to a fine powder at liquid $N_2$ temperatures with a Geno/Grinder®2010 Ball Mill (SPEX Sample Prep®, Metuchen, NJ). To extract protein from plant samples, 4 mL of extraction buffer ((50 mM Tris, pH 8.0, 150 mM Potassium Chloride, 2.5 mM EDTA, 1.5% Polyvinylpolypyrrolidone and Complete EDTA Free protease inhibitor tablets (Roche Diagnostics, Germany)) was added to every 1 gram of fresh weight of tissue. The suspension was slightly agitated on a rocker at 4° C. for 15 minutes. The homogenate was clarified by centrifugation at 6000×g for 15 minutes followed by filtration through a Whatman 0.45 pm filter (GE, Piscataway, NJ). Small molecules and contaminating buffer components are removed by desalting into 50 mM Tris, pH 8.0 using 10 mL Zeba™ Spin desalting columns (Thermo Scientific, IL). Bioassay of the desalted supernatant to determine activity was performed as described above. Active plant samples, their insecticidal activities, and polypeptide sequence identifier are listed in Table 1.

TABLE 1

| Species | Plant ID | Insect Activity | Identifier | Polypeptide |
|---|---|---|---|---|
| *Polypodium musifolium* | PS-8568 | ECB | IPD059Aa | SEQ ID NO: 39 |
| *Asplenium nidus* var. *plicatum* | PS-9146 | WCRW | IPD098Aa | SEQ ID NO: 102 |
| *Selaginella moellendorffii* | NY011 | ECB | IPD108Aa | SEQ ID NO: 131 |
| *Selaginella victoriae* | PS-10890 | WCRW | IPD109Aa | SEQ ID NO: 138 |

Example 3—Isolation and Identification of the IPD059Aa Polypeptide

Insecticidal activity against European corn borer ((ECB) (*Ostrinia nubilalis*)) was observed from a clarified and desalted extraction from *Polypodium musifolium* (PS-8568) plant tissue. This insecticidal activity exhibited heat and protease sensitivity indicating proteinaceous nature.

*Polypodium musifolium* (PS-8568) plant tissue was removed from storage at −80° C. and ground to a fine powder at liquid Nitrogen temperatures with a Geno/Grinder® 2010 Ball Mill (SPEX Sample Prep®, Metuchen, NJ). The protein was extracted from the plant tissue by adding extraction buffer ((50 mM Tris, pH 8.0, 150 mM Potassium Chloride, 2.5 mM EDTA, 1.5% Polyvinylpolypyrrolidone and Complete EDTA Free protease inhibitor tablets (Roche Diagnostics, Germany)) at a ratio of four mL per every one gram of fresh weight of tissue. The sample was kept in suspension by light agitation on a platform rocker at 4° C. for 15 minutes. The homogenate was clarified by centrifugation at 6000×g for 15 minutes followed by filtration through a Whatman 0.45 pm filter (GE Healthcare, Piscataway, NJ). PS-8568 was desalted into 50 mM Tris, pH 8.0 using 10 mL Zeba™ Spin desalting columns (Thermo Scientific, IL) before loading onto a 5 mL HiTrap™Q-FF column (GE Healthcare, Piscataway, NJ) that was equilibrated in the same buffer. A linear 30 column volume gradient from 0.0 M to 0.6 M NaCl in 50 mM Tris, pH 8.0 was used to elute bound protein. The eluted fractions and flow-through were assayed against ECB in the bioassay described above. Activity against ECB was detected from the flow-through fraction that did not bind to the resin. The flow-through fractions were pooled and buffer exchanged on a 10 mL Zeba™ Spin desalting column (Thermo Scientific, IL) into 50 mM Sodium Formate, pH 4.4 and loaded onto a 1 mL Mono S® column (GE Healthcare) equilibrated in the same buffer. A 70 column volume linear gradient from 0% to 80% elution buffer (50 mM Sodium Formate pH 4.4, 1.0 M NaCl) was run and 1 mL fractions of eluted protein were collected. The eluted protein fractions were bioassayed as previously described and ECB activity was detected in fractions eluting at ~3.8-8.2 mS/cm² conductivity. The active Mono S® fractions were pooled, concentrated on a 10 kD MWCO filter (Millipore, MA) and loaded onto a Superdex™ 75 10/300 GL™ column (GE Healthcare, Piscataway, NJ) as a polishing step. An isocratic gradient with 50 mM Tris, pH 8.0 was applied and the 0.5 mL eluted fractions assayed against ECB. Based on LDS-PAGE, the active fraction contained one protein band at approximately 19 kDa and was designated as IPD059Aa (SEQ ID NO: 39).

Protein identification was performed by Mass Spectrometry (MS) analysis after protein digestion with trypsin. Proteins for MS identification were obtained after running the sample on an LDS-PAGE gel stained with Coomassie™

Brilliant Blue G-250 Stain. The band of interest were excised from the gel, de-stained, reduced with dithiothreitol and then alkylated with Iodoacetamide. Following overnight digestion with trypsin, liquid chromatography-tandem mass spectrometry (LC-MSMS) analysis for tryptically-digested peptides was conducted using electrospray ion source on a QToF Premiere™ mass spectrometer (Waters®, Milford, MA) coupled with a NanoAcquity™ nano-LC system (Waters®, Milford, MA) with a gradient from 2% acetonitrile, 0.1% formic acid to 60% acetonitrile, 0.1% formic acid.

The resulting LCMS data were analyzed using Protein Lynx Global Server (Waters®, Milford, MA) to generate DeNovo sequence data. The amino acid sequences were BLAST™ (Basic Local Alignment Search Tool; Altschul, et al., (1993) *J. Mol. Biol.* 215:403-410; see also ncbi.nlm.nih-.gov/BLAST/, which can be accessed using the www prefix) searched against public and DUPONT-PIONEER internal databases that included plant protein sequences. Amino acid sequences were aligned with proteins in a proprietary DUPONT-PIONEER plant protein database.

The N-terminal sequence of the protein was determined by Edman Degradation sequencing on a Procise® 494 protein sequencer (Thermo Scientific, Waltham, MA). A protein sequence was also identified having an N-terminal deletion of residues 1-28 of IPD059Aa (SEQ ID NO: 39) starting at the Aspartic Acid at position 29 and the resulting polypeptide was designated as IPD059AaTR1 (SEQ ID NO: 78).

Example 4—Transcriptomic Sequencing of *Polypodium musifolium, Asplenium Nidus* var. *plicatum, Selaginella Moellendorffii* and *Selaginella victoriae* and Cloning of cDNAs Transcriptomes for Polypodium musifolium, (Id. #PS-8568), Asplenium nidus var. plicatum (Id. #PS-9146), Selaginella moellendorffii (Id. #NYO11) and *Selaginella victoriae*, (Id. #PS-10890) were prepared as follows. Total RNA was isolated from frozen tissues by use of a RNeasy® kit (Qiagen®) for total RNA isolation. Sequencing libraries from the resulting total RNA were prepared using the TruSeq™ mRNA-Seq kit and protocol from Illumina®, Inc. (San Diego, CA). Briefly, mRNAs were isolated via attachment to oligo(dT) beads, fragmented to a mean size of 180 nt, reverse transcribed into cDNA by random hexamer prime, end repaired, 3′ A-tailed, and ligated with Illumina® indexed TruSeq™ adapters. Ligated cDNA fragments were PCR amplified using Illumina® TruSeq™ primers and purified PCR products were checked for quality and quantity on the Agilent Bioanalyzer® DNA 7500 chip. Post quality and quantity assessment, 100 ng of the transcript library was normalized by treatment with Duplex Specific Nuclease (DSN) (Evrogen®, Moscow, Russia). Normalization was accomplished by addition of 200 mM Hepes buffer, followed by heat denaturation and 5 hour anneal at 68° C. The annealed library was treated with 2 µL of DSN enzyme for 25 minutes, purified by Qiagen® MinElute® columns according to manufacturer protocols, and amplified 12 cycles using Illumina® adapter specific primers. Final products were purified with Ampure® XP beads (Beckman Genomics, Danvers, MA) and checked for quality and quantity on the Agilent Bioanalyzer® DNA 7500 chip.

Normalized transcript libraries were sequenced according to manufacturer protocols on the Illumina® Genome Analyzer IIx. Each library was hybridized to two flowcell lanes and amplified, blocked, linearized and primer hybridized using the Illumina clonal cluster generation process on cBot®. Sequencing was completed on the Genome Analyzer IIx, generating sixty million 75 bp paired end reads per normalized library.

Example 5—Cloning cDNA Encoding IPD059Aa

Peptide sequences identified for IPD059Aa (SEQ ID NO: 39) by LCMS sequencing (described in Example 2) were searched against the protein sequences predicted by open reading frames (ORFs) from the internal transcriptome for PS-8568 assemblies. The peptides gave a perfect match to a transcript corresponding to the IPD059Aa polypeptide (SEQ ID NO: 39). The transcript sequences were used to design the primers of SEQ ID NO: 139 and SEQ ID NO: 140, which were used to clone the IPD059Aa cDNA sequence (SEQ ID NO: 1) using the HF Advantage® PCR kit (Clontech™, 1290 Terra *Bella* Ave. Mountain View, CA 94043) and the cDNA prepared from the total RNA from Polypodium al., (1993) *J. Mol. Biol.* 215:403-410; see also ncbi.nlm. nih.gov/BLAST/, which can be accessed using the www prefix) searches under default parameters for similarity to sequences. The polynucleotide sequence for IPD059Aa (SEQ ID NO: 1) was analyzed. One distant homolog with 49% identity to the IPD059Aa polypeptide (SEQ ID NO: 39) was found in the NCBI database from *Ceratopteris richardi* (NOl BAC55101) and designated IPD059Fa (SEQ ID NO: 76).

Gene identities conducted by BLAST™ in a DUPONT PIONEER internal transcriptomes database of ferns and other primitive plants identified multiple homologs for IPD059Aa (SEQ ID NO: 39). The IPDS59Aa homologs and the organism they were identified from are shown in Table 2.

TABLE 2

| Identifier | Source | Organism | DNA Seq | AA Seq |
|---|---|---|---|---|
| IPD059Ab | PS-12341 | *Polypodium formosanum 'Cristatum'* | SEQ ID NO: 2 | SEQ ID NO: 40 |
| IPD059Ac | PS-12341 | *Polypodium formosanum 'Cristatum'* | SEQ ID NO: 3 | SEQ ID NO: 41 |
| IPD059Ad | PS-12341 | *Polypodium formosanum 'Cristatum'* | SEQ ID NO: 4 | SEQ ID NO: 42 |
| IPD059Ae | PS-12341 | *Polypodium formosanum 'Cristatum'* | SEQ ID NO: 5 | SEQ ID NO: 43 |
| IPD059Af | PS-12341 | *Polypodium formosanum 'Cristatum'* | SEQ ID NO: 6 | SEQ ID NO: 44 |
| IPD059Ag | PS-12341 | *Polypodium formosanum 'Cristatum'* | SEQ ID NO: 7 | SEQ ID NO: 45 |
| IPD059Ah | PS-12341 | *Polypodium formosanum 'Cristatum'* | SEQ ID NO: 8 | SEQ ID NO: 46 |
| IPD059Ca | PS-9319CF | *Polypodium punctatum 'Serratum'* | SEQ ID NO: 9 | SEQ ID NO: 47 |
| IPD059Cb | PS-9319CF | *Polypodium punctatum 'Serratum'* | SEQ ID NO: 10 | SEQ ID NO: 48 |
| IPD059Cc | PS-7897CF | *Colysis wrightii* (Hook.) Ching | SEQ ID NO: 11 | SEQ ID NO: 49 |
| IPD059Da | PS-9146 | *Asplenium nidus* var. *plicatum* | SEQ ID NO: 12 | SEQ ID NO: 50 |
| IPD059Db | PS-9146 | *Asplenium nidus* var. *plicatum* | SEQ ID NO: 13 | SEQ ID NO: 51 |
| IPD059Ea | PS-9146 | *Asplenium nidus* var. *plicatum* | SEQ ID NO: 14 | SEQ ID NO: 52 |
| IPD059Eb | PS-9146 | *Asplenium nidus* var. *plicatum* | SEQ ID NO: 15 | SEQ ID NO: 53 |
| IPD059Ec | PS-13327 | *Polystichium tsus-simense* | SEQ ID NO: 16 | SEQ ID NO: 54 |
| IPD059Ed | PS-13327 | *Polystichium tsus-simense* | SEQ ID NO: 17 | SEQ ID NO: 55 |
| IPD059Ee | PS-9146 | *Asplenium nidus* var. *plicatum* | SEQ ID NO: 18 | SEQ ID NO: 56 |
| IPD059Ef | PS-9146 | *Asplenium nidus* var. *plicatum* | SEQ ID NO: 19 | SEQ ID NO: 57 |
| IPD059Eg | PS-9146 | *Asplenium nidus* var. *plicatum* | SEQ ID NO: 20 | SEQ ID NO: 58 |
| IPD059Eh | PS-7897CF | *Colysis wrightii* (Hook.) Ching | SEQ ID NO: 21 | SEQ ID NO: 59 |
| IPD059Ei | PS-9146 | *Asplenium nidus* var. *plicatum* | SEQ ID NO: 22 | SEQ ID NO: 60 |
| IPD059Ej | NY009 | *Phyllitis scolopendium 'Angustifolia'* | SEQ ID NO: 23 | SEQ ID NO: 61 |
| IPD059Ek | PS-7897CF | *Colysis wrightii* (Hook.) Ching | SEQ ID NO: 24 | SEQ ID NO: 62 |
| IPD059El | NY012 | *Asplenium trichomanes* | SEQ ID NO: 25 | SEQ ID NO: 63 |
| IPD059Em | NY009 | *Phyllitis scolopendium 'Angustifolia'* | SEQ ID NO: 26 | SEQ ID NO: 64 |
| IPD059En | NY009 | *Phyllitis scolopendium 'Angustifolia'* | SEQ ID NO: 27 | SEQ ID NO: 65 |
| IPD059Eo | NY009 | *Phyllitis scolopendium 'Angustifolia'* | SEQ ID NO: 28 | SEQ ID NO: 66 |
| IPD059Ep | NY009 | *Phyllitis scolopendium 'Angustifolia'* | SEQ ID NO: 29 | SEQ ID NO: 67 |
| IPD059Eq | NY009 | *Phyllitis scolopendium 'Angustifolia'* | SEQ ID NO: 30 | SEQ ID NO: 68 |
| IPD059Er | NY009 | *Phyllitis scolopendium 'Angustifolia'* | SEQ ID NO: 31 | SEQ ID NO: 69 |
| IPD059Es | NY009 | *Phyllitis scolopendium 'Angustifolia'* | SEQ ID NO: 32 | SEQ ID NO: 70 |
| IPD059Et | NY009 | *Phyllitis scolopendium 'Angustifolia'* | SEQ ID NO: 33 | SEQ ID NO: 71 |
| IPD059Eu | NY009 | *Phyllitis scolopendium 'Angustifolia'* | SEQ ID NO: 34 | SEQ ID NO: 72 |
| IPD059Ev | NY012 | *Asplenium trichomanes* | SEQ ID NO: 35 | SEQ ID NO: 73 |
| IPD059Ew | NY012 | *Asplenium trichomanes* | SEQ ID NO: 36 | SEQ ID NO: 74 |
| IPD059Ex | NY012 | *Asplenium trichomanes* | SEQ ID NO: 37 | SEQ ID NO: 75 | musifolium using the SuperScript® II kit (Thermo Fischer Scientific, Waltham, MA) as the template. PCR products were cloned into a pGEM®-T Vector using the pGEM®-T easy kit (Promega, Madison, WI). The clones were sequenced and the IPD059Aa cDNA sequence is shown as SEQ ID NO: 1 and the encoded IPD059Aa polypeptide sequence as SEQ ID NO: 39. Using the DNA of SEQ ID NO: 1 as a template, a sequence with the protein start site at Asp29 was created using the primers of SEQ ID NO: 141 and SEQ ID NO: 140

Example 6—Identification of IPD059Aa Homologs

Gene identities may be determined by conducting BLAST™ (Basic Local Alignment Search Tool; Altschul, et cDNA was generated from source organisms with identified homologs from the internal database by reverse transcription from total RNA. Homologs were PCR amplified from their respective cDNAs using primers designed to the coding sequences of each homolog and subcloned into a plant transient vector containing the DMMV promoter. Cloned PCR products were confirmed by sequencing.

A matrix table of amino acid sequence identity of the IPD059Aa (SEQ ID NO: 39) homologs as calculated using the Needleman-Wunsch algorithm, as implemented in the Needle program (EMBOSS tool suite) is shown in Table 3A-3C. The void parts of the table are not shown.

TABLE 3A

|  | IPD059Ab SEQ ID NO: 40 | IPD059Ac SEQ ID NO: 41 | IPD059Ad SEQ ID NO: 42 | IPD059Ae SEQ ID NO: 43 | IPD059Af SEQ ID NO: 44 | IPD059Ag SEQ ID NO: 45 | IPD059Ah SEQ ID NO: 46 | IPD059Ca SEQ ID NO: 47 |
|---|---|---|---|---|---|---|---|---|
| IPD059Aa | 94.2 | 93.7 | 93.2 | 69.3 | 69.8 | 69.8 | 70.4 | 74 |
| IPD059Ab | — | 99.5 | 98.9 | 73.2 | 73.7 | 73.7 | 74.2 | 74.6 |
| IPD059Ac | — | — | 99.5 | 73.2 | 73.7 | 73.7 | 74.2 | 74.1 |
| IPD059Ad | — | — | — | 73.7 | 73.2 | 74.2 | 73.7 | 74.1 |
| IPD059Ae | — | — | — | — | 97.9 | 99.3 | 98.6 | 58.4 |
| IPD059Af | — | — | — | — | — | 98.6 | 99.3 | 58.4 |
| IPD059Ag | — | — | — | — | — | — | 99.3 | 58.9 |
| IPD059Ah | — | — | — | — | — | — | — | 58.9 |
| IPD059Ca | — | — | — | — | — | — | — | — |
| IPD059Cb | — | — | — | — | — | — | — | — |
| IPD059Cc | — | — | — | — | — | — | — | — |
| IPD059Da | — | — | — | — | — | — | — | — |

|  | IPD059Cb SEQ ID NO: 48 | IPD059Cc SEQ ID NO: 49 | IPD059Da SEQ ID NO: 50 | IPD059Db SEQ ID NO: 51 |
|---|---|---|---|---|
| IPD059Aa | 73.5 | 73.8 | 60.4 | 60.4 |
| IPD059Ab | 74.1 | 73.9 | 59.4 | 62.2 |
| IPD059Ac | 73.7 | 74.4 | 59.4 | 61 |
| IPD059Ad | 73.7 | 74.4 | 59.4 | 61 |
| IPD059Ae | 58.4 | 57.5 | 50 | 50 |
| IPD059Af | 58.4 | 57.5 | 50 | 50 |
| IPD059Ag | 58.9 | 58 | 50.5 | 50.5 |
| IPD059Ah | 58.9 | 58 | 50.5 | 50.5 |
| IPD059Ca | 99.5 | 81.7 | 61 | 61.5 |
| IPD059Cb | — | 81.2 | 59.8 | 59.8 |
| IPD059Cc | — | — | 63.7 | 64.2 |
| IPD059Da | — | — | — | 99.5 |

TABLE 3B

|  | IPD059Ea SEQ ID NO: 52 | IPD059Eb SEQ ID NO: 53 | IPD059Ec SEQ ID NO: 54 | IPD059Ed SEQ ID NO: 55 | IPD059Ee SEQ ID NO: 56 | IPD059Ef SEQ ID NO: 57 | IPD059Eg SEQ ID NO: 58 | IPD059Eh SEQ ID NO: 59 |
|---|---|---|---|---|---|---|---|---|
| IPD059Aa | 57.7 | 57.7 | 56.8 | 57.3 | 60.8 | 59.3 | 58.8 | 58.3 |
| IPD059Ab | 56.7 | 58.9 | 58.2 | 58.7 | 59.6 | 59 | 58.5 | 56.6 |
| IPD059Ac | 56.7 | 58.9 | 58.2 | 58.7 | 59.6 | 60.5 | 60 | 57.1 |
| IPD059Ad | 57.1 | 59.4 | 58.2 | 58.7 | 59.6 | 60.5 | 60 | 57.1 |
| IPD059Ae | 47.4 | 47.4 | 46.6 | 47.1 | 46.7 | 46.5 | 46 | 41.5 |
| IPD059Af | 46.9 | 46.9 | 46.6 | 47.1 | 46.7 | 46.5 | 46 | 40.9 |
| IPD059Ag | 48 | 48 | 47.1 | 47.6 | 47.2 | 47 | 46.5 | 41.5 |
| IPD059Ah | 47.4 | 47.4 | 47.1 | 47.6 | 47.2 | 47 | 46.5 | 41.5 |
| IPD059Ca | 59 | 59.5 | 59.1 | 59.6 | 61.4 | 59.9 | 59.4 | 57.4 |
| IPD059Cb | 59 | 59.5 | 59.1 | 59.6 | 60.9 | 59.4 | 58.9 | 56.9 |
| IPD059Cc | 61.6 | 62.1 | 59.4 | 59.9 | 62.4 | 61 | 60.5 | 56.7 |
| IPD059Da | 81.8 | 81.2 | 79.2 | 80.2 | 76.8 | 77.3 | 76.8 | 46.7 |
| IPD059Db | 81.2 | 81.8 | 79.7 | 80.7 | 77.3 | 77.8 | 77.3 | 46.7 |
| IPD059Ea | — | 99.5 | 74 | 75 | 70.7 | 70.7 | 70.2 | 43.7 |
| IPD059Eb | — | — | 74.5 | 75.5 | 71.2 | 71.2 | 70.7 | 43.7 |
| IPD059Ec | — | — | — | 98.9 | 76.3 | 75.9 | 75.4 | 47.2 |
| IPD059Ed | — | — | — | — | 77.3 | 76.9 | 76.4 | 47.7 |
| IPD059Ee | — | — | — | — | — | 99 | 98.5 | 48.5 |
| IPD059Ef | — | — | — | — | — | — | 99.5 | 48.3 |
| IPD059Eg | — | — | — | — | — | — | — | 47.8 |

TABLE 3B-continued

| | | | | | | | | |
|---|---|---|---|---|---|---|---|---|
| IPD059Eh | — | — | — | — | — | — | — | — |
| IPD059Ei | — | — | — | — | — | — | — | — |
| IPD059Ej | — | — | — | — | — | — | — | — |
| IPD059Ek | — | — | — | — | — | — | — | — |

| | IPD059Ei SEQ ID NO: 60 | IPD059Ej SEQ ID NO: 61 | IPD059Ek SEQ ID NO: 62 | IPD059El SEQ ID NO: 63 |
|---|---|---|---|---|
| IPD059Aa | 58.4 | 59.2 | 58.9 | 56.6 |
| IPD059Ab | 56.9 | 60.7 | 57.1 | 57.8 |
| IPD059Ac | 56.9 | 61.2 | 57.7 | 58.3 |
| IPD059Ad | 57.4 | 60.7 | 57.7 | 58.3 |
| IPD059Ae | 48 | 49.5 | 42 | 45.7 |
| IPD059Af | 47.4 | 49.5 | 41.5 | 45.7 |
| IPD059Ag | 48.5 | 49.5 | 42 | 46.2 |
| IPD059Ah | 48 | 50 | 42 | 46.2 |
| IPD059Ca | 59.5 | 59.1 | 57.8 | 57.8 |
| IPD059Cb | 58.4 | 59.1 | 57.4 | 57.8 |
| IPD059Cc | 61.3 | 58.9 | 57.1 | 59.9 |
| IPD059Da | 90.6 | 76.2 | 47.2 | 73.5 |
| IPD059Db | 90.1 | 76.7 | 47.2 | 74 |
| IPD059Ea | 91.1 | 72.5 | 44.2 | 69.4 |
| IPD059Eb | 90.6 | 73.1 | 44.2 | 69.9 |
| IPD059Ec | 78.1 | 78.6 | 47.7 | 73.8 |
| IPD059Ed | 79.2 | 79.7 | 48.2 | 74.9 |
| IPD059Ee | 75.3 | 77.3 | 49 | 77 |
| IPD059Ef | 75.8 | 76.9 | 48.8 | 76.6 |
| IPD059Eg | 75.3 | 76.4 | 48.3 | 76.1 |
| IPD059Eh | 44.2 | 48.2 | 99.4 | 47.5 |
| IPD059Ei | — | 76.2 | 44.7 | 73.5 |
| IPD059Ej | — | — | 48.7 | 80.6 |
| IPD059Ek | — | — | — | 48 |

TABLE 3C

| | IPD059Em SEQ ID NO: 64 | IPD059En SEQ ID NO: 65 | IPD059Eo SEQ ID NO: 66 | IPD059Ep SEQ ID NO: 67 | IPD059Eq SEQ ID NO: 68 | IPD059Er SEQ ID NO: 69 | IPD059Es SEQ ID NO: 70 | IPD059Et SEQ ID NO: 71 |
|---|---|---|---|---|---|---|---|---|
| IPD059Aa | 49.5 | 49.1 | 48.6 | 49.1 | 49.5 | 49.1 | 50.7 | 49.3 |
| IPD059Ab | 50.5 | 50 | 49.5 | 50 | 50.5 | 50 | 50.9 | 49.5 |
| IPD059Ac | 50.7 | 50.2 | 49.8 | 50.2 | 50.7 | 50.2 | 50.9 | 49.5 |
| IPD059Ad | 50.7 | 50.2 | 49.8 | 50.2 | 50.7 | 50.2 | 50.9 | 49.5 |
| IPD059Ae | 40.8 | 40.4 | 39.9 | 40.4 | 40.8 | 40.4 | 40.8 | 40.7 |
| IPD059Af | 40.8 | 40.4 | 39.9 | 40.4 | 40.8 | 40.4 | 40.8 | 40.7 |
| IPD059Ag | 41.3 | 40.8 | 40.4 | 40.8 | 41.3 | 40.8 | 41.3 | 41.1 |
| IPD059Ah | 41.3 | 40.8 | 40.4 | 40.8 | 41.3 | 40.8 | 41.3 | 41.1 |
| IPD059Ca | 51.4 | 50.9 | 50.5 | 50.9 | 51.4 | 50.9 | 50.7 | 50.5 |
| IPD059Cb | 51.4 | 50.9 | 50.5 | 50.9 | 51.4 | 50.9 | 50.7 | 50.5 |
| IPD059Cc | 52.8 | 52.3 | 51.9 | 52.3 | 52.8 | 52.3 | 54.2 | 54 |
| IPD059Da | 50 | 49.5 | 49.1 | 50 | 50.5 | 50 | 50.9 | 51.2 |
| IPD059Db | 50 | 49.5 | 49.1 | 50 | 50.5 | 50 | 50 | 49.8 |
| IPD059Ea | 45.6 | 45.6 | 45.1 | 45.6 | 46 | 46 | 49.3 | 47.2 |
| IPD059Eb | 45.6 | 45.6 | 45.1 | 45.6 | 46 | 46 | 47.4 | 47.7 |
| IPD059Ec | 46.5 | 46 | 46.5 | 46.9 | 46.5 | 46 | 47.4 | 47.7 |
| IPD059Ed | 46.9 | 46.5 | 46.9 | 47.4 | 46.9 | 46.5 | 47.9 | 48.1 |
| IPD059Ee | 49.8 | 49.3 | 49.3 | 50.2 | 50.2 | 49.8 | 50.2 | 50.5 |
| IPD059Ef | 50.5 | 50 | 50 | 50.9 | 50.9 | 50.5 | 51.9 | 52.1 |
| IPD059Eg | 50 | 49.5 | 49.5 | 50.5 | 50.5 | 50 | 51.4 | 51.6 |
| IPD059Eh | 39.6 | 39.2 | 39.6 | 40.1 | 39.6 | 39.2 | 38.7 | 36.8 |
| IPD059Ei | 48.6 | 48.6 | 48.1 | 48.6 | 49.1 | 49.1 | 49.5 | 50.2 |
| IPD059Ej | 46.2 | 45.8 | 45.8 | 48.6 | 48.6 | 48.1 | 49.5 | 48.8 |
| IPD059Ek | 40.1 | 39.6 | 40.1 | 40.6 | 40.1 | 39.6 | 39.2 | 37.3 |
| IPD059El | 46 | 45.6 | 45.1 | 45.6 | 46 | 45.6 | 47.2 | 48.4 |
| IPD059Em | — | 99.5 | 99.1 | 98.6 | 99.1 | 98.6 | 96.7 | 94.8 |
| IPD059En | — | — | 99.5 | 98.1 | 98.6 | 99.1 | 96.2 | 95.3 |
| IPD059Eo | — | — | — | 98.6 | 98.1 | 98.6 | 95.7 | 94.8 |
| IPD059Ep | — | — | — | — | 99.5 | 99.1 | 97.2 | 95.3 |
| IPD059Eq | — | — | — | — | — | 99.5 | 97.6 | 95.8 |
| IPD059Er | — | — | — | — | — | — | 97.2 | 96.2 |
| IPD059Es | — | — | — | — | — | — | — | 98.1 |
| IPD059Et | — | — | — | — | — | — | — | — |

TABLE 3C-continued

| | | | | | | | | |
|---|---|---|---|---|---|---|---|---|
| IPD059Eu | — | — | — | — | — | — | — | — |
| IPD059Ev | — | — | — | — | — | — | — | — |
| IPD059Ew | — | — | — | — | — | — | — | — |

| | IPD059Eu SEQ ID NO: 72 | IPD059Ev SEQ ID NO: 73 | IPD059Ew SEQ ID NO: 74 | IPD059Ex SEQ ID NO: 75 |
|---|---|---|---|---|
| IPD059Aa | 51.6 | 53.1 | 52.9 | 53.8 |
| IPD059Ab | 51.4 | 55.6 | 55.1 | 55.6 |
| IPD059Ac | 51.4 | 56 | 55.6 | 56 |
| IPD059Ad | 51.4 | 56 | 55.6 | 56 |
| IPD059Ae | 42.5 | 44 | 43.5 | 44 |
| IPD059Af | 42.5 | 44 | 43.5 | 44 |
| IPD059Ag | 43 | 44.4 | 44 | 44.4 |
| IPD059Ah | 43 | 44.4 | 44 | 44.4 |
| IPD059Ca | 53.7 | 56.9 | 55.9 | 56.9 |
| IPD059Cb | 53.7 | 56.9 | 55.9 | 56.9 |
| IPD059Cc | 57.2 | 56.9 | 56.4 | 57.3 |
| IPD059Da | 54.9 | 67.1 | 66.7 | 67.6 |
| IPD059Db | 53.5 | 68.6 | 68.1 | 69.1 |
| IPD059Ea | 49.1 | 65.6 | 65.1 | 64.7 |
| IPD059Eb | 49.5 | 65.6 | 65.1 | 64.7 |
| IPD059Ec | 51.9 | 68.6 | 68.6 | 69.6 |
| IPD059Ed | 52.3 | 69.6 | 69.6 | 70.5 |
| IPD059Ee | 53.7 | 67.9 | 67.9 | 68.9 |
| IPD059Ef | 55.3 | 68.4 | 68.4 | 69.4 |
| IPD059Eg | 54.8 | 67.9 | 67.9 | 68.9 |
| IPD059Eh | 39.2 | 42.7 | 42.2 | 42.7 |
| IPD059Ei | 52.1 | 68.6 | 68.1 | 68.1 |
| IPD059Ej | 52.6 | 74.4 | 74 | 75 |
| IPD059Ek | 39.6 | 43.1 | 42.7 | 43.1 |
| IPD059El | 51.6 | 72 | 71.5 | 72.5 |
| IPD059Em | 90.1 | 47.8 | 47.3 | 46.9 |
| IPD059En | 89.6 | 47.3 | 46.9 | 46.4 |
| IPD059Eo | 89.2 | 47.3 | 46.9 | 46.4 |
| IPD059Ep | 90.6 | 49.5 | 49.1 | 48.6 |
| IPD059Eq | 91 | 49.5 | 49.1 | 48.6 |
| IPD059Er | 90.6 | 49.1 | 48.6 | 48.2 |
| IPD059Es | 93.4 | 50.2 | 49.8 | 49.3 |
| IPD059Et | 94.3 | 50.5 | 50 | 49.5 |
| IPD059Eu | — | 52.7 | 52.3 | 52.7 |
| IPD059Ev | — | — | 99 | 98.6 |
| IPD059Ew | — | — | — | 98.6 |

A Phylogenetic tree of the IPD059 homologs is shown in FIG. 1. Amino acid sequence alignments of selected subgroups of the IPD059 homologs are shown in FIG. 2, FIG. 3, and FIG. 4.

Example 7—Transient Expression of IPD059Aa and Homologs in Soybean or Bushbean Leaves and Insect Bioassay To confirm activity of IPD059Aa (SEQ ID NO: 39) the corresponding gene was cloned into a transient expression system under control of the dMMV promoter (Dey, et. al., (1999) *Plant Mol. Biol.* 40:771-782) was utilized. The agro-infiltration method of introducing an *Agrobacterium* cell suspension to plant cells of intact tissues so that reproducible infection and subsequent plant derived transgene expression may be measured or studied is well known in the art (Kapila, et. al., (1997) *Plant Science* 122:101-108). Briefly, excised leaf disks of soybean (*Glycine max*) or intact California Small White (*Phaseolus vulgaris*) variety bush bean, were agro-infiltrated with normalized bacterial cell cultures of test and control strains. After 4 days leaf disks were infested with 4 neonates of European corn borer (*Ostrinia nubialis*) alone. Control leaf discs were generated with *Agrobacterium* containing only a DsRed2 fluorescence marker (Clontech™, 1290 Terra *Bella* Ave. Mountain View, CA 94043) expression vector. Leaf discs from non-infiltrated plants were included as a second control. The consumption of green leaf tissue was scored three days after infestation.

The transiently expressed IPD059Aa (SEQ ID NO: 39), protected leaf discs from consumption by the infested insects while total green tissue consumption was observed for the negative control and untreated tissue (Table 4).

TABLE 4

| | Transient expression | |
|---|---|---|
| Protein expressed | Soy | Bush bean |
| IPD059Aa (SEQ ID NO: 39) | 6.2 (++) | 7.8 (+++) |
| dsRED | 2.4 (−) | 1.8 (−) |

| Value | Description |
|---|---|
| 1 | leaf disk is greater than 90% consumed |
| 2 | leaf disk is 70-80% consumed |
| 3 | leaf disk is 60-70% consumed |
| 4 | leaf disk is 50-60% consumed |
| 5 | leaf disk is 40-50% consumed |

TABLE 4-continued

| | |
|---|---|
| 6 | leaf disk is less than 30% consumed |
| 7 | leaf disk is less than 10% consumed |
| 8 | leaf disk has only a few pinholes |
| 9 | leaf disk is untouched by the insect |

The activity spectrums for tested IPD059Aa homologs are summarized in Table 5, where a "+++" indicates an average activity score of <=10% of leaf disc consumed, a "++" indicates an average activity score of 11-50% leaf disc consumed, a "+" indicates an average activity score of 51-70% leaf disc consumed, and a "−" indicates an average activity score of >70% leaf disc consumed.

TABLE 5

| Identifier | Polypeptide | SBL | CEW | FAW | ECB |
|---|---|---|---|---|---|
| IPD059Aa | SEQ ID NO: 39 | − | − | − | +++ |
| IPD059Ab | SEQ ID NO: 40 | − | − | + | +++ |
| IPD059Ac | SEQ ID NO: 41 | − | − | + | +++ |
| IPD059Ad | SEQ ID NO: 42 | − | − | + | +++ |
| IPD059Ae | SEQ ID NO: 43 | − | − | − | − |
| IPD059Af | SEQ ID NO: 44 | − | − | − | − |
| IPD059Ag | SEQ ID NO: 45 | − | − | − | − |
| IPD059Ah | SEQ ID NO: 46 | − | − | − | − |
| IPD059Ca | SEQ ID NO: 47 | − | − | + | +++ |
| IPD059Cb | SEQ ID NO: 48 | − | − | + | +++ |
| IPD059Cc | SEQ ID NO: 49 | − | − | + | +++ |
| IPD059Da | SEQ ID NO: 50 | − | − | + | +++ |
| IPD059Db | SEQ ID NO: 51 | − | − | + | +++ |
| IPD059Ea | SEQ ID NO: 52 | − | − | − | − |
| IPD059Eb | SEQ ID NO: 53 | − | − | − | + |
| IPD059Ec | SEQ ID NO: 54 | − | − | + | +++ |
| IPD059Ed | SEQ ID NO: 55 | − | − | + | +++ |
| IPD059Ee | SEQ ID NO: 56 | − | − | − | + |
| IPD059Ef | SEQ ID NO: 57 | − | − | − | + |
| IPD059Eg | SEQ ID NO: 58 | − | − | − | + |
| IPD059Eh | SEQ ID NO: 59 | − | − | − | − |
| IPD059Ei | SEQ ID NO: 60 | − | − | + | +++ |
| IPD059Ej | SEQ ID NO: 61 | − | − | + | +++ |
| IPD059Ek | SEQ ID NO: 62 | − | − | − | − |
| IPD059El | SEQ ID NO: 63 | − | − | + | +++ |
| IPD059Em | SEQ ID NO: 64 | − | − | + | + |
| IPD059En | SEQ ID NO: 65 | − | − | − | ++ |
| IPD059Eo | SEQ ID NO: 66 | − | − | − | ++ |
| IPD059Ep | SEQ ID NO: 67 | − | − | − | + |
| IPD059Eq | SEQ ID NO: 68 | − | − | − | + |
| IPD059Er | SEQ ID NO: 69 | − | − | − | + |
| IPD059Es | SEQ ID NO: 70 | − | − | + | + |
| IPD059Et | SEQ ID NO: 71 | − | − | − | − |
| IPD059Eu | SEQ ID NO: 72 | − | − | + | +++ |
| IPD059Ev | SEQ ID NO: 73 | − | − | + | +++ |
| IPD059Ew | SEQ ID NO: 74 | − | − | − | + |
| IPD059Ex | SEQ ID NO: 75 | − | − | − | +++ |

Example 8—Isolation and Identification of the IPD098Aa Polypeptide

Insecticidal activity against Western corn rootworm ((WCRW) (*Diabrotica virgifera*)) was observed from a clarified and desalted extraction of Asplenium nidus var. plicatum (PS-9146) plant tissue. This insecticidal activity exhibited heat and protease sensitivity indicating proteinaceous nature.

Asplenium nidus var. plicatum (PS-9146) plant tissue was removed from storage at −80° C. and ground to a fine powder at liquid $N_2$ temperatures with a Geno/Grinder®2010 Ball Mill (SPEX Sample Prep®, Metuchen, NJ). The protein was extracted from the plant tissue by adding extraction buffer ((50 mM Tris, pH 8.0, 150 mM Potassium Chloride, 2.5 mM EDTA, 1.5% Polyvinylpolypyrrolidone and Complete EDTA Free protease inhibitor tablets (Roche Diagnostics, Germany)) at a ratio of 4 mL per 1 gram of fresh weight of tissue. The suspension was gently agitated on a rocker at 4° C. for 15 minutes. The homogenate was clarified by centrifugation at 6000×g for 15 minutes followed by filtration through a Whatman 0.45 pm filter (GE Healthcare, Piscataway, NJ). PS-9146 was desalted into 50 mM Tris, pH 8.0 using a 10 mL Zeba™ Spin desalting columns (Thermo Scientific, IL) and was split into 3 equal volumes. The split supernatants were loaded separately onto a 1 mL HiTrap™ Q-HP column (GE Healthcare, Piscataway, NJ) equilibrated in 50 mM Tris, pH 8.0 and a linear 70 column volume gradient from 0 M to 0.7 M NaCl in 50 mM Tris, pH 8.0 was applied. The unbound and eluted protein fractions were collected and assayed against WCRW in the in-vitro bioassay described above. Activity against WCRW was detected in fractions eluting at approximately 10.2-15.2 $mS/cm^2$. The fractions were pooled and concentrated on a 3 kDa MWCO filter (Pall Life Sciences, Port Washington, NY) and loaded onto a HiLoad™ 16/60 Superdex 200 size exclusion column (GE Healthcare, Piscataway, NJ). An isocratic gradient of 50 mM Tris, pH 8.0 was applied and the eluted 1 mL fractions were assayed against WCRW. The active fractions were combined, diluted to lower the NaCl concentration and injected onto a 1 mL Mono Q® column ((GE Healthcare, Piscataway, NJ) equilibrated in 50 mM Tris, pH 8.0. A 25 column volume linear gradient from 0% to 50% Elution Buffer (50 mM Tris pH 8.0, 1.0 M NaCl) was performed to generate 1 mL fractions of eluted protein. The eluted proteins were bioassayed as previously described and WCRW activity was detected in fractions eluting at ~17.6-25.0 $mS/cm^2$ conductivity. Based on LDS-PAGE the active fractions contained a protein band at approximately 17 kDa which was designated, IPD098Aa.

Proteins for MS identification were obtained after running the sample on an LDS-PAGE gel stained with Coomassie™ Brilliant Blue G-250 stain. The band of interest were excised from the gel, de-stained, reduced with dithiothreitol and then alkylated with iodoacetamide. Following overnight digestion with trypsin, liquid chromatography-tandem mass spectrometry (LC-MSMS) analysis for tryptically-digested peptides was conducted using electrospray ion source on a QToF Premiere™ mass spectrometer (Waters®, Milford, MA) coupled with a NanoAcquity™ nano-LC system (Waters®, Milford, MA) with a gradient from 2% acetonitrile, 0.1% formic acid to 60% acetonitrile, 0.1% formic acid.

Protein identification was performed by database searches using Mascot® (Matrix Science, 10 Perrins Lane, London NW3 1QY UK). The searches were conducted against an in-house transcriptome database containing transcripts from the Asplenium nidus var. plicatum (PS-9146) source plant and the public protein database Swiss-Prot using the Mascot search engine (Matrix Science). Protein identification was also performed by taking the resulting LCMS data which was analyzed using Protein Lynx Global Server (Waters®, Milford, MA) to generate DeNovo sequence data. The amino acid sequences were BLAST™ (Basic Local Alignment Search Tool; Altschul, et al., (1993) *J. Mol. Biol.* 215:403-410; see also ncbi.nlm.nih.gov/BLAST/, which can be accessed using the www prefix) searched against public and DUPONT-PIONEER internal databases that included plant protein sequences. Amino acid sequences were aligned with proteins in a proprietary DUPONT-PIONEER plant protein database.

The N-terminal sequence of the protein was determined by Edman Degradation sequencing on a Procise® 494 protein sequencer (Thermo Scientific, Waltham, MA). The resulting amino acid sequence was used to verify the true N-terminus of the protein to be Glycine.

Example 9—Cloning and *E. coli* Expression of IPD098Aa cDNA was generated from RNA sample PS-9146 by reverse transcription using the SuperScript® II kit (Thermo Fischer Scientific, Waltham, MA). The IPD098Aa cDNA (SEQ ID NO: 79) was PCR amplified from PS-9146 cDNA using the primers of SEQ ID NO: 142 and SEQ ID NO: 143. The cDNA was then cloned into the NdeI/BamHI sites of pET24 (Novagen) in frame with a C-terminal His-tag for purification. The clones were sequenced and the IPD098Aa cDNA sequence is shown as SEQ ID NO: 79 and the encoded IPD098Aa polypeptide sequence as SEQ ID NO: 102 pET24 plasmid DNA, containing the respective IPD098 gene insert, was transformed into competent BL21-DE3 *E. coli* cells for recombinant protein expression. *E. coli* cells were grown overnight at 37° C. with 40 µg/mL Kanamycin selection and then inoculated to a fresh 2xYT medium (1:50) and further grown to an optical density of about 0.8. At that point cells were chilled in the presence of 1 mM IPTG and further grown at 16° C. for 16 hours to induce protein expression. The *E. coli* expressed proteins were purified by immobilized metal ion chromatography using Ni-NTA agarose (Qiagen, Germany) according to the manufacturer's protocols.

Example 10—Identification of IPD098Aa Homologs

Gene identities may be determined by conducting BLAST™ (Basic Local Alignment Search Tool; Altschul, et al., (1993) *J. Mol. Biol.* 215:403-410; see also ncbi.nlm.nih-.gov/BLAST/, which can be accessed using the www prefix) searches under default parameters for similarity to sequences. The polynucleotide sequence for IPD098Aa (SEQ ID NO: 79) was analyzed. Gene identities conducted by BLAST™ in a DUPONT PIONEER internal plant transcriptomes database identified multiple homologs of IPD098Aa protein (SEQ ID NO: 102). Additional homologs of IPD098Aa (SEQ ID NO: 102) having a low level of sequence identity were identified in public databases. The IPD098Aa homologs and the organism they were identified from are shown in Table 6.

A matrix table of amino acid sequence identity of the IPD098Aa homologs as calculated using the Needleman-Wunsch algorithm, as implemented in the Needle program (EMBOSS tool suite) is shown in Table 7A-7B. The void parts of the table are not shown.

TABLE 6

| Identifier | Source | Organism | DNA Seq | AA Seq |
|---|---|---|---|---|
| IPD098Aa | PS-9146 | *Asplenium nidus* var. *plicatum* | SEQ ID NO: 79 | SEQ ID NO: 102 |
| IPD098Ab | PS-9146 | *Asplenium nidus* var. *plicatum* | SEQ ID NO: 80 | SEQ ID NO: 103 |
| IPD098Ac | PS-9146 | *Asplenium nidus* var. *plicatum* | SEQ ID NO: 81 | SEQ ID NO: 104 |
| IPD098Ba | PS-9146 | *Asplenium nidus* var. *plicatum* | SEQ ID NO: 82 | SEQ ID NO: 105 |
| IPD098Bb | PS-8566 | *Asplenium australasicum* | SEQ ID NO: 83 | SEQ ID NO: 106 |
| IPD098Bc | PS-9140 | *Asplenium* x *kenzoi Sa. Kurata* | SEQ ID NO: 84 | SEQ ID NO: 107 |
| IPD098Bd | PS-9140 | *Asplenium* x *kenzoi Sa. Kurata* | SEQ ID NO: 85 | SEQ ID NO: 108 |
| IPD098Be | PS-8566 | *Asplenium australasicum* | SEQ ID NO: 86 | SEQ ID NO: 109 |
| IPD098Bf | PS-8566 | *Asplenium australasicum* | SEQ ID NO: 87 | SEQ ID NO: 110 |
| IPD098Bg | PS-9140 | *Asplenium* x *kenzoi Sa. Kurata* | SEQ ID NO: 88 | SEQ ID NO: 111 |
| IPD098Bh | PS-9140 | *Asplenium* x *kenzoi Sa. Kurata* | SEQ ID NO: 89 | SEQ ID NO: 112 |
| IPD098Bi | PS-9140 | *Asplenium* x *kenzoi Sa. Kurata* | SEQ ID NO: 90 | SEQ ID NO: 113 |
| IPD098Da | PS-8570 | *Adiantum capillus-veneris L.* | SEQ ID NO: 91 | SEQ ID NO: 114 |
| IPD098Db | PS-9092 | *Platycerium wandae* | SEQ ID NO: 92 | SEQ ID NO: 115 |
| IPD098Ea | PS-9140 | *Asplenium* x *kenzoi Sa. Kurata* | SEQ ID NO: 93 | SEQ ID NO: 116 |
| IPD098Eb | PS-9140 | *Asplenium* x *kenzoi Sa. Kurata* | SEQ ID NO: 94 | SEQ ID NO: 117 |
| IPD098Fa | Accession # XP_002988395.1 | *Selaginella moellendorffii* | SEQ ID NO: 95 | SEQ ID NO: 118 |
| IPD098Ga | Accession # XP_002973581 | *Selaginella moellendorffii* | SEQ ID NO: 96 | SEQ ID NO: 119 |
| IPD098Gb | Accession # XP_002978886 | *Selaginella moellendorffii* | SEQ ID NO: 97 | SEQ ID NO: 120 |
| IPD098Gc | Accession # XP_002977210; XP_002977211 (1aa difference) | *Selaginella moellendorffii* | SEQ ID NO: 98 | SEQ ID NO: 121 |
| IPD098Gd | Accession # XP_002965364 | *Selaginella moellendorffii* | SEQ ID NO: 99 | SEQ ID NO: 122 |
| IPD098Ge | Accession # XP_002977211 | *Selaginella moellendorffii* | SEQ ID NO: 100 | SEQ ID NO: 123 |
| IPD098Gf | NCBI-BAA03951 | *Aspergillus fumigatus* | SEQ ID NO: 101 | SEQ ID NO: 124 |

TABLE 7A

| | IPD098Ab SEQ ID NO: 103 | IPD098Ac SEQ ID NO: 104 | IPD098Ba SEQ ID NO: 105 | IPD098Bb SEQ ID NO: 106 | IPD098Bc SEQ ID NO: 107 | IPD098Bd SEQ ID NO: 108 | IPD098Be SEQ ID NO: 109 | IPD098Bf SEQ ID NO: 110 | IPD098Bg SEQ ID NO: 111 | IPD098Bh SEQ ID NO: 112 | IPD098Bi SEQ ID NO: 113 |
|---|---|---|---|---|---|---|---|---|---|---|---|
| IPD098Aa | 92.8 | 97.8 | 82.7 | 87.8 | 87.8 | 83.5 | 88.5 | 87.8 | 81.3 | 82.7 | 74.1 |
| IPD098Ab | — | 94.9 | 89.9 | 87.7 | 88.4 | 84.1 | 88.4 | 87.7 | 81.2 | 83.3 | 72.5 |
| IPD098Ac | — | — | 84.8 | 89.1 | 89.9 | 85.5 | 89.9 | 89.1 | 82.6 | 84.8 | 74.6 |
| IPD098Ba | — | — | — | 89.1 | 89.9 | 84.1 | 89.9 | 89.1 | 81.2 | 83.3 | 72.5 |
| IPD098Bb | — | — | — | — | 99.3 | 87 | 99.3 | 98.6 | 84.1 | 86.2 | 77.5 |
| IPD098Bc | — | — | — | — | — | 87.7 | 98.6 | 97.8 | 84.8 | 87 | 77.5 |
| IPD098Bd | — | — | — | — | — | — | 87.7 | 87 | 95.6 | 97.8 | 82.5 |
| IPD098Be | — | — | — | — | — | — | — | 99.3 | 84.8 | 87 | 77.5 |
| IPD098Bf | — | — | — | — | — | — | — | — | 84.1 | 86.2 | 77.5 |
| IPD098Bg | — | — | — | — | — | — | — | — | — | 96.4 | 86.5 |
| IPD098Bh | — | — | — | — | — | — | — | — | — | — | 83.2 |

TABLE 7B

| | IPD098Da SEQ ID NO: 114 | IPD098Db SEQ ID NO: 115 | IPD098Ea SEQ ID NO: 116 | IPD098Eb SEQ ID NO: 117 | IPD098Fa SEQ ID NO: 118 | IPD098Ga SEQ ID NO: 119 | IPD098Gb SEQ ID NO: 120 | IPD098Gc SEQ ID NO: 121 | IPD098Gd SEQ ID NO: 122 | IPD098Ge SEQ ID NO: 123 | IPD098Gf SEQ ID NO: 124 |
|---|---|---|---|---|---|---|---|---|---|---|---|
| IPD098Aa | 64 | 59.7 | 54.3 | 54.3 | 31.9 | 39.9 | 32.4 | 31.9 | 31.9 | 31.9 | 34.9 |
| IPD098Ab | 63.8 | 60.1 | 56.1 | 56.1 | 30.9 | 37.8 | 31.5 | 30.9 | 30.9 | 30.9 | 33.8 |
| IPD098Ac | 65.2 | 60.1 | 56.1 | 56.1 | 32 | 39.9 | 32.6 | 32 | 32 | 32 | 35.1 |
| IPD098Ba | 63 | 60.9 | 56.1 | 56.1 | 30.9 | 36.5 | 31.5 | 30.9 | 30.9 | 30.9 | 31.5 |
| IPD098Bb | 63 | 59.4 | 57.6 | 57.6 | 33.1 | 39.9 | 33.7 | 33.1 | 33.1 | 33.1 | 35.1 |
| IPD098Bc | 63.8 | 59.4 | 58.3 | 58.3 | 32.6 | 39.2 | 33.1 | 32.6 | 32.6 | 32.6 | 35.1 |
| IPD098Bd | 63.8 | 59.4 | 55.8 | 55.8 | 31.7 | 38.1 | 32.2 | 31.7 | 31.7 | 31.7 | 34.7 |
| IPD098Be | 63.8 | 60.1 | 56.8 | 56.8 | 32.6 | 39.2 | 33.1 | 32.6 | 32.6 | 32.6 | 35.8 |
| IPD098Bf | 63 | 59.4 | 56.8 | 56.8 | 32.6 | 39.2 | 33.1 | 32.6 | 32.6 | 32.6 | 35.8 |
| IPD098Bg | 62.3 | 57.2 | 54.3 | 54.3 | 30 | 37.4 | 30.5 | 30 | 30 | 30 | 35.7 |
| IPD098Bh | 63 | 58.7 | 55.1 | 55.1 | 31.1 | 38.8 | 31.6 | 31.1 | 31.1 | 31.1 | 34 |
| IPD098Bi | 55.8 | 52.1 | 47.8 | 47.8 | 27.2 | 33.1 | 27.7 | 27.2 | 27.2 | 27.2 | 32.1 |
| IPD098Da | — | 62.3 | 49.3 | 49.3 | 32.8 | 36.7 | 33.3 | 32.8 | 32.8 | 32.8 | 34.2 |
| IPD098Db | — | — | 42.4 | 42.4 | 30.2 | 38.9 | 30.7 | 30.2 | 30.2 | 30.2 | 31.8 |
| IPD098Ea | — | — | — | 99.3 | 27.7 | 31.9 | 28.2 | 27.7 | 27.7 | 27.7 | 28.5 |
| IPD098Eb | — | — | — | — | 27.7 | 31.9 | 28.2 | 27.7 | 27.7 | 27.7 | 28.5 |
| IPD098Fa | — | — | — | — | — | 58.1 | 94.2 | 97.7 | 97.1 | 98.3 | 26 |
| IPD098Ga | — | — | — | — | — | — | 59.1 | 57.5 | 58.1 | 58.1 | 27.6 |
| IPD098Gb | — | — | — | — | — | — | — | 94.8 | 94.2 | 95.4 | 26.4 |
| IPD098Gc | — | — | — | — | — | — | — | — | 98.3 | 99.4 | 26.4 |
| IPD098Gd | — | — | — | — | — | — | — | — | — | 98.8 | 26 |
| IPD098Ge | — | — | — | — | — | — | — | — | — | — | 26 |

Example 11—IPD098Aa and Homologs Expressed in *E. coli* and Insect Bioassay

A series of concentrations of the purified IPD98Aa homologs were assayed against coleopteran WCRW (*Diabrotica virgifera*). To measure insecticidal activities against WCRW (*Diabrotica virgifera*) bioassays were conducted using 25 μL of the purified protein samples mixed with 35 μL artificial WCRW diet (Bio-Serv F9800B based) in each of a 96 well bioassay plate. A variable number of neonate *Diabrotica virgifera* neonates (3 to 9) were placed into each well of the 96 well plate. The assay was run for four days at 25° C. with no light and then scored for mortality and stunting. The results are shown in Table 8.

TABLE 8

| Identifier | Polypeptide | Activity | Effect on WCRW |
|---|---|---|---|
| IPD098Aa | SEQ ID NO: 102 | Y | death at 51 ppm |
| IPD098Ab | SEQ ID NO: 103 | Y | death at 248 ppm |
| IPD098Ba | SEQ ID NO: 105 | Y | stunting at 85 ppm |

TABLE 8-continued

| Identifier | Polypeptide | Activity | Effect on WCRW |
|---|---|---|---|
| IPD098Bb | SEQ ID NO: 106 | Y | stunting at 250 ppm |
| IPD098Bc | SEQ ID NO: 107 | Y | mild stunting at 348 ppm |
| IPD098Bd | SEQ ID NO: 108 | Y | mild stunting at 946 ppm |
| IPD098Da | SEQ ID NO: 114 | Y | death at 1407 ppm |
| IPD098Db | SEQ ID NO: 115 | Y | mild stunting at 338 ppm |
| IPD098Ea | SEQ ID NO: 116 | N | inactive at 917 ppm |
| IPD098Fa | SEQ ID NO: 118 | No soluble expression | ND |

Example 12—Mode of Action of IPD098Aa

Bioactivity of purified recombinant protein incorporated into artificial diet revealed toxicity of IPD098Aa polypeptide (SEQ ID NO: 102) to Western corn rootworm (WCRW) larvae. To understand the mechanism of IPD098Aa polypeptide (SEQ ID NO: 102) toxicity, specific binding of the purified protein with WCRW midgut tissue was evaluated by in vitro competition assays. Midguts were isolated from third instar WCRW larvae to prepare brush border membrane vesicles (BBMV) following a method modified from Wolfersberger et al. (Comp Bioch Physiol 86A: 301-308, 1987) using aminopeptidase enzymatic activity to track enrichment. BBMVs represent the apical membrane component of the epithelial cell lining of insect midgut tissue and therefore serve as a model system for how insecticidal proteins interact within the gut following ingestion.

Recombinant IPD098Aa (SEQ ID NO: 102) was expressed and purified from an *E. coli* expression system utilizing a carboxy-terminal poly-histidine fusion tag (10× His). The full length purified protein was labeled with Alexa-Fluor® 488 (Life Technologies) and unincorporated fluorophore was separated from labeled protein using buffer exchange resin (Life Technologies, A30006) following manufacturer's recommendations. Prior to binding experiments, proteins were quantified by gel densitometry following Simply Blue® (Thermo Scientific) staining of SDS-PAGE resolved samples that included BSA as a standard.

Binding buffer consisted of 20 mM Bis-Tris, 137 mM NaCl, 2.7 mM KCl pH 6.0, 0.1% Tween®20 and 2× of Complete EDTA-free Protease Inhibitors (Roche, 05956 489 001) pH 6.0. To demonstrate specific binding and to evaluate affinity, BBMVs (10 ug) were incubated with 40 nM Alexa-labeled IPD098Aa polypeptide (SEQ ID NO: 102) in 100 μL of binding buffer for 1 hr. at RT in the absence and presence of increasing concentrations of unlabeled IPD098Aa polypeptide (SEQ ID NO: 102). Centrifugation at 20000xg was used to pellet the BBMVs to separate unbound toxin remaining in solution. The BBMV pellet was then washed twice with binding buffer to eliminate remaining unbound toxin. The final BBMV pellet (with bound fluorescent toxin) was solubilized in reducing Laemmli sample buffer, heated to 100OC for 5 minutes, and subjected to SDS-PAGE using 3-8% Tris-Acetate polyacrylamide gels (Life Technologies). The amount of Alexa-labeled IPD098Aa polypeptide (SEQ ID NO: 102) in the gel from each sample was measured by a digital fluorescence imaging system (Image Quant LAS4010 GE Healthcare). Digital images were analyzed by densitometry software (Phoretix 1D, TotalLab, Ltd.)

The apparent affinity of IPD098Aa polypeptide (SEQ ID NO: 102) for WCRW BBMVs was estimated based on the concentration of unlabeled protein that was needed to reduce the binding of Alexa-labeled IPD098Aa polypeptide (SEQ ID NO: 102) by 50% ($EC_{50}$ value). This value was approximately 1.4 μM for IPD098Aa polypeptide (SEQ ID NO: 102) binding with WCRW BBMVs (FIG. 1).

Example 13—Isolation and Identification of the IPD108Aa Polypeptide

Insecticidal activity against European corn borer ((ECB) (*Ostrinia nubilalis*)) was observed from a clarified and desalted extraction from Selaginella erythropus (NY011) plant tissue. This insecticidal activity exhibited heat and protease sensitivity indicating proteinaceous nature.

Protein isolation was from a frozen tissue sample of NYO11 (Selaginella erythropus) that had been stored at −80° C. For each gram of tissue, 5 mL extraction buffer (100 mM Tris, 150 mM KCl, 2.5 mM EDTA, 1.5% Polyvinylpolypyrrolidone (PVPP), pH 8 with protease inhibitors) was used. The plant material was pulverized at liquid $N_2$ temperatures with a Geno/Grinder® (600 rpm, 2 min, 2×), extraction buffer was then added and the suspension rocked for 30 minutes before centrifuging at 20000xg for 10 minutes. The supernatant was transferred to a fresh tube, and buffer (1/2 volume compared to initial) was added to the tissue and the extraction repeated.

The supernatant was filtered and concentrated with 10 kDa MWCO filters to perform several runs on a single Superdex™ 200 (GE Healthcare) size exclusion column. Active fractions were collected and desalted into 20 mM Tris, pH 8 before running on an 8 mL Mono Q® column (GE Healthcare). The Mono Q® chromatography was performed with a 25 column volume gradient (Buffer B: 20 mM Tris+0.5 M NaCl, pH 8) collecting 1.5 mL fractions. Active fractions (12.0-16.2 mS/cm) were pooled and desalted into 25 mM BisTris, pH 6.8, loaded onto a 4 mL Mono P® column (GE Healthcare) and eluted with 100% B Polybuffer® 74 (GE Healthcare), pH 4.4-diluted 1:15). Active fractions were pooled and desalted into 20 mM MES, pH 6.5, loaded onto a 1 mL Mono Q® column employing a 30 column volume gradient to Buffer B: 20 mM MES, 0.25 M NaCl, pH 6.5) and 1 mL fractions were collected. Activity was associated with fractions corresponding to 10.2-12.3 mS/cm. Mass Spec was used for in-solution and in-gel sample analysis and a transcript was identified that aligned with activity that was designated as IPD108Aa (SEQ ID NO: 131).

Example 14—Cloning and *E. coli* Expression of IPD108Aa

Peptide sequences identified for IPD108Aa (SEQ ID NO: 131) by LCMS sequencing (as described in Example 8) were searched against protein sequences predicted by open reading frames (ORFs) from the transcriptome assemblies for *Selaginella erythropus*, NY011. The peptides gave a perfect match to a transcript corresponding to IPD108Aa (SEQ ID NO: 125). The coding sequence was used to design the primers of SEQ ID NO: 144 and SEQ ID NO: 145 to clone the IPD108Aa cDNA sequence. This clone was produced by polymerase chain reaction using cDNA prepared from the total RNA from *Selaginella erythropus*, NYO11 by the SuperScript® II kit (Thermo Fischer Scientific, Waltham, MA) as the template. PCR products were gel purified, digested with BamHI and XhoI restriction enzymes and ligated into a modified pET28a vector (Novagen) with an N-terminal 6xHis tag followed by a thrombin cleavage site, a Maltose Binding Protein tag and a Factor Xa cleavage site. Colonies were sequenced to confirm the clone.

The modified pET28a vector with the IPD108Aa cDNA (SEQ ID NO: 125), encoding the IPD108Aa polypeptide (SEQ ID NO: 131), was transformed into chemically competent BL21 (DE3) cells (Invitrogen®). The transformed *E. coli* cells were grown overnight at 37° C. with kanamycin selection and then inoculated into a fresh 2xYT medium (1:200) and further grown to an optical density (OD600) of about 0.8. Protein expression was induced by adding 1.0 mM IPTG and cells were further grown at 16° C. for 16 hours. The *E. coli* expressed proteins were purified by affinity chromatography using Amylose resin (New England Biolabs, Ipswich, MA) according to the manufacturer's protocols. The purified fractions were dialyzed into 1xPBS buffer (1:400) using 6K MWCO Flextubes (IBI, Peosta, IA) on a stir plate at 4° C. overnight. The eluted protein was used in diet bioassays to evaluate the protein activity on larvae of a diversity of Lepidoptera.

Example 15—Identification of IPD108Aa Homologs

Gene identities may be determined by conducting BLAST™ (Basic Local Alignment Search Tool; Altschul, et al., (1993) *J. Mol. Biol.* 215:403-410; see also ncbi.nlm.nih- .gov/BLAST/, which can be accessed using the www prefix) searches under default parameters for similarity to sequences. The polynucleotide sequence for IPD108Aa (SEQ ID NO: 125) was analyzed. Gene identities conducted by BLAST™ in a DUPONT PIONEER internal plant transcriptomes database identified multiple homologs of IPD108Aa protein (SEQ ID NO: 131). The IPD108Aa homologs and the organism they were identified from are shown in Table 9.

TABLE 9

| IPD108 homolog | Source | Organism | DNA Seq | AA Seq |
|---|---|---|---|---|
| IPD108Da | PS-10887 | *Selaginella victoriae* | SEQ ID NO: 126 | SEQ ID NO: 132 |
| IPD108Dd | PS-12409 | *Athyrium filix-femina* | SEQ ID NO: 127 | SEQ ID NO: 133 |
| IPD108Df | NY015 | *Athyrium niponicum* 'Red Beauty' | SEQ ID NO: 128 | SEQ ID NO: 134 |
| IPD108Dj | PS-12275 | *Onoclea sensibilis* | SEQ ID NO: 129 | SEQ ID NO: 135 |
| IPD108Eb | gi│300146701│gb│EFJ13369.1│ hypothetical protein | *Selaginella moellendorffii* | SEQ ID NO: 130 | SEQ ID NO: 136 |

A matrix table of amino acid sequence identity of the IPD108Aa homologs as calculated using the Needleman-Wunsch algorithm, as implemented in the Needle program (EMBOSS tool suite) is shown in Table 10. The void parts of the table are not shown.

TABLE 10

|  | IPD108Da | IPD108Dd | IPD108Df | IPD108Dj | IPD108Eb |
|---|---|---|---|---|---|
| IPD108Aa | 67 | 63.3 | 63.3 | 62.1 | 53.1 |
| IPD108Da | — | 63 | 62.1 | 60.4 | 50.8 |
| IPD108Dd | — | — | 87.5 | 82.6 | 50.2 |
| IPD108Df | — | — | — | 83.3 | 52.1 |
| IPD108Dj | — | — | — | — | 52 | cDNA was generated from source organisms with identified homologs from the internal database by reverse transcription from total RNA using SuperScript II® First Strand Synthesis Kit (Invitrogen, Carlsbad, CA). Homologs were PCR amplified from their respective cDNA's using primers designed to the coding sequences of each homolog with 5' vector overlapping extensions (Table 11). The IPD108Eb polynucleotide (SEQ ID NO: 130) was synthesized with vector overlapping extensions as gBlocks® Gene Fragments (Integrated DNA Technologies, Coralville, IA).

TABLE 11

| Gene Name | Forward Primer SEQ ID | Reverse Primer SEQ ID |
|---|---|---|
| IPD108Da | SEQ ID NO: 146 | SEQ ID NO: 147 |
| IPD108Dd | SEQ ID NO: 148 | SEQ ID NO: 149 |
| IPD108Df | SEQ ID NO: 150 | SEQ ID NO: 151 |
| IPD108Dj | SEQ ID NO: 152 | SEQ ID NO: 153 |

The PCR products and synthesized sequence containing the IPD108Aa homolog sequences were subcloned into the modified pET28a vector (Novagen®) in frame with an N-terminal 6× His tag followed by a thrombin cleavage site, a MBP tag, and a Factor Xa cleavage site digested with BamHI/XhoI (New England Biolabs, Ipswich, MA) for PCR products and BamHI for synthesized sequence using the Gibson Assembly® Master Mix (New England Biolabs, Ipswich, MA). Cloned PCR products were confirmed by sequencing.

Chemically competent BL21 (DE3) cells (Invitrogen®) were transformed with plasmid DNA containing the IPD108 homologs for recombinant protein expression. The transformed *E. coli* cells were grown overnight at 37° C. with kanamycin selection and then inoculated to a fresh 2xYT medium (1:100) and further grown to an optical density of about 0.8-1.2. Protein expression was induced by adding 1.0 mM IPTG and cells were further grown at 16° C. for 16 hours. The *E. coli* expressed proteins were purified by affinity chromatography using Amylose resin (New England Biolabs, Ipswich, MA) according to the manufacturer's protocols. The purified fractions were dialyzed into 50 mM Carbonate buffer (pH 10.0) using 6K MWCO Flextubes (IBI, Peosta, IA) on a stir plate at 4° C. overnight. The eluted protein was used in diet bioassays to evaluate the protein activity on larvae of a diversity of Lepidoptera.

Example 16—IPD108 Homologs Expressed in *E. coli* and Insect Bioassay

Bioassays against the five pest species, Corn earworm (CEW) (*Helicoverpa zea*), European corn borer (ECB) (*Ostrinia nubialis*), fall armyworm (FAW) (*Spodoptera frugiperda* JE Smith), Soybean looper (SBL) (*Pseudoplusia includens*), and velvet bean caterpillar (VBC) (*Anticarsia gemmatalis* Hubner) were conducted on purified N-6xHis-MBP-IPD108 homologs incorporated into an agar-based Lepidoptera diet (Southland Products Inc., Lake Village, AR) in a 96-well plate format. Four replicates were used per sample. Samples were diluted into the diet, aliquoted into the wells, and two to five neonate insects were placed into each well of the plate. After four days of incubation at 27° C. larvae were scored for mortality or severity of stunting. The scores were recorded numerically as dead (3), severely stunted (2) (little or no growth but alive and equivalent to a 1$^{st}$ instar larvae), stunted (1) (growth to second instar but not equivalent to controls), or normal (0). The activity results are shown in Table 12.

TABLE 12

| Identifier | polypeptide | PPM | BCW | CEW | ECB | FAW | SBL | VBC |
|---|---|---|---|---|---|---|---|---|
| IPD108Db | SEQ ID NO: 132 | 375 | 0 | 0 | 2.25 | 0 | 0.5 | 0 |
| IPD108Dd | SEQ ID NO: 133 | 125 | 0 | 0 | 2.25 | 0 | 0.75 | 0 |
| IPD108Df | SEQ ID NO: 134 | 62.5 | 0 | 0 | 2 | 0 | 0 | 0 |

US 12,595,488 B2

135
136

TABLE 12-continued

| Identifier | polypeptide | PPM | BCW | CEW | ECB | FAW | SBL | VBC |
|---|---|---|---|---|---|---|---|---|
| IPD108Dj | SEQ ID NO: 135 | 31.25 | 0 | 0 | 2 | 0 | 0.25 | 0 |
| IPD108Eb | SEQ ID NO: 136 | 375 | 0 | 0 | 1 | 0 | 0 | 0.5 |

Example 17—Isolation and Identification of the
IPD109Aa Polypeptide

Insecticidal activity against Western corn rootworm
((WCRW) (*Diabrotica virgifera*)) was observed from a
clarified and desalted extraction from *Selaginella victoriae*
(PS-10890) plant tissue. This insecticidal activity exhibited
heat and protease sensitivity indicating proteinaceous
nature.

Protein isolation was from a frozen tissue sample of
PS-10890 (*Selaginella victoriae*) that had been stored at
−80° C. For each gram of fresh tissue, 5 mL extraction buffer
(100 mM Tris, 150 mM KCl, 2.5 mM EDTA, 1.5% Poly-
vinylpolypyrrolidone (PVPP), pH 8 with protease inhibitors)
was used. The plant material was pulverized at liquid $N_2$
temperatures with a Geno/Grinder® (600 rpm, 2 min, 2×),
extraction buffer was then added and the suspension rocked
for 30 minutes before centrifuging at 20000×g for 10 min-
utes. The supernatant was transferred to a fresh tube, and
buffer (1/2 volume compared to initial) was added to the
tissue and the extraction repeated.

The supernatant was filtered, concentrated (10 kDa) and
desalted into 20 mM Tris, pH 8. The desalted extract was run
through a tandem of two 5 mL Capto™ Q (GE Healthcare)
columns equilibrated in 20 mM Tris, pH 8. Bound proteins
were eluted with a step gradient of 20 mM Tris+0.5 M NaCl,
pH 8). The Capto™ Q Eluate was desalted into 20 mM
MES, pH 6.5 and loaded onto a 1 mL Mono Q® column
equilibrated in this buffer. Bound proteins were eluted with
a 30 column volume gradient to 20 mM MES+0.4 M NaCl,
pH 6.5, collecting 1 mL fractions. WCRW activity eluted
with fractions corresponding to conductivity range of 12.8-
22.3 mS/cm.

The active Mono Q® fractions were pooled from both
Mono Q® runs and desalted into 25 mM BisTris, pH 7
before running on a 4 mL Mono P® column (GE Health-
care). A 100% B wash (B: Polybuffer 74, pH 4.2-diluted
1:15 with $H_2O$) was used to elute protein and active fractions
were pooled and concentrated before running on 2× Super-
dex™ 200 (GE Healthcare) size exclusion column. The
Superdex™ 200 column run was performed in 100 mM
(NH₄)HCO₃ collecting 1 mL fractions. Active fractions were
pooled and desalted into 20 mM Tris, pH 8.6 before loading
on a 1 mL Mono Q® column, deploying a 0 to 100%, 25
column volume gradient (Buffer B: 20 mM Tris+0.25 M
NaCl, pH 8.6). One mL fractions were collected and con-
centrated with 10 kDa MWCO filtration units before sub-
mitting to bioassay. Activity was associated with fractions
corresponding to 14.4-21.8 mS/cm. Mass Spec was used for
in-solution and in-gel sample analysis and a transcript was
identified that aligned with activity that was designated as
IPD109Aa (SEQ ID NO: 137).

Example 18—Cloning and *E. coli* Expression of
IPD109Aa

The total RNA from a *Selaginella victoriae* PS-10890
sample was obtained and cDNA was generated using Super-
Script® First Strand Synthesis Kit (Invitrogen®, Carlsbad, CA) by reverse transcription. The cDNA was then used as
template for a PCR reaction using KOD Hot Start Master
Mix® (Novagen®, Madison, WI) and the primers of SEQ
ID NO: 154 and SEQ ID NO: 155.

The IPD109Aa cDNA (SEQ ID NO: 137), encoding
IPD109Aa (SEQ ID NO: 138) was subcloned into the
pET28a vector (Novagen®, Madison, WI) using the BamHI/
HindIII restriction sites in frame with an N-terminal 6× His
tag followed by a thrombin cleavage site. The expression
vectors were then amplified and the IPD109Aa cDNA (SEQ
ID NO: 137) was sequence confirmed prior to recombinant
protein expression in *E. coli*. Chemically competent BL21
(DE3) cells (Invitrogen®, Carlsbad, CA) were transformed
with pET28a plasmid DNA, containing the IPD109Aa gene
for recombinant protein expression. The transformed *E. coli*
cells were grown overnight at 37° C. with kanamycin
selection and then inoculated to a fresh 2xYT medium
(1:200) and further grown to an optical density (OD600) of
about 0.8. Protein expression was induced by adding 1.0
mM IPTG and cells were further grown at 16° C. for 16
hours. The *E. coli* expressed proteins were purified by
immobilized metal ion chromatography using Talon™
Cobalt resin (Clonetech, Mountain View, CA) according to
the manufacturer's protocols. The purified fractions were
dialyzed into 1×PBS buffer (1:400) using 6K MWCO Flex-
tubes (IBI, Peosta, IA) on a stir plate at 4° C. overnight. The
purified IPD109Aa protein (SEQ ID NO: 138) was used in
diet bioassays to evaluate the protein activity on larvae of a
diversity of Lepidopteran and Coleopteran pests.

Example 19—*Agrobacterium*-Mediated Stable
Transformation of Maize

For *Agrobacterium*-mediated maize transformation of
insecticidal polypeptides, the method of Zhao is employed
(US Patent Number 5,981). Briefly, immature embryos are
isolated from maize and the embryos contacted with an
*Agrobacterium* Suspension, where the bacteria were capable
of transferring a polynucleotide encoding an insecticidal
polypeptide of the disclosure to at least one cell of at least
one of the immature embryos (step 1: the infection step). In
this step the immature embryos are immersed in an *Agro-
bacterium* suspension for the initiation of inoculation. The
embryos are co-cultured for a time with the *Agrobacterium*
(step 2: the co-cultivation step). The immature embryos are
cultured on solid medium with antibiotic, but without a
selecting agent, for *Agrobacterium* elimination and for a
resting phase for the infected cells. Next, inoculated
embryos are cultured on medium containing a selective
agent and growing transformed callus is recovered (step 4:
the selection step). The immature embryos are cultured on
solid medium with a selective agent resulting in the selective
growth of transformed cells. The callus is then regenerated
into plants (step 5: the regeneration step), and calli grown on
selective medium are cultured on solid medium to regener-
ate the plants.

For detection of the insecticidal polypeptide in leaf tissue
4 lyophilized leaf punches/sample are pulverized and resus-
pended in 100 µL PBS containing 0.1% TWEEN™ 20

(PBST), 1% beta-mercaoptoethanol containing 1 tablet per 7 mL of complete Mini proteinase inhibitor (Roche 1183615301). The suspension is sonicated for 2 minutes and then centrifuged at 4° C., 20,000 g for 15 minutes. To a supernatant aliquot 1/3 volume of 3× NuPAGE® LDS Sample Buffer (Invitrogen™ (CA, USA), 1% B-ME containing 1 tablet per 7 mL complete Mini proteinase inhibitor was added. The reaction is heated at 80° C. for 10 minutes and then centrifuged. A supernatant sample is loaded on 4-12% Bis-Tris Midi gels with MES running buffer as per manufacturer's (Invitrogen™) instructions and transferred onto a nitrocellulose membrane using an iBlot® apparatus (Invitrogen™). The nitrocellulose membrane is incubated in PBST containing 5% skim milk powder for 2 hours before overnight incubation in affinity-purified rabbit anti-insecticidal polypeptide in PBST overnight. The membrane is rinsed three times with PBST and then incubated in PBST for 15 minutes and then two times 5 minutes before incubating for 2 hours in PBST with goat anti-rabbit-HRP for 3 hours. The detected proteins are visualized using ECL Western Blotting Reagents (GE Healthcare) and Kodak® Biomax® MR film. For detection of the insecticidal protein in roots the roots are lyophilized and 2 mg powder per sample is suspended in LDS, 1% beta-mercaptoethanol containing 1 tablet/7 mL Complete Mini proteinase inhibitor is added. The reaction is heated at 80° C. for 10 minutes and then centrifuged at 4° C., 20,000 g for 15 minutes. A supernatant sample is loaded on 4-12% Bis-Tris Midi gels with MES running buffer as per manufacturer's (Invitrogen™) instructions and transferred onto a nitrocellulose membrane using an iBlot® apparatus (Invitrogen™). The nitrocellulose membrane is incubated in PBST containing 5% skim milk powder for 2 hours before overnight incubation in affinity-purified polyclonal rabbit anti-insecticidal antibody in PBST overnight. The membrane is rinsed three times with PBST and then incubated in PBST for 15 minutes and then two times 5 minutes before incubating for 2 hours in PBST with goat anti-rabbit-HRP for 3 hrs. The antibody bound insecticidal proteins are detected using ECL™ Western Blotting Reagents (GE Healthcare) and Kodak® Biomax® MR film.

Transgenic maize plants positive for expression of the insecticidal proteins are tested for pesticidal activity using standard bioassays known in the art. Such methods include, for example, root excision bioassays and whole plant bioassays. See, e.g., US Patent Application Publication Number US 2003/0120054.

Example 20—Expression Vector Constructs for Expression of Insecticidal Polypeptides in Plants The plant expression vectors, can be constructed to include a transgene cassette containing the coding sequence pf the insecticidal polypeptide, under control of the *Mirabilis* Mosaic Virus (MMV) promoter [Dey N and Maiti IB, 1999, *Plant Mol. Biol.* 40(5):771-82] in combination with an enhancer element. These constructs can be used to generate transgenic maize events to test for efficacy against corn rootworm provided by expression of the insecticidal polypeptide of the disclosure.

T0 greenhouse efficacy of the events can be measured by root protection from Western corn rootworm. Root protection is measured according to the number of nodes of roots injured (CRWNIS=corn rootworm node injury score) using the method developed by Oleson, et al. (2005) [*J. Econ Entomol.* 98(1):1-8]. The root injury score is measured from "0" to "3" with "0" indicating no visible root injury, "1" indicating 1 node of root damage, "2" indicating 2 nodes or root damage, and "3" indicating a maximum score of 3 nodes of root damage. Intermediate scores (e.g. 1.5) indicate additional fractions of nodes of damage (e.g. one and a half nodes injured).

The above description of various illustrated embodiments of the disclosure is not intended to be exhaustive or to limit the scope to the precise form disclosed. While specific embodiments of and examples are described herein for illustrative purposes, various equivalent modifications are possible within the scope of the disclosure, as those skilled in the relevant art will recognize. The teachings provided herein can be applied to other purposes, other than the examples described above. Numerous modifications and variations are possible in light of the above teachings and, therefore, are within the scope of the appended claims.

These and other changes may be made in light of the above detailed description. In general, in the following claims, the terms used should not be construed to limit the scope to the specific embodiments disclosed in the specification and the claims.

The entire disclosure of each document cited (including patents, patent applications, journal articles, abstracts, manuals, books or other disclosures) in the Background, Detailed Description, and Examples is herein incorporated by reference in their entireties.

Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight; temperature is in degrees centigrade; and pressure is at or near atmospheric.

```
                        SEQUENCE LISTING

Sequence total quantity: 156
SEQ ID NO: 1           moltype = DNA   length = 564
FEATURE                Location/Qualifiers
source                 1..564
                       mol_type = other DNA
                       organism = Polypodium musifolium
SEQUENCE: 1
atggcggcga ctaaggcggt attggcagtc tgcagttgca taatagtact catggcgtc   60
atgatcagcg gaggattggc cagcgacgag ccgacatggc aggaggtctt gacaacggca  120
cgcacgaacg tggtatatgg acccagcaac acgtacacca tcaggtcaat gacctctggg  180
atagggtatc tctttaggtt cttctttggc ctggggttcc caggcgaagc ggtccgaacg  240
gacaccacga tcaccatggg tcgcaatgga gatgcctcgg ccatttatgc ctgcatcgac  300
ggcagacttc ggttagtggc caccaacacc tccggcacgc ctcagaacgc tttgattcgc  360
gtgcgcttca acagcaccga cggctactac cgcctgcaga tcacgcaggc ctcaccggct  420
gtctacgttc agtttgttct tctctcccaa ggcggcatcc tctgcaccgc aggcctaccc  480
```

-continued

```
ggcacgcctc tcacctttac ctcctcctcc tcctcggacc tgcgcgtcct tcatcaagtg  540
gtcgacagct cctcccttta ctag                                         564

SEQ ID NO: 2            moltype = DNA  length = 570
FEATURE                 Location/Qualifiers
source                  1..570
                        mol_type = other DNA
                        organism = Polypodium formosanum
SEQUENCE: 2
atggcggcga ctaaggcggt attggcagtc tgcagttgta taatagtact catgggcgtc  60
gacatgatca gcggaggatt ggccagcaac gagccgacat ggcaggaggt cttgacaacg  120
gcacgcacga acgtggtgta tggagccagc aacacgtaca ccatctggtc acagacctct  180
gggattgggt atctctttag gttcttcttt ggcctggggt tcccaggcga agcggtccga  240
acggacacca ccatcaccat gggtcgcaat ggagatgcct cggccattta tgcctgcatc  300
gacggcagac ttcaggtagt ggccaccaac acctccggca cgcctcagaa cgctttgatt  360
cgcgtgcgct acaacagcac cgacggctac taccgcctgc agatcacgca ggcctcaccg  420
gctgtctacg ttcagtttgt tcttctctcc caaggcggca tcctctgcac cgcaggccta  480
cccggcacgc ctctcacctt tacctcctcc tcctcctcct cctcggacct gcgcgtcctt  540
catcaagtgg tcgacagctc ctccctggcc                                   570

SEQ ID NO: 3            moltype = DNA  length = 570
FEATURE                 Location/Qualifiers
source                  1..570
                        mol_type = other DNA
                        organism = Polypodium formosanum
SEQUENCE: 3
atggcggcga ctaaggcggt attggcagtc tgcagttgca taatagtact catgggcgcc  60
gacatgatca gcggaggatt ggccagcaac gagccgacat ggcaggaggt cttgacaact  120
gcacgcacga acgtggtgta tggagccagc aacacgtaca ccatctggtc acagacctct  180
gggattgggt atctctttag gttcttcttt ggcctggggt tcccaggcga agcggtccga  240
acggacacca ccatcaccat gggtcgcaat ggagatgcct cggccattta tgcctgcatc  300
gacggcagac ttcaggtagt ggccaccaac acctccggca cgcctcagaa cgctttgatt  360
cgcgtgcgct acaacagcac cgacggctac taccgcctgc agatcacgca ggcctcaccg  420
gctgtctacg ttcagtttgt tcttctctcc caaggcggca tcctctgcac cgcaggccta  480
cccggcacgc ctctcacctt tacctcctcc tcctcctcct cctcggacct gcgcgtcctt  540
catcaagtgg tcgacagctc ctccctggcc                                   570

SEQ ID NO: 4            moltype = DNA  length = 570
FEATURE                 Location/Qualifiers
source                  1..570
                        mol_type = other DNA
                        organism = Polypodium formosanum
SEQUENCE: 4
atggcggcga cgaaggcggt attggcagtc tgcagttgca taatagtact catgggcgcc  60
gacatgatca gcggaggatt ggccagcaac gagccgacat ggcaggaggt cttgacaact  120
gcacgcacga acgtggtgta tggagccagc aacacgtaca ccatctggtc acagacctct  180
gggattgggt atctctttag gttcttcttt ggcctggggt tcccaggcga agcggtccga  240
acggacacca ccatcaccat gggtcgcaat ggagatgcct cggccattta tgcctgcatc  300
gacggcagac ttcaggtagt ggccaccaac acctccggca cgcctcagaa cgctttgatt  360
cgcgtgcgct acaacagcac cgacggctac taccgcctgc agatcacgca ggcctcaccg  420
gctgtctacg ttcagtttgt tcttctctcc caaggcggca tcctctgcac cgcaggccta  480
cccggcacgc ctgtccacctt tacctcctcc tcctcctcct cctcggacct gcgcgtcctt  540
catcaagtgg tcgacagctc ctccctggcc                                   570

SEQ ID NO: 5            moltype = DNA  length = 426
FEATURE                 Location/Qualifiers
source                  1..426
                        mol_type = other DNA
                        organism = Polypodium formosanum
SEQUENCE: 5
atgagcaaca cgtacaccat ctggtcacag acctctggga ttgggtatct ctttaggttc  60
ttctttggcc tggggttccc aggcgaagcg gtccgaacgg acaccaccat caccatgggt  120
cgcaatggat atgcctcggc catttatgcc tgcatcgacg gcagacttca ggtagtggcc  180
accaacacct ccggcacgcc tcagaacgct ttgattcgcg tgcgctacaa cagcaccgac  240
ggctactacc gcctgcagat cacgcaggcc tcaccggctg tctacgttca gtttgttctt  300
ctctcccaag gcggcatcct ctgcaccgca ggcctacccg gcacgcctgt caccttttacc  360
tcctcctcct cctcctcctc ggacctgcgc gtccttcatc aagtggtcga cagctcctcc  420
ctggcc                                                             426

SEQ ID NO: 6            moltype = DNA  length = 426
FEATURE                 Location/Qualifiers
source                  1..426
                        mol_type = other DNA
                        organism = Polypodium formosanum
SEQUENCE: 6
atgagcaaca cgtacaccat ctggtcacag acctctggga ttgggtatct ctttaggttc  60
ttctttggcc tggggttccc aggcgaagcg gtccgaacga acaccaccat caccatgggt  120
cgcaatggag atgcctcggc catttatgcc tgcatcgacg gcagacttca ggtagtggcc  180
accaacacct ccggcacgcc tcagaacgct ttgattcgcg tgcgctacaa cagcaccgac  240
```

-continued

```
ggctactacc gcctgcagat cacgcaggcc tcaccggctg tctacgttca gtttgttctt      300
ctctcccaag gcggcatcct ctgcaccgca ggcctacccg gcacgcctct cacctttacc      360
tcctcctcct cctcctcctc ggacctgcgc gtccttcatc aagtggtcga cagctcctcc      420
ctggcc                                                                 426
```

SEQ ID NO: 7                        moltype = DNA   length = 426
FEATURE                             Location/Qualifiers
source                              1..426
                                    mol_type = other DNA
                                    organism = Polypodium formosanum
SEQUENCE: 7

```
atgagcaaca cgtacaccat ctggtcacag acctctggga ttgggtatct ctttaggttc      60
ttctttggcc tggggttccc aggcgaagcg gtccgaacgg acaccaccat caccatgggt     120
cgcaatggag atgcctcggc catttatgcc tgcatcgacg gcagacttca ggtagtggcc     180
accaacacct ccggcacgcc tcagaacgct ttgattcgcg tgcgctacaa cagcaccgac     240
ggctactacc gcctgcagat cacgcaggcc tcaccggctg tctacgttca gtttgttctt     300
ctctcccaag gcggcatcct ctgcaccgca ggcctacccg gcacgcctgt cacctttacc     360
tcctcctcct cctcctcctc ggacctgcgc gtccttcatc aagtggtcga cagctcctcc     420
ctggcc                                                                 426
```

SEQ ID NO: 8                        moltype = DNA   length = 426
FEATURE                             Location/Qualifiers
source                              1..426
                                    mol_type = other DNA
                                    organism = Polypodium formosanum
SEQUENCE: 8

```
atgagcaaca cgtacaccat ctggtcacag acctctggga ttgggtatct ctttaggttc      60
ttctttggcc tggggttccc aggcgaagcg gtccgaacgg acaccaccat caccatgggt     120
cgcaatggag atgcctcggc catttatgcc tgcatcgacg gcagacttca ggtagtggcc     180
accaacacct ccggcacgcc tcagaacgct ttgattcgcg tgcgctacaa cagcaccgac     240
ggctactacc gcctgcagat cacgcaggcc tcaccggctg tctacgttca gtttgttctt     300
ctctcccaag gcggcatcct ctgcaccgca ggcctacccg gcacgcctct cacctttacc     360
tcctcctcct cctcctcctc ggacctgcgc gtccttcatc aagtggtcga cagctcctcc     420
ctggcc                                                                 426
```

SEQ ID NO: 9                        moltype = DNA   length = 659
FEATURE                             Location/Qualifiers
source                              1..659
                                    mol_type = other DNA
                                    organism = Polypodium punctatum
SEQUENCE: 9

```
atggcgacga agacattgtt ggcagtctgc ggttgcatac taatactcat gggcgtcatg      60
atcagcggag gatcggccgc tgacgagaca tggcaggagg tcctgacgag ggcgggaaca     120
aacgtggttt atgggcccag caataectac atcatctggt caacagagtc ctggataggc     180
tatgtctttg ggttcttctt tggcctggga tttgacgggg aggcggtgag aaccgacaca     240
accgtcacgt tgggtagaaa cggagacgca tcctccattt atgcctgcat tgatggcaag     300
cttgagctgg tgcccaccaa cagctccggc acgcctcaga atgctttgat tcgcgtgcgt     360
tacaatagca ccgatggcta ctaccggctg cagatcacgg aggcctctcc cgccgtctac     420
gttcagtttg ttcttctctc ccaaggcggc atcctctgca ctgcaggcct ccctggcacg     480
cctatcgtct tcacctccac ctcctcctcc tcctccgtgt cccccaaccg ccgccaggga     540
ccggccttgg tctacacgcc cgacatgcac gtcctccgtc aggtggtcga cagctcctcc     600
ctggcctagc cgccttgcag tcagtttgta ttacaaagct cactacgccg ataaaacaa     659
```

SEQ ID NO: 10                       moltype = DNA   length = 659
FEATURE                             Location/Qualifiers
source                              1..659
                                    mol_type = other DNA
                                    organism = Polypodium punctatum
SEQUENCE: 10

```
atggcgacga agacattgtt gacagtctgc ggttgcatac taatactcat gggcgtcatg      60
atcagcggag gatcggccgc tgacgagaca tggcaggagg tcctgacgag ggcgggaaca     120
aacgtggttt atgggcccag caataectac atcatctggt caacagagtc ctggataggc     180
tatgtctttg ggttcttctt cggcctggga tttgacgggg aggcggtgag aaccgacaca     240
accgtcacgt tgggtagaaa cggagacgca tcctccattt atgcctgcat tgatggcaag     300
cttgagctgg tgcccaccaa cagctccggc acgcctcaga atgctttgat tcgcgtgcgt     360
tacaatagca ccgatggcta ctaccggctg cagatcacgg aggcctctcc cgccgtctac     420
gttcagtttg ttcttctctc ccaaggcggc atcctctgca ctgcaggcct ccctggcacg     480
cctatcgtct tcacctccac ctcctcctcc tcctccgtgt cccccaaccg ccgccaggga     540
ccggccttgg tctacacgcc cgacatgcac gtcctccgtc aggtggtcga cagctcctcc     600
ctggcctagc cgccttgcag tcagtttgta ttacaaagct cactacgccg ataaaacaa     659
```

SEQ ID NO: 11                       moltype = DNA   length = 600
FEATURE                             Location/Qualifiers
source                              1..600
                                    mol_type = other DNA
                                    organism = Colysis wrightii
SEQUENCE: 11

```
atggcgacga aggcggtatc ggcaatctgc ggttgcataa tgatactcat gggcgccatg      60
atcagcggag cattggccga tgacgagaca tggcaggagg tcctgacgac ggcgggaacg     120
```

```
aacgtggtgt ttggagccag taacacgtac accatccggt caagggaatc cgggataggc  180
tatctcttca ggttctactt tggcctgggg ggcgaggggg aaccggtgcg aacagacacc  240
accgtcacat tgggtcgcaa cggagatgca tcgagaattt actcctgcaa cgatggcacg  300
ctggagttgg tggcgaccaa ctcctctggt acgcctcaga gtgctctgat tcgcgtgcgc  360
tacaacagca ctgacggcta ctaccggctg cagatccagg aagcctcccc ggctgtctac  420
gttcagtttg ttcttctctc ccaaggtggc attctctgca ccgctggtct ccccggtaca  480
cctattgtat tcgaatcctc ctcctcctcc tccctctcca gccgccctct ggggccggtg  540
ttagtctaca cgccagacat ggacgtcctc cgtcaggtgg tggacagttc ctccctggcc  600

SEQ ID NO: 12           moltype = DNA  length = 576
FEATURE                 Location/Qualifiers
source                  1..576
                        mol_type = other DNA
                        organism = Asplenium nidus
SEQUENCE: 12
atggcaaaca agggaggggt tgtcgcagtg ctctggctga tgacggtgag ctctgtgttg  60
atgatggggt gcaatacggt ggccggggat gatgagacat ggcaggaagt gctcaccaca  120
gctggcacga acgtggtgtt cggggctagc aacacctaca cgatttgggc tcgggacata  180
gggatagggt atctctttag gttcttcttc gggctggggt ctacgggaga ggcggtgcgg  240
accgacacga ctgtcacgtt gggcgcctat ggcgatgcat ccagggtcta cgcttgcact  300
gacggcaagc tgcagctggt ggccgtaaac tccagtggca cgccagagaa cgccattatt  360
cgcgtgcgct acaacagcac cgaccggaac tatcggctac agatcacaga gaactcccct  420
gccgtctttg tgcagttcac ttaccttttcc cagggcggcc ttctctgcac ctctgggggtt  480
gcaggcaccc caatccgttt cacctttttcc tcctcttctt cccttgatca cgtggatgag  540
ccggccaccg ttgtcctacg tcaagtggtt gacgcc                             576

SEQ ID NO: 13           moltype = DNA  length = 576
FEATURE                 Location/Qualifiers
source                  1..576
                        mol_type = other DNA
                        organism = Asplenium nidus
SEQUENCE: 13
atggcaacca agggaggggt tgtcgcagtg ctctggctga tgacggtgag ctctgtgttg  60
atgatggggt gcaatacggt ggccggggat gatgagacat ggcaggaagt gctcaccaca  120
gctggcacga acgtggtgtt cggggctagc aacacctaca cgatttgggc tcgggacata  180
gggatagggt atctctttag gttcttcttc gggctggggt ctacgggaga ggcggtgcgg  240
accgacacga ctgtcacgtt gggcgcctat ggcgatgcat ccagggtcta cgcttgcact  300
gacggcaagc tgcagctggt ggccgtaaac tccagtggca cgccagagaa cgccattatt  360
cgcgtgcgct acaacagcac cgaccggaac tatcggctac agatcacaga gaactcccct  420
gccgtctttg tgcagttcac ttaccttttcc cagggcggcc ttctctgcac ctctgggggtt  480
gcaggcaccc caatccgttt cacctttttcc tcctcttctt cccttgatca cgtggatgag  540
ccggccaccg ttgtcctacg tcaagtggtt gacgcc                             576

SEQ ID NO: 14           moltype = DNA  length = 576
FEATURE                 Location/Qualifiers
source                  1..576
                        mol_type = other DNA
                        organism = Asplenium nidus
SEQUENCE: 14
atggcaaaca agggaggggt tgtggtagcc ttctggctaa tgatagtgag ctgctctgtg  60
ttactggggt gcaacacggt ggccggggacc gatgagacat ggcaggaagt gctgaccaca  120
gccggcacga atgtggtgtt cggggctagc aacacctaca ccattcggtc tcaggaaacc  180
ggaatagggt atctctttag gttctacttc gagctggggg ctacgggaga ggcggtgcgg  240
accgacacga ctgtcacgct gggcgccttt ggagatgcat ccaggatcta cgcttgcgtt  300
gacggcaagc tggagcgggt ggccgtaaac tcctccggga cgccagagaa tgccattttt  360
cgcgtgcgct acaacagcac tagcagcagc tacctgcttc agatcacgga gaactcgcct  420
gccgtctttg ttcagttcac ttaccttttcc ctaggcggcc ttctctgcac ctctggggtc  480
gcaggcaccc cagtccgctt cacttctgcc tcctcctctt cccatggtca cgtggatgag  540
ccggccactg ttgacctgcg tcaagtggtt gacgcc                             576

SEQ ID NO: 15           moltype = DNA  length = 576
FEATURE                 Location/Qualifiers
source                  1..576
                        mol_type = other DNA
                        organism = Asplenium nidus
SEQUENCE: 15
atggcaacca agggaggggt tgtggtagcc ttctggctaa tgatagtgag ctgctctgtg  60
ttactggggt gcaacacggt ggccggggacc gatgagacat ggcaggaagt gctgaccaca  120
gccggcacga atgtggtgtt cggggctagc aacacctaca ccattcggtc tcaggaaacc  180
ggaatagggt atctctttag gttctacttc gagctggggg ctacgggaga ggcggtgcgg  240
accgacacga ctgtcacgct gggcgccttt ggagatgcat ccaggatcta cgcttgcgtt  300
gacggcaagc tggagcgggt ggccgtaaac tcctccggga cgccagagaa tgccattttt  360
cgcgtgcgct acaacagcac tagcagcagc tacctgcttc agatcacgga gaactcgcct  420
gccgtctttg ttcagttcac ttaccttttcc ctaggcggcc ttctctgcac ctctggggtc  480
gcaggcaccc cagtccgctt cacttctgcc tcctcctctt cccatggtca cgtggatgag  540
ccggccactg ttgacctgcg tcaagtggtt gacgcc                             576

SEQ ID NO: 16           moltype = DNA  length = 561
FEATURE                 Location/Qualifiers
```

```
source                    1..561
                          mol_type = other DNA
                          organism = Polystichium tsus-simense
SEQUENCE: 16
atggcaacca agggaggtgt agtgctagtg tgcttgtgca tgatagcgtt ggggtgcaat   60
acagtggccg gcgatgacga gacatggcag gaggtgctga caacagacgg cgcgaacgtg  120
gtgtatgggg cgaacaacac ctacaccatc tgggcgcggg acattggaat cgggtatctc  180
tacaggttct tctttggact ggggtttacg ggcactgcag tgcggtcaga cacggccgtc  240
acgctgggtg cctttgcaga ttcaaccagg atctatgctt gcactgacgg caaactggag  300
ctggtggccg tgaactccag cggcacgcca gcgaatgcca tcattcgcgt gcgctacaac  360
agcaccgaca gcaactaccg gctgcagatc acggagaact ccctgccgt cttcgttcag   420
ttcacctacc tctccctggg cggcctcctc tgcacctctg gcgtgtcggg caccccatc   480
cgcttcacct cttcctcctc tgcgtccat gatcacctgc atgagccggc caccgttgcc   540
ctgcgtcagg tggtcgagac c                                            561
```

```
SEQ ID NO: 17          moltype = DNA  length = 561
FEATURE                Location/Qualifiers
source                 1..561
                       mol_type = other DNA
                       organism = Polystichium tsus-simense
SEQUENCE: 17
atggcaacca agggaggtgt agtgctagtg tgcttgtgca tgatagcgtt ggggtgcaat   60
acagtggccg gcgatgacga gacatggcag gaggtgctga caacagacgg cgcgaacgtg  120
gtgtatgggg cgaacaacac ctacaccatc tgggcgcggg acattggaat cgggtatctc  180
tacaggttct tctttggact ggggtttacg ggcactgcag tgcggacaga cacggccgtc  240
acgctgggtg cctttgcaga ttcaaccagg atctatgctt gcactgacgg caaactggag  300
ctggtggccg tgaactccag cggcacgcca gcgaatgcca tcattcgcgt gcgctacaac  360
agcaccgaca gcaactaccg gctgcagatc acggagaact ccctgccgt cttcgttcag   420
ttcacctacc tctccctggg cggcctcctc tgcacctctg gcgtggcggg caccccatc   480
cgcttcacct cttcctcctc tgcgtccat gatcacctgc atgagccggc caccgttgcc   540
ttgcgtcagg tggtcgagac c                                            561
```

```
SEQ ID NO: 18          moltype = DNA  length = 591
FEATURE                Location/Qualifiers
source                 1..591
                       mol_type = other DNA
                       organism = Asplenium nidus
SEQUENCE: 18
atggcaacca agggagcagt tgttgcggtg tgctgcctcg tgctggtgag cgccatgttc   60
atggggtgca cgacggtagc cggggacgac gagacatggc aggaagtgct gacaacagcc  120
ggcacgactg tggtgtatgg ggctaccaac acctacacga tccaggccat ggacattgga  180
atcaggtatc tgtattactt tttcttcggg ctggggtata cgggagatgc ggtgcggacg  240
gacacggccg tcacgttggg cgacctcggc gacgcgtcc aaatctacgc ctgcactgac   300
ggcaaactgg agctggtggc cgtcaactct agcggcacgc cgcagaatgc catcattcgc  360
gttcgctaca acagcaccga cggcaactac gggctgcaga tcaccgagaa ctcacctgcc  420
gtcttcgttc agtttactta cctctcgctg gcggcctcc tctgcacctc cggggtcgca   480
ggcacccca tccgcttcat ctcttcctcc tctgcttccc ataatcatat cctgcataag   540
ccggccacca ctgtgtcct gcgtcaggtg gtggacgcct catcatccac c             591
```

```
SEQ ID NO: 19          moltype = DNA  length = 594
FEATURE                Location/Qualifiers
source                 1..594
                       mol_type = other DNA
                       organism = Asplenium nidus
SEQUENCE: 19
atggcaacca agggagctgt tgttgcggtg tgctgcctcg tgctggtgag cgccatattg   60
ttcatggggt gcacgacggt agccggggac gacgagacat ggcaggaagt gctgacaaca  120
gccggcacga ctgtggtgta tggggctacc aacacctaca cgatccaggc catggacatt  180
ggaatcaggt atctctatta ctttttcttc gggctggggt atacgggaga tgcggtgcgg  240
acggacacgg ccgtcacgtt gggcgacctc ggcgacgcgt cccaaatcta cgcctgcact  300
gacggcaaac tggagctggt ggccgtcaac tctagcggca cgccgcagaa tgccatcatt  360
cgcgttcgct acaacagcac cgacggcaac tacgggctgc agatcaccga gaactcacct  420
gccgtcttcg ttcagtttac ttacctctcg ctgggcggcc tcctctgcac ctccggggtc  480
gcaggcaccc ccatccgctt catctcttcc tcctctgctt cccataatca tatcctgcat  540
aagccggcca ccactggtgt cctgcgtcag gtggtggacg cctcatcatc cacc         594
```

```
SEQ ID NO: 20          moltype = DNA  length = 594
FEATURE                Location/Qualifiers
source                 1..594
                       mol_type = other DNA
                       organism = Asplenium nidus
SEQUENCE: 20
atggcaacca agggagctgt tgttgcggtg tgctgcctcg tgctggtgag cgccatattg   60
ttcatggggt gcacgacggt agccggggac gacgagacat ggcaggaagt gctgacaaca  120
gccggcacga ctgtggtgta tggggctacc aacacctaca cgatccaggc catggacatt  180
ggaatcaggt atctctatta ctttttcttc gggctgggt atacgggaga tgcggtgcgg   240
acggacacgg ccgtcacgtt gggcgacctc ggcgacgcgt cccaaatcta cgcctgcact  300
gacgacaaac tggagctggt ggccgtcaac tctagcggca cgccgcagaa tgccatcatt  360
cgcgttcgct acaacagcac cgacggcaac tacgggctgc agatcaccga gaactcacct  420
```

```
gccgtcttcg ttcagtttac ttacctctcg ctgggcggcc tcctctgcac ctccggggtc   480
gcaggcaccc ccatccgctt catctcttcc tcctctgctt cccataatca tatcctgcat   540
aagccggcca ccactggtgt cctgcgtcag gtggtggacg cctcatcatc cacc          594

SEQ ID NO: 21            moltype = DNA  length = 540
FEATURE                  Location/Qualifiers
source                   1..540
                         mol_type = other DNA
                         organism = Colysis wrightii
SEQUENCE: 21
atggctatga aggcaatatt ggcagtctgc tgttgcataa taatactaat gggcgccatg   60
atcagcggag gatcggccgc tgacgagaca tggcaggagg tcctaattac gaacacgggg   120
tcgaaggtag tgtatgggac caacaacaag tatgttatca gggcaatgga cttgcggtta   180
ggctatgccc acaagtttta cttcggccta gggtacgagg gggacccggt gcgaacagac   240
acgaccctca caataggttg caatggtaat gcatcgacca tctactcctg catcgatggc   300
aagatgaaga cggtgcccac ttgcaccacc tccggcatgt cgcagaatgc tttgattcgc   360
gtgcgctaca acagcactga cggctactac cggcttcaga tcacggaatc ctacccggcc   420
gtgtacgttg agtttgttta ttcttcccaa ggttccatat tctgcaccgc aggcctcctc   480
ggcacaccta ttgaatttcc ccacgactac ttctcctcct ccttctctca gggttgcctt   540

SEQ ID NO: 22            moltype = DNA  length = 576
FEATURE                  Location/Qualifiers
source                   1..576
                         mol_type = other DNA
                         organism = Asplenium nidus
SEQUENCE: 22
atggcaaaca agggaggggt tgtcgcagtg ctctggctga tgacggtgag ctctgtgttg   60
atgatggggt gcaatacggt ggccggggat gatgagacat ggcaggaagt gctcaccaca   120
gctggcacga acgtggtgtt cggggctagc aacacctaca cgatttgggc tcgggacata   180
gggataggggt atctctttag gttcttcttc gggctggggg ctacgggaga gggcggtgtg   240
accgacacga ctgtcacgct gggcgccttt ggagatgcat ccaggatcta cgcttgcgtt   300
gacggcaagc tggagcgggt ggccgtaaac tcctccggga cgccagaaa tgccattttt   360
cgcgtgcgct acaacagcac tagcagcagc tacctgcttc agatcacgga gaactcgcct   420
gccgtctttg ttcagttcac ttacctttcc ctaggcggcc tttctctgcac ctctggggtc   480
gcaggcaccc cagtccgctt cacttctgcc tcctcctctt cccatggtca cgtggatgag   540
ccggccactg ttgacctgcg tcaagtggtt gacgcc                               576

SEQ ID NO: 23            moltype = DNA  length = 570
FEATURE                  Location/Qualifiers
source                   1..570
                         mol_type = other DNA
                         organism = Phyllitis scolopendrium
SEQUENCE: 23
atggcaacaa ctaagggagt agtagtacta gtgtgctggt taatgatggt gagcgcagtg   60
tttataggggt gcaatacagt ggcgggcgac acatttcagg aggtgttgac aacagccggc   120
gctaacgtgg tgtatggggc taccaacacc tacaccattt gggcgcagga cattggaatc   180
gggtatctct ataagttctt cttcgggctg gggtatacgg gggacggagac   240
acggccgtca cgctgggtgc ctctggaaat gcgtccaaca tctacgcttg cactgacggc   300
aaactggagc tggtggccgt aaactccagt ggcacgccac agaatgctct cattcgcgtg   360
cgctacaaca gcactgacag ctactaccgg ctgcagatca cggaggcctc ccctgcagtc   420
tacgttcagt tcacttacct ctccctgggc ggctcctct gcacctctgg cgtcgcaggc   480
tcgccctcc aattcacctc ttcttcctct tcttcccatg aacacctgca tgagccggct   540
actataaccc tgcgtcaggt ggttgacacc                                      570

SEQ ID NO: 24            moltype = DNA  length = 540
FEATURE                  Location/Qualifiers
source                   1..540
                         mol_type = other DNA
                         organism = Colysis wrightii
SEQUENCE: 24
atggctatga aggcaatatt ggcagtctgc tgttgcataa taatactaat gggcgccatg   60
atcagcggag gatcggccgc tgacgagaca tggcaggagg tcctaattac gaacacgggg   120
tcgaaggtag tgtatgggac caacaacaag tatgttatca gggcaatgga cttgcggtta   180
ggctatgccc acaagtttta cttcggccta gggtacgagg gggacccggt gcgaacagac   240
acgaccctca caataggttg caatggtaat gcatcgacca tctactcctg catcgatggc   300
aagatgaaga cggtgcccac ttgcaccacc tccggcatgt cgcagaatgc tttgattcgc   360
gtgcgctaca acagcactga cggctactac cggcttcaga tcacggaatc ctacccggcc   420
gtgtacgttg agtttgttta ttcttcccaa ggttccattc tctgcaccgc aggcctcctc   480
ggcacaccta ttgaatttcc ccacgactac ttctcctcct ccttctctca gggttgcctt   540

SEQ ID NO: 25            moltype = DNA  length = 585
FEATURE                  Location/Qualifiers
source                   1..585
                         mol_type = other DNA
                         organism = Asplenium trichomanes
SEQUENCE: 25
atgacaacca agggagtagc agtactagtg tgctggttag tgatggtgag cgcagtgttt   60
atgaggtgca atacagtggc cggcgatgcg agacatggc aggaggtgct gacaacagac   120
agcacgaacg tggtgtatgg ggctagcaac acctacacca tttgggccct ggatatggga   180
```

-continued

```
atcctctacc tcggtgagtt cttcttcggg ctggggtata cgggagatgt ggtgaggaca   240
gacacggccc tcacgatggg cgcctttgga gatgcctcca atatctatgc ttgcagtgac   300
ggcaaattgg agctggtggc cgtgaacacc agcggcacgc cacaaaatgc cctcattcgc   360
gtgcgctaca acagcaccga caccagttac agactgcaga tcacagaggc ctcccctgct   420
gtctttgttc agttcactta cctctccctg ggtggcctcc tctgcacctc gggggtggca   480
ggatccccca tccgcttcat ctcttcttcc tcgacctctt cccatgatca cctgcagcac   540
gtcaagccgg ccactatgac cggcctgcgt caggtggtcg acgcc              585
```

```
SEQ ID NO: 26            moltype = DNA   length = 633
FEATURE                  Location/Qualifiers
source                   1..633
                         mol_type = other DNA
                         organism = Phyllitis scolopendrium
SEQUENCE: 26
atggcggggt tgaaggcggc ggtggcgatg cgcgtgatgt tctgctgctg gtcggtgatc   60
atgatactga gcaaggcgcc gcgggtggtt catgcacagg acgaggagac atttgaggag   120
gtgacgacga gaaatgggtc gaccgtggtg tacgagccag gcaatacgta caccatatgg   180
tcaagggagt cggggatcgg gtattacccg ttccacttcg ggctggggtt tgaggggctt   240
gcgatgcgaa cagacacgcc catcaccatg ggactgggat cagatgccag ccgaatctat   300
gcctgtgtca acggcacgct cagacgtgtg gccacggacc ctgagtgtac gcctgacaat   360
gccttgattc gcgtgcggct caacagcact gacaactact accgcctgca gatcactcag   420
acgttgcctc ccgtttatgt gcaacttgtc ctgctcagtc aaggcggcct tctctgcacc   480
tccgacctcc ctggcactcc tatccaattc agcgccgtgt cgtcgaccac ctccaccttc   540
accccacatg tcccggctac tgatccgggg cttgtttacg agctgggcgc cgataatacg   600
cacatcctcc gtcaggtggt cgacggctca acc                                633
```

```
SEQ ID NO: 27            moltype = DNA   length = 633
FEATURE                  Location/Qualifiers
source                   1..633
                         mol_type = other DNA
                         organism = Phyllitis scolopendrium
SEQUENCE: 27
atggcggggt tgaaggcggc ggtggcgatg cgcgtgatgt tctgctgctg gtcggtgatc   60
atgatactga gcaaggcgcc gcgggtggtt catgcacagg acgaggagac atttgaggag   120
gtgacgacga gaaatgggtc gaccgtggtg tacgagccag gcaatacgta caccatatgg   180
tcaagggagt cggggatcgg gtattacccg ttccacttcg ggctggggtt tgaggggctt   240
gcgatgcgaa cagacacgcc catcaccatg ggactgggat cagatgccag ccgaatctat   300
gcctgtgtca acggcacgct cagacgtgtg gccacggacc ctgagtgtac gcctgacaat   360
gccttgattc gcgtgcggct caacagcact cacaactact accgcctgca gatcactcag   420
acgttgcctc ccgtttatgt gcaacttgtc ctgctcagtc aaggcggcct tctctgcacc   480
tccgacctcc ctggcactcc tatccaattc agcgccgtgt cgtcgaccac ctccaccttc   540
accccacatg tcccggctac tgatccgggg cttgtttacg agctgggcgc cgataatacg   600
cacatcctcc gtcaggtggt cgacggctca acc                                633
```

```
SEQ ID NO: 28            moltype = DNA   length = 633
FEATURE                  Location/Qualifiers
source                   1..633
                         mol_type = other DNA
                         organism = Phyllitis scolopendrium
SEQUENCE: 28
atggcggggt tgaaggcggc ggtggcgatg cgcgtgatgt tctgctgctg gtcggtgatc   60
atgatactga gcaaggcgcc gcgggtggtt catgcacagg acgaggagac atttgaggag   120
gtgacgacga gaaatgggtc gaccgtggtg tacggagcca acaatacgta caccatatgg   180
tcaagggagt cggggatcgg gtattacccg ttccacttcg ggctggggtt tgaggggctt   240
gcgatgcgaa cagacacgcc catcaccatg ggactgggat cagatgccag ccgaatctat   300
gcctgtgtca acggcacgct cagacgtgtg gccacggacc ctgagtgtac gcctgacaat   360
gccttgattc gcgtgcggct caacagcact cacaactact accgcctgca gatcactcag   420
acgttgcctc ccgtttatgt gcaacttgtc ctgctcagtc aaggcggcct tctctgcacc   480
tccgacctcc ctggcactcc tatccaattc agcgccgtgt cgtcgaccac ctccaccttc   540
accccacatg tcccggctac tgatccgggg cttgtttacg agctgggcgc cgataatacg   600
cacatcctcc gtcaggtggt cgacggctca acc                                633
```

```
SEQ ID NO: 29            moltype = DNA   length = 633
FEATURE                  Location/Qualifiers
source                   1..633
                         mol_type = other DNA
                         organism = Phyllitis scolopendrium
SEQUENCE: 29
atggcggggt tgaaggcggc ggtggcgatg cgcgtgatgt tctgctgctg gtcggtgatc   60
atgatactga gcaaggcgcc gcgggtggtt catgcacagg acgaggagac atttgaggag   120
gtgacgacga gaaatgggtc gaccgtggtg tacggagcca acaatacgta caccatatgg   180
tcaagggagt cggggatcgg gtattacccg ttccacttcg ggctggggtt tgaggggctt   240
gcgatgcgaa cagacacgcc catcaccatg ggactgggat cagatgccag ccgaatctat   300
gcctgtgtca acggcacgct cagacgtgtg gccacggacc ctgagtgtac gcctgacaat   360
gccttgattc gcgtgcggct caacagcact gacaactact accgcctgca gatcactcag   420
acgttgcctc ccgtttatgt gcaacttgtc ctgctcagtc aaggcggcct tctctgcacc   480
tccgacctcc ctggcactcc tatccaattc agcgccgtgt cgtcgaccac ctccaccttc   540
accccacatg tcccggctac tgatccgggg cttgtttacg agctgggcgc cgataatacg   600
cacatcctcc gtcaggtggt cgacgcctca gcc                                633
```

-continued

```
SEQ ID NO: 30            moltype = DNA   length = 633
FEATURE                  Location/Qualifiers
source                   1..633
                         mol_type = other DNA
                         organism = Phyllitis scolopendrium
SEQUENCE: 30
atggcggggt tgaaggcggc ggtggcgatg cgcgtgatgt tctgctgctg gtcggtgatc   60
atgatactga gcaaggcgcc gcgggtggtt catgcacagg acgaggagac atttgaggag   120
gtgacgacga gaaatgggtc gaccgtggtg tacggagcca gcaatacgta caccatatgg   180
tcaagggagt cggggatcgg gtattacccg ttccacttcg ggctggggtt tgaggggctt   240
gcgatgcgaa cagacacgcc catcaccatg ggactgggat cagatgccag ccgaatctat   300
gcctgtgtca acggcacgct cagacgtgtg gccacggacc ctgagtgtac gcctgacaat   360
gccttgattc gcgtgcggct caacagcact gacaactact accgcctgca gatcactcag   420
acgttgcctc ccgtttatgt gcaacttgtc ctgctcagtc aaggcggcct tctctgcacc   480
tccgacctcc ctggcactcc tatccaattc agcgccgtgt cgtcgaccac ctccaccttc   540
accccacatg tcccggctac tgatccgggg cttgtttacg agctgggcgc tgataatacg   600
cacatcctcc gtcaggtggt cgacgcctca gcc                                633

SEQ ID NO: 31            moltype = DNA   length = 633
FEATURE                  Location/Qualifiers
source                   1..633
                         mol_type = other DNA
                         organism = Phyllitis scolopendrium
SEQUENCE: 31
atggcggggt tgaaggcggc ggtggcgatg cgcgtgatgt tctgctgctg gtcggtgatc   60
atgatactga gcaaggcgcc gcgggtggtt catgcacagg acgaggagac atttgaggag   120
gtgacgacga gaaatgggtc gaccgtggtg tacggagcca gcaatacgta caccatatgg   180
tcaagggagt cggggatcgg gtattacccg ttccacttcg ggctggggtt tgaggggctt   240
gcgatgcgaa cagacacgcc catcaccatg ggactgggat cagatgccag ccgaatctat   300
gcctgtgtca acggcacgct cagacgtgtg gccacggacc ctgagtgtac gcctgacaat   360
gccttgattc gcgtgcggct caacagcact cacaactact accgcctgca gatcactcag   420
acgttgcctc ccgtttatgt gcaacttgtc ctgctcagtc aaggcggcct tctctgcacc   480
tccgacctcc ctggcactcc tatccaattc agcgccgtgt cgtcgaccac ctccaccttc   540
accccacatg tcccggctac tgatccgggg cttgtttacg agctgggcgc cgataatacg   600
cacatcctcc gtcaggtggt cgacgcctca gcc                                633

SEQ ID NO: 32            moltype = DNA   length = 633
FEATURE                  Location/Qualifiers
source                   1..633
                         mol_type = other DNA
                         organism = Phyllitis scolopendrium
SEQUENCE: 32
atggcggggt tgaaggcggc ggtggcgatg cgcgtgatgt tctgctgttg gttggtgatc   60
atgatactga gcaaggcacc gcgggtggtt catgcacacg acgaggagac atttgaggag   120
gtgacgacga cagatgggtc gatcgtggtg tacggagcca gcaatacgta caccatatgg   180
tcaagggagt cggggatcgg gtattacccg ttccacttcg ggctggggtt tgaggggctt   240
gcgatgcgaa cagacacgcc catcaccatg ggactgggat cagatgccag ccgaatctat   300
gcctgtgtca acggcacgct cagacgtgtg gccacggacc ctgagtgtac gcctgacaat   360
gccttgattc gcgtgcggct caacagcact gacaactact accgcctgca gatcactcag   420
acgttgcctc ccgtttatgt gcaacttgtc ctgctcagtc aaggcggcct tctctgcacc   480
tccgacctcc ctggcactcc tatccaattc agcgccgtgt cgtcgaccac ctccaccttc   540
accccacatg tcccggctac tgatccgggg cttgtttacg agctgggcgc tgataatacg   600
cacatcctcc gtcaggtggt cgacgcctca gcc                                633

SEQ ID NO: 33            moltype = DNA   length = 636
FEATURE                  Location/Qualifiers
source                   1..636
                         mol_type = other DNA
                         organism = Phyllitis scolopendrium
SEQUENCE: 33
atggcggggt tgaaggcggc ggcggtggcg atgcgcgtga tgttctgctg ttggttggtg   60
atcatgatac tgagcaaggc accgcggggtg gttcatgcac acgacgagga gacatttgag   120
gaggtgacga cgacagatgg gtcgatcgtg gtgtacggag ccagcaatac gtacaccata   180
tggtcaaggg agtcgdggat cgggtattac ccgttccact tcgggctggg gtttgagggg   240
cttgcggtgc gaacagacac agccatcacc atgggactgg gatcagatgc cagccgaatc   300
tatgcctgtg tcaacggcac gctcagacgt gtggccacgg accctgagtg tacgcctgac   360
aatgccttga ttcgcgtgcg gctcaacagc actcacaact actaccgcct gcagatcact   420
cagacgttgc ctcccgttta tgtgcaactt gtcctgctca gtcaaggcgg ccttctctgc   480
acctccgacc tccctggcac tcctatccaa ttcagcgccg tgtcgtcgac cacctccacc   540
ttcacccca c atgtcccggc tactgatccg gggcttgttt acgagctggg cgccgataat   600
acgcacatcc tccgtcaggt ggtcgacgcc tcagcc                             636

SEQ ID NO: 34            moltype = DNA   length = 636
FEATURE                  Location/Qualifiers
source                   1..636
                         mol_type = other DNA
                         organism = Phyllitis scolopendrium
SEQUENCE: 34
```

-continued

```
atggcggggt tgaaggcggc ggcggtggcg atgcgcgtga tgttctgctg ttggttggtg        60
atcatgatac tgagcaaggc accgcggtg gttcatgcac acgacgagga gacatttgag        120
gaggtgacga cgacagatgg gtcgatcgtg gtgtacggag ccagcaatac gtacaccata      180
tggtcaaggc agtcggggat cgggtattac ccgttccact tcgggctggg gtttgagggg       240
cttgcggtgc gaacagacac agccatcacc atgggactgg gaacagatgc cagccgaatc       300
tatgcctgtg tcaacggcac gctcagccta gtggccacgg accctgaggg tacgcctgcg       360
aatgccttga ttcgcgtgcg gctcaacagc actgacaact actaccgcct gcagatcact       420
gagagctcgc ctcccgttta tgtgcaattt gtcctactca gtcaaggcgg ccttctctgc       480
acctccggcc tccctggcac tcctattcaa ttcagcaccg tgtcgtcgac cacctccacc       540
ttcaccccac atgtcccggc tactgatccg gggcttgttt acgagctggg cgccgataat       600
acgcacatcc tccgtcaggt ggtcgacgcc tcagcc                                 636
```

```
SEQ ID NO: 35              moltype = DNA   length = 621
FEATURE                    Location/Qualifiers
source                     1..621
                           mol_type = other DNA
                           organism = Asplenium trichomanes
SEQUENCE: 35
atggcaatct gcaagcgatc ggtagctgta gtactagtgt gctggctcac gatggtgagc        60
gctgtgttgc tgctggggtg caatgcaggc gtgccggtcc gcgatgacga gacgtggcag       120
gaggtgctga caacagccgg cgacaacgtg gtttatgggg ctaccaacac ctacaccatt       180
tgggcgcagg acattggaat cgggtatctc tacaggtctc tcttcgggct ggggtatacg      240
ggagatgcgg tgctgacgga cacggccctc acactgggcg cttttcgcaga tgcgtccaac     300
atctacgctt gcaatgccgg cgttctggag cggattgccg tgaacgccag cggcacacca      360
cagaatgccc tcattcgcgt gcgctacaac agcaccgaca gcagctaccg gctgcagatc       420
acggaggcct ctcctgccgt ctacgtccag ttcacctacc tctccctgg cggcctcctc       480
tgcacctctg gcgtcgcagg cacccccatc cgcttcacct cttcctccag ctcttcttcc      540
cacgatgcag tgaaccgaca tcatgggccg gccaccacaa ctgcgcccct cctgcgacag      600
gtggtggtgg aggcggaggc c                                                 621
```

```
SEQ ID NO: 36              moltype = DNA   length = 621
FEATURE                    Location/Qualifiers
source                     1..621
                           mol_type = other DNA
                           organism = Asplenium trichomanes
SEQUENCE: 36
atggcaatct gcaagcgatc ggtagctgta gtactagtgt gctggctcac gatggtgagc        60
gctgtgttgc tgctggggtg caatgcaggc gtgccggtcc gcgatgacga gacgtggcag       120
gaggtgctga caacagccgg cgacaacgtg gtttatgggg ctaccaacac ctacaccatt       180
tgggcgcagg acattggaat cgggtatctc tacaggttct tcttcgggct ggggtatacg      240
ggagatgcgg tgctgacgga cacggccctc acactgggcg ctttcgcaga tgcgtccaac      300
atctacgctt gcaatgccgg cgttctggag cggattgccg tgaacgccag cggcacacca      360
cagaatgccc tcattcgcgt gcgctacaac agcaccgaca gcagctaccg gctgcagatc       420
acggaggcct ctcctgccgt ctacgtccag ttcacctacc tctccctgtg cggcctcctc      480
tgcacctctg gcgtcgcagg cacccccatc cgcttcacct cttcctccag ctcttcttcc      540
cacgatgcag tgcaccggca tcatgggccg gccaccacaa ctgcgcccct cctgcgacag      600
gtggtggtgg aggcggaggc c                                                 621
```

```
SEQ ID NO: 37              moltype = DNA   length = 621
FEATURE                    Location/Qualifiers
source                     1..621
                           mol_type = other DNA
                           organism = Asplenium trichomanes
SEQUENCE: 37
atggcaatct gcaagcgatc ggtagctgta gtactagtgt gctggctcac gatggtgagc        60
gctgtgttgc tgctggggtg caatgcaggc attccggtcc gcgatgacga gacatggcaa       120
gaggtgctga caacagccgg cgacaacgtg gtttatgggg ctaccaacac ctacaccatt       180
tgggcgcagg acattggaat cgggtatctc tacaggttct tctttgggct ggggtatacg      240
ggagatgccg tgctgacgga cacggccctc acactgggcg ctttcgcaga tgcgtccaac      300
atctacgctt gcaatgccgg cgttctggag cttattgccg tgaacgccag cggcacacca      360
cagaatgccc tcattcgcgt gcgctacaac agcaccgaca gcagctaccg gctgcagatc       420
acggaggcct ccctgccgt ctacgtccag ttcacctacc tctccctggg cggcctcctc       480
tgcacctctg gcgtcgcagg cacccccatc cgcttcacct cttcctccag ctcttcttcc      540
cacgatgcag tgcaccggca tcatgggccg gccaccacaa ctgcgcccct cctgcgacag      600
gtggtggtgg aggcggaggc c                                                 621
```

```
SEQ ID NO: 38              moltype = DNA   length = 807
FEATURE                    Location/Qualifiers
source                     1..807
                           mol_type = other DNA
                           organism = Ceratopteris richardii
SEQUENCE: 38
cgcgcctgcc tctgatctac agtcccgatt gcaatgaaga gaatcgtagt agttccagcc        60
gccctcttcg tgatcgcgct caccatgctg agctgcggtc accctgcta cggggcggct       120
gtgctcacaa gtgccggcac acctgtggtg tttggaaccc cgcccagata cacgctatgg      180
tcccgggaat ccggaattgg gtataatggc ttcttcttcg ggctcggctt tcccggagat      240
cctgtataca cggacaccac cattaccatg ggatccttct ggtctggtgg tggtccgtcg      300
aatatctatg catgtaggga tggtttcctc accttcatcc ccgtcagctc cgagctcaca      360
ccacaagatg ccattatccg cgtgcgcttc aacagcactg acaactctta ccgccttcag      420
```

```
ataactgagg ctaacccccc cgtctacgtt caactggcgc ttctctcgca aggcggcctc   480
ctctgcaccc caggcgttcc tggcacccct atgcggttca gcctccggtc ctccaaagat   540
gagaacctcc ctcagcagat gagccatgtg ctccatgagg tcgttgacac cgcttgaacg   600
tctgccgcaa ggtcattgtc tccgctttct tccttctgtg cttgtcctta gcgcttcatc   660
gctttgcagc cccctatgtg aagtttgtat ttagtatgtt gccccacatg taacaagttc   720
ttcttcaata attattggca cagcaaacta cgcagtaaaa aaaaaaaaaa aaaaaaaaaa   780
aaaaaaaaag cggccgcctg aattcta                                       807
```

```
SEQ ID NO: 39          moltype = AA   length = 187
FEATURE                Location/Qualifiers
source                 1..187
                       mol_type = protein
                       organism = Polypodium musifolium
SEQUENCE: 39
MAATKAVLAV CSCIIVLMGV MISGGLASDE PTWQEVLTTA RTNVVYGPSN TYTIRSMTSG   60
IGYLFRFFFG LGFPGEAVRT DTTITMGRNG DASAIYACID GRLRLVATNT SGTPQNALIR   120
VRFNSTDGYY RLQITQASPA VYVQFVLLSQ GGILCTAGLP GTPLTFTSSS SSDLRVLHQV   180
VDSSSLS                                                            187
```

```
SEQ ID NO: 40          moltype = AA   length = 190
FEATURE                Location/Qualifiers
source                 1..190
                       mol_type = protein
                       organism = Polypodium formosanum
SEQUENCE: 40
MAATKAVLAV CSCIIVLMGV DMISGGLASN EPTWQEVLTT ARTNVVYGAS NTYTIWSQTS   60
GIGYLFRFFF GLGFPGEAVR TDTTITMGRN GDASAIYACI DGRLQVVATN TSGTPQNALI   120
RVRYNSTDGY YRLQITQASP AVYVQFVLLS QGGILCTAGL PGTPLTFTSS SSSSSDLRVL   180
HQVVDSSSLA                                                         190
```

```
SEQ ID NO: 41          moltype = AA   length = 190
FEATURE                Location/Qualifiers
source                 1..190
                       mol_type = protein
                       organism = Polypodium formosanum
SEQUENCE: 41
MAATKAVLAV CSCIIVLMGA DMISGGLASN EPTWQEVLTT ARTNVVYGAS NTYTIWSQTS   60
GIGYLFRFFF GLGFPGEAVR TDTTITMGRN GDASAIYACI DGRLQVVATN TSGTPQNALI   120
RVRYNSTDGY YRLQITQASP AVYVQFVLLS QGGILCTAGL PGTPLTFTSS SSSSSDLRVL   180
HQVVDSSSLA                                                         190
```

```
SEQ ID NO: 42          moltype = AA   length = 190
FEATURE                Location/Qualifiers
source                 1..190
                       mol_type = protein
                       organism = Polypodium formosanum
SEQUENCE: 42
MAATKAVLAV CSCIIVLMGA DMISGGLASN EPTWQEVLTT ARTNVVYGAS NTYTIWSQTS   60
GIGYLFRFFF GLGFPGEAVR TDTTITMGRN GDASAIYACI DGRLQVVATN TSGTPQNALI   120
RVRYNSTDGY YRLQITQASP AVYVQFVLLS QGGILCTAGL PGTPVTFTSS SSSSSDLRVL   180
HQVVDSSSLA                                                         190
```

```
SEQ ID NO: 43          moltype = AA   length = 142
FEATURE                Location/Qualifiers
source                 1..142
                       mol_type = protein
                       organism = Polypodium formosanum
SEQUENCE: 43
MSNTYTIWSQ TSGIGYLFRF FFGLGFPGEA VRTDTTITMG RNGYASAIYA CIDGRLQVVA   60
TNTSGTPQNA LIRVRYNSTD GYYRLQITQA SPAVYVQFVL LSQGGILCTA GLPGTPVTFT   120
SSSSSSSSDLR VLHQVVDSSS LA                                           142
```

```
SEQ ID NO: 44          moltype = AA   length = 142
FEATURE                Location/Qualifiers
source                 1..142
                       mol_type = protein
                       organism = Polypodium formosanum
SEQUENCE: 44
MSNTYTIWSQ TSGIGYLFRF FFGLGFPGEA VRTNTTITMG RNGDASAIYA CIDGRLQVVA   60
TNTSGTPQNA LIRVRYNSTD GYYRLQITQA SPAVYVQFVL LSQGGILCTA GLPGTPLTFT   120
SSSSSSSSDLR VLHQVVDSSS LA                                           142
```

```
SEQ ID NO: 45          moltype = AA   length = 142
FEATURE                Location/Qualifiers
source                 1..142
                       mol_type = protein
                       organism = Polypodium formosanum
SEQUENCE: 45
MSNTYTIWSQ TSGIGYLFRF FFGLGFPGEA VRTDTTITMG RNGDASAIYA CIDGRLQVVA   60
```

```
TNTSGTPQNA LIRVRYNSTD GYYRLQITQA SPAVYVQFVL LSQGGILCTA GLPGTPVTFT   120
SSSSSSSDLR VLHQVVDSSS LA                                              142

SEQ ID NO: 46              moltype = AA  length = 142
FEATURE                    Location/Qualifiers
source                     1..142
                           mol_type = protein
                           organism = Polypodium formosanum
SEQUENCE: 46
MSNTYTIWSQ TSGIGYLFRF FFGLGFPGEA VRTDTTITMG RNGDASAIYA CIDGRLQVVA   60
TNTSGTPQNA LIRVRYNSTD GYYRLQITQA SPAVYVQFVL LSQGGILCTA GLPGTPLTFT   120
SSSSSSSDLR VLHQVVDSSS LA                                              142

SEQ ID NO: 47              moltype = AA  length = 202
FEATURE                    Location/Qualifiers
source                     1..202
                           mol_type = protein
                           organism = Polypodium punctatum
SEQUENCE: 47
MATKTLLAVC GCILILMGVM ISGGSAADET WQEVLTRAGT NVVYGPSNTY IIWSTESWIG   60
YVFGFFFGLG FDGEAVRTDT TVTLGRNGDA SSIYACIDGK LELVPTNSSG TPQNALIRVR   120
YNSTDGYYRL QITEASPAVY VQFVLLSQGG ILCTAGLPGT PIVFTSTSSS SSVSPNRRQG   180
PALVYTPDMH VLRQVVDSSS LA                                              202

SEQ ID NO: 48              moltype = AA  length = 202
FEATURE                    Location/Qualifiers
source                     1..202
                           mol_type = protein
                           organism = Polypodium punctatum
SEQUENCE: 48
MATKTLLTVC GCILILMGVM ISGGSAADET WQEVLTRAGT NVVYGPSNTY IIWSTESWIG   60
YVFGFFFGLG FDGEAVRTDT TVTLGRNGDA SSIYACIDGK LELVPTNSSG TPQNALIRVR   120
YNSTDGYYRL QITEASPAVY VQFVLLSQGG ILCTAGLPGT PIVFTSTSSS SSVSPNRRQG   180
PALVYTPDMH VLRQVVDSSS LA                                              202

SEQ ID NO: 49              moltype = AA  length = 200
FEATURE                    Location/Qualifiers
source                     1..200
                           mol_type = protein
                           organism = Colysis wrightii
SEQUENCE: 49
MATKAVSAIC GCIMILMGAM ISGALADDET WQEVLTTAGT NVVFGASNTY TIRSRESGIG   60
YLFRFYFGLG GEGEPVRTDT TVTLGRNGDA SRIYSCNDGT LELVATNSSG TPQSALIRVR   120
YNSTDGYYRL QITEASPAVY VQFVLLSQGG ILCTAGLPGT PIVFESSSSS SLSSRPLGPV   180
LVYTPDMDVL RQVVDSSSLA                                                 200

SEQ ID NO: 50              moltype = AA  length = 192
FEATURE                    Location/Qualifiers
source                     1..192
                           mol_type = protein
                           organism = Asplenium nidus
SEQUENCE: 50
MANKGGVVAV LWLMTVSSVL MMGCNTVAGD DETWQEVLTT AGTNVVFGAS NTYTIWARDI   60
GIGYLFRFFF GLGSTGEAVR TDTTVTLGAY GDASRVYACT DGKLQLVAVN SSGTPENAII   120
RVRYNSTDRN YRLQITENSP AVFVQFTYLS QGGLLCTSGV AGTPIRFTFS SSSSLDHVDE   180
PATVVLRQVV DA                                                        192

SEQ ID NO: 51              moltype = AA  length = 192
FEATURE                    Location/Qualifiers
source                     1..192
                           mol_type = protein
                           organism = Asplenium nidus
SEQUENCE: 51
MATKGGVVAV LWLMTVSSVL MMGCNTVAGD DETWQEVLTT AGTNVVFGAS NTYTIWARDI   60
GIGYLFRFFF GLGSTGEAVR TDTTVTLGAY GDASRVYACT DGKLQLVAVN SSGTPENAII   120
RVRYNSTDRN YRLQITENSP AVFVQFTYLS QGGLLCTSGV AGTPIRFTFS SSSSLDHVDE   180
PATVVLRQVV DA                                                        192

SEQ ID NO: 52              moltype = AA  length = 192
FEATURE                    Location/Qualifiers
source                     1..192
                           mol_type = protein
                           organism = Asplenium nidus
SEQUENCE: 52
MANKGGVVVA FWLMIVSCSV LLGCNTVAGT DETWQEVLTT AGTNVVFGAS NTYTIRSQET   60
GIGYLFRFYF ELGATGEAVR TDTTVTLGAF GDASRIYACV DGKLERVAVN SSGTPENAIF   120
RVRYNSTSSS YLLQITENSP AVFVQFTYLS LGGLLCTSGV AGTPVRFTSA SSSSHGHVDE   180
PATVDLRQVV DA                                                        192
```

```
SEQ ID NO: 53          moltype = AA  length = 192
FEATURE                Location/Qualifiers
source                 1..192
                       mol_type = protein
                       organism = Asplenium nidus
SEQUENCE: 53
MATKGGVVVA FWLMIVSCSV LLGCNTVAGT DETWQEVLTT AGTNVVFGAS NTYTIRSQET   60
GIGYLFRFYF ELGATGEAVR TDTTVTLGAF GDASRIYACV DGKLERVAVN SSGTPENAIF  120
RVRYNSTSSS YLLQITENSP AVFVQFTYLS LGGLLCTSGV AGTPVRFTSA SSSSHGHVDE  180
PATVDLRQVV DA                                                      192

SEQ ID NO: 54          moltype = AA  length = 187
FEATURE                Location/Qualifiers
source                 1..187
                       mol_type = protein
                       organism = Polystichium tsus-simense
SEQUENCE: 54
MATKGGVVLV CLCMIALGCN TVAGDDETWQ EVLTTDGANV VYGANNTYTI WARDIGIGYL   60
YRFFFGLGFT GTAVRSDTAV TLGAFADSTR IYACTDGKLE LVAVNSSGTP ANAIIRVRYN  120
STDSNYRLQI TENSPAVFVQ FTYLSLGGLL CTSGVSGTPI RFTSSSSASH DHLHEPATVA  180
LRQVVET                                                            187

SEQ ID NO: 55          moltype = AA  length = 187
FEATURE                Location/Qualifiers
source                 1..187
                       mol_type = protein
                       organism = Polystichium tsus-simense
SEQUENCE: 55
MATKGGVVLV CLCMIALGCN TVAGDDETWQ EVLTTDGANV VYGANNTYTI WARDIGIGYL   60
YRFFFGLGFT GTAVRTDTAV TLGAFADSTR IYACTDGKLE LVAVNSSGTP ANAIIRVRYN  120
STDSNYRLQI TENSPAVFVQ FTYLSLGGLL CTSGVAGTPI RFTSSSSASH DHLHEPATVA  180
LRQVVET                                                            187

SEQ ID NO: 56          moltype = AA  length = 197
FEATURE                Location/Qualifiers
source                 1..197
                       mol_type = protein
                       organism = Asplenium nidus
SEQUENCE: 56
MATKGAVVAV CCLVLVSAMF MGCTTVAGDD ETWQEVLTTA GTTVVYGATN TYTIQAMDIG   60
IRYLYYFFFG LGYTGDAVRT DTAVTLGDLG DASQIYACTD GKLELVAVNS SGTPQNAIIR  120
VRYNSTDGNY GLQITENSPA VFVQFTYLSL GGLLCTSGVA GTPIRFISSS SASHNHILHK  180
PATTGVLRQV VDASSST                                                 197

SEQ ID NO: 57          moltype = AA  length = 198
FEATURE                Location/Qualifiers
source                 1..198
                       mol_type = protein
                       organism = Asplenium nidus
SEQUENCE: 57
MATKGAVVAV CCLVLVSAIL FMGCTTVAGD DETWQEVLTT AGTTVVYGAT NTYTIQAMDI   60
GIRYLYYFFF GLGYTGDAVR TDTAVTLGDL GDASQIYACT DGKLELVAVN SSGTPQNAII  120
RVRYNSTDGN YGLQITENSP AVFVQFTYLS LGGLLCTSGV AGTPIRFISS SSASHNHILH  180
KPATTGVLRQ VVDASSST                                                198

SEQ ID NO: 58          moltype = AA  length = 198
FEATURE                Location/Qualifiers
source                 1..198
                       mol_type = protein
                       organism = Asplenium nidus
SEQUENCE: 58
MATKGAVVAV CCLVLVSAIL FMGCTTVAGD DETWQEVLTT AGTTVVYGAT NTYTIQAMDI   60
GIRYLYYFFF GLGYTGDAVR TDTAVTLGDL GDASQIYACT DDKLELVAVN SSGTPQNAII  120
RVRYNSTDGN YGLQITENSP AVFVQFTYLS LGGLLCTSGV AGTPIRFISS SSASHNHILH  180
KPATTGVLRQ VVDASSST                                                198

SEQ ID NO: 59          moltype = AA  length = 180
FEATURE                Location/Qualifiers
source                 1..180
                       mol_type = protein
                       organism = Colysis wrightii
SEQUENCE: 59
MAMKAILAVC CCIIILMGAM ISGGSAADET WQEVLITNTG SKVVYGTNNK YVIRAMDLRL   60
GYAHKFYFGL GYEGDPVRTD TTLTIGCNGN ASTIYSCIDG KMKTVPTCTT SGMSQNALIR  120
VRYNSTDGYY RLQITESYPA VYVEFVYSSQ GSIFCTAGLL GTPIEFPHDY FSSSFSQGCL  180

SEQ ID NO: 60          moltype = AA  length = 192
FEATURE                Location/Qualifiers
source                 1..192
```

```
                              mol_type = protein
                              organism = Asplenium nidus
SEQUENCE: 60
MANKGGVVAV LWLMTVSSVL MMGCNTVAGD DETWQEVLTT AGTNVVFGAS NTYTIWARDI    60
GIGYLFRFFF GLGATGEAVR TDTTVTLGAF GDASRIYACV DGKLERVAVN SSGTPENAIF   120
RVRYNSTSSS YLLQITENSP AVFVQFTYLS LGGLLCTSGV AGTPVRFTSA SSSSHGHVDE   180
PATVDLRQVV DA                                                       192

SEQ ID NO: 61                 moltype = AA  length = 190
FEATURE                       Location/Qualifiers
source                        1..190
                              mol_type = protein
                              organism = Phyllitis scolopendrium
SEQUENCE: 61
MATTKGVVVL VCWLMMVSAV FIGCNTVAGD TFQEVLTTAG ANVVYGATNT YTIWAQDIGI    60
GYLYKFFFGL GYTGDVVRTD TAVTLGASGN ASNIYACTDG KLELVAVNSS GTPQNALIRV   120
RYNSTDSYYR LQITEASPAV YVQFTYLSLG GLLCTSGVAG SPLQFTSSSS SSHEHLHEPA   180
TITLRQVVDT                                                          190

SEQ ID NO: 62                 moltype = AA  length = 180
FEATURE                       Location/Qualifiers
source                        1..180
                              mol_type = protein
                              organism = Colysis wrightii
SEQUENCE: 62
MAMKAILAVC CCIIILMGAM ISGGSAADET WQEVLITNTG SKVVYGTNNK YVIRAMDLRL    60
GYAHKFYFGL GYEGDPVRTD TTLTIGCNGN ASTIYSCIDG KMKTVPTCTT SGMSQNALIR   120
VRYNSTDGYY RLQITESYPA VYVEFVYSSQ GSILCTAGLL GTPIEFPHDY FSSSFSQGCL   180

SEQ ID NO: 63                 moltype = AA  length = 195
FEATURE                       Location/Qualifiers
source                        1..195
                              mol_type = protein
                              organism = Asplenium trichomanes
SEQUENCE: 63
MTTKGVAVLV CWLVMVSAVF MRCNTVAGDA ETWQEVLTTD STNVVYGASN TYTIWALDMG    60
ILYLGEFFFG LGYTGDVVRT DTALTMGAFG DASNIYACSD GKLELVAVNT SGTPQNALIR   120
VRYNSTDTSY RLQITEASPA VFVQFTYLSL GGLLCTSGVA GSPIRFISSS STSSHDHLQH   180
VKPATMTGLR QVVDA                                                    195

SEQ ID NO: 64                 moltype = AA  length = 211
FEATURE                       Location/Qualifiers
source                        1..211
                              mol_type = protein
                              organism = Phyllitis scolopendrium
SEQUENCE: 64
MAGLKAAVAM RVMFCCWSVI MILSKAPRVV HAQDEETFEE VTTRNGSTVV YGASNTYTIW    60
SRESGIGYYP FHFGLGFEGL AMRTDTPITM GLGSDASRIY ACVNGTLRRV ATDPECTPDN   120
ALIRVRLNST DNYYRLQITQ TLPPVYVQLV LLSQGGLLCT SDLPGTPIQF SAVSSTTSTF   180
TPHVPATDPG LVYELGADNT HILRQVVDGS T                                  211

SEQ ID NO: 65                 moltype = AA  length = 211
FEATURE                       Location/Qualifiers
source                        1..211
                              mol_type = protein
                              organism = Phyllitis scolopendrium
SEQUENCE: 65
MAGLKAAVAM RVMFCCWSVI MILSKAPRVV HAQDEETFEE VTTRNGSTVV YGASNTYTIW    60
SRESGIGYYP FHFGLGFEGL AMRTDTPITM GLGSDASRIY ACVNGTLRRV ATDPECTPDN   120
ALIRVRLNST HNYYRLQITQ TLPPVYVQLV LLSQGGLLCT SDLPGTPIQF SAVSSTTSTF   180
TPHVPATDPG LVYELGADNT HILRQVVDGS T                                  211

SEQ ID NO: 66                 moltype = AA  length = 211
FEATURE                       Location/Qualifiers
source                        1..211
                              mol_type = protein
                              organism = Phyllitis scolopendrium
SEQUENCE: 66
MAGLKAAVAM RVMFCCWSVI MILSKAPRVV HAQDEETFEE VTTRNGSTVV YGANNTYTIW    60
SRESGIGYYP FHFGLGFEGL AMRTDTPITM GLGSDASRIY ACVNGTLRRV ATDPECTPDN   120
ALIRVRLNST HNYYRLQITQ TLPPVYVQLV LLSQGGLLCT SDLPGTPIQF SAVSSTTSTF   180
TPHVPATDPG LVYELGADNT HILRQVVDGS T                                  211

SEQ ID NO: 67                 moltype = AA  length = 211
FEATURE                       Location/Qualifiers
source                        1..211
                              mol_type = protein
                              organism = Phyllitis scolopendrium
SEQUENCE: 67
```

-continued

```
MAGLKAAVAM RVMFCCWSVI MILSKAPRVV HAQDEETFEE VTTRNGSTVV YGANNTYTIW   60
SRESGIGYYP FHFGLGFEGL AMRTDTPITM GLGSDASRIY ACVNGTLRRV ATDPECTPDN  120
ALIRVRLNST DNYYRLQITQ TLPPVYVQLV LLSQGGLLCT SDLPGTPIQF SAVSSTTSTF  180
TPHVPATDPG LVYELGADNT HILRQVVDAS A                                211

SEQ ID NO: 68            moltype = AA  length = 211
FEATURE                  Location/Qualifiers
source                   1..211
                         mol_type = protein
                         organism = Phyllitis scolopendrium
SEQUENCE: 68
MAGLKAAVAM RVMFCCWSVI MILSKAPRVV HAQDEETFEE VTTRNGSTVV YGASNTYTIW   60
SRESGIGYYP FHFGLGFEGL AMRTDTPITM GLGSDASRIY ACVNGTLRRV ATDPECTPDN  120
ALIRVRLNST DNYYRLQITQ TLPPVYVQLV LLSQGGLLCT SDLPGTPIQF SAVSSTTSTF  180
TPHVPATDPG LVYELGADNT HILRQVVDAS A                                211

SEQ ID NO: 69            moltype = AA  length = 211
FEATURE                  Location/Qualifiers
source                   1..211
                         mol_type = protein
                         organism = Phyllitis scolopendrium
SEQUENCE: 69
MAGLKAAVAM RVMFCCWSVI MILSKAPRVV HAQDEETFEE VTTRNGSTVV YGASNTYTIW   60
SRESGIGYYP FHFGLGFEGL AMRTDTPITM GLGSDASRIY ACVNGTLRRV ATDPECTPDN  120
ALIRVRLNST HNYYRLQITQ TLPPVYVQLV LLSQGGLLCT SDLPGTPIQF SAVSSTTSTF  180
TPHVPATDPG LVYELGADNT HILRQVVDAS A                                211

SEQ ID NO: 70            moltype = AA  length = 211
FEATURE                  Location/Qualifiers
source                   1..211
                         mol_type = protein
                         organism = Phyllitis scolopendrium
SEQUENCE: 70
MAGLKAAVAM RVMFCCWLVI MILSKAPRVV HAHDEETFEE VTTTDGSIVV YGASNTYTIW   60
SRESGIGYYP FHFGLGFEGL AMRTDTPITM GLGSDASRIY ACVNGTLRRV ATDPECTPDN  120
ALIRVRLNST DNYYRLQITQ TLPPVYVQLV LLSQGGLLCT SDLPGTPIQF SAVSSTTSTF  180
TPHVPATDPG LVYELGADNT HILRQVVDAS A                                211

SEQ ID NO: 71            moltype = AA  length = 212
FEATURE                  Location/Qualifiers
source                   1..212
                         mol_type = protein
                         organism = Phyllitis scolopendrium
SEQUENCE: 71
MAGLKAAAVA MRVMFCCWLV IMILSKAPRV VHAHDEETFE EVTTTDGSIV VYGASNTYTI   60
WSRESGIGYY PFHFGLGFEG LAVRTDTAIT MGLGSDASRI YACVNGTLRR VATDPECTPD  120
NALIRVRLNS THNYYRLQIT QTLPPVYVQL VLLSQGGLLC TSDLPGTPIQ FSAVSSTTST  180
FTPHVPATDP GLVYELGADN THILRQVVDA SA                               212

SEQ ID NO: 72            moltype = AA  length = 212
FEATURE                  Location/Qualifiers
source                   1..212
                         mol_type = protein
                         organism = Phyllitis scolopendrium
SEQUENCE: 72
MAGLKAAAVA MRVMFCCWLV IMILSKAPRV VHAHDEETFE EVTTTDGSIV VYGASNTYTI   60
WSRESGIGYY PFHFGLGFEG LAVRTDTAIT MGLGTDASRI YACVNGTLSL VATDPEGTPA  120
NALIRVRLNS TDNYYRLQIT ESSPPVYVQF VLLSQGGLLC TSGLPGTPIQ FSTVSSTTST  180
FTPHVPATDP GLVYELGADN THILRQVVDA SA                               212

SEQ ID NO: 73            moltype = AA  length = 207
FEATURE                  Location/Qualifiers
source                   1..207
                         mol_type = protein
                         organism = Asplenium trichomanes
SEQUENCE: 73
MAICKRSVAV VLVCWLTMVS AVLLLGCNAG VPVRDDETWQ EVLTTAGDNV VYGATNTYTI   60
WAQDIGIGYL YRFFFGLGYT GDAVLTDTAL TLGAFADASN IYACNAGVLE RIAVNASGTP  120
QNALIRVRYN STDSSYRLQI TEASPAVYVQ FTYLSLGGLL CTSGVAGTPI RFTSSSSSSS  180
HDAVNRHHGP ATTTAPLLRQ VVVEAEA                                     207

SEQ ID NO: 74            moltype = AA  length = 207
FEATURE                  Location/Qualifiers
source                   1..207
                         mol_type = protein
                         organism = Asplenium trichomanes
SEQUENCE: 74
MAICKRSVAV VLVCWLTMVS AVLLLGCNAG VPVRDDETWQ EVLTTAGDNV VYGATNTYTI   60
WAQDIGIGYL YRFFFGLGYT GDAVLTDTAL TLGAFADASN IYACNAGVLE RIAVNASGTP  120
```

```
QNALIRVRYN STDSSYRLQI TEASPAVYVQ FTYLSLCGLL CTSGVAGTPI RFTSSSSSSS    180
HDAVHRHHGP ATTTAPLLRQ VVVEAEA                                       207

SEQ ID NO: 75           moltype = AA  length = 207
FEATURE                 Location/Qualifiers
source                  1..207
                        mol_type = protein
                        organism = Asplenium trichomanes
SEQUENCE: 75
MAICKRSVAV VLVCWLTMVS AVLLLGCNAG IPVRDDETWQ EVLTTAGDNV VYGATNTYTI     60
WAQDIGIGYL YRFFFGLGYT GDAVLTDTAL TLGAFADASN IYACNAGVLE LIAVNASGTP    120
QNALIRVRYN STDSSYRLQI TEASPAVYVQ FTYLSLGGLL CTSGVAGTPI RFTSSSSSSS    180
HDAVHRHHGP ATTTAPLLRQ VVVEAEA                                       207

SEQ ID NO: 76           moltype = AA  length = 187
FEATURE                 Location/Qualifiers
source                  1..187
                        mol_type = protein
                        organism = Ceratopteris richardii
SEQUENCE: 76
MKRIVVVPAA LFVIALTMLS CGHPCYGAAV LTSAGTPVVF GTPPRYTLWS RESGIGYNGF     60
FFGLGFPGDP VYTDTTITMG SFWSGGGPSN IYACRDGFLT FIPVSSELTP QDAIIRVRFN    120
STDNSYRLQI TEANPPVYVQ LALLSQGGLL CTPGVPGTPM RFSLRSSKDE NLPQQMSHVL    180
HEVVDTA                                                             187

SEQ ID NO: 77           moltype = DNA  length = 480
FEATURE                 Location/Qualifiers
source                  1..480
                        mol_type = other DNA
                        organism = Polypodium musifolium
SEQUENCE: 77
gacgagccga catggcagga ggtcttgaca acggcacgca cgaacgtggt atatggaccc     60
agcaacacgt acaccatcag gtcaatgacc tctgggatag ggtatctctt taggttcttc    120
tttggctcgg ggttcccagg cgaagcggtc cgaacggaca ccacgatcac catgggtcgc    180
aatggagatg cctcggccat ttatgcctgc atcgacggca gacttcggtt agtggccacc    240
aacacctccg gcacgcctca gaacgctttg attcgcgtgc gcttcaacag caccgacggc    300
tactaccgcc tgcagatcac gcaggcctca ccggctgtct acgttcagtt tgttcttctc    360
tcccaaggcg gcatcctctg caccgcaggc ctacccggca cgcctctcac ctttacctcc    420
tcctcctcct cggacctgcg cgtccttcat caagtggtca acagctcctc cctttcctag    480

SEQ ID NO: 78           moltype = AA  length = 159
FEATURE                 Location/Qualifiers
source                  1..159
                        mol_type = protein
                        organism = Polypodium musifolium
SEQUENCE: 78
DEPTWQEVLT TARTNVVYGP SNTYTIRSMT SGIGYLFRFF FGLGFPGEAV RTDTTITMGR     60
NGDASAIYAC IDGRLRLVAT NTSGTPQNAL IRVRFNSTDG YYRLQITQAS PAVYVQFVLL    120
SQGGILCTAG LPGTPLTFTS SSSSDLRVLH QVVDSSSLS                          159

SEQ ID NO: 79           moltype = DNA  length = 417
FEATURE                 Location/Qualifiers
source                  1..417
                        mol_type = other DNA
                        organism = Asplenium nidus
SEQUENCE: 79
atggggtacg cgcagtgggt aagggtaacg ctgaagaatg catctgcaag cggctcgctg     60
gaggtgaagc aggcgaccct gcaatggggc aaatggttca aacccttgcc cgcgcccgag    120
ggcgacaagg agacggaggt ggcgtcgccc ggcggggata ccttccagaa agacgcgccg    180
ctcgtcttcg ccagctgcgg gcgcgagaac tcaacctcgg gcacccaagg cagcgtggag    240
atttgggacg gctccatcct cgtggtcaaa atcgcgtggg actgcccta cgtgggcagc    300
aactccacct ccctctccga ccaaaactct gactacgttg tgcagcaggt ccctgccagc    360
gtctctaccg gcgggcccct gggcaacatc acctacacca tcgttaaact gcccgct       417

SEQ ID NO: 80           moltype = DNA  length = 414
FEATURE                 Location/Qualifiers
source                  1..414
                        mol_type = other DNA
                        organism = Asplenium nidus
SEQUENCE: 80
atggggtacg cgcagtgggt aagggtaacg ctgaagaatg catctgcaag cggctcgctg     60
gaggtgaagc aggcgaccct gcaatggggc aaatggttca aacccttgcc cgcgcccgag    120
ggcgacaagg agacggaggt ggcgtcgccc ggcggggata ccttccagaa agacgcgccg    180
ctcgtcttcg ccagctgcgg gcgcgagaac tcaacctcgg gcacccaagg cagcgtggag    240
atttgggacg gctccatcct cgtggtcaaa atcgcgtggg actgcccctt tttaggcagc    300
aactcgacct ccctctccaa ccaaagctct gactacgtcg tgcagcaggt ccctgccagc    360
gtctctacca cggggccct ggacaacatc acctacacct cgtgaaact ggca           414

SEQ ID NO: 81           moltype = DNA  length = 414
```

-continued

```
FEATURE                Location/Qualifiers
source                 1..414
                       mol_type = other DNA
                       organism = Asplenium nidus
SEQUENCE: 81
atggggtacg cgcagtgggt aagggtaacg ctgaagaatg catctgcaag cggctcgctg    60
gaggtgaagc aggcgaccct gcaatggggc aaatggttca aacccttgcc cgcgcccgag   120
ggcgacaagg agacggaggt ggcgtcgccc ggcgggggata ccttccagaa agacgcgccg   180
ctcgtttttcg ccagctgcgg gcgcgagaac tcaacctcgg gcacccaagg cagcgtggag   240
atttgggacg gctccatcct cgtggtcaaa atcgcgtggg actgcccta cgtgggcagc   300
aactccacct ccctctccga ccaaaaactct gactacgttg tgcagcaggt ccctgccagc   360
gtctctaccg gcgggcccct gggcaacatc acctacacct tcgtgaaact ggca          414

SEQ ID NO: 82           moltype = DNA   length = 414
FEATURE                Location/Qualifiers
source                 1..414
                       mol_type = other DNA
                       organism = Asplenium nidus
SEQUENCE: 82
atggggtacg cgcagtgggt aagggtaacg ctgaagagcg ctgctgcaag cggctcgctg    60
gaagtgaagc aggcgaccct gcaatggggc aaatggtacc aacccatgcc cgcgcccgag   120
ggcgacaagg atacggaggt ggcgtcgccg ggcggggata cctccagac agactcgccg   180
ctcgtctttg cctgctgcgg gcgcgaggac tcaccctcgg gcacccaggg cagcgtggag   240
atctgggacg cctccactct cgtggtcaaa atcgcgtggg actgcccctt tttaggcagc   300
aactcgacct ccctctccaa ccaaagctct gactacgtcg tgcagcaggt ccctgccagc   360
gtctctacca acggggcccct ggacaacatc acctacacct tcgtgaaact ggca          414

SEQ ID NO: 83           moltype = DNA   length = 414
FEATURE                Location/Qualifiers
source                 1..414
                       mol_type = other DNA
                       organism = Asplenium australasicum
SEQUENCE: 83
atggggtacg cgcagtgggt aagggtaacg ctgaagaatg cttctgcaag cggctcgctg    60
gaagtgaagc aggcgaccct gcaatggggc aaatggtacc aacccatgcc cgcgcccgag   120
ggcgacaagg atacggaggt ggcgtcgccg ggcggggaca cctccagaa agactcgccg   180
ctcgtctttg ccagctgcgg gcgcgaggac tcaccctcgg gcacccaagg cagcgtggag   240
atttgggatg gctccacact cgtggtcaaa atcgcctggg actgccccta cgtgggcagc   300
aactccacct ccctcaccga ccaaagctct gactacgttg tgcagcaggt ccctgcaagc   360
gtctctaccg gcgggcccct ggaggacatc acctacaccg tcgtgaaact ggca          414

SEQ ID NO: 84           moltype = DNA   length = 414
FEATURE                Location/Qualifiers
source                 1..414
                       mol_type = other DNA
                       organism = Phyllitis scolopendrium
SEQUENCE: 84
atggggtacg cgcagtgggt aagggtaacg ctgaagaatg cttctgcaag cggctcgctg    60
gaagtgaagc aggcgaccct gcaatggggc aaatggtacc aacccatgcc cgcgcccgag   120
ggcgacaagg atacggaggt ggcgtcgccg ggcggggaca cctccagaa agactcgccg   180
ctcgtctttg ccagctgcgg gcgcgaggac tcaccctcgg gcacccaagg cagcgtggag   240
atttgggatg gctccacact cgtggtcaaa atcgcctggg actgccccta cgtgggcagc   300
aactccacct ccctcaccga ccaaagctct gactacgttg tgcagcaggt ccctgcaagc   360
gtctctaccg gcgggcccct ggaggacatc acctacacct tcgtgaaact ggca          414

SEQ ID NO: 85           moltype = DNA   length = 411
FEATURE                Location/Qualifiers
source                 1..411
                       mol_type = other DNA
                       organism = Phyllitis scolopendrium
SEQUENCE: 85
atggggtacg cgcagtgggt aagggtaacg ctgaagaatg cttctgcaag cggctcgctg    60
gaagtgaagc aggcgaccct gcagtggggc aaatggttcc aacccatgcc gcccgatggc   120
gacaaggata cggaggtggc gtcgccaggc ggggccgctc tccagaaagg ctcgccgctc   180
gtctttgcca gctgcgggcg ccaggagtca ccctcgggca cccaaggcag cgtggaggtc   240
tgggacggct ccactctcgt ggtcaaaatc gcctgggact gccccctatat cggcaagaac   300
tccacctccc tcaccgcgca aaactctgac tacgttgtgc agcagagccc cgccagtgtc   360
tctaccgatg gggccctggg caacatcacc tacaccttcg tgaaactggc a             411

SEQ ID NO: 86           moltype = DNA   length = 414
FEATURE                Location/Qualifiers
source                 1..414
                       mol_type = other DNA
                       organism = Asplenium australasicum
SEQUENCE: 86
atggggtacg cgcagtgggt aagggtaacg ctgaagaatg cttctgcaag cggctcgctg    60
gaagtgaagc aggcgaccct gcaatggggc aaatggtacc aacccatgcc cgcgcccgag   120
ggcgacaagg atacggaggt ggcgtcgccg ggcggggaca cctccagaa agactcgccg   180
ctcgtctttg ccagctgcgg gcgcgaggac tcaccctcgg gcacccaagg cagcgtggag   240
```

```
atttgggatg gctccacact cgtggtcaaa atcgcctggg actgcccta cgtgggcagc    300
aactccacct ccctcaccga ccaaagctct gactacgttg tgcagcaggt ccctgcaagc    360
gtctctaccg gcggggccct ggagaacatc acctacaccg tcgtgaaact ggca          414

SEQ ID NO: 87          moltype = DNA  length = 414
FEATURE                Location/Qualifiers
source                 1..414
                       mol_type = other DNA
                       organism = Asplenium australasicum
SEQUENCE: 87
atggggtacg cgcagtgggt aagggtaacg ctgaagaatg cttctgcaag cggctcgctg    60
gaagtgaagc aggcgaccct gcaatggggc aaatggtacc aacccatgcc cgcgcgcgag    120
ggcgacaagg atacggaggt ggcgtcgccg ggcggggaca cctcccagaa agactcgccg    180
ctcgtctttg ccagctgcgg gcgcgaggac tcaccctcgg gcacccaagg cagcgtggag    240
atttgggatg gctccacact cgtggtcaaa atcgcctggg actgcccta cgtgggcagc    300
aactccacct ccctcaccga ccaaagctct gactacgttg tgcagcaggt ccctgcaagc    360
gtctctaccg gcggggccct ggagaacatc acctacaccg tcgtgaaact ggca          414

SEQ ID NO: 88          moltype = DNA  length = 399
FEATURE                Location/Qualifiers
source                 1..399
                       mol_type = other DNA
                       organism = Phyllitis scolopendrium
SEQUENCE: 88
atggggtacg cgcagtgggt aagggtaacg ctgaagaatg gttctgcaag cggctcgctg    60
gaagtgaagc aggcgaccct gcagtggggc aaatggttcc aacccatgcc gcccatgtgc    120
gacaaggata cggaggtggc gtcgccaggc gggggcacct ccagaaagg ctcgccgctc    180
gtctttgcca gctgcgggcg cgaggagtca ccctcgggca cccaaggcag cgtggaggtc    240
tgggacggct ccactctcgt ggtcaaaatc gcctgggact gccctatat cggcaagaac    300
tccacctccc tcaccgcgca aaactctgac tacgttgtgc agcagagccc cgccagtgtc    360
tctaccgatg gggccctggg caacatcacc tacaccttc                           399

SEQ ID NO: 89          moltype = DNA  length = 411
FEATURE                Location/Qualifiers
source                 1..411
                       mol_type = other DNA
                       organism = Phyllitis scolopendrium
SEQUENCE: 89
atggggtacg cgcagtgggt aagggtaacg ccgaagaatg gttctgcaag cggctcgctg    60
gaagtgaagc aggcgaccct gcagtggggc aaatggttcc aacccatgcc gcccgatggc    120
gacaaggata cggaggtggc gtcgccaggc gggggcacct ccagaaagg ctcgccgctc    180
gtctttgcca gctgcgggcg cgaggagtca ccctcgggca cccaaggcag cgtggaggtc    240
tgggacggct ccactctcgt ggtcaaaatc gcctgggact gccctatat cggcaagaac    300
tccacctccc tcaccgcgca aaactctgac tacgttgtgc agcagagccc cgccagtgtc    360
tctaccgatg gggccctggg caacatcacc tacaccttcg tgaaactggc a             411

SEQ ID NO: 90          moltype = DNA  length = 372
FEATURE                Location/Qualifiers
source                 1..372
                       mol_type = other DNA
                       organism = Phyllitis scolopendrium
SEQUENCE: 90
atggggtacg cgcagtgggt aagggtaacg ctgaagaatg gttctgcaag cggctcgctg    60
gaagtgaagc aggcgaccct gcagtggggc aaatggttcc aacccatgcc gtccgatggc    120
tacaaggata cggaggtggc gtcgccaggc gggggcacct ccagaaaag ctcgtcgctc    180
gtctttgcca gctgcgggcg cgaggagtca ccctcgggca cccaaggcag cgtggagatc    240
tgggacggct ccactctcgt ggtcaaaatc gcctgggact gcctctatat cggcaagaac    300
tccacctccc tcaccgacca aaactctgac tacgttgtgc agcagagccc cgccagtgtc    360
tctacacctt cg                                                        372

SEQ ID NO: 91          moltype = DNA  length = 411
FEATURE                Location/Qualifiers
source                 1..411
                       mol_type = other DNA
                       organism = Adiantum capillus-veneris
SEQUENCE: 91
atggggtacg ctcagtgggt tagggtgacg ttgaaaactg tgtcaagtgg gacactggaa    60
gtgaagcgag cacaaacatc atatggcaag tggtacgagc cgttgcctgc accgagggt    120
aacaaggatt ctgaggtggc ttcaccggga ggggcaacct tcgatgcggc gacccctctc    180
ctgtttgcaa cctgcgggcg agataactcg ccctcgggtg ctacaggctc tgtggagata    240
tgggatggag acgtgaaagt ggtaatcatc aaatgggatt gccctatat tggcagcaac    300
tctctcgagt tgggcgagca gaacaatgca tatatcatcc agcagaaacc ggctagtgtc    360
tcaaacagtg gggccatcgg aaatgtggag tacactttcg tcaaagtcag c             411

SEQ ID NO: 92          moltype = DNA  length = 414
FEATURE                Location/Qualifiers
source                 1..414
                       mol_type = other DNA
                       organism = Platycerium wandae
```

```
SEQUENCE: 92
atggggtacg atcagtgggt tagggtgacg ctgcaggcgg cgacgagtgg gctcaagttc   60
gaagtgaaga atgccgggac gacatggggt aagtggtaca aagcgacacc accaccggag  120
gggcagaagg atacagaggt ggcttctccc ggtggaggta cctttgagaa agactccccc  180
ctcctctttg cagcctgcgg gcgagagaac tctccttctg gtgtggaagc tagtatagag  240
atatacgagg gagacacgaa agtggtaaaa atctactgga gttgcccttt catcggcagc  300
aacagcgtca atatctctga gcaaacaac gactatgtcg ttcagcagaa acctgccagt  360
tctcctgcat ccggagccat tggcaacctt gagtatgtca ttgccaagct tgcc         414

SEQ ID NO: 93            moltype = DNA  length = 405
FEATURE                  Location/Qualifiers
source                   1..405
                         mol_type = other DNA
                         organism = Phyllitis scolopendrium
SEQUENCE: 93
atggggtacg agcagtcggt aagaataacg ctgaggactc tttctgacgt cacgctagag   60
ttgaagggag cgaccttggt taacggcaaa tggtatgatc ccactgctgc caacaaggat  120
gttgacgcga tatcgccaga cgaccggacc ttctaccaca acggcacgcc cctcgtcttt  180
gccagctgcg ggctcaagga ctcagactcg ggcacccaag gctctgtaga gatttgggaa  240
ggcgaaaatc aagtggttaa aatcgcctgg aactgcccct acaccggcaa caacttcacc  300
tccctcgaca accaaagctc taactacgtt gtgcagcagg tccccaccaa cgtcgttcac  360
accgggcagt tgggcgacat cgcctacacc tttgcgaaag tggca               405

SEQ ID NO: 94            moltype = DNA  length = 405
FEATURE                  Location/Qualifiers
source                   1..405
                         mol_type = other DNA
                         organism = Phyllitis scolopendrium
SEQUENCE: 94
atggggtacg agcagtcggt aagaataacg ctgaggactc tttctgacgt cacgctagag   60
ttgaagggag cgaccttggt taacggcaaa tggtatgatc ccactgctgc caacaaggat  120
gttgacgcga tatcgccaga cgaccggacc ttctaccaca acggcacgcc cctcgtcttt  180
gccagctgcg ggctcaagga ctcagactcg ggcacccaag gctctgtaga gatttgggaa  240
ggcgaaaatc aagtggttaa aatcgcctgg aactgcccct acaccggcaa caacttcacc  300
tccctcgaca accaaagctc taactacgtt gtgcagcagg tccccaccaa cgtcgttcac  360
atcgggcagt tgggcgacat cgcctacacc tttgcgaaag tggca               405

SEQ ID NO: 95            moltype = DNA  length = 519
FEATURE                  Location/Qualifiers
source                   1..519
                         mol_type = other DNA
                         organism = Phyllitis scolopendrium
SEQUENCE: 95
atgtccagca gctccttcct ggtggcgctg ctgtgcgttt ctatcggtag cctggcatct   60
gccgcttccg caggtgaaaa agactctgtt tctatcttcc aggtaactga tggcaagctg  120
ggtggttacc cgcagtgggt atccttcaaa atcactaacc tgggccgtga taccctggag  180
gtaaaaaatt cttttctgtc ttacggtaaa tggtataagt acccgaacaa aaacaacgat  240
ggctctgcac cgggtggcat tactattgca gccggcgcga ctagcccaaa tcctccattc  300
gcagcttgcg gtcgtcaagg ctctccaagc ggtaccaccg gcggcttcga catctacacg  360
aaaggtttta aggtcgcgac cattcatttc gactgtccgt atactggctc taacaaactg  420
tctgtatccg acgaatgtaa aaaattgcgtt gtgcagctgc cgagctttag cacctctggt  480
gcactgggtg acctggtgct gaaagtggta gcgctggtc                        519

SEQ ID NO: 96            moltype = DNA  length = 420
FEATURE                  Location/Qualifiers
source                   1..420
                         mol_type = other DNA
                         organism = Phyllitis scolopendrium
SEQUENCE: 96
ttgagaggat atcctcagtg ggtatctttc aagataacaa acctgggacc agacacctta   60
gtagtgagaa actccgtctt accatggggg aaatggtaca agtacccaaa taagggcatt  120
gatggtagct ctccgggtgg ggtaacgatt gcatcaggag caacctctcc cacccccacca  180
tttgctcat gtggaagaga aaactctcca tctgggacta aaggtacgtt tgacctctat  240
gccaaggaca tcaaagttgc cactatatac tttgattgtc cctacattgg cagcaataag  300
ctgtctgtcc aatatgcgtg caacacttgt gttgtgcagc ttcctcctt ttctacttct  360
ggtcccttag gagaccttgt aatcaaagtg gtggcactcg taaatcttga ggctgaagct  420

SEQ ID NO: 97            moltype = DNA  length = 510
FEATURE                  Location/Qualifiers
source                   1..510
                         mol_type = other DNA
                         organism = Phyllitis scolopendrium
SEQUENCE: 97
atgttgagtt cttctttcct tctagcattg ctatccctat ctattgggggg cttagcttct   60
gctggagaag aggactcggt ttctatcttt caagtcaccg atggcaagtt gggaggatat  120
cctcagtggg tatccttcaa gatcacaaac ttgggacgag acaccttaga agtgaaaaac  180
tccttcttat catatggaaa gtggtataag tacccaaata agaacgatga tggcagtgca  240
ccaggtggga taaccatcgc tgcaggagca acctctccca acccgccatt tgctgcatgt  300
ggaaggcaag gttctccatc tgggactaca ggtggatttg acatctatac gaagggcttc  360
```

-continued

```
aaagttgcca ctatacactt tgattgtcca tacactggca gtaataagct gtctgtcagc   420
gatgagtgca agaattgtgt tgtgcagctt ccgtcctttt ctacgtccgg tgcgctggga   480
gaccttgtac tcaaagtggt ggcactagtt                                     510

SEQ ID NO: 98              moltype = DNA   length = 519
FEATURE                    Location/Qualifiers
source                     1..519
                           mol_type = other DNA
                           organism = Phyllitis scolopendrium
SEQUENCE: 98
atgtcgagtt cttctttcct tctagcattg ctttgcatat ccattgggag cttagcttct   60
gctgcttcgg ctggagaaga ggactcggtt tctatctttc aagtcaccga tggaaagttg   120
ggaggatatc ctcagtgggt atccttcaag atcacaaacc tgggacgaga caccttagaa   180
gtgaaaaact ccttcttatc atatggaaag tggtataagt acccaaataa gaacaatgat   240
ggcagtgcac caggtgggat aaccattgct gctggagcaa cctctcccaa cccggcattt   300
gctgcatgtg gaaggcaagg ttctccatct gggactacag gtggatttga catctatacg   360
aagggcttca aagttgccac tatacacttt gattgtccat acactggcag taataagctg   420
tctgtcagcg atgagtgcaa gaattgtgtt gtgcagcttc cgtccttttc tacttccggt   480
gcgctgggag accttgtact caaagtggtg gcactagtt                          519

SEQ ID NO: 99              moltype = DNA   length = 519
FEATURE                    Location/Qualifiers
source                     1..519
                           mol_type = other DNA
                           organism = Phyllitis scolopendrium
SEQUENCE: 99
atgtcgagtt cttctttcct tctagcattg ctttgcatat ccattgggag cttagcttct   60
gctgcttcgg ctggagaaga ggactcggtt tctatttttc aagtcaccga tggaaagttg   120
agaggatatc ctcagtgggt atccttcaag atcacaaacc tgggacgaga caccttagaa   180
gtgaaaaact ccttcttatc atatggaaag tggtataagt acccaaataa gaacaatgat   240
ggcagcgcac caggtgggat aaccattgct gctggagcaa cctctcccaa cccgccattt   300
gctgcatgtg gaaggcaagg ttctccatct gggactacag gtggatttga catctatacg   360
aagggcttca aagttgccac tatacacttt gattgtccat acactggcag taataagctg   420
tctgtcagcg atgagtgcaa gaattgtgtt gtgcagcttc cgtccttttc tacttccggt   480
gcgctgggag accttgtact caaagtggtg gtactagtt                          519

SEQ ID NO: 100             moltype = DNA   length = 519
FEATURE                    Location/Qualifiers
source                     1..519
                           mol_type = other DNA
                           organism = Phyllitis scolopendrium
SEQUENCE: 100
atgtcgagtt cttctttcct tctagcattg ctttgcatat ccattgggag cttagcttct   60
gctgcttcgg ctggagaaga ggactcggtt tctatctttc aagtcaccga tggaaagttg   120
ggaggatatc ctcagtgggt atccttcaag atcacaaacc tgggacgaga caccttagaa   180
gtgaaaaact ccttcttatc atatggaaag tggtataagt acccaaataa gaacaatgat   240
ggcagcgcac caggtgggat aaccattgct gcaggagcaa cctctcccaa cccgccattt   300
gctgcatgtg gaaggcaagg ttctccatct gggactacag gtggatttga catctatacg   360
aagggcttca aagttgccac tatacacttt gattgtccat acactggcag taataagctg   420
tctgtcagcg atgagtgcaa gaattgtgtt gtgcagcttc cgtccttttc tacttccggt   480
gcgctgggag accttgtact caaagtggtg gcactagtt                          519

SEQ ID NO: 101             moltype = DNA   length = 393
FEATURE                    Location/Qualifiers
source                     1..393
                           mol_type = other DNA
                           organism = Phyllitis scolopendrium
SEQUENCE: 101
atggcatcgg tccaagctta cgcacagtgg gttacggttc atctcatcaa tagcatgtct   60
tccgagacct tgagtatcaa gaatgctagt ctctcctggg gcaagtggta caaggacggt   120
gacaaggacg ccgaaatcac aagtgaagat gtccagcaaa agacggcacc cccaggcggt   180
tccgtgaacg tcaactcttg cggtcgcagc gacgcttcga gtggaacgac gggaggtttt   240
gatttgtatg acggcaatac caagattgga agagtccact gggactgtcc atggggttct   300
aaaaccaacg atttcgatgt tggagagaga aacaaaaatt actgggtcga aattggaacg   360
tggaacaagt atggtggtgc cattggcaac tgt                                393

SEQ ID NO: 102             moltype = AA   length = 139
FEATURE                    Location/Qualifiers
source                     1..139
                           mol_type = protein
                           organism = Asplenium nidus
SEQUENCE: 102
MGYAQWVRVT LKNASASGSL EVKQATLQWG KWFKPLPAPE GDKETEVASP GGDTFQKDAP   60
LVFASCGREN STSGTQGSVE IWDGSILVVK IAWDCPYVGS NSTSLSDQNS DYVVQQVPAS   120
VSTGGPLGNI TYTIVKLPA                                                139

SEQ ID NO: 103             moltype = AA   length = 138
FEATURE                    Location/Qualifiers
source                     1..138
```

-continued

```
                        mol_type = protein
                        organism = Asplenium nidus
SEQUENCE: 103
MGYAQWVRVT LKNASASGSL EVKQATLQWG KWFKPLPAPE GDKETEVASP GGDTFQKDAP  60
LVFASCGREN STSGTQGSVE IWDGSILVVK IAWDCPFLGS NSTSLSNQSS DYVVQQVPAS  120
VSTNGALDNI TYTFVKLA                                                138

SEQ ID NO: 104        moltype = AA  length = 138
FEATURE               Location/Qualifiers
source                1..138
                        mol_type = protein
                        organism = Asplenium nidus
SEQUENCE: 104
MGYAQWVRVT LKNASASGSL EVKQATLQWG KWFKPLPAPE GDKETEVASP GGDTFQKDAP  60
LVFASCGREN STSGTQGSVE IWDGSILVVK IAWDCPYVGS NSTSLSDQNS DYVVQQVPAS  120
VSTGGPLGNI TYTFVKLA                                                138

SEQ ID NO: 105        moltype = AA  length = 138
FEATURE               Location/Qualifiers
source                1..138
                        mol_type = protein
                        organism = Asplenium nidus
SEQUENCE: 105
MGYAQWVRVT LKSAAASGSL EVKQATLQWG KWYQPMPAPE GDKDTEVASP GGETFQTDSP  60
LVFACCGRED SPSGTQGSVE IWDASTLVVK IAWDCPFLGS NSTSLSNQSS DYVVQQVPAS  120
VSTNGALDNI TYTFVKLA                                                138

SEQ ID NO: 106        moltype = AA  length = 138
FEATURE               Location/Qualifiers
source                1..138
                        mol_type = protein
                        organism = Asplenium australasicum
SEQUENCE: 106
MGYAQWVRVT LKNASASGSL EVKQATLQWG KWYQPMPAPE GDKDTEVASP GGDTSQKDSP  60
LVFASCGRED SPSGTQGSVE IWDGSTLVVK IAWDCPYVGS NSTSLTDQSS DYVVQQVPAS  120
VSTGGALEDI TYTVVKLA                                                138

SEQ ID NO: 107        moltype = AA  length = 138
FEATURE               Location/Qualifiers
source                1..138
                        mol_type = protein
                        organism = Phyllitis scolopendrium
SEQUENCE: 107
MGYAQWVRVT LKNASASGSL EVKQATLQWG KWYQPMPAPE GDKDTEVASP GGDTSQKDSP  60
LVFASCGRED SPSGTQGSVE IWDGSTLVVK IAWDCPYVGS NSTSLTDQSS DYVVQQVPAS  120
VSTGGALEDI TYTFVKLA                                                138

SEQ ID NO: 108        moltype = AA  length = 137
FEATURE               Location/Qualifiers
source                1..137
                        mol_type = protein
                        organism = Phyllitis scolopendrium
SEQUENCE: 108
MGYAQWVRVT LKNASASGSL EVKQATLQWG KWFQPMPPDG DKDTEVASPG GGTFQKGSPL  60
VFASCGRQES PSGTQGSVEV WDGSTLVVKI AWDCPYIGKN STSLTAQNSD YVVQQSPASV  120
STDGALGNIT YTFVKLA                                                 137

SEQ ID NO: 109        moltype = AA  length = 138
FEATURE               Location/Qualifiers
source                1..138
                        mol_type = protein
                        organism = Asplenium australasicum
SEQUENCE: 109
MGYAQWVRVT LKNASASGSL EVKQATLQWG KWYQPMPAPE GDKDTEVASP GGDTSQKDSP  60
LVFASCGRED SPSGTQGSVE IWDGSTLVVK IAWDCPYVGS NSTSLTDQSS DYVVQQVPAS  120
VSTGGALENI TYTVVKLA                                                138

SEQ ID NO: 110        moltype = AA  length = 138
FEATURE               Location/Qualifiers
source                1..138
                        mol_type = protein
                        organism = Asplenium australasicum
SEQUENCE: 110
MGYAQWVRVT LKNASASGSL EVKQATLQWG KWYQPMPARE GDKDTEVASP GGDTSQKDSP  60
LVFASCGRED SPSGTQGSVE IWDGSTLVVK IAWDCPYVGS NSTSLTDQSS DYVVQQVPAS  120
VSTGGALENI TYTVVKLA                                                138

SEQ ID NO: 111        moltype = AA  length = 133
FEATURE               Location/Qualifiers
```

```
source                  1..133
                        mol_type = protein
                        organism = Phyllitis scolopendrium
SEQUENCE: 111
MGYAQWVRVT LKNGSASGSL EVKQATLQWG KWFQPMPPDG DKDTEVASPG GGTFQKGSPL   60
VFASCGREES PSGTQGSVEV WDGSTLVVKI AWDCPYIGKN STSLTAQNSD YVVQQSPASV  120
STDGALGNIT YTF                                                    133

SEQ ID NO: 112          moltype = AA   length = 137
FEATURE                 Location/Qualifiers
source                  1..137
                        mol_type = protein
                        organism = Phyllitis scolopendrium
SEQUENCE: 112
MGYAQWVRVT PKNGSASGSL EVKQATLQWG KWFQPMPPDG DKDTEVASPG GGTFQKGSPL   60
VFASCGREES PSGTQGSVEV WDGSTLVVKI AWDCPYIGKN STSLTAQNSD YVVQQSPASV  120
STDGALGNIT YTFVKLA                                                137

SEQ ID NO: 113          moltype = AA   length = 124
FEATURE                 Location/Qualifiers
source                  1..124
                        mol_type = protein
                        organism = Phyllitis scolopendrium
SEQUENCE: 113
MGYAQWVRVT LKNGSASGSL EVKQATLQWG KWFQPMPSDG YKDTEVASPG GGTFQKSSSL   60
VFASCGREES PSGTQGSVEI WDGSTLVVKI AWDCLYIGKN STSLTDQNSD YVVQQSPASV  120
STPS                                                              124

SEQ ID NO: 114          moltype = AA   length = 137
FEATURE                 Location/Qualifiers
source                  1..137
                        mol_type = protein
                        organism = Adiantum capillus-veneris
SEQUENCE: 114
MGYAQWVRVT LKTVSSGTLE VKRAQTSYGK WYEPLPAPEG NKDSEVASPG GATFDAATPL   60
LFATCGRDNS PSGATGSVEI WDGDVKVVII KWDCPYIGSN SLELGEQNNA YIIQQKPASV  120
SNSGAIGNVE YTFVKVS                                                137

SEQ ID NO: 115          moltype = AA   length = 138
FEATURE                 Location/Qualifiers
source                  1..138
                        mol_type = protein
                        organism = Platycerium wandae
SEQUENCE: 115
MGYDQWVRVT LQAATSGLKF EVKNAGTTWG KWYKATPPPE GQKDTEVASP GGGTFEKDSP   60
LLFAACGREN SPSGVEASIE IYEGDTKVVK IYWSCPFIGS NSVNISEQNN DYVVQQKPAS  120
SPASGAIGNL EYVIAKLA                                               138

SEQ ID NO: 116          moltype = AA   length = 135
FEATURE                 Location/Qualifiers
source                  1..135
                        mol_type = protein
                        organism = Phyllitis scolopendrium
SEQUENCE: 116
MGYEQSVRIT LRTLSDVTLE LKGATLVNGK WYDPTAANKD VDAISPDDRT FYHNGTPLVF   60
ASCGLKDSDS GTQGSVEIWE GENQVVKIAW NCPYTGNNFT SLDNQSSNYV VQQVPTNVVH  120
TGQLGDIAYT FAKVA                                                  135

SEQ ID NO: 117          moltype = AA   length = 135
FEATURE                 Location/Qualifiers
source                  1..135
                        mol_type = protein
                        organism = Phyllitis scolopendrium
SEQUENCE: 117
MGYEQSVRIT LRTLSDVTLE LKGATLVNGK WYDPTAANKD VDAISPDDRT FYHNGTPLVF   60
ASCGLKDSDS GTQGSVEIWE GENQVVKIAW NCPYTGNNFT SLDNQSSNYV VQQVPTNVVH  120
IGQLGDIAYT FAKVA                                                  135

SEQ ID NO: 118          moltype = AA   length = 173
FEATURE                 Location/Qualifiers
source                  1..173
                        mol_type = protein
                        organism = Phyllitis scolopendrium
SEQUENCE: 118
MSSSSFLVAL LCVSIGSLAS AASAGEKDSV SIFQVTDGKL GGYPQWVSFK ITNLGRDTLE   60
VKNSFLSYGK WYKYPNKNND GSAPGGITIA AGATSPNPPF AACGRQGSPS GTTGGFDIYT  120
KGFKVATIHF DCPYTGSNKL SVSDECKNCV VQLPSFSTSG ALGDLVLKVV ALV         173

SEQ ID NO: 119          moltype = AA   length = 140
```

-continued

```
FEATURE                  Location/Qualifiers
source                   1..140
                         mol_type = protein
                         organism = Phyllitis scolopendrium
SEQUENCE: 119
LRGYPQWVSF KITNLGPDTL VVRNSVLPWG KWYKYPNKGI DGSSPGGVTI ASGATSPTPP   60
FAACGRENSP SGTEGTFDLY AKEIKVATIY FDCPYIGSNK LSVQYACNTC VVQLPSFSTS   120
GPLGDLVIKV VALVNLEAEA                                               140

SEQ ID NO: 120          moltype = AA  length = 170
FEATURE                  Location/Qualifiers
source                   1..170
                         mol_type = protein
                         organism = Phyllitis scolopendrium
SEQUENCE: 120
MLSSSFLLAL LSLSIGGLAS AGEEDSVSIF QVTDGKLGGY PQWVSFKITN LGRDTLEVKN   60
SFLSYGKWYK YPNKNDDGSA PGGITIAAGA TSPNPPFAAC GRQGSPSGTT GGFDIYTKGF   120
KVATIHFDCP YTGSNKLSVS DECKNCVVQL PSFSTSGALG DLVLKVVALV             170

SEQ ID NO: 121          moltype = AA  length = 173
FEATURE                  Location/Qualifiers
source                   1..173
                         mol_type = protein
                         organism = Phyllitis scolopendrium
SEQUENCE: 121
MSSSSFLLAL LCISIGSLAS AASAGEEDSV SIFQVTDGKL GGYPQWVSFK ITNLGRDTLE   60
VKNSFLSYGK WYKYPNKNND GSAPGGITIA AGATSPNPAF AACGRQGSPS GTTGGFDIYT   120
KGFKVATIHF DCPYTGSNKL SVSDECKNCV VQLPSFSTSG ALGDLVLKVV ALV         173

SEQ ID NO: 122          moltype = AA  length = 173
FEATURE                  Location/Qualifiers
source                   1..173
                         mol_type = protein
                         organism = Phyllitis scolopendrium
SEQUENCE: 122
MSSSSFLLAL LCISIGSLAS AASAGEEDSV SIFQVTDGKL RGYPQWVSFK ITNLGRDTLE   60
VKNSFLSYGK WYKYPNKNND GSAPGGITIA AGATSPNPPF AACGRQGSPS GTTGGFDIYT   120
KGFKVATIHF DCPYTGSNKL SVSDECKNCV VQLPSFSTSG ALGDLVLKVV VLV         173

SEQ ID NO: 123          moltype = AA  length = 173
FEATURE                  Location/Qualifiers
source                   1..173
                         mol_type = protein
                         organism = Phyllitis scolopendrium
SEQUENCE: 123
MSSSSFLLAL LCISIGSLAS AASAGEEDSV SIFQVTDGKL GGYPQWVSFK ITNLGRDTLE   60
VKNSFLSYGK WYKYPNKNND GSAPGGITIA AGATSPNPPF AACGRQGSPS GTTGGFDIYT   120
KGFKVATIHF DCPYTGSNKL SVSDECKNCV VQLPSFSTSG ALGDLVLKVV ALV         173

SEQ ID NO: 124          moltype = AA  length = 131
FEATURE                  Location/Qualifiers
source                   1..131
                         mol_type = protein
                         organism = Phyllitis scolopendrium
SEQUENCE: 124
MASVQAYAQW VTVHLINSMS SETLSIKNAS LSWGKWYKDG DKDAEITSED VQQKTAPPGG   60
SVNVNSCGRS DASSGTTGGF DLYDGNTKIG RVHWDCPWGS KTNDFDVGER NKNYWVEIGT   120
WNKYGGAIGN C                                                       131

SEQ ID NO: 125          moltype = DNA  length = 1416
FEATURE                  Location/Qualifiers
source                   1..1416
                         mol_type = other DNA
                         organism = Phyllitis scolopendrium
SEQUENCE: 125
atgggaacac ctgttaatct tgttgcaaca ctgcctcggt tcatagcaat caaagggac   60
aatggtctct acttggctct caagccaagc ggtatcctca cctttgatgc ttcgagaga   120
acacgccttg caactcacga ggtcctttac aatgccgatg aatccacatt catcattcgc   180
tctgccaacg gtcgattctg gaagcgtgac tccagtggtc gggtctatgc caacttggaa   240
gagccaccag caacgacaca ggcggatgct cgattcaagc tcgttcatct cgacacttct   300
gacaaactgg cctttcagtc tgcaaaagac aaccgctacc tcaaaaggta cctagccagt   360
gaaaatggat acaacgctgt tatgacaagc cttgacgtgc atactaaggt agaggtgagt   420
gatgcatccg agtatgcagt ctctctgcct cgctacatct tcttgaaggg gaacaatggt   480
aagtacgtcc atatcagtta tgaaagaagt tacgcatggt tgaagttcca cggcgatgaa   540
cccggtaact tgtggggaat agctgaggtg gttccattgc ttaatggcag cgtagcactg   600
tacagtccac acgcaacaag attttggcgc aacagcacca attggatctg ggcagatgct   660
caaagggacg agattgccac caacgctagg tgccactttg agcccatcaa gctgagcagc   720
agcatgttgc cattccggag catcttcaac gatcgtatat gcaaacgtct cactgactat   780
tggactgaca gcatgaatgc tgctgctgcg aacacgaatg atgttgacac aagactcaca   840
```

```
gtcagcgaag ctacttttgc aaagtctgtt ttcgatgtga aatacctttt gaacctggca  900
tccaccagcg agcagaggcc ccttgccgtt gcgcatggct cagctcgtaa cgattcgcct  960
tacactctgg acatggctgt gacggccatc atctcacaga ctgtgtcccg gagcaggacc  1020
tggtccaact cgttcacctt cagtcagtct gtgactacat ccttcaaggc tggctttcca  1080
atccttgctg aaggcaaggt tgaggtggaa atcggattcg agcagaactt ctccaacgaa  1140
tggggccaga ccacggaaca gaatattgga ttcgagactc agtacactgt gaaggatgtt  1200
cctcccgggg gaacggcctc cgtgactgtg gttttgcagct cggccaaaat gcgcatcccc  1260
ttcacgtaca agtctaaaga cactgctcca gatggcatag acaggccaac tatggagtac  1320
attgatggca tttacgaagg agtggatgct tacaaaatag aagctcagat aagcggctcc  1380
gccaaaagct acaatgttcc tgctaagcta ccactt                            1416
```

```
SEQ ID NO: 126          moltype = DNA   length = 1461
FEATURE                 Location/Qualifiers
source                  1..1461
                        mol_type = other DNA
                        organism = Selaginella victoriae
SEQUENCE: 126
atggcagccc ctgcagatcc agttgcgact ctgcctcgct acatagcaat caaaggtgat  60
aatggcaact atttgacgct cacatcagac ggcatgctca agttcgactc ctccgagagg  120
aaccggcttg ccactcacga ggtactgtac aacgaggatg agtccacctt cgtcatccgc  180
tcccagaaca agcgtttctg gacggagcgc aatggctgga tctgcgctag ttgggaaggt  240
cagccaccaa cagcagccaa caaagatgct cgcttcagc tcgttcagct cgggacgggc  300
aaactggctt tccaattcgc caagaacgac aactatctca agcggtacaa cagcggcatc  360
aatggataca aggcagcggt ggcaagcccc gaccagtaca cggagattga ggtgagtgat  420
gcttccgagt accccgtctc cttgccgcag tacatctacc ttaaagggaa caatggtaaa  480
tacgtccaca tctactatat ggacaaccgg aagtggctta agtaccatgg tgaaggacct  540
gataacttgt ggggaatgag cgaggttcat tacctccttg acgggcagcat agcactgtac  600
agtccggaat caacctactt ctggcgcaat agcaccaact ggatctggac agacgccagc  660
aagaatgaat atatcgacaa cacaaggtgc cactttgagc cggtgaaact gagcagcaac  720
atgatagcat tgaagagcaa gtttaacaat cagttctgca aaaggctgac cgactactgg  780
tcggactcta tgaacgctgc cgcaggcagc acgagcgacg tggagacaag gctgactgtc  840
agcgaggctg tgagcggaaa atatgtattc gatgttaagt acctgctcaa cctggcgtcc  900
acaaccgatc agaagcctct cgcagttgca tacggttcac aagtcaacaa ctccccctac  960
cagaccgact taaccgtgac ggccatcgta tcacaatcgg tgagcaggag ccggacgtgg  1020
tccaactcct tcaccttcag ccagtccgtg accaccgagt tcaaggctgg attcccgttc  1080
ctggcggaag gaaaggttga agttcagatc ggttttgagc agagtttctc aaacgagtgg  1140
ggagagacca cggaggaaaa tattgaattt cagactcagt atgttgtcaa ggacgtccca  1200
cctggaggcc aggcatctgt gaccgtgatc tgtagcgcgg ccaaaatgcg gattccgttc  1260
atgtatacgt ccaaggatac tgctcctgac ggtgtagaca gcgagcat gcagtacatt  1320
gatggtatat atgaaggtgt ggatgcctat aagatcgaag cagaaataaa cggctcggct  1380
ggaaaggaaa cgcaaaggct tccgttgaag cccgctggca tagagaaagt gaagtttgtt  1440
gctcctgatc ctacagcgga g                                            1461
```

```
SEQ ID NO: 127          moltype = DNA   length = 1455
FEATURE                 Location/Qualifiers
source                  1..1455
                        mol_type = other DNA
                        organism = Athyrium filix-femina
SEQUENCE: 127
atggcagcaa atccagtagc acttctgccg agatacattg cactcaaggg cgacaatggc  60
atgtatctgt cgctcaagtc cgacggcctt ctcaccttcg acgctgcaga gatgacacgg  120
ctggcaactc acgaggtgct ctacaacgag gacgacccctg actccacctt catcatccgc  180
tcccagaaca tgcgcttctg gaggcgagac tctgccaact ggatccgcgc cgaccgtgag  240
gccgatcagc caccctcagc gggtgagcac gctgcaaggt tcacgctggt cacgctggcg  300
tcgggcaagc tggcctttcg gtccgcggtg gacagccgct acatcaagcg ctacgatgcc  360
ggttcgctca agggctacaa cgccctggtg ccatccccgg accagtatag cgcggttgag  420
gtgagcgacg cttgggagta tgccatctcc ctgccgcgct acatcttcct caagggcaac  480
aatggcatgt acatgcagac ctacaacgag cgctccatca attggctcaa attccacggc  540
agcgaccctg gaaacctcta tggcacctct gaggttattc ccctcctcga tggcagcctc  600
gcattctaca acccacagac cgaccgcttc tggcgcaaca gcaccaactg gatatgacg  660
gactccagca ggagtgatgc cctcaccaac accaggtgcc atttcgagcc cataaggctc  720
agccgaagca tgctcgccct gcggaacaag ttcaacaacc acatctgcaa gcgcctgacc  780
gactattggg agaactgtct caatgctgca gccagcaaca cgtccgatgc caccacgcat  840
ctcacggtca gcgaggccgc caacggacgg caggttttcg acatcaagta tctgctcaat  900
ttggcatcca ccagcgacca aaaggtcctc gccgttgggt atggttcgtc tgtcaacaac  960
tcttcctatt tgaccgacct ggtggtgagg gtctcaattt cgcagagcgt gtcgaggagc  1020
tacaccttct ccaactcctt caccttcagc cagactgtgt ccactgaatt caaggccggc  1080
attccgtttt tcggtgaagg caagatcagt gtggagatcg gcctggagca gagcttctcc  1140
aatgagtggg gtgagaccac cgaacaaggc atcgagtttg agacgcaaca cgtcgtcaag  1200
gatgtcccccc ccggcggaag cgcttcagtc accatcactt gcagcaccgc caagatgaga  1260
atccccttca cctacaaatc caaagacagt gctccggacg ggaccgatcg tccaacccaa  1320
caatttgtgg atggcatctt tgaaggagtc gatgcctaca aaatcgaggc actcataagc  1380
gactctgtca agagctatac acttccagtt gccaggagct atgtaggcgc tcctacatca  1440
tctactgaac taatg                                                   1455
```

```
SEQ ID NO: 128          moltype = DNA   length = 1452
FEATURE                 Location/Qualifiers
source                  1..1452
                        mol_type = other DNA
```

```
                         organism = Athyrium niponicum
SEQUENCE: 128
atggcatcat cacctgcaaa cccagtagca cttctgccga gatacattgc agtcaagggc   60
gacaatggca tgtatctgtc gctcaagtcc gacggccttc tcaccttcga cgctgcagag  120
aggacacggc tggcaactca cgaggtgctc tacaacgagg acgaccctgg cgccaccttc  180
atcatccgct cccagaacat gcgcttctgg aggcgagact ctgccaactg gatccgcgcc  240
gaccgtgagg ccgatcagcc accctcagcg gctgacaacg ctgcaaggtt cacgctggtc  300
acgctggcgt cgggcaagct ggcctttcag tccgcgctgg acggcctcta catcaatcgc  360
tacgatctcg gttcgctcaa gggctacaac gccctggcgc gatccccaga ccagtatagc  420
gcggttgagg tgagcgacgc ttgggagtac gccgtctccc tgccgcggta catcttcctc  480
aagggcgaca atggtatgta catgcacgcc tactacgagc gcaacctcaa ttggctcaaa  540
ttccatggca gcgaccctgg aaacctctat ggcacctccg aggttattcc cctccttgat  600
ggcagcctcg cgttctacaa cccacagacc gaccgcttct ggcgcaacgg cggcaactgg  660
gtatttacgg actccagcag gagtgatgcc atcaccaaca ccaggtgcca tttcgagccc  720
ataaggctca gccgaagcat gctcgccgtg aggaacaagt caacaaccca catctgcaag  780
cgtctgagcg actactgggt gaactgtctc aatgctgcag ccagcaacac gtccgacacc  840
accacgcatc tcacggtcag cgaggctgcc aacgacggg aggtcttcga catcaagtat  900
ctgctcaatt tggcatccac aagcgaccaa aggccccttg ccgttgggta tggttcgtcc  960
gtcaacaact cttcctatat gagcgacctg gtggtgaggg tcacaatttc gcagaaagtg 1020
tcgaagagct acaccttctc caactccttc accttcagtc agactgtgac cactgaattc 1080
aaggccggca ttccgttttt cggtgaaggc acggtcagtg tggagatcgg cctggagcaa 1140
agcttctcca atgagtgggg tgagaccacc gaagaaggca tcgagttcga gctgcaacac 1200
gtcgtcaagg atgttccccc cggcggaagg gcttcagtca ccgtcacttg cagcaccgac 1260
aaaatgagaa tcccccttcac ctacaaatcc aaagacagtg ctcccgacgg gaccgatcgt 1320
ccaacccaac aatttgtgga tggcatcttt gaaggagtgg atgcctacaa aatcgaggca 1380
gtcataagcg actccgtcaa gagctatgca attccagttg ccaggagcta tgtaagccgc 1440
cctgcaattg tc                                                     1452

SEQ ID NO: 129          moltype = DNA  length = 1419
FEATURE                 Location/Qualifiers
source                  1..1419
                        mol_type = other DNA
                        organism = Onoclea sensibilis
SEQUENCE: 129
atggcatcgt cacttgcaga cccagtagca cttctgccga gatacattgc aatcaagggc   60
gacaatggca tgtacctggc gctcaagtca gacggccttc tcaccttcga cgctgcagag  120
ataacacggc tggcaactca tgaggtgctc tacaacgtgg acgaccctga cgccacgttc  180
atcatccgct cccaaaacat gcgcttctgg aggcgcgact ctgccaactg gatccgcgcc  240
gaccgtgagg ctgatcagcc accctcagcg ggcgacaccg gtgcaaggtt cacgctggcc  300
aggctggagt cgggcaagct ggcctttcgg tccgcggtgg atggcctcta cctcaatcgc  360
tacaatcggg acctgcacgg ctacaacgcc ttggagcaaa ccccaaacca gtggagcgag  420
gttgaggtga gcgacgcttg ggagcaccca gtctccctgc cgcgccacat cttcctcaag  480
ggggacaatg gcatgtacat gcacacctac aacgagcgta gcctcaattg gctcaagttc  540
catggtaacg atcctggaaa cctctacggc accagcgagg ttctccacct cctggatggc  600
accctcgcat tctacagccc acagaccgac cgcttctggc gcaacagcac caactggata  660
tggacagact ccagcaggag tgatgccctc accaacacca ggtgccattt cgagccaatc  720
aggctcagcc gaagcatggt cgccctaagg aacaagtaca caaacctcat ctgcaagcgt  780
ctcagcgact attgggtgaa ttgcctcaac gctgcagcca gcaacacgtc cgacaccacc  840
acgcatctca cggtgagtga ggctgccaat ggacggcagg tcttcgacgt caagtaccta  900
ctcaatctgg cgtccaccag cgaccaaatg cccctcgcgg ttgggtatgg ttcgtctatc  960
aacaactctt cctatatgac cgacctggtg gtcaggggtct cgatttcgca gagcgtgcca 1020
aagagctaca ccttctccaa ctccttcacc ttcagccaga ccgtgtccac tgagttcacg 1080
gccggcatac cattcttggg tggaggcaag atcagtgtgg agatcggcat ggagcagagc 1140
ttctccaacg agtggggcga gaccacccaa cgagccatcg agttcgagac gcaacacgtt 1200
gtcaaggatg ttccccccgg cggaatggct tcagtcacca tcatttgtag cactgccaag 1260
atgcggatcc ccttcactta caaatccaaa gacagtgctc ctgatgggac agatcgtcca 1320
acccaagagt ttgtggacgg catctttgaa ggggtcgacg cctacaaaat cgaggccgtc 1380
ataagcgact ccgtcaggag ctatgtaatg ccagttgtc                        1419

SEQ ID NO: 130          moltype = DNA  length = 1431
FEATURE                 Location/Qualifiers
source                  1..1431
                        mol_type = other DNA
                        organism = Phyllitis scolopendrium
SEQUENCE: 130
atggccaaat tcgaggtggt atctgcagtt cccactcttc ctcgctacat ctccatccaa   60
ggcgacaacg gcctctacct ggctctcaaa tcggatggtc tggtttcctt tgatgctaaa  120
gagacgaaca acttgacaac ttttgaagtc ctgtatgacg ctgatggtgc cttgctcatt  180
cgatcttctg caaaccgccg tttctggaga cgtgacgcct caaactacat ccgggcaact  240
accctaaatg tcactgatgc tggtcgcttc aaggcttcta agctggacac tggcaatttg  300
gcctttcagt cgactaaaga tgatctgttc ctgaaccgct atgcgagacg tgtggatggc  360
tacaatgccc tggagacagt ccctaaccag tggaccgaag tccgcgttac tgatgcaagc  420
gactatgctg ttcgtcttcc agattacatc tggctgaaag aaacaacgg gaagtatgtc  480
catctgcatt acgagcgaga tctaaattgg ctcaaattcc atggagattc tccttctgat  540
gactggggca ccaaccaagt cattccattg ctcgatggga gtgttgccct gtacaatgtc  600
aaggctggaa aattctggcg gaacagtacc aattggatat gggcagatgt gaacaagcaa  660
gaggatgctg aaagcaatcc gaggtgccat ttcgagcccc tcaaactagg cagcgagata  720
gtggccctca gaaccagtt caatggactc ttctgcaaga ggctaactga ctattggcag  780
agctgcctca atgctggcac cggttccccc aatgactctg aagcacgcct tatagtcggt  840
```

-continued

```
gatgcaacag agaagaggag catcttcaat gtcaagtacc tcatgaatct ggccaccact   900
agtgaccaga aactccagct ggttggtcgt ggctctgcga caaacaattc aagcaacatg   960
atggacatga acgtggtggt caccccttgag aacaaagttt caaagagtag tacgtggtcc  1020
aactccttca ccttcagcca aaaggtgacc acaaccttca aatgtggcgt tcctttcatt  1080
ggcaatgctg agattggcgt ggagattggt actgagcaga cctttgggca tgagtggggt  1140
gagactactg aagaaactgt ccaatttcag actgggtacc ttgtgaaaga tattggacct  1200
ggccagatgg cttcagtgac tgtgacatgt tcaactgcta agatacggat ccccttcacg  1260
tataagtgca aagatactgc ccttggaggc tatgatcgag ggactgtgga ctacattgat  1320
ggtgtttacg aaggagtggc ggcatatgat actagagcca aggttagcaa tggagggatg  1380
gtaaatgaag tcaaactgcg tgcagatgaa gagggccgag catttattct c            1431
```

SEQ ID NO: 131             moltype = AA  length = 472
FEATURE                    Location/Qualifiers
source                     1..472
                           mol_type = protein
                           organism = Phyllitis scolopendrium
SEQUENCE: 131
MGTPVNLVAT LPRFIAIKGD NGLYLALKPS GILTFDASER TRLATHEVLY NADESTFIIR   60
SANGRFWKRD SSGWVYANLE EPPATTQADA RFKLVHLDTS DKLAFQSAKD NRYLKRYLAS  120
ENGYNAVMTS LDVHTKVEVS DASEYAVSLP RYIFLKGNNG KYVHISYERS YAWLKFHGDE  180
PGNLWGIAEV VPLLNGSVAL YSPHATRFWR NSTNWIWADA QRDEIATNAR CHFEPIKLSS  240
SMLAFRSIFN DRICKRLTDY WTDSMNAAAA NTNDVDTRLT VSEATFAKSV FDVKYLLNLA  300
STSEQRPLAV AHGSARNDSP YTLDMAVTAI ISQTVSRSRT WSNSFTFSQS VTTSFKAGFP  360
ILAEGKVEVE IGFEQNFSNE WGQTTEQNIG FETQYTVKDV PPGGTASVTV VCSSAKMRIP  420
FTYKSKDTAP DGIDRPTMEY IDGIYEGVDA YKIEAQISGS AKSYNVPAKL PL           472

SEQ ID NO: 132             moltype = AA  length = 487
FEATURE                    Location/Qualifiers
source                     1..487
                           mol_type = protein
                           organism = Selaginella victoriae
SEQUENCE: 132
MAAPADPVAT LPRYIAIKGD NGNYLTLTSD GMLKFDSSER NRLATHEVLY NEDESTFVIR   60
SQNKRFWTER NGWICASWEG QPPTAANKDA RFKLVQLGTG KLAFQFAKND NYLKRYNSGI  120
NGYKAAVASP DQYTEIEVSD ASEYPVSLPQ YIYLKGNNGK YVHIYYMDNR KWLKYHGEGP  180
DNLWGMSEVH YLLDGSIALY SPESTYFWRN STNWIWTDAS KNEYIDNTRC HFEPVKLSSN  240
MIALKSKFNN QFCKRLTDYW SDSMNAAAGS TSDVETRLTV SEAVSGKYVF DVKYLLNLAS  300
TTDQKPLAVA YGSQVNNSPY QTDLTVTAIV SQSVSRSRTW SNSFTFSQSV TTEFKAGFPF  360
LAEGKVEVQI GFEQSFSNEW GETTEENIEF QTQYVVKDVP PGGQASVTVI CSAAKMRIPF  420
MYTSKDTAPD GVDRPSMQYI DGIYEGVDAY KIEAEINGSA GKETQRLPLK PAGIEKVKFV  480
APDPTAE                                                            487

SEQ ID NO: 133             moltype = AA  length = 485
FEATURE                    Location/Qualifiers
source                     1..485
                           mol_type = protein
                           organism = Athyrium filix-femina
SEQUENCE: 133
MAANPVALLP RYIALKGDNG MYLSLKSDGL LTFDAAEMTR LATHEVLYNE DDPDSTFIIR   60
SQNMRFWRRD SANWIRADRE ADQPPSAGEH AARFTLVTLA SGKLAFRSAV DSRYIKRYDA  120
GSLKGYNALV PSPDQYSAVE VSDAWEYAIS LPRYIFLKGN NGMYMQTYNE RSINWLKFHG  180
SDPGNLYGTS EVIPLLDGSL AFYNPQTDRF WRNSTNWIWT DSSRSDALTN TRCHFEPIRL  240
SRSMLALRNK FNNHICKRLT DYWENCLNAA ASNTSDATTH LTVSEAANGR QVFDIKYLLN  300
LASTSDQKVL AVGYGSSVNN SSYLTDLVVR VSISQSVSRS YTFSNSFTFS QTVSTEFKAG  360
IPFFGEGKIS VEIGLEQSFS NEWGETTEQG IEFETQHVVK DVPPGGSASV TITCSTAKMR  420
IPFTYKSKDS APDGTDRPTQ QFVDGIFEGV DAYKIEALIS DSVKSYTLPV ARSYVGAPTS  480
STELM                                                              485

SEQ ID NO: 134             moltype = AA  length = 484
FEATURE                    Location/Qualifiers
source                     1..484
                           mol_type = protein
                           organism = Athyrium niponicum
SEQUENCE: 134
MASSPANPVA LLPRYIAVKG DNGMYLSLKS DGLLTFDAAE RTRLATHEVL YNEDDPGATF   60
IIRSQNMRFW RRDSANWIRA DREADQPPSA ADNAARFTLV TLASGKLAFQ SALDGLYINR  120
YDLGSLKGYN ALARSPDQYS AVEVSDAWEY AVSLPRYIFL KGDNGMYMHA YYERNLNWLK  180
FHGSDPGNLY GTSEVIPLLD GSLAFYNPQT DRFWRNGGNW VFTDSSRSDA ITNTRCHFEP  240
IRLSRSMLAV RNKFNNHICK RLSDYWVNCL NAAASNTSDT TTHLTVSEAA NGRQVFDIKY  300
LLNLASTSDQ RPLAVGYGSS VNNSSYMSDL VVRVTISQKV SKSYTFSNSF TFSQTVTTEF  360
KAGIPFFGEG TVSVEIGLEQ SFSNEWGETT EEGIEFETQH VVKDVPPGGR ASVTVTCSTA  420
KMRIPFTYKS KDSAPDGTDR PTQQFVDGIF EGVDAYKIEA VISDSVKSYA IPVARSYVSR  480
PAIV                                                               484

SEQ ID NO: 135             moltype = AA  length = 473
FEATURE                    Location/Qualifiers
source                     1..473
                           mol_type = protein
                           organism = Onoclea sensibilis
```

```
SEQUENCE: 135
MASSLADPVA LLPRYIAIKG DNGMYLALKS DGLLTFDAAE ITRLATHEVL YNVDDPDATF  60
IIRSQNMRFW RRDSANWIRA DREADQPPSA GDTGARFTLA RLESGKLAFR SAVDGLYLNR  120
YNRDLHGYNA LEQTPNQWSE VEVSDAWEHP VSLPRHIFLK GDNGMYMHTY NERSLNWLKF  180
HGNDPGNLYG TSEVLHLLDG TLAFYSPQTD RFWRNSTNWI WTDSSRSDAL TNTRCHFEPI  240
RLSRSMVALR NKYNNLICKR LSDYWVNCLN AAASNTSDTT THLTVSEAAN GRQVFDVKYL  300
LNLASTSDQM PLAVGYGSSI NNSSYMTDLV VRVSISQSVS KSYTFSNSFT FSQTVSTEFT  360
AGIPFLGGGK ISVEIGMEQS FSNEWGETTQ RAIEFETQHV VKDVPPGGMA SVTIICSTAK  420
MRIPFTYKSK DSAPDGTDRP TQEFVDGIFE GVDAYKIEAV ISDSVRSYVM PVV         473

SEQ ID NO: 136        moltype = AA  length = 477
FEATURE               Location/Qualifiers
source                1..477
                      mol_type = protein
                      organism = Phyllitis scolopendrium
SEQUENCE: 136
MAKFEVVSAV PTLPRYISIQ GDNGLYLALK SDGLVSFDAK ETNNLTTFEV LYDADGALLI  60
RSSANRRFWR RDASNYIRAT TLNVTDAGRF KASKLDTGNL AFQSTKDDLF LNRYARRVDG  120
YNALETVPNQ WTEVRVTDAS DYAVRLPDYI WLKGNNGKYV HLHYERDLNW LKFHGDSPSD  180
DWGTNQVIPL LDGSVALYNV KAGKFWRNST NWIWADVNKQ EDAESNPRCH FEPLKLGSEI  240
VALKNQFNGL FCKRLTDYWQ SCLNAGTGSP NDSEARLIVG DATEKRSIFN VKYLMNLATT  300
SDQKLQLVGR GSATNNSSNM MDMNVVVTLE NKVSKSSTWS NSFTFSQKVT TTFKCGVPFI  360
GNAEIGVEIG TEQTFGHEWG ETTEETVQFQ TGYLVKDIGP GQMASVTVTC STAKIRIPFT  420
YKCKDTALGG YDRGTVDYID GVYEGVAAYD TRAKVSNGGM VNEVKLRADE EGRAFIL     477

SEQ ID NO: 137        moltype = DNA  length = 696
FEATURE               Location/Qualifiers
source                1..696
                      mol_type = other DNA
                      organism = Selaginella victoriae
SEQUENCE: 137
atggcagcag cggcattcta cgtaccacgc aagtccaatg agctctactt cttcaaggga  60
actcaatatg cacgaatcgg cctcactcca acccctgggt caactgcatc tgacaagctc  120
ctggacggcc ctcacaacat cgtcgacaaa tggccgtcgc tcaagaaggc tggtttcacc  180
acggttgatg aagcgttagc tgttccggga ggccaaggtg agacttactt cttctcaggc  240
accaaaggtg tgctggtgaa ggtgatccct ggcactctgg atgactatat catcgaggga  300
cccttcacca tctccgagag ggagccttac aaggaggctg gcttttgcac catcgacgct  360
gtgcttccgg tcccaaattc tcccacggac gcctacgtct tcagctgtga ccgctacatt  420
cgcatcaacg tggtgaaaga cgctctggtc gggggaccta agaacatcct ctcctactgg  480
ccttccctca aaaagctcgg cttcagcaca gtggacgttg ctttcggcat cccaggcacc  540
actcaagatg cctacttctt cagcggaagc gagtatggcc gtgtgcatgt cgttcctgga  600
actctcgatg acactgtcgt aggcggcccc agcgaggtgg ccgagtactg gccatcgttg  660
gtcaaggctg ggttctactg taaagatcag aacaac                           696

SEQ ID NO: 138        moltype = AA  length = 232
FEATURE               Location/Qualifiers
source                1..232
                      mol_type = protein
                      organism = Selaginella victoriae
SEQUENCE: 138
MAAAAFYVPR KSNELYFFKG TQYARIGLTP TPGSTASDKL LDGPHNIVDK WPSLKKAGFT  60
TVDEALAVPG GQGETYFFSG TKGVLVKVIP GTLDDYIIEG PFTISEREPY KEAGFCTIDA  120
VLPVPNSPTD AYVFSCDRYI RINVVKDALV GGPKNILSYW PSLKKLGFST VDVAFGIPGT  180
TQDAYFFSGS EYGRVHVVPG TLDDTVVGGP SEVAEYWPSL VKAGFYCKDQ NN          232

SEQ ID NO: 139        moltype = DNA  length = 30
FEATURE               Location/Qualifiers
misc_feature          1..30
                      note = cloning primer
source                1..30
                      mol_type = other DNA
                      organism = synthetic construct
SEQUENCE: 139
ggtaatcaaa gatggcggcg actaaggcgg                                  30

SEQ ID NO: 140        moltype = DNA  length = 27
FEATURE               Location/Qualifiers
misc_feature          1..27
                      note = cloning primer
source                1..27
                      mol_type = other DNA
                      organism = synthetic construct
SEQUENCE: 140
ggcggctagg aaagggagga gctgtcg                                     27

SEQ ID NO: 141        moltype = DNA  length = 28
FEATURE               Location/Qualifiers
misc_feature          1..28
                      note = cloning primer
```

-continued

```
source                   1..28
                         mol_type = other DNA
                         organism = synthetic construct
SEQUENCE: 141
ggattgcata tggacgagcc gacatggc                                         28

SEQ ID NO: 142          moltype = DNA   length = 46
FEATURE                 Location/Qualifiers
misc_feature            1..46
                         note = cloning primer
source                   1..46
                         mol_type = other DNA
                         organism = synthetic construct
SEQUENCE: 142
cagcagcggc catatcgaag gtcgtcatat ggggtacgcg cagtgg                     46

SEQ ID NO: 143          moltype = DNA   length = 32
FEATURE                 Location/Qualifiers
misc_feature            1..32
                         note = cloning primer
source                   1..32
                         mol_type = other DNA
                         organism = synthetic construct
SEQUENCE: 143
atggtgggat ccagcgggca gtttaacgat gg                                    32

SEQ ID NO: 144          moltype = DNA   length = 30
FEATURE                 Location/Qualifiers
misc_feature            1..30
                         note = cloning primer
source                   1..30
                         mol_type = other DNA
                         organism = synthetic construct
SEQUENCE: 144
aaggatccat gggaacacct gttaatcttg                                       30

SEQ ID NO: 145          moltype = DNA   length = 35
FEATURE                 Location/Qualifiers
misc_feature            1..35
                         note = cloning primer
source                   1..35
                         mol_type = other DNA
                         organism = synthetic construct
SEQUENCE: 145
ttctcgagtt aaagtggtag cttagcagga acatt                                 35

SEQ ID NO: 146          moltype = DNA   length = 46
FEATURE                 Location/Qualifiers
misc_feature            1..46
                         note = cloning primer
source                   1..46
                         mol_type = other DNA
                         organism = synthetic construct
SEQUENCE: 146
aattaggcat gcgaggatcc atggcagccc ctgcagatcc agttgc                     46

SEQ ID NO: 147          moltype = DNA   length = 53
FEATURE                 Location/Qualifiers
misc_feature            1..53
                         note = cloning primer
source                   1..53
                         mol_type = other DNA
                         organism = synthetic construct
SEQUENCE: 147
cagtggtggt ggtggtggtg ctcgagctac tccgctgtag gatcaggagc aac            53

SEQ ID NO: 148          moltype = DNA   length = 48
FEATURE                 Location/Qualifiers
misc_feature            1..48
                         note = cloning primer
source                   1..48
                         mol_type = other DNA
                         organism = synthetic construct
SEQUENCE: 148
aattaggcat gcgaggatcc atggcagcaa atccagtagc acttctgc                   48

SEQ ID NO: 149          moltype = DNA   length = 53
FEATURE                 Location/Qualifiers
misc_feature            1..53
```

-continued

```
                          note = cloning primer
source                    1..53
                          mol_type = other DNA
                          organism = synthetic construct
SEQUENCE: 149
cagtggtggt ggtggtggtg ctcgagttac attagttcag tagatgatgt agg            53

SEQ ID NO: 150            moltype = DNA   length = 48
FEATURE                   Location/Qualifiers
misc_feature              1..48
                          note = cloning primer
source                    1..48
                          mol_type = other DNA
                          organism = synthetic construct
SEQUENCE: 150
aattaggcat gcgaggatcc atggcatcat cacctgcaaa cccagtag                   48

SEQ ID NO: 151            moltype = DNA   length = 54
FEATURE                   Location/Qualifiers
misc_feature              1..54
                          note = cloning primer
source                    1..54
                          mol_type = other DNA
                          organism = synthetic construct
SEQUENCE: 151
cagtggtggt ggtggtggtg ctcgagctag acaattgcag ggcggcttac atag           54

SEQ ID NO: 152            moltype = DNA   length = 48
FEATURE                   Location/Qualifiers
misc_feature              1..48
                          note = cloning primer
source                    1..48
                          mol_type = other DNA
                          organism = synthetic construct
SEQUENCE: 152
aattaggcat gcgaggatcc atggcatcgt cacttgcaga cccagtag                   48

SEQ ID NO: 153            moltype = DNA   length = 52
FEATURE                   Location/Qualifiers
misc_feature              1..52
                          note = cloning primer
source                    1..52
                          mol_type = other DNA
                          organism = synthetic construct
SEQUENCE: 153
cagtggtggt ggtggtggtg ctcgagctag acaactggca ttacatagct cc             52

SEQ ID NO: 154            moltype = DNA   length = 22
FEATURE                   Location/Qualifiers
misc_feature              1..22
                          note = cloning primer
source                    1..22
                          mol_type = other DNA
                          organism = synthetic construct
SEQUENCE: 154
aaggatccat ggcagcagcg gc                                               22

SEQ ID NO: 155            moltype = DNA   length = 41
FEATURE                   Location/Qualifiers
misc_feature              1..41
                          note = cloning primer
source                    1..41
                          mol_type = other DNA
                          organism = synthetic construct
SEQUENCE: 155
ttaagctttt agttgttctg atctttacag tagaacccag c                         41

SEQ ID NO: 156            moltype = AA   length = 5
FEATURE                   Location/Qualifiers
REGION                    1..5
                          note = fusion linker
source                    1..5
                          mol_type = protein
                          organism = synthetic construct
SEQUENCE: 156
EEKKN                                                                   5
```

That which is claimed:

1. A recombinant polynucleotide encoding an insecticidal polypeptide comprising an amino acid sequence having at least 80% sequence identity compared to an amino acid sequence selected from the group consisting of SEQ ID NO: 131, SEQ ID NO: 132, SEQ ID NO: 133, SEQ ID NO: 134, and SEQ ID NO: 135.

2. The recombinant polynucleotide of claim 1, wherein the polynucleotide is a 3 cDNA.

3. A DNA construct comprising, the recombinant polynucleotide of claim 1 and a heterologous regulatory sequence operably linked to the recombinant polynucleotide.

4. A transgenic plant or plant cell comprising the DNA construct of claim 3.

5. A method of inhibiting growth or killing an agricultural insect pest population, comprising contacting the insect pest population with the transgenic plant or plant cell of claim 3 having an insecticidally-effective amount of the insecticidal polypeptide or with an extract thereof comprising an insecticidally-effective amount of the insecticidal polypeptide.

6. The method of claim 5, wherein the insect pest or insect pest population is resistant to a Bt toxin.

7. A method of controlling insect pest damage to plants comprising providing to an insect pest or pest population for ingestion an insecticidally-effective amount of an insecticidal polypeptide, wherein said insecticidal polypeptide is provided as the transgenic plant or plant cell of claim 3 containing the insecticidal polypeptide or an extract thereof.

8. A transgenic plant or plant cell comprising the recombinant polynucleotide of claim 1.

9. A method of controlling a *Lepidoptera* and/or *Coleoptera* insect infestation of a transgenic plant, the method comprising growing the transgenic plant or plant cell according to claim 8 under conditions sufficient to control said insect infestation.

10. A plant seed comprising the recombinant polynucleotide of claim 1.

* * * * *